(12) United States Patent
Yu et al.

(10) Patent No.: US 11,603,567 B2
(45) Date of Patent: Mar. 14, 2023

(54) FECAL BACTERIAL MARKERS FOR COLORECTAL CANCER

(71) Applicant: The Chinese University of Hong Kong, Hong Kong (CN)

(72) Inventors: Jun Yu, Hong Kong (CN); Joseph Jao Yiu Sung, Hong Kong (CN); Qiaoyi Liang, Hong Kong (CN)

(73) Assignee: The Chinese University of Hong Kong, Hong Kong (CN)

(*) Notice: Subject to any disclaimer, the term of this patent is extended or adjusted under 35 U.S.C. 154(b) by 382 days.

(21) Appl. No.: 16/327,560

(22) PCT Filed: Aug. 23, 2017

(86) PCT No.: PCT/CN2017/098592
§ 371 (c)(1),
(2) Date: Feb. 22, 2019

(87) PCT Pub. No.: WO2018/036503
PCT Pub. Date: Mar. 1, 2018

(65) Prior Publication Data
US 2020/0002769 A1    Jan. 2, 2020

Related U.S. Application Data

(60) Provisional application No. 62/379,635, filed on Aug. 25, 2016.

(30) Foreign Application Priority Data

Apr. 20, 2017  (CN) .......................... 201710261558.9

(51) Int. Cl.
*C12Q 1/6886* (2018.01)
*C12Q 1/689* (2018.01)
*C12Q 1/6827* (2018.01)

(52) U.S. Cl.
CPC .......... *C12Q 1/6886* (2013.01); *C12Q 1/689* (2013.01); *C12Q 1/6827* (2013.01);
(Continued)

(58) Field of Classification Search
CPC ............................. C12Q 1/6886; C12Q 1/689
See application file for complete search history.

(56) References Cited

U.S. PATENT DOCUMENTS

2014/0107092 A1    4/2014  Meyerson et al.

FOREIGN PATENT DOCUMENTS

| CN | 105368944 A | 3/2016 |
| CN | 105473738 A | 4/2016 |

(Continued)

OTHER PUBLICATIONS

Liang, et al. "303 Fecal Bacteria Act as Novel Biomarkers for Non-lnvasive Diagnosis of Colorectal Cancer." Gastroenterology, S-69, 1 page (2016).

(Continued)

*Primary Examiner* — Diana B Johannsen
(74) *Attorney, Agent, or Firm* — Kilpatrick Townsend & Stockton LLP

(57) ABSTRACT

Provided is a non-invasive method for diagnosing colorectal cancer in a subject by detecting enrichment or reduction of certain bacterial species. A kit and device useful for such methods are also provided. In addition, a method for reducing the risk of colon cancer by regulating the pertinent bacterial species in human colon is also provided.

14 Claims, 45 Drawing Sheets

Specification includes a Sequence Listing.

(52) U.S. Cl.
CPC .. *C12Q 2600/112* (2013.01); *C12Q 2600/118* (2013.01); *C12Q 2600/156* (2013.01); *C12Q 2600/158* (2013.01); *G01N 2333/33* (2013.01)

(56) References Cited

FOREIGN PATENT DOCUMENTS

| CN | 105473739 | A | | 4/2016 | |
|---|---|---|---|---|---|
| CN | 105803061 | A | | 7/2016 | |
| EP | 2955232 | A1 | | 12/2015 | |
| WO | 2012/142605 | A1 | | 10/2012 | |
| WO | WO-2015018308 | A1 | * | 2/2015 | ........... C12Q 1/6806 |
| WO | 2016/112488 | A1 | | 7/2016 | |
| WO | 2016/142605 | A1 | | 9/2016 | |

OTHER PUBLICATIONS

Goodman, "Fecal bacteria plus FIT promising in diagnosis of colorectal cancer," HCVHub, pp. 1-4 (2016).
Wong, et al., "Quantitation of faecal *Fusobacterium* improves faecal immunochemical test in detecting advanced colorectal neoplasia", GUT, vol. 66, No. 8, pp. 1441-1448 (2017).
Extended European Search Report for EP Patent Application No. 17842925.4, dated Jun. 2, 2020, 14 pages.
Ahn, et al. "Human gut microbiome and risk for colorectal cancer." Journal of the National Cancer Institute 105, No. 24 (2013): 1907-1911.
Arthur, et al. "Intestinal inflammation targets cancer-inducing activity of the microbiota." science 338, No. 6103 (2012): 120-123.
Baracos, et al. "Investigations of branched-chain amino acids and their metabolites in animal models of cancer." The Journal of nutrition 136, No. 1 (2006) 237S-242S.
Boleij, et al. "Association between *Streptococcus bovis* and colon cancer." Journal of clinical microbiology 47, No. 2 (2009): 516-516.
Castellarin, et al. "Fusobacterium nucleatum infection is prevalent in human colorectal carcinoma." Genome research 22, No. 2 (2012): 299-306.
Chen, et al. "Human intestinal lumen and mucosa-associated microbiota in patients with colorectal cancer." PloS one 7, No. 6 (2012): e39743.
Ciccarelli, et al. "Toward automatic reconstruction of a highly resolved tree of Tife." science 311, No. 5765 (2006): 1283-1287.
Cuevas-Ramos, et al. "*Escherichia coli* induces DNA damage in vivo and triggers genomic instability in mammalian cells." Proceedings of the National Academy of Sciences 107, No. 25 (2010): 11537-11542.
Ding, et al. "Dynamics and associations of microbial community types across the human body." Nature 509, No. 7500 (2014): 357.
Dove, et al. "Intestinal neoplasia in the ApcMin mouse: independence from the microbial and natural killer (beige locus) status." Cancer research 57, No. 5 (1997) 812-814.
Edge, et al. "The American Joint Committee on Cancer: the 7th edition of the AJCC cancer staging manual and the future of TNM." Annals of surgical oncology 17, No. 6 (2010): 1471-1474.
Feng, et al. "Gut microbiome development along the colorectal adenoma-carcinoma sequence." Nature communications 6 (2015): 6528.
Ferlay, et al. GLOBOCAN 2012 v1.0, Cancer Incidence and Mortality Worldwide. KARC CancerBase. Lyon, France: International Agency for Research on Cancer, 2013.) database, located at https://publications.iarc.fr/Databases/Iarc-Cancerbases/GLOBOCAN-2012-Estimated-Cancer-Incidence-Mortality-And-Prevalence-Worldwide-In-2012-V1.0-2012.
Foulkes, "Inherited susceptibility to common cancers." New England Journal of Medicine 359, No. 20 (2008): 2143-2153.
Galvan, et al. "Beyond genome-wide association studies: genetic heterogeneity and individual predisposition to cancer." TRENDS in Genetics 26, No. 3 (2010) 132-141.

Godon, et al. "Molecular microbial diversity of an anaerobic digestor as determined by small-subunit rDNA sequence analysis." Appl. Environ. Microbiol. 63, No. 7 (1997): 2802-2813.
Gonçalves, et al. "Leucine modulates the effect of Walker factor, a proteolysis-inducing factor-like protein from Walker tumours, on gene expression and cellular activity in C2C12 myotubes." Cytokine 64, No. 1 (2013): 343-350.
Grivennikov, et al. "Adenoma-linked barrier defects and microbial products drive IL-23/IL-17-mediated tumour growth." Nature 491, No. 7423 (2012): 254.
Holmes, et al. "Dirichlet multinomial mixtures: generative models for microbial metagenomics." PloS one 7, No. 2 (2012): e30126.
Huang, et al. "Predictive power of quantitative and qualitative fecal immunochemical tests for hemoglobin in population screening for colorectal neoplasm." European Journal of Cancer Prevention 23, No. 1 (2014): 27-34.
Irrazábal, et al. "The multifaceted role of the intestinal microbiota in colon cancer." Molecular cell 54, No. 2 (2014): 309-320.
Jalanka, et al. "Effects of bowel cleansing on the intestinal microbiota." Gut 64, No. 10 (2015): 1562-1568.
Kabat, et al. "A longitudinal study of serum insulin and glucose levels in relation to colorectal cancer risk among postmenopausal women." British journal of cancer 106, No. 1 (2012): 227.
Kanehisa, et al. "KEGG for integration and interpretation of large-scale molecular data sets." Nucleic acids research 40, No. D1 (2011): D109-D114.
Kassinen, et al. "The fecal microbiota of irritable bowel syndrome patients differs significantly from that of healthy subjects." Gastroenterology 133, No. 1 (2007): 24-33.
Knights, et al. "Supervised classification of human microbiota." FEMS microbiology reviews 35, No. 2 (2011): 343-359.
Kostic, et al. "Fusobacterium nucleatum potentiates intestinal tumorigenesis and modulates the tumor-immune microenvironment." Cell host & microbe 14, No. 2 (2013): 207-215.
Kostic, et al. "Genomic analysis identifies association of Fusobacterium with colorectal carcinoma." Genome research 22, No. 2 (2012): 292-298.
Kremer, et al. "Peptostreptococcus micros coaggregates with Fusobacterium nucleatum and non-encapsulated Porphyromonas gingivalis." FEMS microbiology letters 182, No. 1 (2000): 57-61.
Lee, et al. "Accuracy of fecal immunochemical tests for colorectal cancer: systematic review and meta-analysis." Annals of internal medicine 160, No. 3 (2014): 171-181.
Li, et al. "An integrated catalog of reference genes in the human gut microbiome." Nature biotechnology 32, No. 8 (2014): 834.
Li, et al. "SOAP2: an improved ultrafast tool for short read alignment." Bioinformatics 25, No. 15 (2009): 1966-1967.
Lichtenstein, et al. "Environmental and heritable factors in the causation of cancer—analyses of cohorts of twins from Sweden, Denmark, and Finland." New England journal of medicine 343, No. 2 (2000): 78-85.
Markowitz, et al. "IMG: the integrated microbial genomes database and comparative analysis system." Nucleic acids research 40, No. D1 (2011): D115-D122.
McCoy, et al. "Fusobacterium is associated with colorectal adenomas." PloS one 8, No. 1 (2013): e53653.
Nakatsu, et al. "Gut mucosal microbiome across stages of colorectal carcinogenesis." Nature communications 6 (2015): 8727.
Pedersen, et al. "Solobacterium moorei bacteremia: identification, antimicrobial susceptibility, and clinical characteristics." Journal of clinical microbiology 49, No. 7 (2011): 2766-2768.
Peng, et al. "Feature selection based on mutual information: criteria of max-dependency, max-relevance, and min-redundancy." IEEE Transactions on Pattern Analysis & Machine Intelligence 8 (2005): 1226-1238.
Qin, et al. "A metagenome-wide association study of gut microbiota in type 2 diabetes." Nature 490, No. 7418 (2012): 55.
Qin, et al. "A human gut microbial gene catalogue established by metagenomic sequencing." nature 464, No. 7285 (2010): 59.
Rubinstein, et al. "Fusobacterium nucleatum promotes colorectal carcinogenesis by modulating E-cadherin/β-catenin signaling via its FadA adhesin." Cell host & microbe 14, No. 2 (2013): 195-206.
Scanlan, et al. "Culture-independent analysis of the gut microbiota in colorectal cancer and polyposis." Environmental microbiology 10, No. 3 (2008): 789-798.

(56) References Cited

OTHER PUBLICATIONS

Seder, et al. "Clostridium septicum aortitis: report of two cases and review of the literature." Journal of Vascular Surgery 49, No. 5 (2009): 1304-1309.
Shannon, et al. "Cytoscape: a software environment for integrated models of biomolecular interaction networks." Genome research 13, No. 11 (2003): 2498-2504.
Shin, et al. "An increase in the *Akkermansia* spp. population induced by metformin treatment improves glucose homeostasis in diet-induced obese mice." Gut 63, No. 5 (2014): 727-735.
Sobhani, et al. "Microbial dysbiosis in colorectal cancer (CRC) patients." PloS one 6, No. 1 (2011): e16393.
Steer, et al. "*Clostridium hathewayi* sp. nov., from human faeces." Systematic and applied microbiology 24, No. 3 (2001): 353-357.
Storey, et al. "Statistical significance for genomewide studies." Proceedings of the National Academy of Sciences 100, No. 16 (2003): 9440-9445.
Sundqvist, "Taxonomy, ecology, and pathogenicity of the root canal flora." Oral Surgery, Oral Medicine, Oral Pathology 78, No. 4 (1994): 522-530.
Sunagawa, et al. "Metagenomic species profiling using universal phylogenetic marker genes." Nature methods 10, No. 12 (2013): 1196.
Sung, et al. "Increasing incidence of colorectal cancer in Asia: implications for screening." The lancet oncology 6, No. 11 (2005): 871-876.
Sung, et al. "An updated Asia Pacific Consensus Recommendations on colorectal cancer screening." Gut 64, No. 1 (2015): 121-132.
Ulger Toprak, et al. "A possible role of Bacteroides fragilis enterotoxin in the aetiology of colorectal cancer." Clinical microbiology and infection 12, No. 8 (2006): 782-786.
Uronis, et al. "Modulation of the intestinal microbiota alters colitis-associated colorectal cancer susceptibility." PloS one 4, No. 6 (2009): e6026.
Van Duijnhoven, et al. "Blood lipid and lipoprotein concentrations and colorectal cancer risk in the European Prospective Investigation into Cancer and Nutrition." Gut 60, No. 8 (2011): 1094-1102.
Wang, et al. "Conservative fragments in bacterial 16S rRNA genes and primer design for 16S ribosomal DNA amplicons in metagenomic studies." PloS one 4, No. 10 (2009): e7401.
Watanabe, et al. "*Bacteroides clarus* sp. nov., *Bacteroides fluxus* sp. nov. and *Bacteroides oleiciplenus* sp. nov., isolated from human faeces." International journal of systematic and evolutionary microbiology 60, No. 8 (2010): 1864-1869.
Wu, et al. "A human colonic commensal promotes colon tumorigenesis via activation of T helper type 17 T cell responses." Nature medicine 15, No. 9 (2009): 1016.
Yoshioka, et al. "Binding of Actinobacillus actinomycetemcomitans Tipopolysaccharides to Peptostreptococcus micros stimulates tumor necrosis factor a production by macrophage-like cells." Oral microbiology and immunology 20, No. 2 (2005): 118-121.
Yu, et al. "Metagenomic analysis of faecal microbiome as a tool towards targeted non-invasive biomarkers for colorectal cancer." Gut 66, No. 1 (2017): 70-78.
Zackular, et al. "The human gut microbiome as a screening tool for colorectal cancer." Cancer prevention research 7, No. 11 (2014): 1112-1121.
Zeller, et al. "Potential of fecal microbiota for early-stage detection of colorectal cancer." Molecular systems biology 10, No. 11 (2014): 766.
International Search Report in PCT/CN2017/098592, dated Oct. 25, 2017, 6 pages.
Candela, et al. "Inflammation and colorectal cancer, when microbiota-host mutualism breaks." World journal of gastroenterology: WJG 20, No. 4 (2014): 908.
Liang, et al. "Fecal bacteria act as novel biomarkers for noninvasive diagnosis of colorectal cancer." Clinical Cancer Research 23, No. 8 (2017): 2061-2070.

\* cited by examiner

SEQUENCE LISTING

```
<160> NUMBER OF SEQ ID NOS: 89

<210> SEQ ID NO 1
<211> LENGTH: 1062
<212> TYPE: DNA
<213> ORGANISM: Roseburia intestinalis

<400> SEQUENCE: 1
atggaaaaag taaaggcatt ttgtaaacgg aaaaacattg agatatccgt caagcgctac      60
ctgattgatg cacttggtgc gatggcacag ggattatttg catcgctttt gatcggaacg     120
atcatcagta cacttggaac gcagcttaat attccgattc ttgtgacagt cgggacttac     180
gcgaaagcgg cagtcggacc ggcaatggcg atcgaatcg gatatgcact gcaggcagcg      240
cctttagtac tgttttcact tgcggcagtc ggtgcggcgg caaatgaact tggcggggca     300
ggcggaccgc ttgcggtact tgtggttgca atttttgcag cagaatttgg aaaagcagtt     360
tccaaagaga caaaaatcga tattattgtc actccgtttg tgaccatttt tgtcggggtc     420
gcgctttcta tctggtgggc tccggcgatc ggtgcggcag cgagtgcagt cggtaatgcg     480
atcatgtggg caaccgagct gcagccgttt ttcatgggaa tcattgtatc tgtgatcgtc     540
gggattgcac tgacactgcc gatcagcagc gcagcaatct gtgcagcact tggactgacc     600
ggattagccg gtggtgcagc acttgccgga tgctgtgcgc agatggtcgg atttgcagtg     660
gcaagtttcc gtgaaaataa atggggcgga ttgtttgcac agggaatcgg tacatccatg     720
cttcagatgg gtaatatcgt gaaaaatccg cgcatcggc tgccggcgac attggcgtct     780
gcaatcaccg gaccgatcgc aatgtgtctg ttccatttac agatgaatgg tgcagcagtt     840
```

```
tcctccggta tgggaacctg tggactggtc ggacagattg gtgtctatac gggatggatc    900
gcagatattg aagcgggaag caaagctgcc attacaccga tggactggat cggactgatt    960
ttcgtaagct ttcttctgcc gggcgtttta tcatggcttt ttagtgtgtt attccgtaag   1020
atcggctgga tcaaagaagg cgatatgagg ctggacttat aa                      1062

<210> SEQ ID NO 2
<211> LENGTH: 1161
<212> TYPE: DNA
<213> ORGANISM: Bacteroides clarus

<400> SEQUENCE: 2
atgaaaatca acaattagc gaaaagcgca tcattcttgc tggtggcagg ttttatcagt      60
tttactattc cgtcgtgtag cagtgaagaa gaaatcatca tccttcagga tgtaaaagta    120
aacagtgaaa gcttcaatct ggccgaagac ggcagtacga ccatagaagt caaggtagta    180
cccgaaaata ctccaatagc caaagccgta ctcagcacat cattatttaa tgaaagcggt    240
gttttcgaag taacccgact cactcccaaa ggtaacggtg tatggcagat agcagcaaaa    300
gtaaaggact tctcacgcat tcaaaacggt caggacgtaa tactttccgt ctatcaggaa    360
gataatatgt atatccaaac cacattgaaa ataaacgacc catatagcat cgagggtaaa    420
tatacaccgg tccatccgca agcctttact ttctacagtg ccgaagacgg caaactgatg    480
gagattccgt tcatcatcac agccgacaac gcagccgacc ttgccgccat cagctacgac    540
aatataaagg tagtcaatgg caccggaagc tctacaccca gcataagtat cacacatttc    600
gcaatagctc cgatgacagg taaaacaggc ttctatctgc aagtggataa cgcccaactc    660
gaaacggtaa aaaagccat cacaaccatc gcttttttgg actgccgggt tatgataacc    720
ggccctaacg gccgtgttgc ctatactcct gtgcgcctca ttgtttcttc tccgaagtgc    780
atcatcaagg acgaccaact cagcctgctg catacagaat tgtccgcccc ggagtttaat    840
agacaaatca ccatagatat gacccacgat ttttatcgtt tgggcaaaca gaatgataaa    900
acaacctttg aggcgtttga aaaccgaggc ttgtataact cacaaggaga atggcagat    960 gcagaccctc agttcatttc gttgggttat accactcagg gcaaaaatac aacatgtaac   1020
gtaactttaa acatgatgc cacaattcct gcaatcggca cttaccacat ggtagaacgc   1080
ctaaaaggat attgggaata tgacggaaag aaatatccga ccgtttgtac agacctgcaa   1140
ttccaaatca cgattaaata a                                             1161

<210> SEQ ID NO 3
<211> LENGTH: 1935
<212> TYPE: DNA
<213> ORGANISM: Lachnoclostridium sp.

<400> SEQUENCE: 3
aatatccgat atggcaacgg agctctggta gtagtccggg caagggaaaa ccttgtacat     60
ggcgaagcag agcagattac cttcaatact aaaatattag aaaggtgcgt gaggcatttg    120
agaaatccga ttgaagtatt gaaaactcta caagagaaag caggcaacga gaactatcaa    180
tttgaacgcc tgtaccgaaa tctgtacaac gaggagtttt ccctattggc atacggaaat    240
ctctctgcaa agagggaaa tctgaccaag ggaacagacg gcgccacaat agacggaatg    300
ggaatggagc ggattcgcaa gctgattgaa agcctgcgga accacagtta ccagccgtcc    360
cctgcgagac gtgcctatat cccaaaatct aatggaaaac ggcgtccgtt aggcataccc    420
```

| | |
|---|---|
| tctgttgacg ataagctggt gcaggaagtt gtgaggttaa ttctcgaaag tgtgtatgaa | 480 |
| agcaatttt ctgaacattc gcatggtttt agaccgaaca ggagctgtca cacggcactg | 540 |
| acccagattc aaagaaactt cacaggggtt aaatggttca ttgaggggga catcaaaggt | 600 |
| tattttgaca ccatcgacca ccatatcctt gtggatattt aagaaggcg cataaaggac | 660 |
| gaatacctaa tctcgctgat atggaaattt ctgaaagccg atacttaga agactggaaa | 720 |
| ttcaatccta cctattccgg cactccgcaa ggctcggtca tcagtccaat acttgccaat | 780 |
| atctacctta acgaattcga tacctatgtt gaagaataca tagagaaatt caaccgtggt | 840 |
| aaaagacgtg aaagaaacag tgagtatcgc ttttatagtg atggcgcatc gaaactgagg | 900 |
| gtaaagtacc gcgggttatg ggaataatg acagccgatg aaaagaaaa agccaaatgt | 960 |
| gaagtaaatg agctcatgaa aaaagcaaaa cagattccag ctatgaatcc gatggacagc | 1020 |
| aattaccgcc gtctgctcta ttgcaggtat gcggatgatt ttatttgcgg agtaatcgga | 1080 |
| agcaaggaag atgcagaaac catcaaggct gattttagcc ggtacctgaa agaaaagctg | 1140 |
| ggactggata tgtcggaaga aagacactg attacacact caaacgaaaa agcggcgttc | 1200 |
| cttggctacg aaatcgctgt ttccagaagc aatgaataca aaaagataag caacggacag | 1260 |
| aaggcaagaa cctttaatgg gcgtgttcat ctatttatgc cacataataa atgggttaag | 1320 |
| aagctgacca gttgcggagc aatggaaatc aaacagcagg acggcaaaga aatatggaaa | 1380 |
| ccgcaggcga ggaaagacct catcaacaaa gagccgattg aaatcctaag catttacaat | 1440 |
| gccgaaattc gtgggctgta caattattat tgtttggcaa gcaacgtatg caagctgcag | 1500 |
| aaatattact acatcatgga atacagcatg taccagacgt tgcagcgaa gtaccgtgat | 1560 |
| aatttgcgga aaacgattaa caagcatacc cgaaacggcg tgtttggtgt cagctacact | 1620 |
| acaaaaccg gcaacgagaa acgggcgaca ttcgtgaaag gaagcttcca aaaacggact | 1680 |
| gtcagcttag attacagtga tgaaatcccc tcttatcctg ccgcaaaata tagtcggaaa | 1740 |
| aacggcttaa ttgagcggtt acagggtgga aaatgtgaac tatgcggaca gcagaccgac | 1800 |
| aatgtaaaag ttcatcatgt caggaagctg aaagaattag ccggtatgaa agaatgggaa | 1860 |
| agaaaaatgg ttcagatgaa cagaaaaact ctggttgttt gtaatacatg ttatggaaac | 1920 |
| ataacaggca agtaa | 1935 |

<210> SEQ ID NO 4
<211> LENGTH: 930
<212> TYPE: DNA
<213> ORGANISM: Parvimonas micra

<400> SEQUENCE: 4

| | |
|---|---|
| aatcaattta gaattggttt atcaagaatg gagagagttg ttagagaaag aatgtcaact | 60 |
| caagatccag accttgctac gcctcaagga cttattaata taagacctct tgttgcgtct | 120 |
| ttaaaagaat tcttcggttc ttcacaatta tcacaattca tggatcaaaa caatccactt | 180 |
| gcagaactta ctcataagag aagattatca gcattaggac ctggtggtct tagtagagat | 240 |
| agagcaggat acgaagtaag agacgttcat gaaagtcact acggaagaat ttgtccgata | 300 |
| gaaactccag aaggtccaaa catcggtctt attacttctc ttacaactta tgcaagagtt | 360 |
| gatcaatatg gatttattga aacaccatat cgtgttgtaa ataatggaat tgctacaaag | 420 |
| gacattgttt atttaactgc tgatgaagaa gatgaagtta ttatcgctca agccaatgaa | 480 |
| ccacttgatg aaaatggacg ttttgtaaac gaaagagtaa gtggtcgtgg tattaatggc | 540 |
| gaaaatgata tttatccaag agatacaatt caacttatgg acgtttctcc tcaacaaatt | 600 |

```
gtatcagttg gtacagcaat gattcctttc cttgaaaatg acgatgctac tcgtgcgttg    660
atgggttcaa acatgcaaag acaagcagtg cctctacttg ttactgaagc tcctattgta    720
ggaaccggta tagaacataa agcggcaaga gatagtggtg ttgttatcat tgctaaaaat    780
tcaggaattg ttacaaaagt tgatagtgat gaaattcata ttaaaagaga tttagataat    840
gtagttgata aatatagatt acttaaattt aaacgttcaa atcaaggaac aacaattaat    900
caaagaccta tagttaatga aaatgacaga                                     930

<210> SEQ ID NO 5
<211> LENGTH: 687
<212> TYPE: DNA
<213> ORGANISM: Fusobacterium nucleatum

<400> SEQUENCE: 5
tctgcaaaag aaaaagttgc tgcattagtt gctgcattaa aagcagatgg atatgatttt     60
actgttggta tccctcttga tacaccaata ggaaaatctg aaagagttgt aagtgctggt    120
aaagggattg agataaaaa gaatatgaag ctaattgaaa acttagcaaa acaagctgga    180
gcttctattg ttcttctcg tccagtggca gaaacattgc aatatgtacc tcttgaccgt    240
tatgtaggaa tgtcaggaca aaaatttgtt ggaaaccttt atatagcttg tggaatttca    300
ggagctttac aacatttaaa aggaattaaa gatgcaacaa caatagttgc tataaataca    360
aactcaaatg ctccaatatt taagaatgca gactatggaa tagttggaga tttagcagaa    420
attttacctt tattaactaa ggaattagat aatggagaag ctaaaaaaga tgcaccacct    480
atgaagaaaa tgaagagagt tatacctaga gtagtgtata gtcctcatgt atatgtatgt    540
agtggttgtg acatgaata caatcctgat ttaggagatg aagattctga cataaaacca    600
ggaactagat ttaaagattt accagaagat tggacttgtc ctgattgtgg agatccaaaa    660
tctggatata tagatgcaaa aaaataa                                        687

<210> SEQ ID NO 6
<211> LENGTH: 627
<212> TYPE: DNA
<213> ORGANISM: Clostridium hathewayi

<400> SEQUENCE: 6
atgcctatac ttcagcagct tctcacatta gtagagcagc acttcggtaa caaatgcgaa     60
atcgtgcttc atgatctgac aaaggattac aaccatacca ttgtcgatat ccgaaacgga    120
gacattaccc atcgttccat cggggctgc ggaagcaact tagggctgga agtcctgcgc    180
ggaaccgtgc tggatgggga tcgttttaac tatgttacca ccacacagga cggaaagatt    240
ctccgttcct catcgatcta tctaaaaaat gatcagggcg aggtcatcgg atcgatctgc    300
gtgaacctgg atatcacaga gacacttcag tttgaagggt atttacgcca gtttaaccag    360
tttgacagct ttacttccaa cgacgaggag attttcgctc ccgacgtgaa taatcttctc    420
agccatctga ttcagatggg acaggaacag atcggaaagc ctgcgctgga gatgaacaag    480
aacgagaaga ttgagtttat ccgtttcctt gaccagaaag gagcattcct catcacgaag    540
tccggggaac agatctgtga acttctggga atcagcaaat ttacctttta taattacctt    600
gaaagcagcc gcagccagtc ggattcg                                        627

<210> SEQ ID NO 7
<211> LENGTH: 1305
<212> TYPE: DNA
```

<213> ORGANISM: Unknown
<220> FEATURE:
<223> OTHER INFORMATION: Description of Unknown:
    m7 sequence

<400> SEQUENCE: 7

```
atgttagcaa tcgtaggttt attaactatc ctggtcgtaa tgtttctgat tatgacaaaa      60
aaatgttcga ctctggtcgc actgattgca gttcccatga ttgcatgtgt tattgtgggt     120
cagggcgccg atatgggagg gtacataacg gccggtatca aaagtgtggc cgccaccgga     180
gtcatgttta tttttgcagt ggccttttc ggtgtcatgg gtgatgtggg tgcatttgaa      240
atcgtagtga ataaaatact caggattatt gggaaagatc ctttgaaaat ctgtatcggc     300
acgctgatta tcacattgat gacccacctg gacggctccg gcgcaacgac atttttgatc    360
acaataccgg cgctgctgcc gatatacgat aaattgaaga tggatcggcg tgtgctggca     420
actatagtgg cggcaggagc aggaaccatg aatctcgtcc cttggggagg gccgacgatc     480
cgagcagcga cggcactgga ggtctcactg accgagcttt acaatcctat gattgtccct     540
cagctttgcg gagtcgccgc ctgcgtgaca gtggcggtga tgtttggcct gaaggaacgg     600
aaacgtttaa aagggactct ggaatctgtt tcggtagagc ctccgaaatt tgaggactta     660
ccggaggagg agagagtgaa acgccgtccc caccttgtct ggtttaacat tctgctcatt    720
atagttacaa ttgtgtcatt ggttatggag cttttgccgc cggccggctg ttttatggcg     780
gcgctgtgca tcgcaatgct ggttaactac cgtgatttaa aggatcaggg aaaacggatg    840
gacgagcatg cggtagcggc catgatgatg gcatccaccc tgtttggcgc aggctgcttt    900
accggtatcc tgggaggctg cggcatgctg gaagcgatgg cccagggact ctgtgatatt    960
ctcccggtag ccattatggg tcacattgcg attttggtgg cagttttctc catgcctctg    1020
tcgctgatgt tcgatccgga cagcttctac tatgcagtac ttccggtaat tgcagtggcg    1080
gccgaggtgg ccggtgttcc ggcattggca gtgggccgcg cggcgatatg cggacagatt    1140
actgttggat tccccatttc accactgact ccatccacct tccttctgac aggactaacg    1200
ggcgtggatc tcggggacca tcagaagcac agtttcgtgt ggctgtggct gatttccctg    1260
acgattgtgc tggttgccgt ggtgatgggc gtaattccgg tatag                   1305
```

<210> SEQ ID NO 8
<211> LENGTH: 504
<212> TYPE: DNA
<213> ORGANISM: Clostridium scindens

<400> SEQUENCE: 8

```
atggttgcac ttgtatggct actgattgaa atgaaatata aaatcagtgt cccatctcca     60
ctgttgctca gcatggttta caaactttttg cttccggcta tgcctgccta tcttctggct   120
aaaatcccct ctgggaaatt aacggccagc ttgagaagaa tgccgatttc tacccatatc    180
atgcttgtat tgatcgtcat gctccgcttt gcgccgactg tgctgcatga atttggagaa    240
gtcagggaag ccatgaaaat tcgtggcttc ttaaaatcgg tcggtaatgt tttgaggcat    300
ccaatggaca cgttggaata cgccattgtt ccgatggtgt tccgctcctt aaagatcgcg    360
gacgagttag cagcttctgc catagtcagg ggaattgaaa gccctacaa gaaagaaagc    420
tactatgtca gccggatcgc tgcgctggat tactttttga ttgttgtcag cgtgggagct    480
gccgtgtgct gctgtctttt atag                                          504
```

<210> SEQ ID NO 9

-continued

```
<211> LENGTH: 750
<212> TYPE: DNA
<213> ORGANISM: Ruminococcus obeum

<400> SEQUENCE: 9
atgaaaggaa aaagagttat tgcaggcatt ctgcttgcag gaattttagc agttaccctg      60
gcagggtgta aaacacaga taacactaaa gaagaatcag aaaagccggt tattaccctc     120
ggcagcgata gctatccacc atacaattat ctgaatgagg atggtgtacc gacgggcata     180
gatgtggaac tagctacaga agctttcaaa agaatgggat atcaggtgaa tgtcgtccaa     240
atcaactggg aggagaaaaa agaactggta gagagtggaa agatcgattg tatcatgggt     300 tgttttcta tggaaggacg tcttgacgat taccgctggg caggggcgta catagcaagc     360
cgtcaggttg tagcggtaaa tgaggacagt gatatttata aattgagtga ccttgaggga     420
aagaacctgg ctgtccagtc cacaactaaa ccggaagtta tatttctgaa ccggttggat     480
aagagaatcc acaaactggg aaatctgatc agtcttggac accgcgagct gatatataca     540
tttcttggga aaggatatgt agatgcagtt gccgcacatg aggaatcaat catccagtat     600
atgaaggatt atgacataga cttccgtatc ctggaagaat cgctgatgat tacggggata     660
ggtgttgctt tcgcaaaaga tgatgacaga ggaattgtga gcagatggac cagacccttg     720
aagaaatgcg taaggatggc acgtctttga                                      750

<210> SEQ ID NO 10
<211> LENGTH: 594
<212> TYPE: DNA
<213> ORGANISM: Unknown
<220> FEATURE:
<223> OTHER INFORMATION: Description of Unknown:
      m10 sequence

<400> SEQUENCE: 10
atggcaatgc tcactgtaga aaatatcaat gtatattacg gcgtgatcca cgcccttaaa      60
gacatctcct ttcaggtaaa cgaaggcgag atcgtcgcac tgatcggcgc aaacggtgcc     120
ggcaaaacca ccaccctgca gactgtcagc ggcatgctga gcgcaaagtc cggttcgatc     180
cgatttcagg atcaggagat ttccagaatg ccggagcaca aaatcgtgaa gcagggaatt     240
tcccacgtcc ccgaaggacg ccggatgttc tccaatctga cggttttgga aaacctgaaa     300
atgggcgctt acaccagaaa agacaagcag gaaatcaaca attccctgga atggtttat      360 gagcggtttc cccgcttaaa ggaacgtacc cgccagctgg caggaactct ttccggcggt     420
gaacagcaga tgcttgcaat gggacgtgca ctgatgtctc atccgaagat catccttctg     480
gatgaaccgt ctatgggact ttcaccgatt tttgtaaatg agatttttcga aattatcaag     540 aaagtcagtg cagccggcac gaccgtactt ctggtagagc agaatgcaaa gaaa          594

<210> SEQ ID NO 11
<211> LENGTH: 708
<212> TYPE: DNA
<213> ORGANISM: Unknown
<220> FEATURE:
<223> OTHER INFORMATION: Description of Unknown:
      m11 sequence

<400> SEQUENCE: 11
gcagcttcaa actacgacct ttgtacaaca atccttagaa atgaatgggg atacgatggt      60
atcgtaatga ctgactggtg ggccaagatg aacgacgttg tagaaggtgg cgaagaatca     120
aatcaggata caagagatat ggttcgctca cagaacgacg tatatatggt tgtaaacaat     180
```

```
aacggcgcag aagttaactc aaacaacgac aacacagaga aatcaattaa agagggaaga      240
cttacaatcg gagaacttca gcgagctgca atcaacatct gcaacttcat tctttcagca      300
cctgttattg aaagagaatt agttgacaca gacgttgcaa acattacga ttcagttcca       360 aatgatcagg ccaagtatga agtatttaac attgaaaaag acaataaggt aatgttcaat      420
agcggagcag aagcaacatt ggaagttgaa gacgaagggg aatacacaat tattgttaac      480
atctcatttg acaagtccaa cttatcacag tcaacagtaa acgttaatgc aacggcaca      540 acaatggtag taatccagac taatggaaca gacggcaact ggattacaca gaagctttgc      600
aaggttaaac ttgacaaggg tgtatacaac ttaaaacttg aagaagtatt agcaggaatc      660
aaagttaaat atattcagtt taagaagatt cctaagaaaa ataaataa                   708

<210> SEQ ID NO 12
<211> LENGTH: 1401
<212> TYPE: DNA
<213> ORGANISM: Faecalibacterium prausnitzii

<400> SEQUENCE: 12
atgccgaacg aacgacatta ctccaatgaa ctgaatctgg aaagcgtggg catcaatctg      60
ccctacaaca tgcaggccga gcagagcgtg ctgggtgcgg tgctgctcaa gccggaaaca      120
ctgaccgacc tggttgagat catccggccg gaaatgttct acaccggca gaacgcccaa      180 atttattcgg aaatgctccg gctgttcacc agcgaccaga ccattgattt cgtcaccctg      240
ctggacgcgg tcatctcaga cggcgtgttt cccagcgcgg acgaggcgaa agtctacctg      300
accggtctgg ccgagacggt gcccagcatc tccaacgtga agcctacgc ccagatcgtg      360 caggaaaaat atctggtccg ccagctcatg ggtgtggcga agatatctt gcaggatgcg      420 ggcgacgagc cggacgcgga cctgctgctg gaaaacgccg agcagcgcat ttatgagatc      480
cgctccgggc gggattccag cgccctgacg ccccttcctt ccagcatggt ggaaacgctg      540
accaatctgc agaagatcag cggcccggat gccgataagt acaagggcat ccctacaggc      600
ttccgcctgc tggacaccgt gctcaccggc cttggccgcg cgaccttat tattctggct      660 gcccgccccg gtatgggcaa gaccagtttt gcgctgaaca ttgccacccg cgtggccatg      720
cagcagaaag taccggtggc catcttcagc ctcgaaatga ccaaggagca gctgaccaac      780
cggatcctct cggcggaggc cggcatcgac agccaggcgt ccgcaccgg cgccctccgg      840 gcggaggact gggagtacct ggcccttgcc accgagaagc tccatgacgc gcccatttat      900
atggatgaca cctcgggcat caccatcacc gagatgaaag ccaagatccg ccgggtgaac      960
caggacccca gccgcccaa tgtggggctc atcgtcatcg actatctgca gctgatgacc      1020
acgggccagc gcaccgagaa ccgtgtacag gagatcagct ccatcacccg aaacctcaag      1080
atcatggcca aagagatgaa tgtgcccatc attgcgctga gccagctgtc ccgtgcggtg      1140
gaaaagcagg gcaacaactc ctcccaccgc cccagctgt ccgacctgcg tgattccggt      1200
tccatcgagc aggacgccga ctgcgtgctg ttcctctacc gtgattctta ttacgccagc      1260
cagaacccgg acggtgccga ggtggacgcc gacacggccg agtgcatcgt ggccaaaaac      1320
cgccacggtg agaccagtac cgtgccgctg ggctgggatg tgcccacac ccgctttatg      1380 gatgtggact tcaaacgctg a                                                1401

<210> SEQ ID NO 13
<211> LENGTH: 777
<212> TYPE: DNA
```

<213> ORGANISM: Ruminococcus bicirculans

<400> SEQUENCE: 13

| | |
|---|---|
| atgaagaata tgataaaaat atttgaaaat gacgaattcg gaaaagtgag aacagtcatt | 60 |
| aaggacggcg aaccgtggct tgtaggaaaa gatgttgcgg aaattttagg gtattccaac | 120 |
| acaagggacg ctctttcacg tcatgtggat accgaggata aaaccaccgt cgtgatttcc | 180 |
| gacagtggtt caaattacaa gagcaagacc actattatca atgaaagcgg cttttacagc | 240 |
| ttagttctct caagcaaaat gccgagagcc aaagagttca ggcgttgggt gaccgccgaa | 300 |
| gtcctcccca ccatcagacg caccggcggc tacgtttcca acgaggatat gttcatcaaa | 360 |
| aactatctcc cctttctcga cgagccatac cgtgacctgt tccgacttca aatgaccatt | 420 |
| atcaacaagc tgaatgaacg tatccgccac gatcagccgc tggtggagtt tgcgaatcag | 480 |
| gtgtcaaata ccgataatct tatcgacatg aacgcaatgg caaagcttgc gagagcggaa | 540 |
| aatatccccg tcggcagaaa caagctttac ggctggctga aggaaaagg tgtgcttatg | 600 |
| gcaaacaatc tgccgtatca ggcttttatc gaccgcggat attttccgt aaaggagtcg | 660 |
| gtgtttgaaa ctgcgactat gacaaagact tatcagcaga cgtttgttac gggcaggggg | 720 |
| cagcagttcg tcataaattt gctgaagaaa tattatggga aggaggtttt gcaataa | 777 |

<210> SEQ ID NO 14
<211> LENGTH: 858
<212> TYPE: DNA
<213> ORGANISM: Faecalibacterium prausnitzii

<400> SEQUENCE: 14

| | |
|---|---|
| atctccaaac tggaaaaaac gctgcgggca cggttcccga aaacgcagca gggcgaactg | 60 |
| ctggccgggg cggtgctggc cttctgcctg ccggtgggca cctttctgct cacaagcgcc | 120 |
| gtgtgccttc tggcggcaaa atcagcccc tggctcggcc ttgccgtgca gatgttctgg | 180 |
| tgcgggcagg cgctggcggc aaagggactt gtgcaggaga gccggaacgt ttacaacaag | 240 |
| ctggtaaagc ccgacctgcc cgccgcccgc aaggcgtga gccgcatcgt ggggcgggac | 300 |
| accgagaacc tgaccgccga gggcgtgacc aaggctgccg tggagactgt ggccgagaat | 360 |
| gccagcgacg gcgtgattgc gccgctgctg tacatgctgc tgggcggcgc gccgctggcg | 420 |
| ctgacctaca aggccgtcaa caccatggac agcatggtgg gctacaaaaa cgagaccctat | 480 |
| ctctacttcg gccgggcggc ggcaaagctg gacgatatgg caaactacat tcccagccgc | 540 |
| cttgccgccc tgctgtgggc ggcggctgct gccctgaccg gcaacgatgc caaaggcgcg | 600 |
| tggcgcatct ggcggcggga ccggcgcaat cacgccagcc caacagcgc ccagaccgaa | 660 |
| agcgcctgcg ccggtgcgct gggcgtgcag ctggccgggc cggcctacta ctttggcgaa | 720 |
| tactacccga aacccaccat cggcgatgcc ctgcgcccca ttgagccgca ggacatcctg | 780 |
| cggggccgacc gcatgatgta cgccgccagc attctggcgc tggtgctcgg gcttgtgata | 840 |
| cgggggttcg ttgtatga | 858 |

<210> SEQ ID NO 15
<211> LENGTH: 945
<212> TYPE: DNA
<213> ORGANISM: Faecalibacterium prausnitzii

<400> SEQUENCE: 15

| | |
|---|---|
| atgaacagag aaacggtgaa catggtgcgc agtccgattt ctgtggaggg gaacatccgg | 60 |
| cttgttccgt attatccggc ctacgataca gcacttgcgt ggtatcagga tgcacagctc | 120 |

```
tgcaaacagg tagataacag ggacttcgtt tatgatttgc cgctgctgaa gcggatgtat      180
cattatctgg acacacacgg ggaactgttt tatattgagt atcggggtgt gctttgtggt      240
gacgtcagcc tgcggacgac cggcgagctg ccatcgtca tctgcaagga gtaccagaat       300
aaacacatcg gcggaaggt catcgaaaaa atgctggagc tggctcggga aggggcttg        360 gcggagtgct cgcgcacat ctattctttc aatacccagt cgcagaaaat gtttgaatcc       420
attggctttg tcccacagga cgaagaacgc tatatctaca aattgcaaaa aggagaaccg      480
actatgacaa aactgactct ggaagaaaag caggagctca tccggatggc ccttgcggcc     540
agggagaggg cttacgtgcc ttacagcgac tttatggtgg gcgctgccct gcgcgccgag     600
gatggccgtg tctttaccgg ctgccatgtg gagaatgccg cctttacccc caccagctgc    660
gccgagcgca ccgcgctgtt caaagccgtg agcgagggcg tgaccaaatt tacgacatc     720 gccgtggtag gctcccgccg gggcgagatc aatcagcaga tcacctcgcc ctgcggcgtc   780
tgccgtcagg cactgtttga gtttggcggc ccggagctga acgtcatcat ggccaaaacg    840
ccggatgatt tcatggagcg cagcatggat gagctgctgc cctttggctt cggtccctcc   900
aatgtggcgg gcaacaaggc cgtggaagag gaagaaaaag gctga                    945
```

<210> SEQ ID NO 16
<211> LENGTH: 1206
<212> TYPE: DNA
<213> ORGANISM: Unknown
<220> FEATURE:
<223> OTHER INFORMATION: Description of Unknown:
      m16 sequence

<400> SEQUENCE: 16

```
atgaggttat tttttgatat ggtatgtaac ggcagggcat tgcaaaatgt acaaatgtat      60
aaattgaata tggttttaga tgtacacccc tatgctatta cagcaccgtc aaaaactggt     120
ggccgttggc agacatatgt aaaggaaggt gataagcgta agattataag ggcttcttca     180
aaggaaaaac taatggacaa attatatact gcctattttg ttcaaaatgg tgtttctggt     240
atgaccatgg acaagctttt tctcgaatgg ttagcttata aggaatgtat cacaaatagt    300
atgaatacga ttcgcagaca tgaacaacac tggaaaagt atttttcagga tatttcccca    360 aataaggtat cttcctatga tcgtctggaa ttgcagaaag aatgtaatca gttaataaaa    420
gttaataacc tttcttccaa agaatggcag aatgtaaaaa caattctttt aggtatgttt    480
gactatgcct ttgaaaaagg atatattaat acaaacccca tgcccagtat aaaaatcact   540
gttaaattcc gtcaggtcaa taaaagagt ggtaggactg aaacatatca gacagacgaa     600
tacaaagcac ttatgcaata tctagatgca gaatatacag ctacagaaga ccttgcttta    660
ttggctgtta aatttgattt ttttattgga tgccgtgttg ctgagttggt agctctcaag   720
tggtgtgatg ttgaaaatct acggcattta catatttgta gggaagaggt taagagtct    780 gtccgtgttg gtgatacctg gaaagatgtt tataccgttt cagagcatac taagacatat   840
acagaccggt ctataaattt agttcctaat gcgattgcta ttttaaatca tatccgtctt   900
aaaatggctt ataatgtatc tgacgatgat tatatcttta cccggaacgg ttcccggatc   960
acttcacgcc agattaatta tattcttgaa aaagcatgta caaaactggg aattatgatt  1020
aagaggtcgc ataaggtaag aaaaacggtt gcaagtcgtc tcaatgtcgg tgaggttccg   1080
ttagattcta ttcgtgagct gttaggtcat gcaaatttaa gcactacact aagttatatt  1140
tataatccgt tatcggaaaa agaaacctat aacctgatgt ccagagcctt ggggaaagtt  1200
```

```
caatag                                                         1206

<210> SEQ ID NO 17
<211> LENGTH: 336
<212> TYPE: DNA
<213> ORGANISM: Clostridium sporogenes

<400> SEQUENCE: 17
atggcgattg atactgaatt agcaaaaaga ttacgttcat atcgtaattt taaacattta    60
acacaaaaag atgttgctgc gcatttaaat gttcctcatt ctgcaatttc cgatatagaa   120
aatggtaaaa gagacattac tgttagcgag ttaaaagtgt tttcaaattt atatggtaga   180
agtgtagaag aaattatgag cgggaaaaaa tatgactatt ataatattgc caatatcgct   240
cgtttactta ctgaacttcc tgatgatgat ttaaaagaaa tcatgtttat tattgaatat   300
aaaagaaaaa gaaatgaaga acgtcatttg aaataa                             336

<210> SEQ ID NO 18
<211> LENGTH: 816
<212> TYPE: DNA
<213> ORGANISM: Treponema sp.

<400> SEQUENCE: 18
atggccaaaa cacctatcgt agataagggg tgcttcatat cgaatgatgt taaaaggtca    60
atagttttaa acctatgtga gactaagtca atggatctaa ttgcaagaga cactgtgta   120 tctcctagta gtgttgccag aatacttcgt ttaactgaag ataggagaag aaaaaattat   180
cttcctagga ttctatcaat agacgaattc aagtcagtaa atacagttga tgcgtctatg   240
agtgtaaatt taactgattt agaaggcggt cataattttg atatcctggt ggataggagg   300
caaagatacc tctttgagta cttttaattcc tatcccttga aggtcagaaa aagggtagaa   360
tatgtgacta cagacatgta taagccatat attgatcttg ccaagaaggt ctttccaaat   420
gccaatattg tggtagataa attccatata gtacagctct tgacaagaga gctaaacaag   480
ttaaggataa atgagatgaa gaagcttaat accaggtcta gagagtataa atactgaag    540 agatactgga aaatacccct taggaagaag agagacttaa acagtatata ttttttacaag   600 aataggcact ttaaaaatat gaccagttca attgatatat tagactatat gttaaaggaa   660
tttcccaact taaaagaggc ctatgatttt tatcaaaact tcctattaag tatatctaat   720
aatgatgtcg ctatgcttga agacattcta aatactagga ctgatgaaat tcccatgtgt   780
tttaggaaga gtataaaaag ccttaaaaag cttaga                             816

<210> SEQ ID NO 19
<211> LENGTH: 432
<212> TYPE: DNA
<213> ORGANISM: Unknown
<220> FEATURE:
<223> OTHER INFORMATION: Description of Unknown:
      m19 sequence

<400> SEQUENCE: 19
tatttttaca agaataggca ctttaaaaat atgaccagtt cagttgatat attagattat    60
atgttaaaag aatttcccaa cttaaaagat gcctatgatt tttatcaaaa cttcctatta   120
agtatatcta ataatgatgt ggctatgctt gaagatattc taaatactag gactgataaa   180
ataccaatgt gttttaggaa gagtataaaa agccttaaaa agtttagaaa gtatgtggta   240
aattcactga aatatgacta tacgaatgcc atggtggagg gtaaaaacaa caagataaag   300
```

| | |
|---|---|
| gtaattaaaa gagtatccta cggatatagg agttttagga attttaaggc aaggataatg | 360 |
| ctaatggaaa ggtataaaat acaaaagggc aacatccata gttatcagtt tgctatggat | 420 |
| gctgccgcat aa | 432 |

<210> SEQ ID NO 20
<211> LENGTH: 873
<212> TYPE: DNA
<213> ORGANISM: Unknown
<220> FEATURE:
<223> OTHER INFORMATION: Description of Unknown:
      m20 sequence

<400> SEQUENCE: 20

| | |
|---|---|
| atgaaacgta tttattaac tggagcaagt ggatttatag gtaaaaacat taaagagaca | 60 |
| ttaaacagta aatatgacat atggagcccg tcaagccagg agctggattt aaaagatacc | 120 |
| gaatgcgttg aagcatattt gaagcagcat tctttcgatg taatattgca tgcagcaaat | 180 |
| tgtaatgata caaggaattc catatcagca tacgatgtac tcaatggaaa tctcagaatg | 240 |
| ttttttaacc tagagagatg ttctcactat tatggaaaaa tgatttattt tgggtctggg | 300 |
| gcagaatatg acagaagtaa taacatccct aatatgtcag aggactattt tgataccagt | 360 |
| gttccgaaag atgcttacgg actttcaaaa tatattatgg caaaagcctg tttaaatcag | 420 |
| aagaacattt atgaattgtg tttatttgga gtatacggaa aatatgagga atgggagaga | 480 |
| agatttatct ctaatgcgat atgtcgtgca ttaaagggta tggatattac gcttcataaa | 540 |
| aatgtatact ttgattattt gtgggtagat gacctcataa aaattattc ttttttcatt | 600 |
| gagaaagata acttgaggta caagaggtac aatgtgtgta gaggcgagaa ggttgatcta | 660 |
| tattcgctgg cagtacaggt aaagaagact ttggatagcg aatgttcaat attagttggt | 720 |
| gagcctggat ggaagaggga gtatactgcg ataacaata gaatgttgaa cgaaatgaat | 780 |
| ggtttatctt ttacaaaact ggaagtgacg atagctgaat tgtgtgaata ttataaagag | 840 |
| catttatcag aaatagttac tgaaaaattg taa | 873 |

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

| | |
|---|---|
| cggatttgca gtggcaagtt | 20 |

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

| | |
|---|---|
| tgattgcaga cgccaatgtc | 20 |

<210> SEQ ID NO 23
<211> LENGTH: 23
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 23
cgtgaaaaat ccgcgcatct ggc                                          23

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tccatccgca agcctttact                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcttccggtg ccattgacta                                              20

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ttcatcatca cagccgacaa cgca                                         24

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aatgggaatg gagcggattc                                              20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cctgcaccag cttatcgtca a                                            21

<210> SEQ ID NO 29
<211> LENGTH: 26
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 29
aagcctgcgg aaccacagtt accagc                                          26

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aagaatggag agagttgtta gagaaagaa                                       29

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttgtgataat tgtgaagaac cgaaga                                          26

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
aactcaagat ccagaccttg ctacgcctca                                      30

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttgtaagtgc tggtaaaggg attg                                            24

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cattcctaca taacggtcaa gaggta                                          26

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic

```
                                      probe

<400> SEQUENCE: 35
agcttctatt ggttcttctc gtccagtggc                                    30

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttcaataaaa gtggcaggtc aag                                           23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
taacaacaca tgcaggtcaa tgg                                           23

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
actcgaaccc ccaaccctcg gttt                                          24

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gggctgcgga agcaactta                                                19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gatgacctcg ccctgatcat                                               20

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 41
accaccacac aggacggaaa gattctcc                                        28

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tcggcacgct gattatcaca                                                 20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cacacgccga tccatcttc                                                  19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
acccacctgg acggctccgg                                                 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aagatcgcgg acgagttagc                                                 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gctcccacgc tgacaacaat                                                 20

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 47
aaagctacta tgtcagccgg atcgctgc                                              28

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cctggcaggg tgtaaaaaca c                                                     21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tatgcccgtc ggtacaccat                                                       20

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
ccggttatta ccctcggcag cga                                                   23

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aatgggcgct tacaccagaa                                                       20

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tcaccgccgg aaagagttc                                                        19

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
```
ttccccgctt aaaggaacgt acccg                                              25

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cagaagcaac attggaagtt gaa                                                23

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tgtaatccag ttgccgtctg ttc                                                23

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
tcaacagtaa acgttaatgc caacggca                                           28

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cggccggaaa tgttctacac                                                    20

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gaaacacgcc gtctgagatg a                                                  21

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59

-continued ccagaccatt gatttcgtca ccctgc                                    26

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctggtggagt ttgcgaatca                                           20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cagccagccg taaagcttgt                                           20

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
cggaaaatat ccccgtcggc aga                                       23

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gggcaccttt ctgctcaca                                            19

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cgggctttac cagcttgttg                                           20

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
aaaaatcagc ccctggctcg gc                                        22

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtgcgcagtc cgatttctgt                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cagcggcaaa tcataaacga                                              20

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
tccgtattat ccggcctacg atacagca                                     28

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
agctttttct cgaatggtta gctta                                        25

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctgcaattcc agacgatcat agg                                          23

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
aatacgattc gcagacatga acaacactgg                                   30

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
aaagatgttg ctgcgcatt                                               19

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tttcccgctc ataatttctt c                                            21

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
aaatgttcct cattctgcaa tttccga                                      27

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tcctatccct tgaaggtcag a                                            21

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tgtcaagagc tgtactatat ggaattt                                      27

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
ttgccaagaa ggtctttcca aatgc                                        25

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tgtggtaaat tcactgaaat atgact                                          26

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tccattagca ttatccttgc c                                               21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
accctccacc atggcattcg t                                               21

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tgtgtgtaga ggcgagaagg                                                 20

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ccattcattt cgttcaacat tc                                              22

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
ccctcttcca tccaggctca cc                                              22

<210> SEQ ID NO 84

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cgtcagctcg tgycgtgag                                            19

<210> SEQ ID NO 85
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cgtcrtcccc rccttcc                                              17

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
ttaagtcccr yaacgagcgc aaccc                                     25

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cgtcagctcg tgtcgtgag                                            19

<210> SEQ ID NO 88
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cgtcgtcccc accttcc                                              17

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
ttaagtccca caacgagcgc aaccc                                     25

FECAL BACTERIAL MARKERS FOR COLORECTAL CANCER

RELATED APPLICATIONS

This application claims priority to U.S. Provisional Patent Application No. 62/379,635, filed on Aug. 25, 2016, and Chinese Patent Application No. 201710261558.9, filed Apr. 20, 2017, the contents of both are hereby incorporated by reference in the entirety for all purposes.

REFERENCE TO SUBMISSION OF A SEQUENCE LISTING AS A TEXT FILE

The Sequence Listing written in file 080015-1127430-020010US SL.txt created on Jun. 19, 2019, 41,769 bytes, submitted electronically in ASCII format, is hereby incorporated by reference in its entirety for all purposes.

BACKGROUND OF THE INVENTION

Colorectal cancer is the third most common cancer worldwide, accounting for about 10% of all cancer cases diagnosed annually. It is a deadly disease with serious impact on human health. During the year of 2012, for instance, 1.4 million new cases of colorectal cancers were diagnosed globally, and nearly 700,000 deaths from the disease were recorded. Incidence of colorectal cancers is substantially higher in developed countries, where more than 65% of cases are found. Men are more likely to suffer from this disease than women.

Diagnosis of colorectal cancer can be challenging. Although family history may provide useful implications for diagnosis, vast majority of the disease (greater than 75-95%) occurs in people with little or no genetic risk. Symptoms of colorectal cancer also can vary significantly, depending on the location of the cancer in the colon, and whether it has spread elsewhere in the body. Depending on how early colorectal cancer is diagnosed, its prognosis can vary from very good to very grim: it is highly curable with surgery when the cancer mass remains confined within the wall of the colon; on the other hand, once colorectal cancer has spread, it is usually not curable, with medical intervention focusing on improving quality of life and alleviating symptoms. On average, the 5-year survival rate in the United States is around 65%.

Because of the high prevalence of colorectal cancer and the vital importance of early diagnosis on patients' life expectancy, there exists an urgent need for new and more effective methods for early diagnosis of colorectal cancer, especially in a non-invasive manner. It was previously known that changes in the gut microbial composition are associated with colorectal cancer (CRC), but causality is yet to be established. For example, *Fusobacterium nucleatum* is thought to potentiate intestinal tumorigenesis through recruitment of infiltrating immune cells and via activation of β-catenin signaling. Fecal microbiota thus holds promise for early non-invasive diagnosis of CRC. However, a simple and affordable targeted approach to diagnosing CRC from fecal samples is still lacking. This invention fulfills this and other related needs.

BRIEF SUMMARY OF THE INVENTION

The present inventors have identified several bacterial species that are significantly correlated with human colorectal cancer (CRC) and therefore can serve as diagnostic markers for early detection of CRC by non-invasive analysis of patient stool samples. More specifically, the inventors show that, compared with normal individuals, certain bacterial species, such as *Parvimonas micra, Solobacterium moorei*, and *Clostridium hathewayi*, are significantly enriched in stool samples from CRC patients, whereas the presence of other bacterial species, such as *Bacteroides clarus* and *Roseburia intestinalis*, is significantly reduced in CRC patient stool. Such increased or decreased presence of these bacterial species results in higher or lower levels of signature DNA, RNA, and protein species unique to these species, which in turn can be used for detection, both qualitatively and quantitatively, the abnormally enriched/suppressed bacteria population in the samples, thus providing critical information relating to the presence of or a heightened risk of CRC in a human subject, including an increased risk of recurrence of CRC after initial treatment (e.g., surgical intervention, chemotherapy, and/or radiation therapy) in a patient who has been diagnosed of the disease. Conversely, specific suppression or activation of these bacterial species can be prophylactically practiced for reducing an individual's risk of developing CRC at a future time.

As such, in the first aspect, the present invention provides a method for assessing the risk for colon cancer in a subject, i.e., the likelihood of colon cancer being present in the subject, and/or the likelihood of the subject developing the disease at a later time, and/or the likelihood of a patient having recurring colon cancer (e.g., after initial treatment of the disease when first diagnosed). The method generally relies on the detection of an increase or decrease in the population of relevant bacterial species (see, e.g., Table S8 of Example 1 and Table 7 of Example 2), genera (see, e.g., Table S10 of Example 1), or phyla (see, e.g., Table S11 of Example 1), or in the level of certain bacterial gene markers indicative of the relevant bacterial species/genera/phyla (see, e.g., Tables S12 and S13 of Example 1) in a patient stool sample when compared with a control value expected in a healthy subject's stool.

For example, the claimed method comprises the steps of: (a) quantitatively determining level of at least one of the bacterial species of *Parvimonas micra, Solobacterium moorei, Bacteroides clarus, Roseburia intestinalis*, and *Clostridium hathewayi* in a stool sample taken from the subject; (b) comparing the level obtained in step (a) with a standard control; (c) determining the level obtained in step (a) as increased or decreased from the standard control; and (d) determining the subject as having an increased risk for colon cancer.

In some embodiments, the level of at least one of *Parvimonas micra* and *Solobacterium moorei* is determined in step (a), and the level of at least one of *Parvimonas micra* and *Solobacterium moorei* is determined as increased from the standard control in step (c). In other embodiments, the level of at least one of *Bacteroides clarus, Roseburia intestinalis*, and *Clostridium hathewayi* is determined.

In some embodiments, step (a) comprises determining the level of a DNA, RNA, or protein unique to at least one of *Parvimonas micra, Solobacterium moorei, Bacteroides clarus, Roseburia intestinalis*, and *Clostridium hathewayi*. In some embodiments, step (a) comprises determining the level of a DNA unique to at least one of *Parvimonas micra, Solobacterium moorei, Bacteroides clarus, Roseburia intestinalis*, and *Clostridium hathewayi*. In some embodiments, step comprises determining the level of a DNA unique to each of *Bacteroides clarus* and *Clostridium hathewayi*, optionally further comprising determining the level of a DNA unique to *Fusobacterium nucleatum*. For example, step (a) comprises determining the levels of gene markers m1704941 (Fn), m2736705 (Ch), m3246804 (m7), and m370640 (Bc), optionally further comprising determining the level of gene marker m181682 (Ri).

In some embodiments, an increase is determined in step (c) for m1704941 (Fn), m2736705 (Ch), and m3246804 (m7), and a decrease is determined in step (c) for m370640 (Bc) and m181682 (Ri). In some embodiments, step (a) comprises determining the level of gene marker m1696299 (*P. micra*), optionally further comprising determining the level of gene marker m1704941 (Fn). In some embodiments, an increase is determined in step (c) for m1696299 (*P. micra*) and m1704941 (Fn). In some embodiments, step (a) comprises a polynucleotide amplification reaction, such as a polymerase chain reaction (PCR), especially a quantitative PCR (qPCR).

In some embodiments, when the subject is determined as having an increased risk for colon cancer, a repeat of step (a) is performed at a later time using another stool sample from the subject at the later time. When an increase is detected in the level obtained at the repeated step (a) as compared to the level from the original step (a), it indicates a heightened risk of colon cancer; conversely, a decrease indicates a lessened risk for colon cancer.

In some embodiments, when the subject is determined as having an increased risk for colon cancer, a further step is performed: administering to the subject an effective amount of an inhibitor of at least one of the bacterial species shown to be enriched (such as *Parvimonas micra* and *Solobacterium moorei*) and/or an activator for one or more bacterial species shown to have a decreased presence (such as *Bacteroides clarus* and *Roseburia intestinalis*).

In some cases, an alternative marker for *Fusobacterium nucleatum*, the nusG gene, may be used for quantitatively measuring the presence of the bacterium in a sample. Exemplary primer/probe sequences for this marker are provided in Table A of Example 1 (Fn-target 2) and in Table 8 of Example 2.

In a second aspect, the present invention provides a kit for detecting colon cancer in a subject. The kit includes these components: (1) a standard control that provides an average amount of at least one of *Parvimonas micra, Solobacterium moorei, Bacteroides clarus, Roseburia intestinalis*, and *Clostridium hathewayi* in a stool sample; and (2) an agent that specifically and quantitatively identifies a DNA, RNA, or protein unique to at least one of *Parvimonas micra, Solobacterium moorei, Bacteroides clarus, Roseburia intestinalis*, and *Clostridium hathewayi*.

In some embodiments, the agent is a polynucleotide probe that specifically binds the DNA or RNA, or the agent is an antibody that specifically binds the protein. The agent optionally can comprise a detectable moiety. In some embodiments, the kit further comprises a set of two oligonucleotide primers for specifically amplifying at least a segment or full length of the DNA or a reverse-transcribed DNA from the RNA or a complement thereof in an amplification reaction. Exemplary sets of oligonucleotide primers are presented in Table S27 of Example 1 and Table 8 of Example 2, as well as in Table A of Example 1. In some embodiments, the kit further comprises an instruction manual.

In a third aspect, the present invention provides a method for prophylactically treating colon cancer or reducing the risk of developing colon cancer in a subject at a later time. The method comprises the step of administering to the subject an effective amount of an inhibitor or activator/enhancer for at least one of the pertinent bacterial species such as *Parvimonas micra, Solobacterium moorei, Bacteroides clarus, Roseburia intestinalis*, and *Clostridium hathewayi*, such that a bacterial species found enriched in a CRC patient stool is to be depressed or inhibited, whereas a bacterial species found decreased in a CRC patient stool is to be activated or promoted. In some embodiments, the inhibitor is for at least one of *Parvimonas micra, Solobacterium moorei*, and *Clostridium hathewayi*, whereas the activator/enhancer is for at least one of *Bacteroides clarus* and *Roseburia intestinalis*. In some embodiments, the inhibitor is a nucleic acid encoding an antisense RNA, miRNA, or siRNA, for example, a nucleic acid encoding an antisense RNA, miRNA, or siRNA against at least one of the gene markers m1696299 and m2736705. The nusG gene, as an alternative marker for *Fusobacterium nucleatum*, may be used for practicing every aspect of the present invention as described herein.

In a related aspect, the present invention provides use of a modulator (i.e., inhibitor or activator) of pertinent bacterial species for manufacturing a medicament for prophylactically treating colon cancer in accordance with the description above and herein.

Figures 12A, 12B:
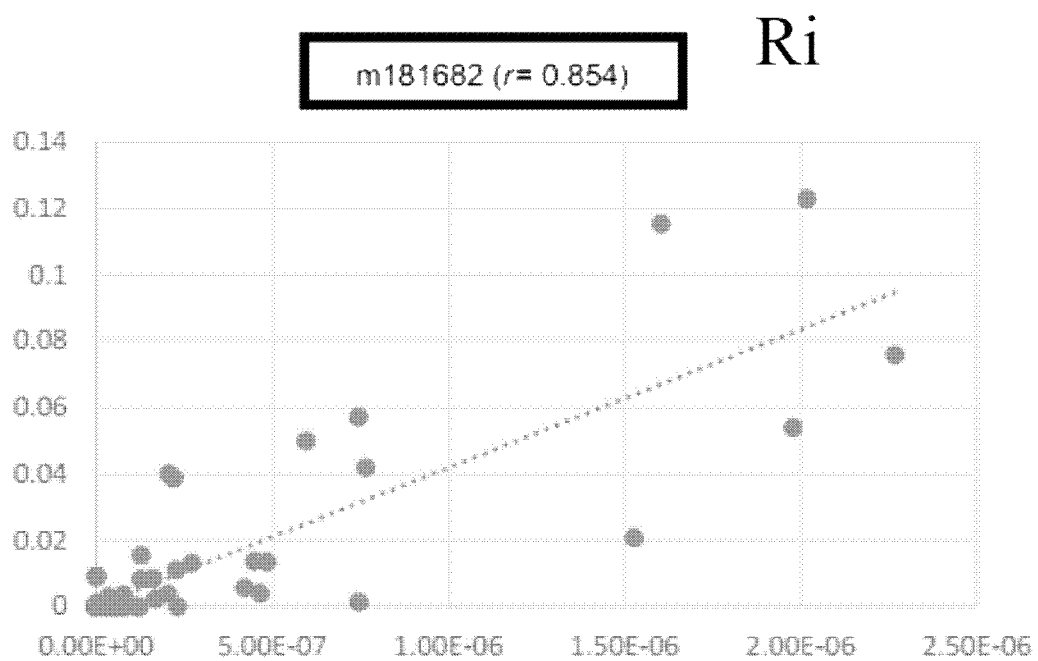
Figure 12C:
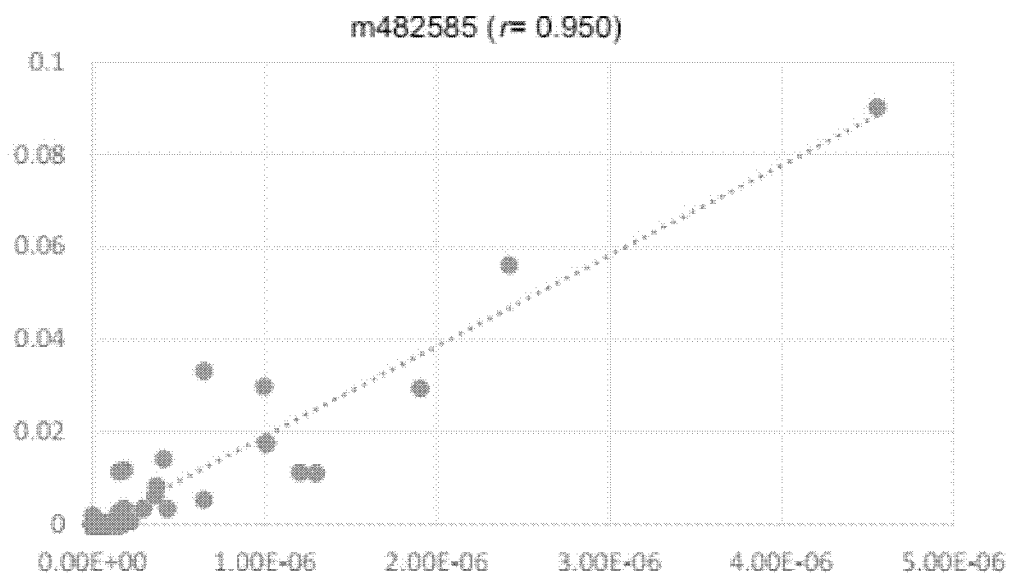
Figure 12D:
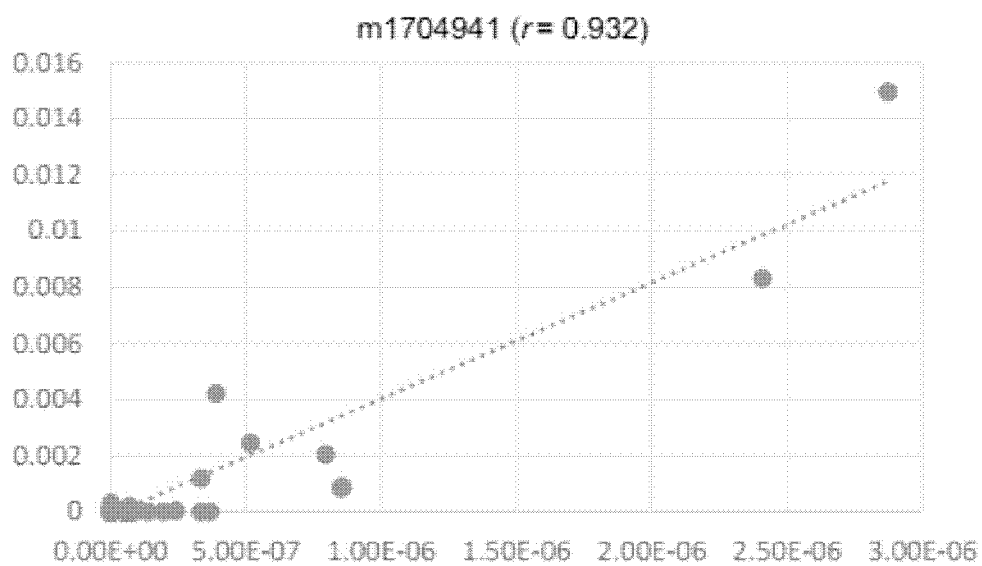

PC1 and PC5 show moderate separation between gut microbiomes of CRC patients and control individuals based on gene profiles, and are associated with CRC status. See FIG. 12 for comparing a PCA of 140,455 significant gene markers where a moderate separation is observed, and FIG. 2A where a strong separation is observed.

Figure 11:
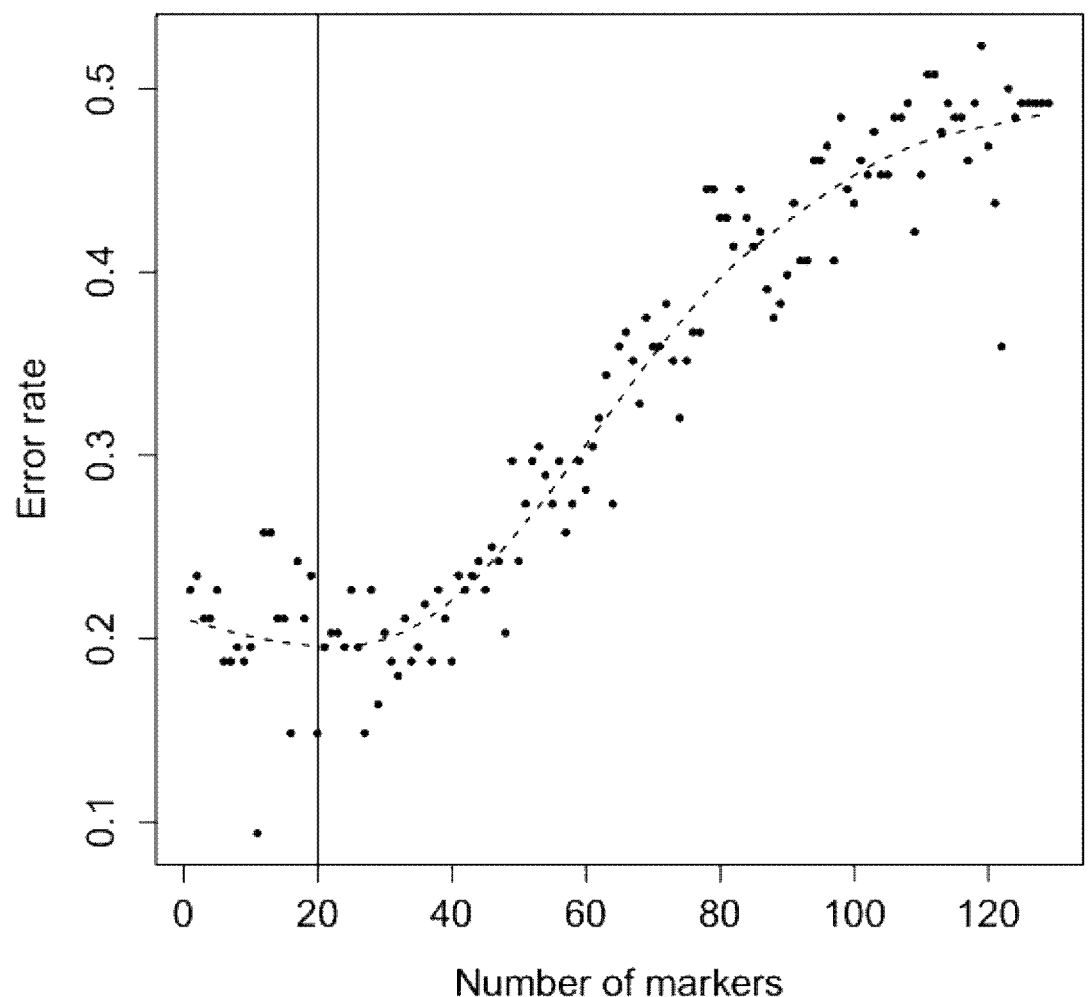

FIG. 11: Distribution of P-value association statistics of all microbial genes in cohort C1.

The association analysis of CRC p-value distribution identified a disproportionate over-representation of strongly associated markers at lower P-values, with the majority of genes following the expected P-value distribution under the null hypothesis. This suggests that the significant markers likely represent true rather than spurious associations.

FIG. 12A-FIG. 12D: 2-dimensional histogram of abundance-vs-occurrence rate of CRC-associated gene markers.

The CRC-associated gene markers selection was based on the significant enrichment in CRC case or healthy control. We computed the occurrence rate and median relative abundance for the CRC-enriched gene makers and healthy control-enriched gene makers in all 128 samples from C1, and generated a 2-Dimensional histogram following previously described methods' to show the distribution of all marker genes. Control-enriched gene makers are mostly present in continuous occurrence rate and high relative abundance. CRC-enriched gene makers are mostly present in low occurrence rate and low abundance.

Figure 13A:
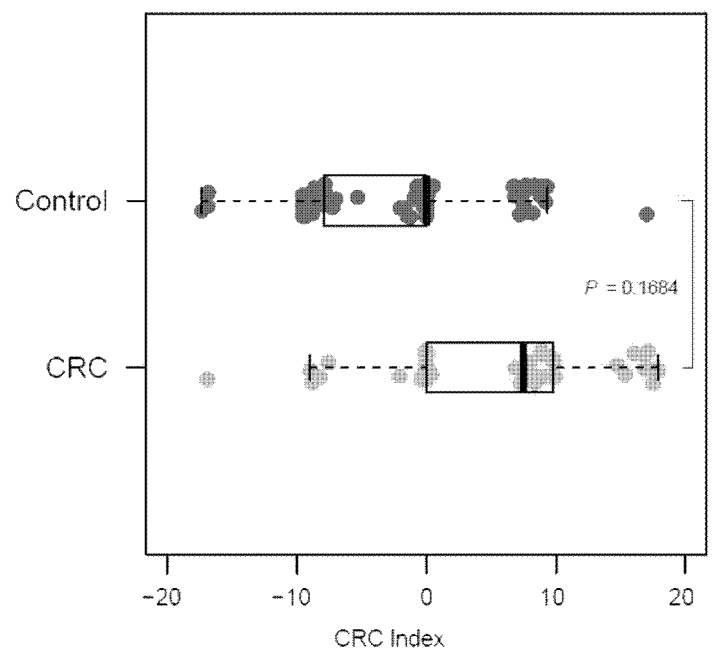
Figure 13B:
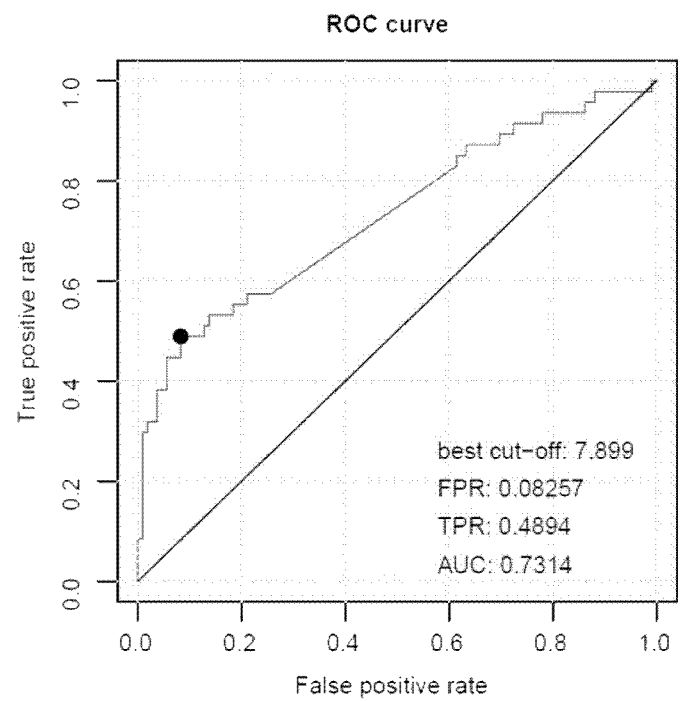

FIG. 13A-FIG. 13B: Enrichment of *Solobacterium moorei* and *Peptostreptococcus stomatis* in CRC patient microbiomes in cohort C1.

Figure 14A:
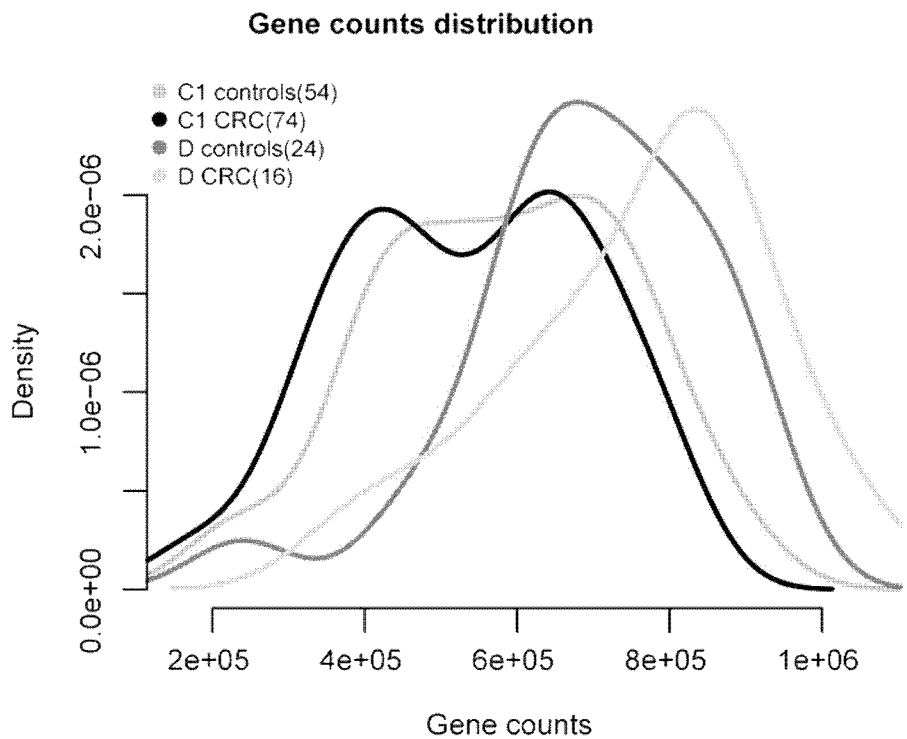

FIG. 14A: A co-occurrence network deduced from 85 MLGs significantly associated with colorectal cancer. Each MLG with more than 100 genes and at least 50% genes annotated to a single species was annotated with species name. The remaining MLGs were named Con or CRC MLGs according to their enrichment in control and CRC samples, respectively. Species are rearranged in two sides based on their enrichment in CRC or healthy microbiomes. Spearman correlation coefficient values lower than −0.5 (negative correlation) are indicated as light grey edges, and coefficient values higher than 0.5 (positive correlation) are indicated as dark grey edges. Node size indicates the number of genes within the MLG, and node color shows their taxonomic annotation.

Figure 14B:
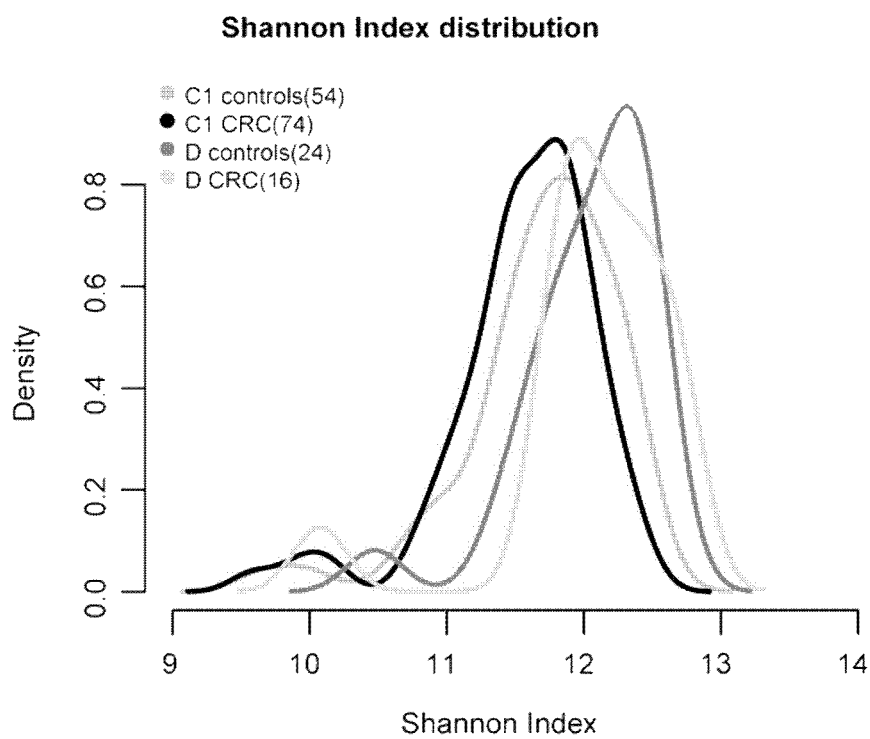

FIG. 14B: A co-occurrence network deduced from 28 IMG species significantly associated with colorectal cancer. Node size indicates the average of relative abundance for each species. See legend for panel A for other details.

Figure 15A:
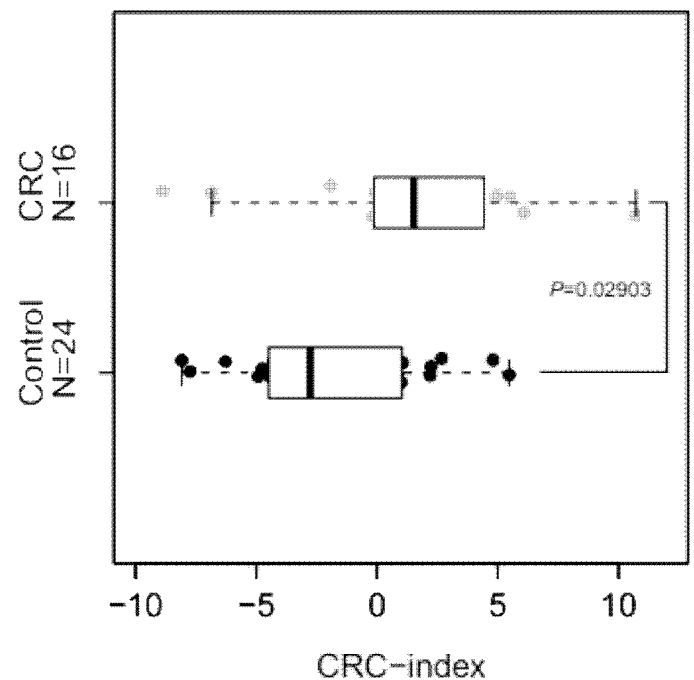

FIG. 15A: IMG species annotation using clean reads to IMG version 400.

Figure 15B:
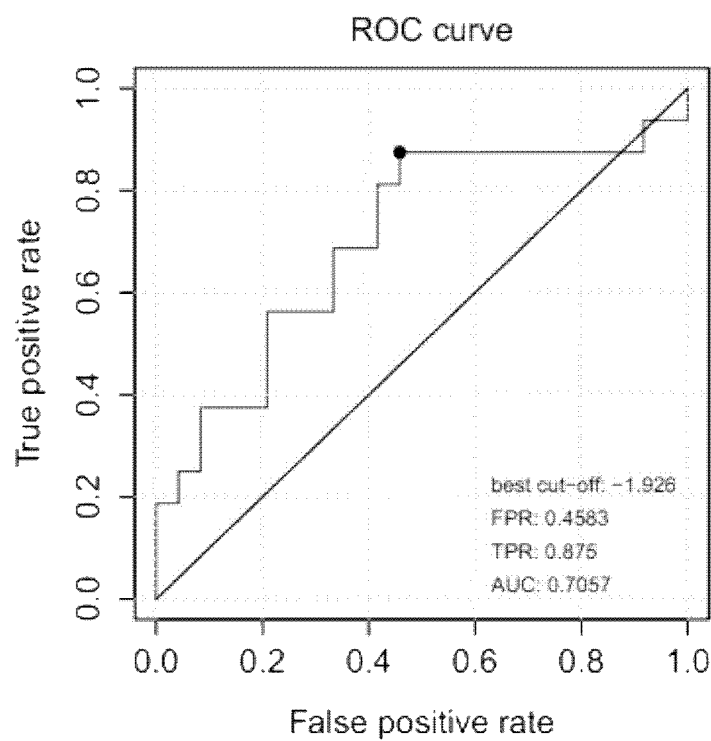
Figure 16A:
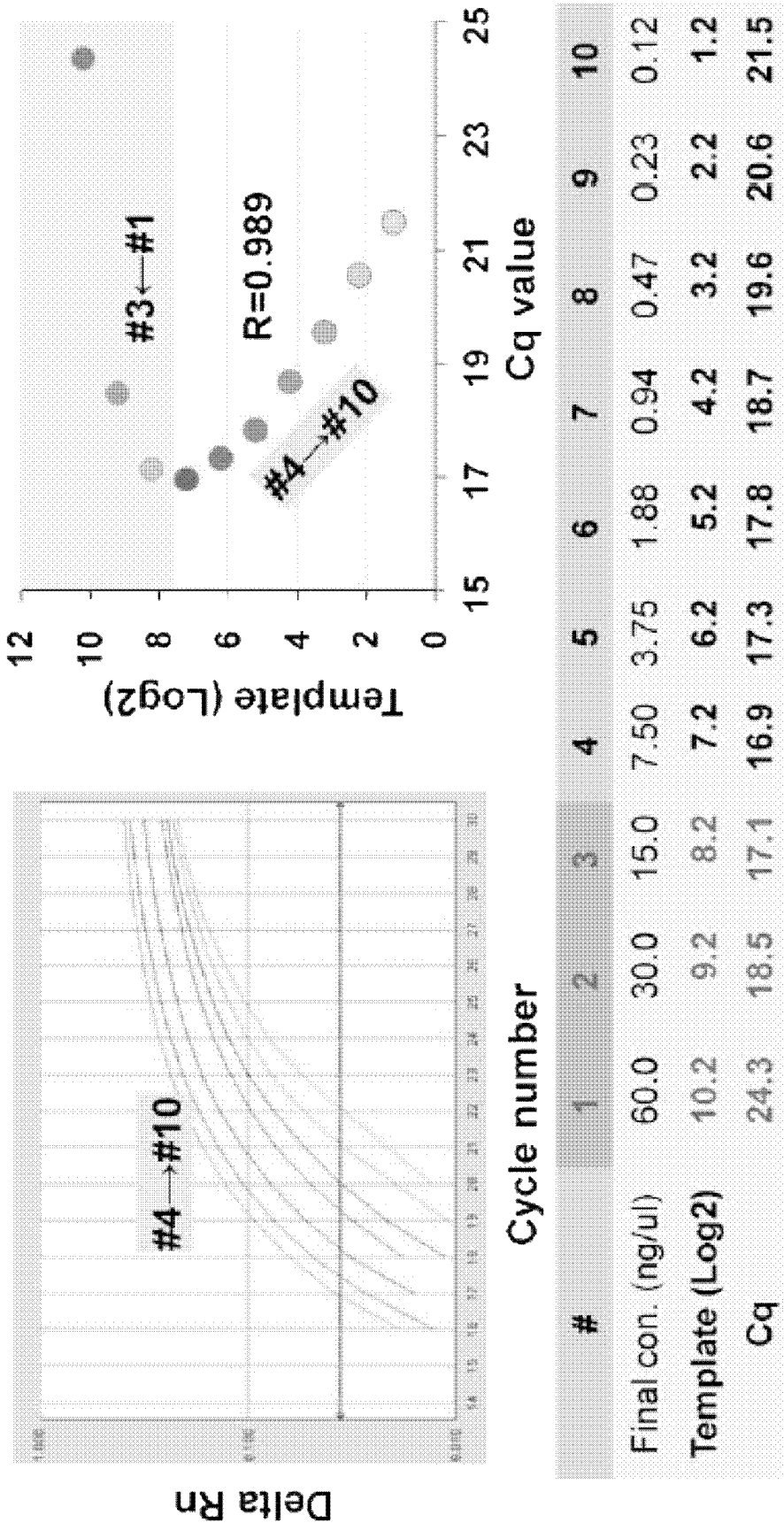
Figure 16B:
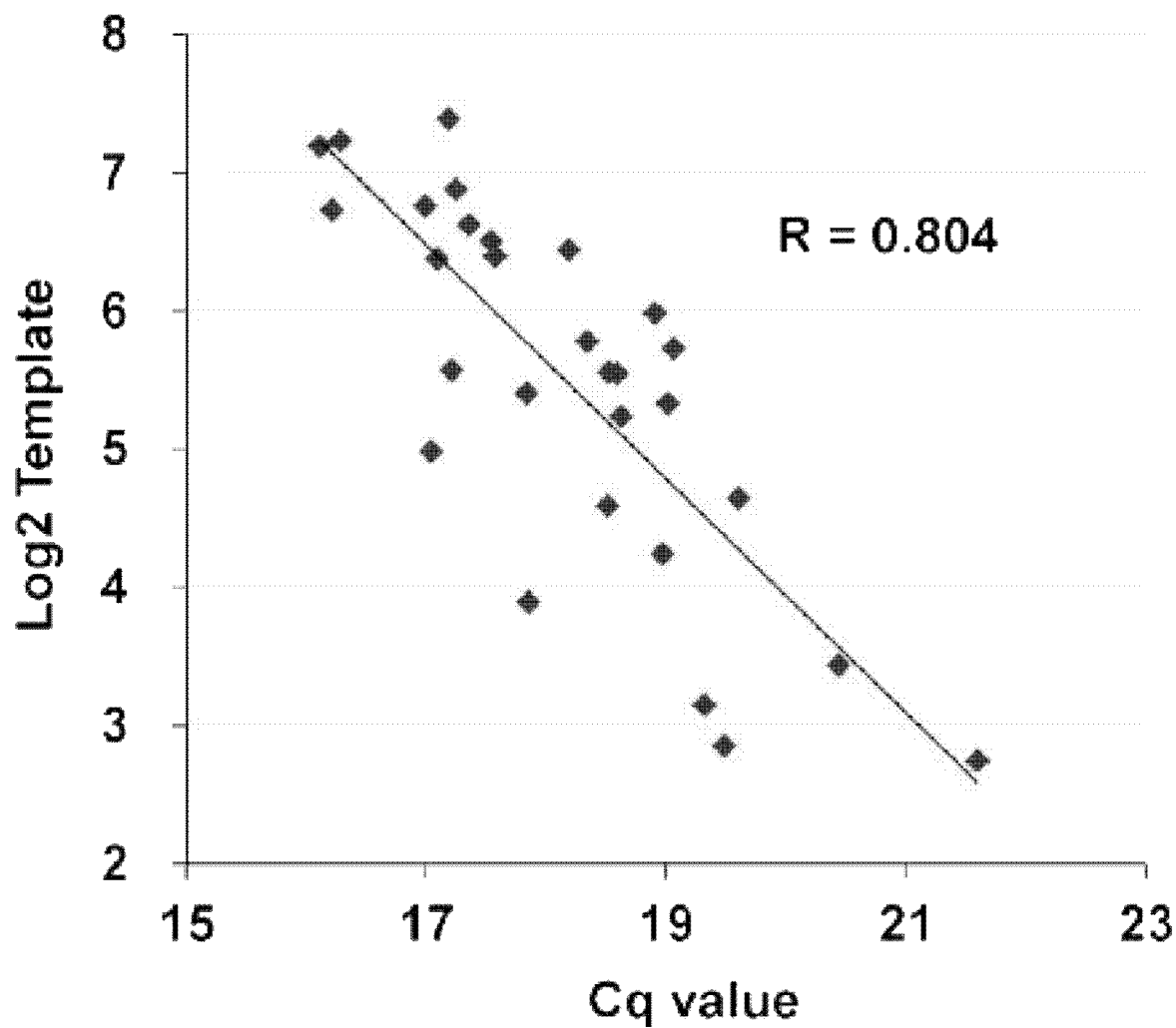
Figure 16C:
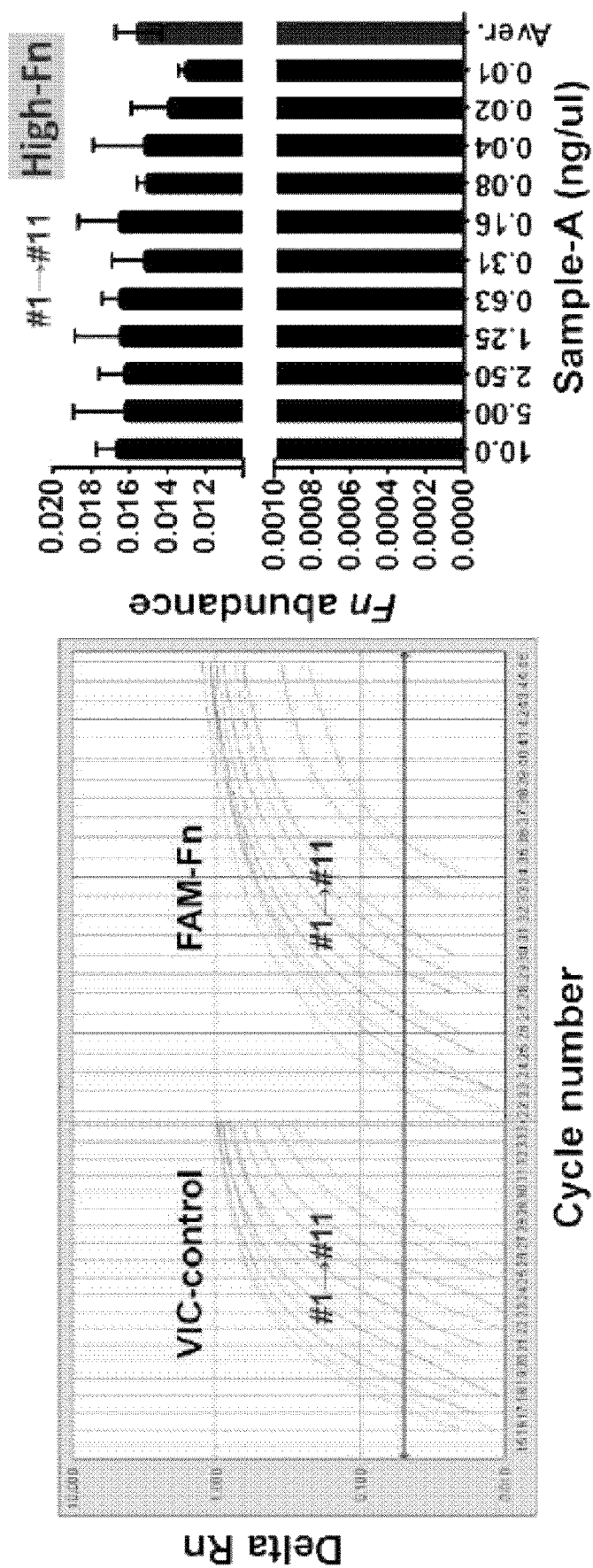
Figure 16D:
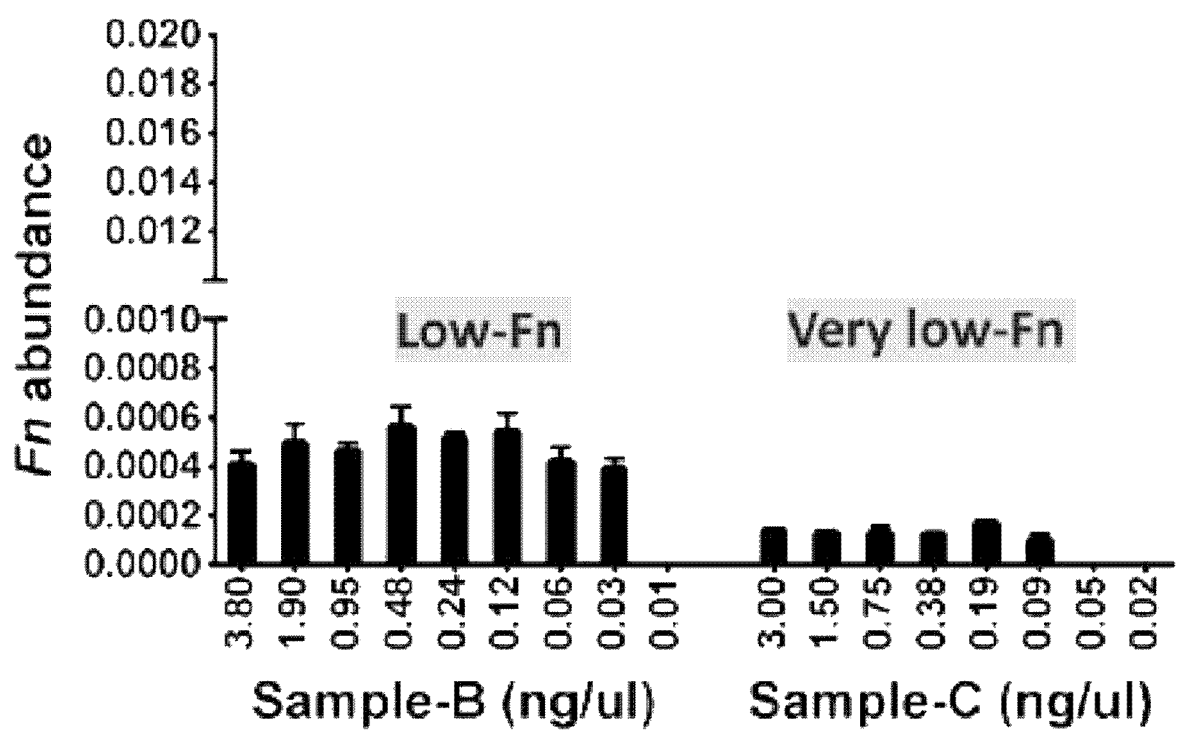

FIG. 15B: mOTU species using published methods[28].

FIG. 16A-FIG. 16D: Minimum redundancy maximum relevance (mRMR) method to identify 20 gene markers that differentiate colorectal cancer cases from controls in cohort C1.

Incremental search was performed using the mRMR method which generated a sequential number of subsets. For each subset, the error rate was estimated by a leave-one-out cross-validation (LOOCV) of a linear discrimination classifier. The optimum subset with the lowest error rate contained 20 gene markers.

Figure 17A:
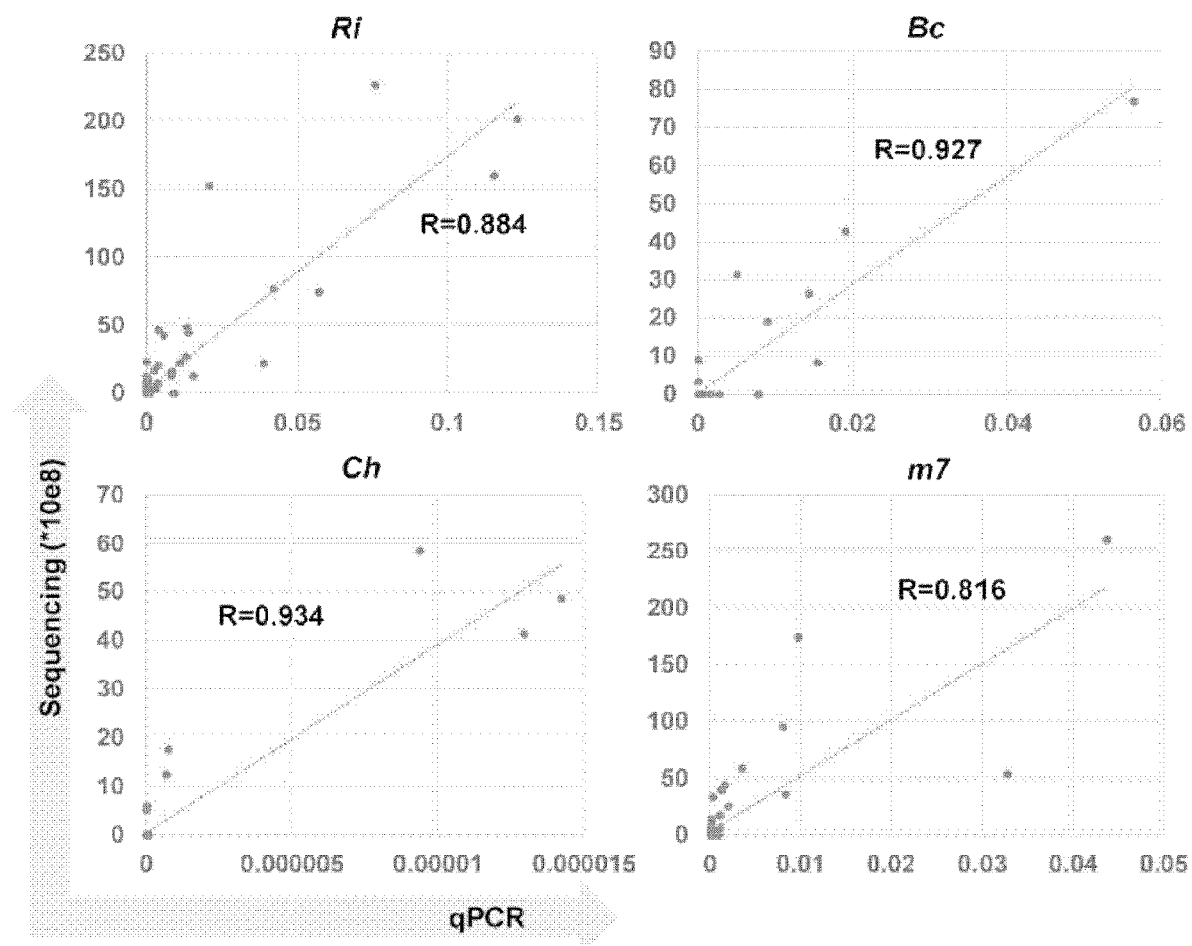
Figure 17B:
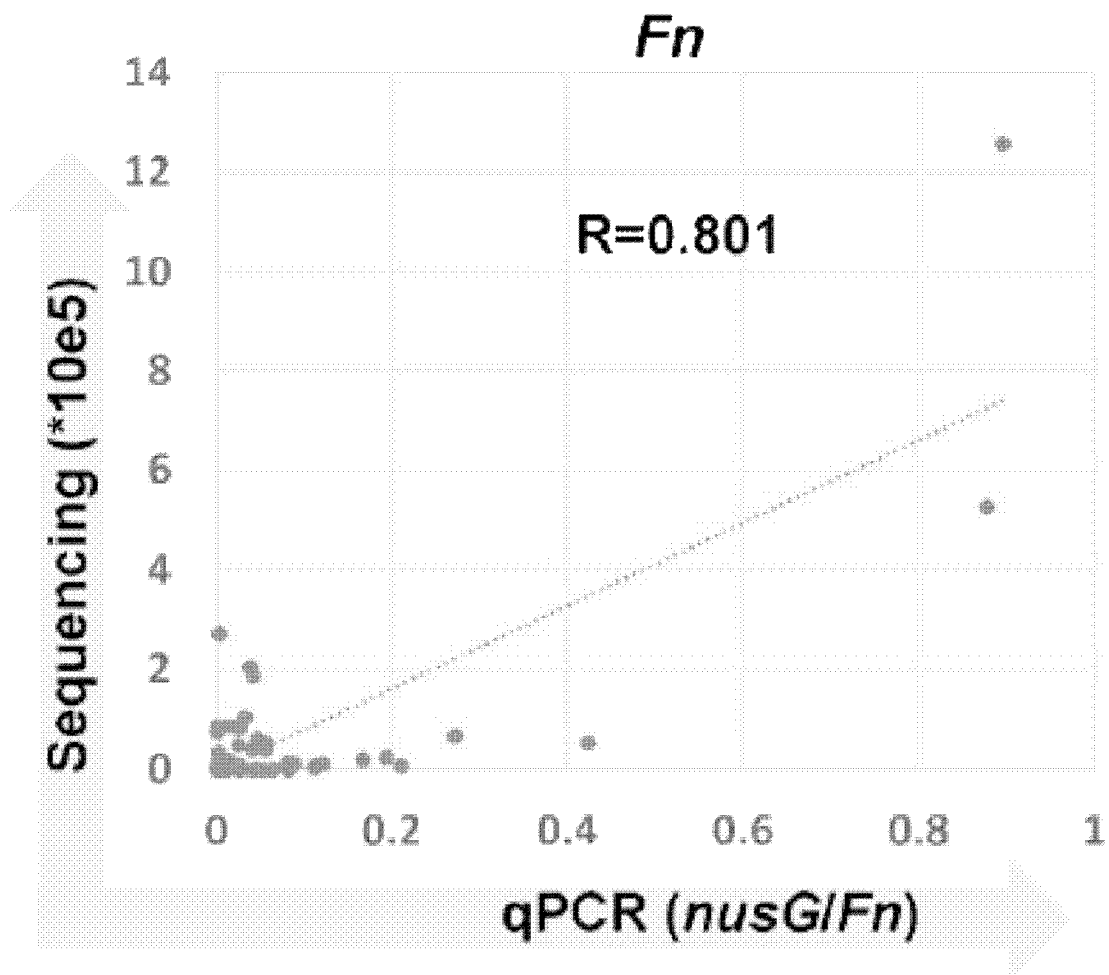

FIG. 17A-FIG. 17B: Correlation between quantification by the metagenomic approach versus quantitative polymerase chain reaction (qPCR) for four gene markers.

Figure 18A:
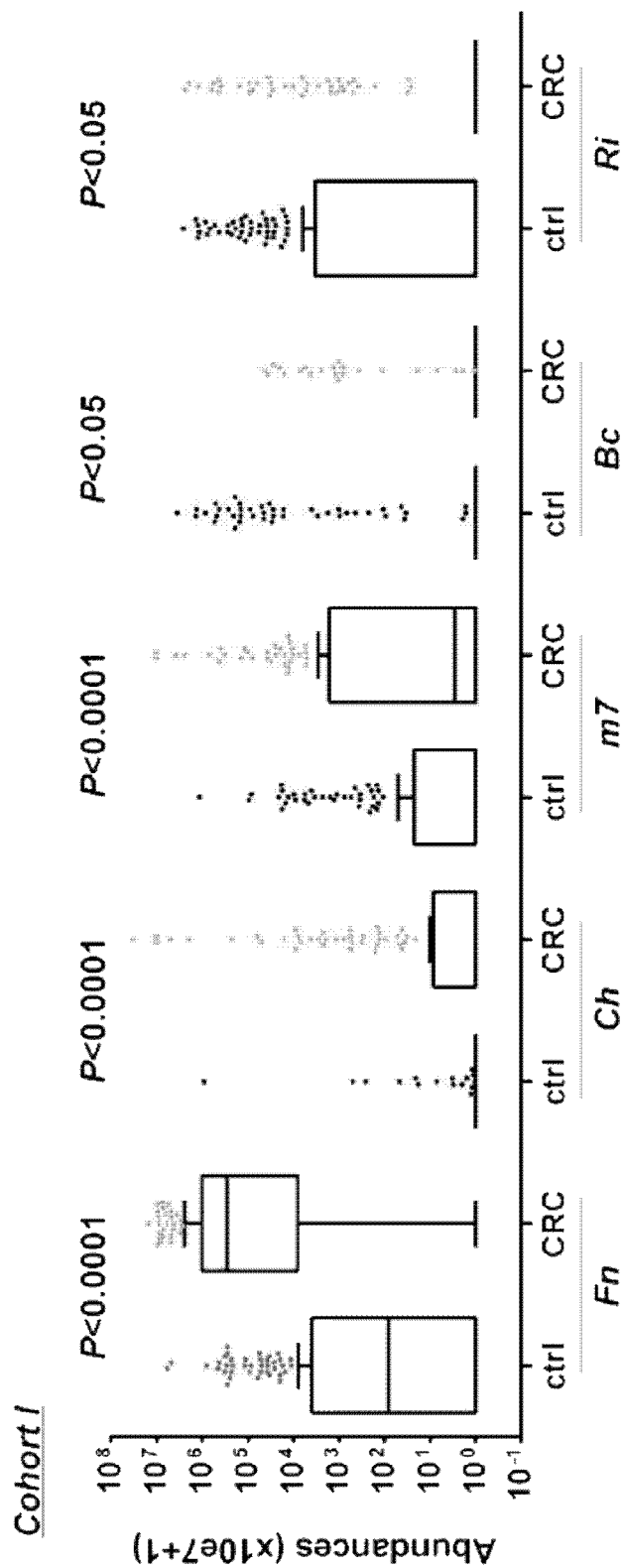
Figure 18B:
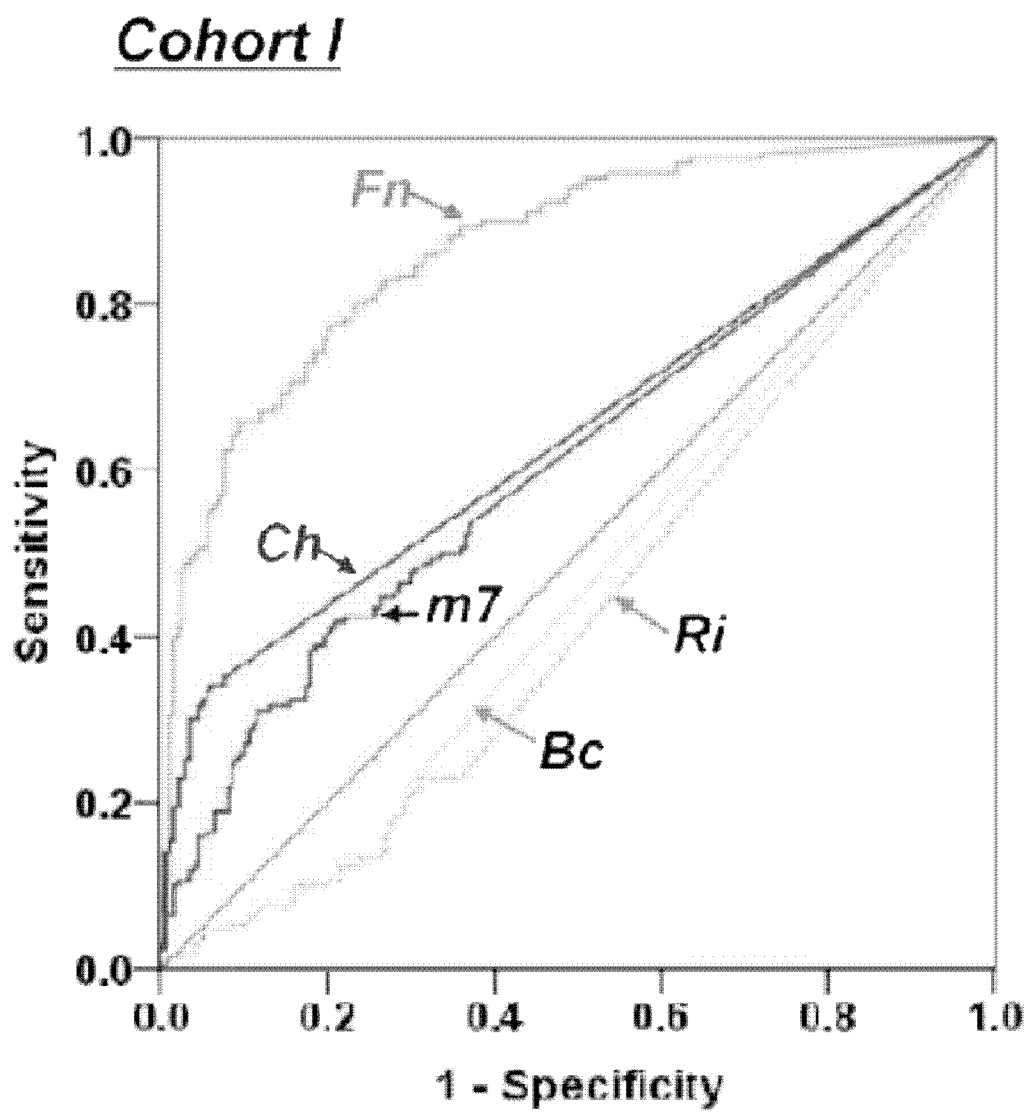
Figure 18C:
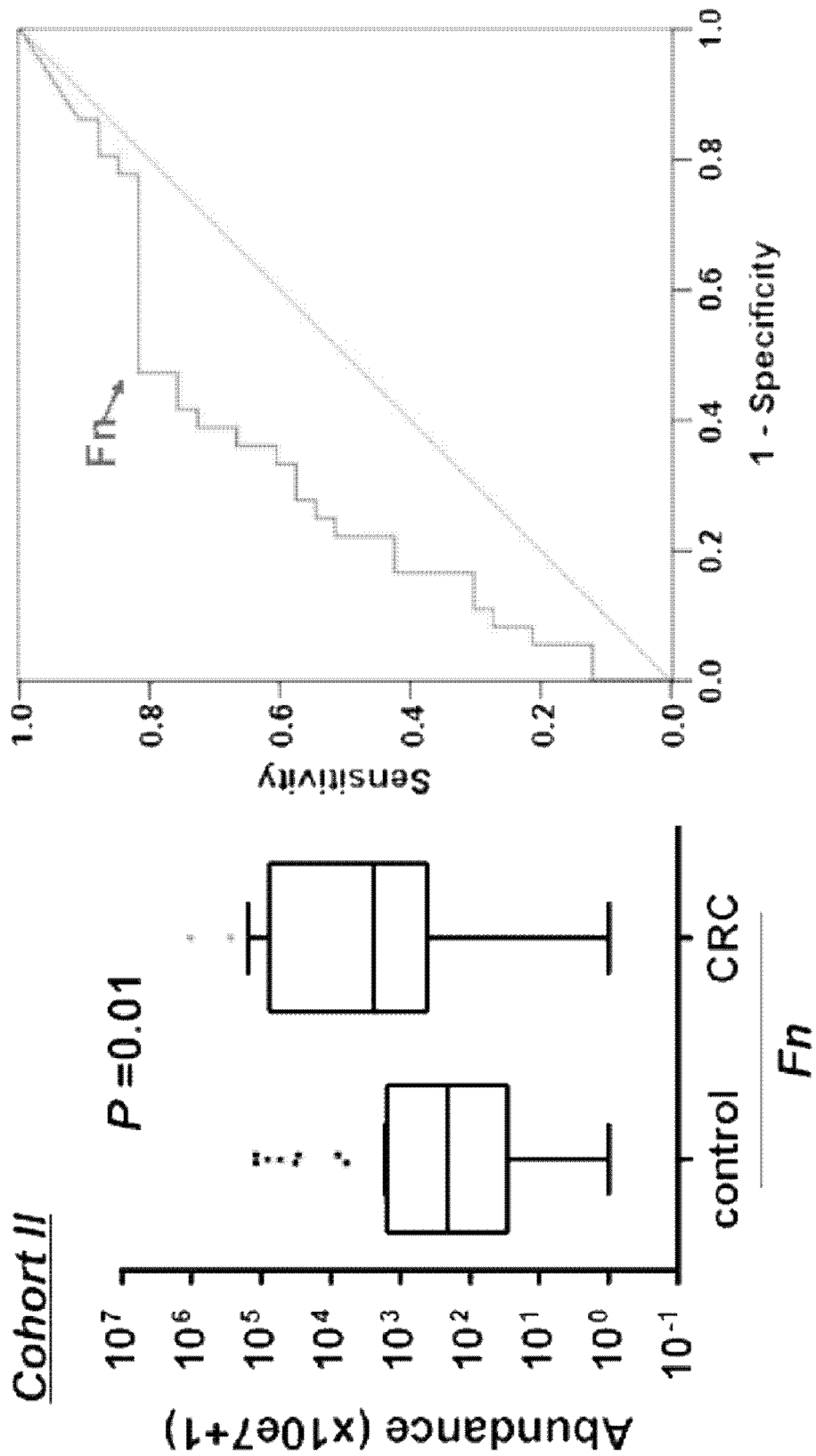
Figure 19A:
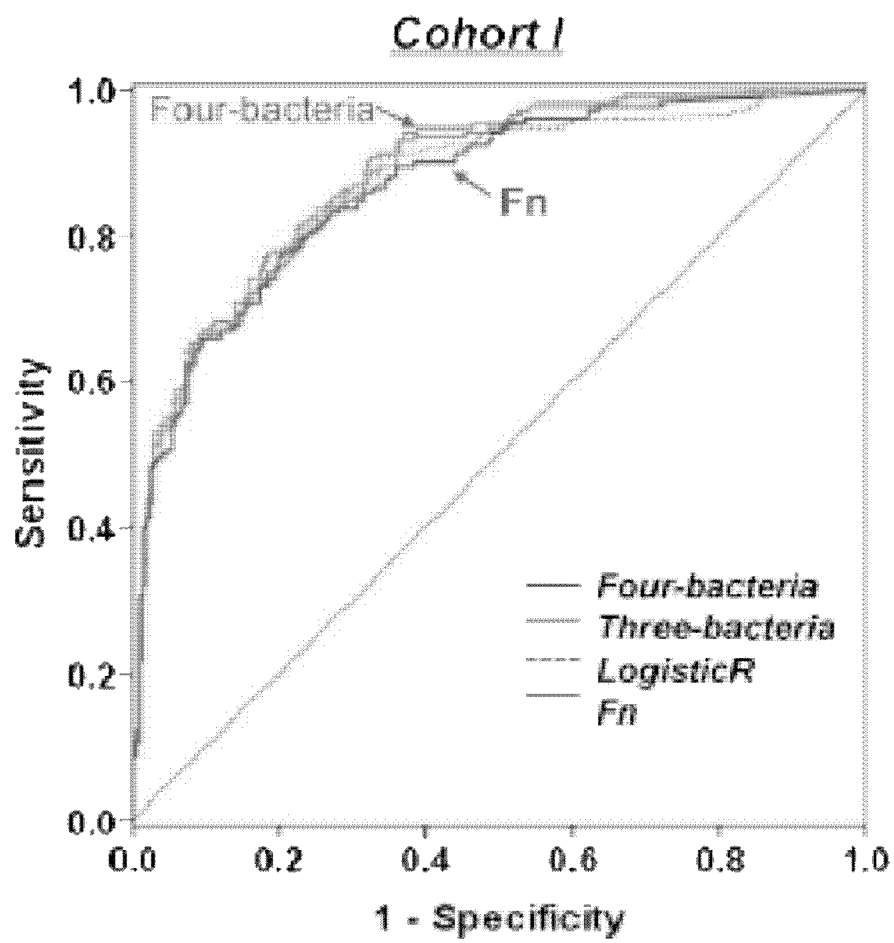
Figure 19B:
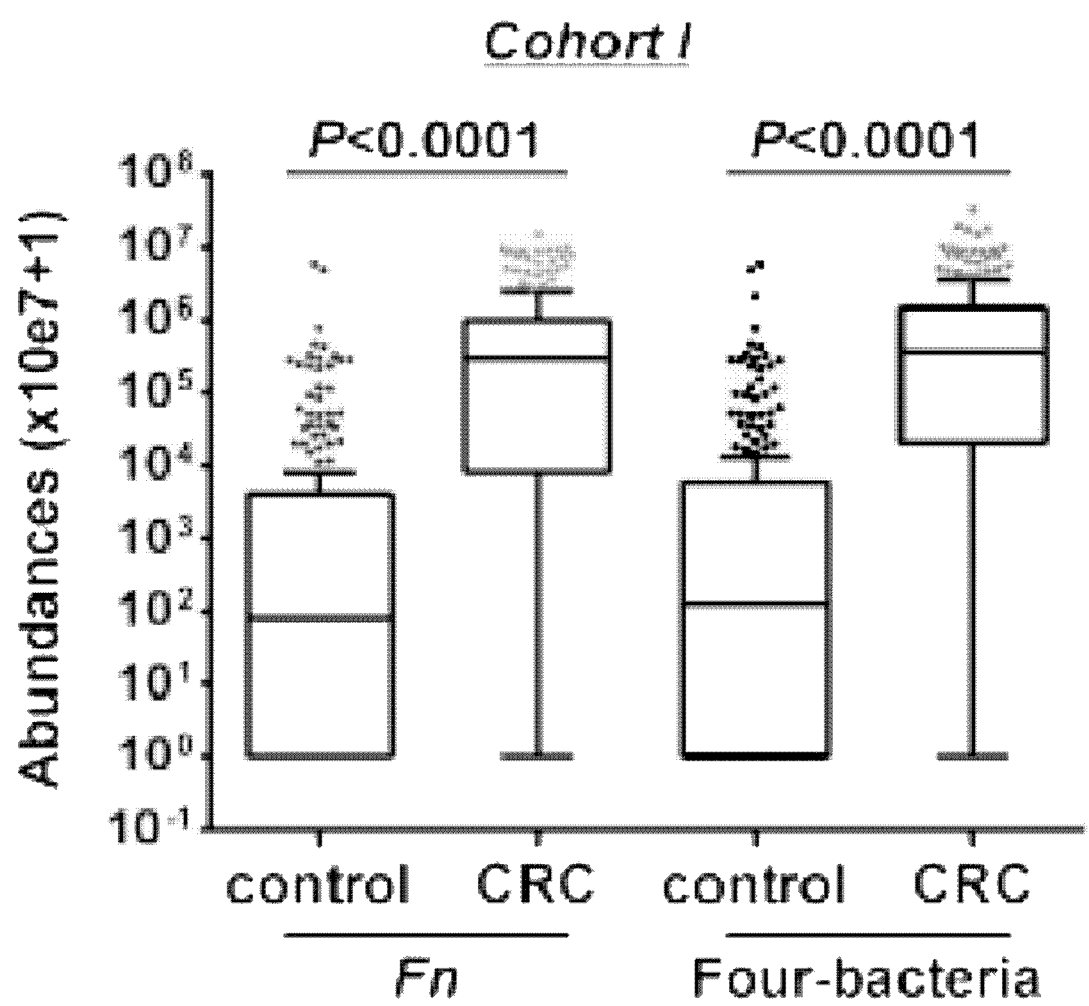
Figure 19C:
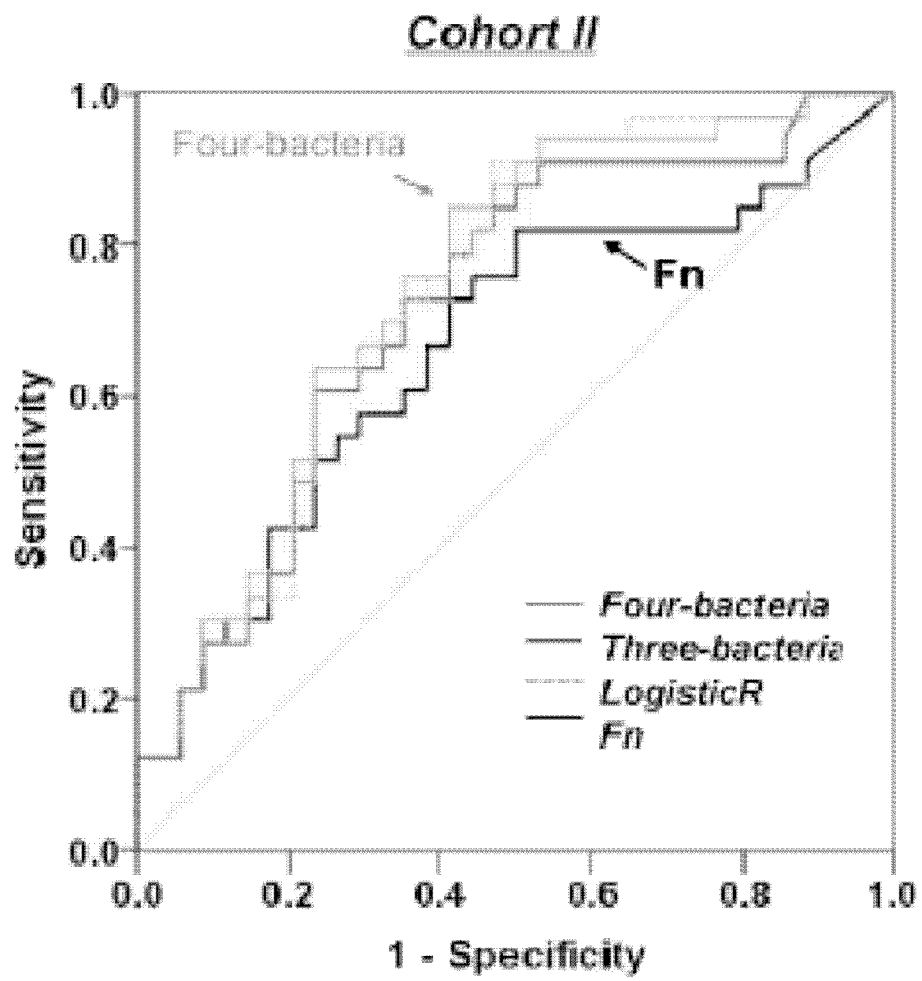
Figure 19D:
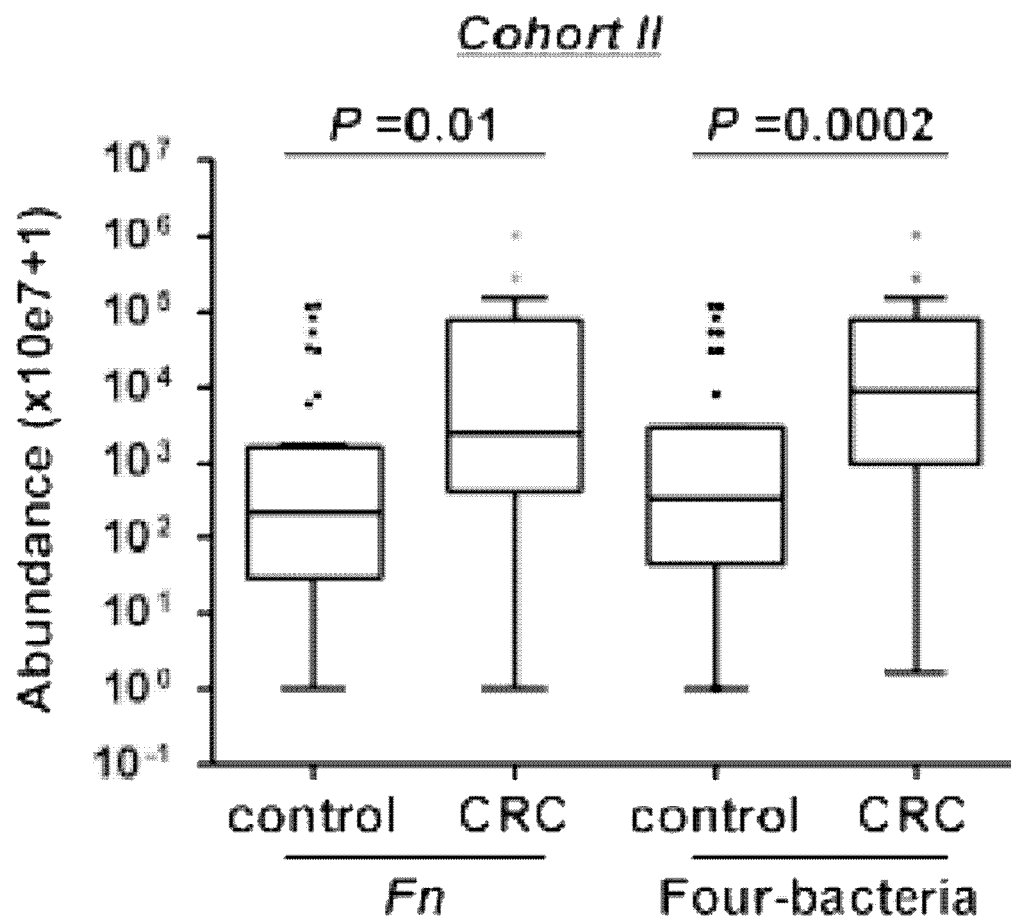

FIG. 18A-FIG. 18C: Evaluating CRC index from four markers in Chinese cohort C2 of 156 individuals.

CRC index based on qPCR abundance of 4 gene markers shows marginal separation of CRC and control microbiomes. ROC analysis reveals moderate potential for classification using CRC index, with an area under the curve of 0.73.

FIGS. 19A-FIG. 19D: Comparison of gene richness (gene count) and alpha-diversity (Shannon index) distribution in cohorts.

Figure 20:
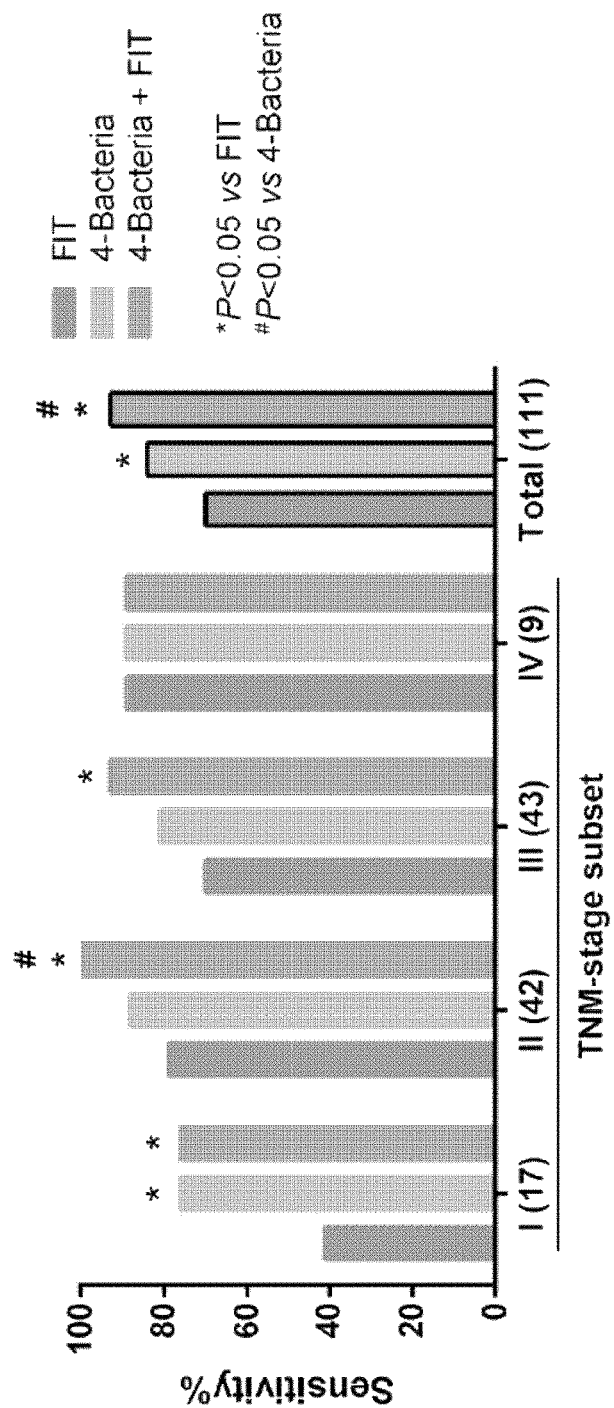

FIG. 20: Evaluating CRC index in cohort D consisting of 40 individuals.

CRC index based on 20 gene markers shows marginal separation of CRC and control microbiomes. ROC analysis reveals moderate potential for classification using CRC index, with an area under the curve of 0.71.

Figure 21:
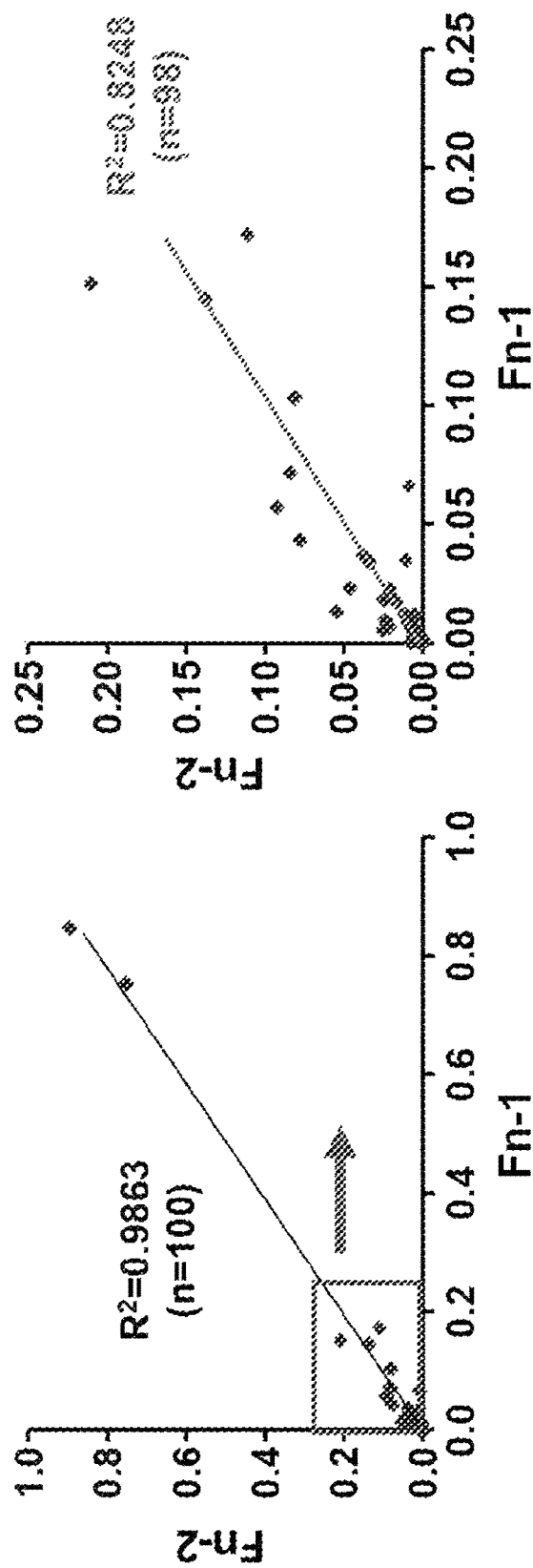

FIG. 21: Good consistency in quantification of nusG/*F. nucleatum* was achieved by two experimenters using our convenient platform.

Figure 22A:
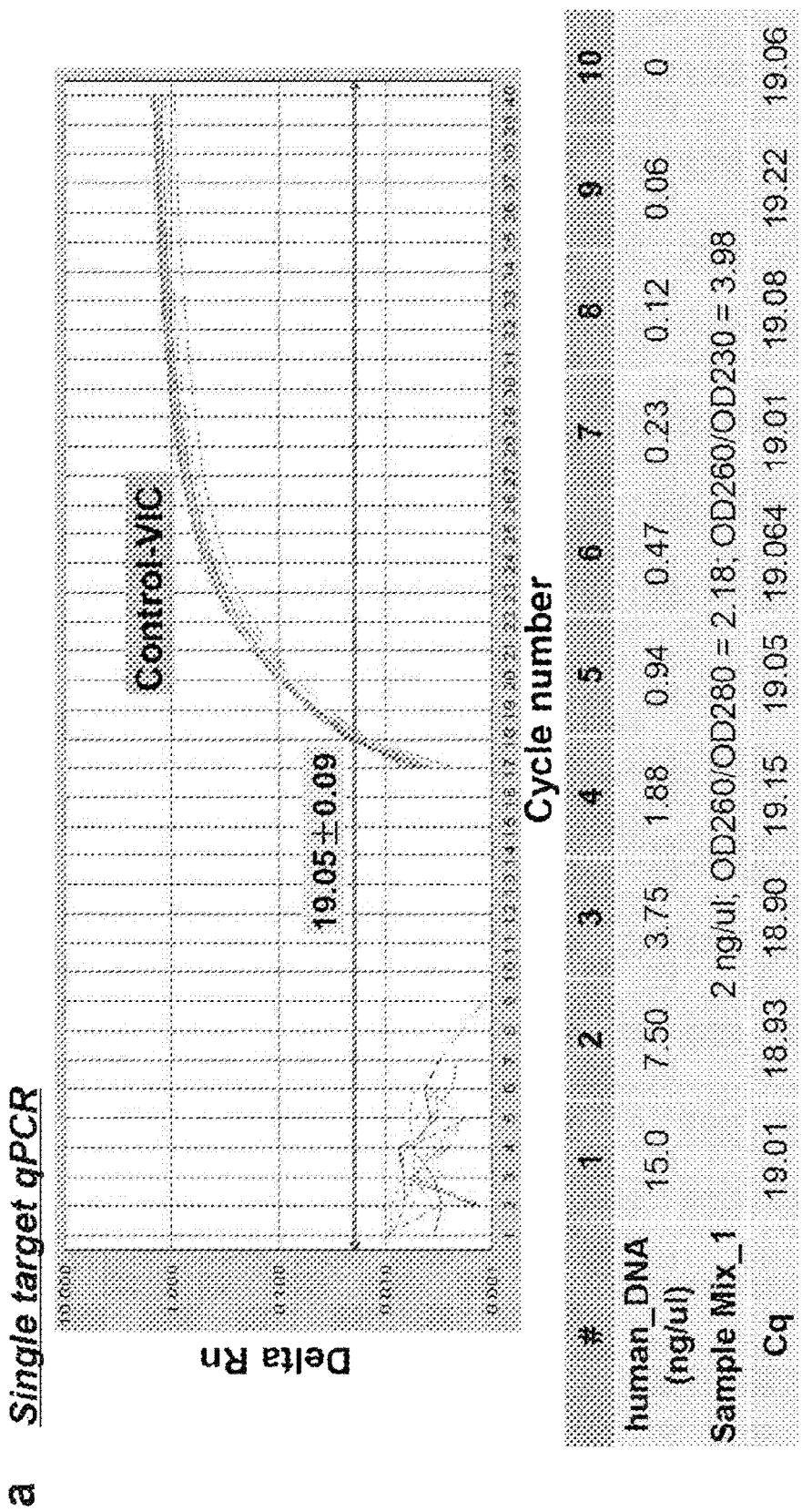
Figure 22B:
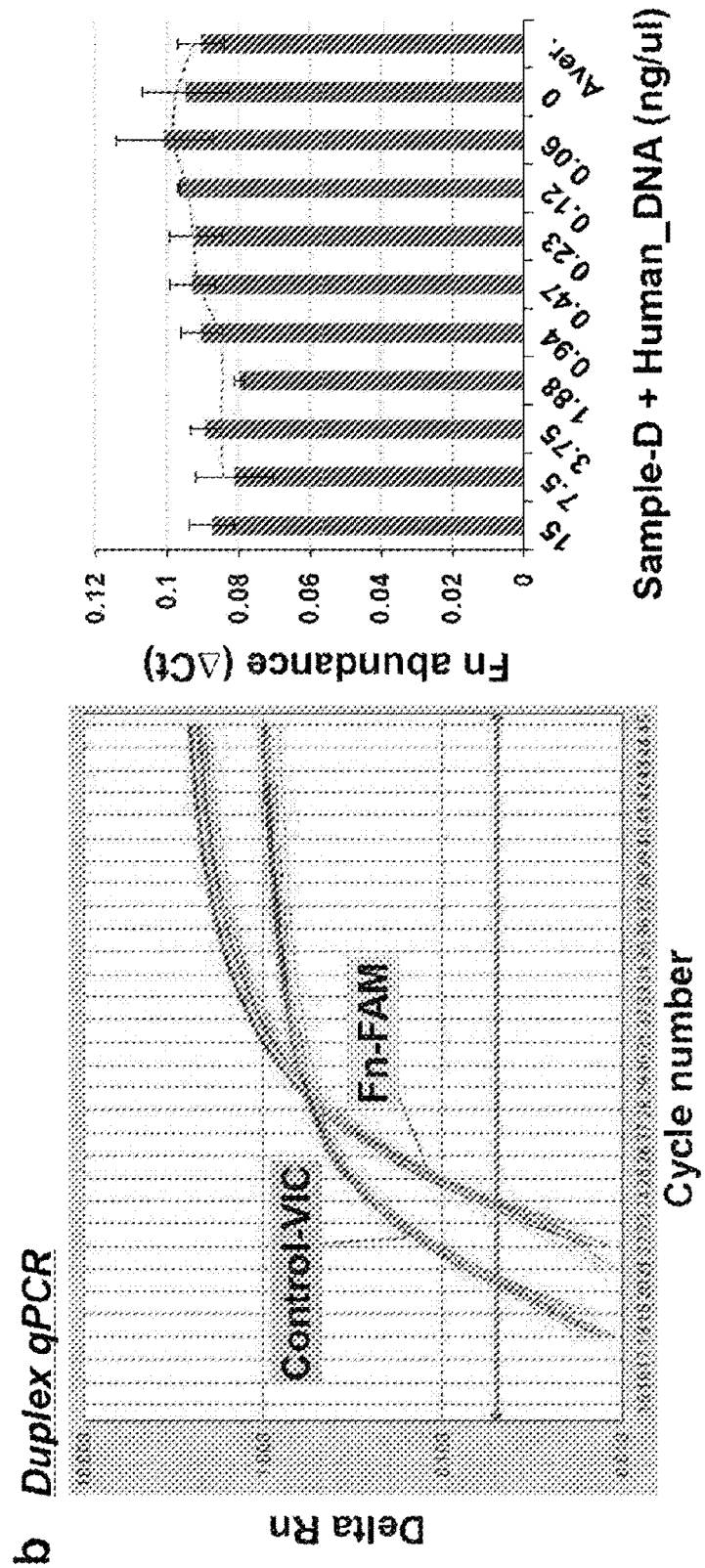

FIG. 22A: A representative example of qPCR evaluation of the internal control on a mixture of 10 randomly selected fecal samples added with different concentrations of human DNA. FIG. 22B: A representative example of duplex qPCR evaluation of the internal control and *F. nucleatum* on a randomly selected fecal sample added with different concentrations of human DNA.

DESCRIPTION OF THE SEQUENCE

SEQ ID NO: 1 is the nucleotide sequence of the gene marker m181682 (Ri).
SEQ ID NO: 2 is the nucleotide sequence of the gene marker m370640 (Bc).
SEQ ID NO: 3 is the nucleotide sequence of m482585.
SEQ ID NO: 4 is the nucleotide sequence of m1696299.
SEQ ID NO: 5 is the nucleotide sequence of the gene marker m1704941 (Fn).
SEQ ID NO: 6 is the nucleotide sequence of the gene marker m2736705 (Ch).
SEQ ID NO: 7 is the nucleotide sequence of the gene marker m3246804 (m7).
SEQ ID NO: 8 is the nucleotide sequence of m2040133.
SEQ ID NO: 9 is the nucleotide sequence of m1559769.
SEQ ID NO: 10 is the nucleotide sequence of m1804565.
SEQ ID NO: 11 is a nucleotide sequence of m2206475.
SEQ ID NO: 12 is the nucleotide sequence of m3319526.
SEQ ID NO: 13 is the nucleotide sequence of m3611706.
SEQ ID NO: 14 is the nucleotide sequence of m3976414.
SEQ ID NO: 15 is the nucleotide sequence of m4171064.
SEQ ID NO: 16 is the nucleotide sequence of m4256106.
SEQ ID NO: 17 is the nucleotide sequence of m2211919.
SEQ ID NO: 18 is the nucleotide sequence of m2361423.
SEQ ID NO: 19 is the nucleotide sequence of m3173495.
SEQ ID NO: 20 is the nucleotide sequence of m3531210.

Definitions

In this disclosure the terms "colorectal cancer (CRC)" and "colon cancer" have the same meaning and refer to a cancer of the large intestine (colon), the lower part of human digestive system, although rectal cancer often more specifically refers to a cancer of the last several inches of the colon, the rectum. A "colorectal cancer cell" is a colon epithelial cell possessing characteristics of colon cancer and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, the term "gene expression" is used to refer to the transcription of a DNA to form an RNA molecule encoding a particular protein or the translation of a protein encoded by a polynucleotide sequence. In other words, both mRNA level and protein level encoded by a gene of interest are encompassed by the term "gene expression level" in this disclosure.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half-life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that has at least 80% sequence identity, preferably 85%, 90%, 91%, 92%, 93, 94%, 95%, 96%, 97%, 98%, 99%, or 100% identity, to a reference sequence, when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average level of a pertinent bacterial DNA or RNA or protein found in stool sample of a healthy subject not suffering from or at risk of developing CRC). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

The term "inhibiting" or "inhibition," as used herein, refers to any detectable negative effect on a target biological process, such as RNA transcription, protein expression, cell proliferation, cellular signal transduction, cell proliferation, tumorigenicity, metastatic potential, and recurrence of a disease/condition. Typically, an inhibition is reflected in a decrease of at least 10%, 20%, 30%, 40%, or 50% in target process (e.g., level of a pertinent bacterial DNA, RNA, or protein) upon application of an inhibitor, when compared to a control where the inhibitor is not applied.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the DNA or RNA sequence of a pertinent bacterial species. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table A of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., a pertinent bacterial DNA, RNA, or protein, that is present in an established disease-free stool sample, e.g., a stool sample from an average healthy individual who has not been diagnosed with CRC or is known to have increased risk of developing CRC. The standard control value is suitable for the use of a method of the present invention, to serve as a basis for comparing the amount of pertinent bacterial DNA, RNA, or protein that is present in a test sample. An established sample serving as a standard control provides an average amount of pertinent bacterial DNA, RNA, or protein that is typical for a stool sample of an average, healthy human without any colon disease especially CRC as conventionally defined, preferably without any increased risk of developing the disease. A standard control value may vary depending on the nature of the sample as well as other factors such as the gender, age, ethnicity of the subjects based on whom such a control value is established.

The term "average," as used in the context of describing a human who is healthy, free of any colon disease (especially CRC) as conventionally defined, refers to certain characteristics, especially the level of certain pertinent bacterial DNA, RNA, or protein, found in the person's stool sample, that are representative of a randomly selected group of healthy humans who are free of any colon diseases (especially CRC) and free of known risk of developing the disease. This selected group should comprise a sufficient number of humans such that the average level or amount of the pertinent bacterial DNA, RNA, or protein found in the stool among these individuals reflects, with reasonable accuracy, the corresponding level/amount of these DNA, RNA, or protein in the general population of healthy humans. In addition, the selected group of humans generally have a similar age to that of a subject whose stool sample is tested for indication of colon cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., a pertinent bacterial DNA, RNA, or protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding an antisense RNA is the amount of said polynucleotide to achieve a decreased level of a corresponding RNA or protein expression or biological activity in a bacterial species, such that the risk, symptoms, severity, and/or recurrence change of colon cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, colon cancer. Subjects also include individuals currently undergoing therapy that seek manipulation of the therapeutic regimen. Subjects or individuals in need of treatment include those that demonstrate symptoms of colon cancer or are at risk of suffering from colon cancer or its symptoms. For example, a subject in need of treatment includes individuals with a genetic predisposition or family history for colon cancer, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of a bacterial species are used to refer to inhibitory, activating, or modulating molecules, respectively, identified using in vitro and in vivo assays for binding to pertinent bacterial DNA, RNA, or protein or for their effect on bacterial survival or proliferation. The term "modulator" includes inhibitors and activators. Inhibitors are agents that, e.g., partially or totally block binding, decrease, prevent, delay activation, inactivate, desensitize, or down regulate the level or amount of the pertinent bacterial DNA, RNA, or protein, potentially by suppressing the growth or survival of the bacterial species. In some cases, the inhibitor directly or indirectly binds to a bacterial DNA or RNA, such as an antisense molecule. Inhibitors, as used herein, are synonymous with inactivators and antagonists. Activators are agents that, e.g., stimulate, increase, facilitate, enhance activation, sensitize or up regulate the level or amount of a pertinent bacterial DNA, RNA, or protein, potentially by promoting growth or survival of the bacterial species. Inhibitors, activators, and modulators can be macromolecules such as polynucleotides, polypeptides including antibodies and antibody fragments, or they can be small molecules including carbohydrate-containing molecules, siRNAs, RNA aptamers, and the like.

DETAILED DESCRIPTION OF THE INVENTION

I. Introduction

Colorectal cancer patients often face a grim prognosis when the disease is detected in its later stages. Early detection of colorectal cancer is therefore critical for improving patient survival rate. While it was previously known that the bacterial population existing in human gut plays a role in the tumorigenesis and progression of colorectal cancer, inadequate information is available for the development of a non-invasive diagnostic tool that allows fast and reliable detection of the disease based on fecal bacterial markers.

The present inventors discovered for the first time that increased presence of certain bacterial species in stool, as demonstrated by increased level of pertinent bacterial DNA, RNA, or protein, are correlated with the presence or heightened risk of colorectal cancer in a patient. This discovery of enrichment of pertinent bacterial species in the colon of colorectal cancer patients provides important means for early detection of colorectal cancer in a non-invasive manner, as well as implications in the monitoring or treatment of the disease. Generally, a higher than normal level of the pertinent bacterial DNA, RNA, or protein seen in a stool sample from a test subject, who may or may not exhibit any signs of colon disorder or anomaly, indicates a high likelihood that the subject already has or will later develop colorectal cancer. The recognition of such heightened risk allows immediate treatment of the patient if further diagnostic methods confirm the presence of the disease, or allows close monitoring and/or preventive measure to be applied to the patient if the disease has not yet occurred.

In their first study, the inventors discovered significant enrichment of novel species, including *Parvimonas micra* and *Solobacterium moorei*, and a strong co-occurrence network between them in the fecal microbiomes of patients with CRC. They identified 20 gene markers that significantly differentiate CRC-associated and control microbiomes in a Chinese cohort, and trans-continental validation of four of them in a Danish cohort. The four gene markers were further validated in published cohorts from the French and Austrian cohorts with areas under the receiver-operating curve (AUC) of 0.72 and 0.77. Quantitative PCR abundance of two gene markers (butyryl-CoA dehydrogenase from *F. nucleatum*, and RNA polymerase subunit (3, rpoB, from *P. micra*) clearly separates CRC microbiomes from controls in an independent Chinese cohort consisting of 47 cases and 109 healthy controls, with AUC=0.84 and odds ratio of 23. The four microbial gene markers shared between the Chinese, Danish, Austrian, and French cohorts suggest that, even though different populations may have different gut microbial community structures, signatures of CRC-associated microbial dysbiosis could have universal features. These observations provide a step further towards affordable early diagnosis of CRC by targeted analysis of metagenomics biomarkers in fecal samples.

In their second study, the inventors identified by metagenome sequencing that the abundances of five bacterial candidates, including *Fusobacterium nucleatum* (Fn), *Bacteroides clarus* (Bc), *Roseburia intestinalis* (Ri), *Clostridium hathewayi* (Ch), and one undefined species (m7) are significantly different in fecal samples of CRC patients in comparison to healthy controls as shown in duplex-qPCR assays. The value of fecal Fn as a stool-based biomarker for CRC diagnosis is corroborated (sensitivity of 77.7%, specificity of 79.5%). A simple linear combination of four bacterial marker candidates (Fn, Bc, Ch, and m7) improves the diagnostic ability of Fn alone for CRC. An increased performance of Fn (sensitivity 92.8%, specificity 79.8%) and four-bacteria (sensitivity 92.8%, specificity 81.5%) was achieved in combination with fecal immunochemical test (FIT) as biomarkers for the detection of CRC.

This invention describes a probe-based internal control assay for quantification of bacterial DNA content and further duplex qPCR assays for quantification of our newly identified fecal bacterial markers by metagenome sequencing. The internal control assay is well established and optimized with the following aspects: 1) a degenerate primer-probe set was designed with amplicon size suitable for qPCR quantification (<150 bp) targeting a conserved region of 16S rRNA genes, covering >90% of the eubacterial population within the Ribosomal Database Project Release version 10.8; 2) Using well-optimized experiment protocol, Cq values correlated well with Log2 DNA quantities ($R2=0.6466$). In short, the present inventors have established a reliable platform for convenient translational application of new bacterial markers. The stool-based CRC-associated bacteria identified by the metagenome sequencing study described herein can serve as novel biomarkers for the non-invasive diagnosis of CRC patients.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of a pertinent bacterial DNA or RNA, and synthetic oligonucleotides (e.g., primers) can be verified using, e.g., the chain termination method for double-stranded templates of Wallace et al., Gene 16: 21-26 (1981).

III. Acquisition of Samples and Analysis of Bacterial DNA or RNA

The present invention relates to measuring the level or amount of a signature DNA or RNA for one or more bacterial species found in a person's stool sample as a means to detect the presence, to assess the risk of developing, and/or to monitor the progression or treatment efficacy of colon cancer, including assessing the likelihood of disease recurrence. Thus, the first steps of practicing this invention are to obtain a stool sample from a test subject and extract DNA or RNA from the sample.

A. Acquisition and Preparation of Stool Samples

A stool sample is obtained from a person to be tested or monitored for colon cancer using a method of the present invention. Collection of a stool sample from an individual can be easily achieved either in a clinic or at patient's home. An appropriate amount of stool is collected and may be stored according to standard procedures prior to further preparation. The analysis of bacterial DNA or RNA found in a patient's stool sample according to the present invention may be performed using established techniques. The methods for preparing stool samples for nucleic acid extraction are well-known among those of skill in the art. See, e.g., Yu et al., *Gut.* 2015 Sep. 25. pii: gutjnl-2015-309800. doi: 10.1136/gutjnl-2015-309800.

B. Extraction and Quantitation of DNA and RNA

Methods for extracting DNA from a biological sample are well-known and routinely practiced in the art of molecular biology (e.g., described by Sambrook and Russell, *Molecular Cloning: A Laboratory Manual* 3d ed., 2001). RNA contamination should be eliminated to avoid interference with DNA analysis.

Likewise, there are numerous methods for extracting mRNA from a biological sample. The general methods of mRNA preparation can be followed, see, e.g., Sambrook and Russell, supra; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used. It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of DNA or RNA Level

Once DNA or mRNA is extracted from a sample, the amount of a predetermined bacterial DNA or RNA (such as 16s rDNA or RNA encoded by a bacterial gene unique to the bacterial species) may be quantified. The preferred method for determining the DNA or RNA level is an amplification-based method, e.g., by polymerase chain reaction (PCR), including reverse transcription-polymerase chain reaction (RT-PCR) for RNA quantitative analysis.

While a bacterial DNA is directly subject to amplification, bacterial RNA must be first reverse transcribed. Prior to the amplification step, a DNA copy (cDNA) of the target RNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well-known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target bacterial DNA or RNA is typically used in practicing the present invention, one of skill in the art will recognize, however, that amplification of these DNA or RNA species in a sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of DNA or mRNA in the sample. For a review of branched-DNA signal amplification for direct quantitation of nucleic acid sequences in clinical samples, see Nolte, *Adv. Clin. Chem.* 33:201-235, 1998.

2. Other Quantitative Methods

The target bacterial DNA or RNA can also be detected using other standard techniques, well known to those of skill in the art. Although the detection step is typically preceded by an amplification step, amplification is not required in the methods of the invention. For instance, the DNA or RNA may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard comparison is an indication of the presence of a target DNA or RNA, the amount of which may then be compared to the control based on the intensity of the band. Alternatively, oligonucleotide probes specific to the target bacterial DNA or RNA can be used to detect the presence of such DNA or RNA species and indicate the amount of bacterial DNA or RNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., a bacterial 16s rDNA, can be labeled by any one of several methods typically used to detect the presence of hybridized nucleic acids. One common method of detection is the use of autoradiography using probes labeled with $^3H$, $^{125}I$, $^{35}S$, $^{14}C$ or $^{32}P$, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well-known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255:137-149, 1983.

IV. Quantitation of Bacterial Proteins

A. Preparing Samples for Bacterial Protein Detection

The presence of relevant bacterial species in a sample also can be quantitatively determined by analysis of one or more proteins unique to the bacteria. Stool sample from a subject is used in the practice of the present invention and can be obtained and processed for analysis according to known methods or as described in the previous section.

B. Determining the Level of A Bacterial Protein

A protein, e.g., one that is indicative of a bacterium's identity, can be detected using a variety of immunological assays. In some embodiments, a sandwich assay can be performed by capturing the target protein from a test sample with an antibody having specific binding affinity for the protein. The protein then can be detected with a labeled antibody having specific binding affinity for it. Such immunological assays can be carried out using microfluidic devices such as microarray protein chips. A protein of interest (e.g., a protein unique to a bacterial species) can also be detected by gel electrophoresis (such as 2-dimensional gel electrophoresis) and western blot analysis using specific antibodies. Alternatively, standard immunohistochemical techniques can be used to detect a target protein, using the appropriate antibodies. Both monoclonal and polyclonal antibodies (including antibody fragment with desired binding specificity) can be used for specific detection of the target protein. Antibodies and their binding fragments with specific binding affinity to a particular protein can be generated by known techniques.

Other methods may also be employed for measuring the level of a marker protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any colon disease (especially any form of tumor such as colon cancer) as conventionally defined is first selected. These individuals are within the appropriate parameters, if applicable, for the purpose of screening for and/or monitoring colon cancer using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of pertinent bacteria, their DNA, mRNA, or protein in the stool sample obtained from the group can be reasonably regarded as representative of the normal or average level among the general population of healthy people. Preferably, the selected group comprises at least 10 human subjects.

Once an average value for the bacteria, their marker DNA, mRNA, or protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Prophylactic Treatment of Colon Cancer

By illustrating the correlation of enrichment of certain bacterial species in human gut and colon cancer, the present invention provides a preventive measure for prophylactically treating patients who are at an increased risk of later developing colon cancer: by way of suppressing the pertinent bacterial species and reducing their presence in the patients' gut. Conversely, certain other bacterial species have been shown by the present inventors as having a depressed or less than normal population in CRC patient's colon. A preventive measure can then be devised for prophylactically treating patients who are at an increased risk of later developing colon cancer: by way of promoting the pertinent bacterial species and increasing/restoring their presence in the patients' colon.

As used herein, prophylactic treatment of colon cancer encompasses preventing or delaying the onset of one or more of the relevant symptoms of the disease, including reducing mortality or likelihood of disease recurrence among patients who have already received initial treatment. Inhibitors of the pertinent bacterial species can be of virtually any chemical and structural nature: they may be polypeptides (e.g., antibody, antibody fragment, aptamer), polynucleotides (e.g., antisense DNA/RNA, small inhibitory RNA, or micro RNA), and small molecules. As long as they possess confirmed inhibitory effect against the target bacteria (e.g., suppression of bacterial proliferation or induced death of bacterial cells), such inhibitors may be useful for suppressing development of colon cancer cells in a patient's gut and therefore useful for treating colon cancer. Similarly, an activator the pertinent bacterial species can be of virtually any chemical and structural nature, so long as they possess confirmed enhancing effect on the target bacteria (e.g., promoting bacterial proliferation or suppressing death of bacterial cells).

In addition, upon detecting the enrichment of certain bacterial species in a patient's gut, which is shown by the present inventors as relevant to colon cancer, one may establish the presence of colon cancer in the patient or an increased risk of later developing the disease in the patient. As a result of this determination, the patient may be subject to subsequent therapies or preventive/monitoring measures, especially those fitting certain profiles, such as those with a family history of colon cancer, such that the symptoms of these conditions may be prevented, eliminated, ameliorated, reduced in severity and/or frequency, or delayed in their onset. For example, a physician may prescribe both pharmacological and non-pharmacological treatments such as lifestyle modification (e.g., reduce body weight by 5% or more, assume a healthier life style including following a high fibre/low salt diet and maintaining a higher level of physical activities such as walking for at least 150 minutes weekly, and undergo regularly scheduled screening/examination such as colonoscopy every 5 years). In some cases, when the presence of colon cancer is confirmed by way of other diagnostic means (e.g., colonoscopy), aggressive treatment may be used such as surgical intervention as well as radio- and/or chemo-therapy.

A. Modulators of Pertinent Bacterial Species

Suppression of a bacterial species can be achieved through the use of inhibitor nucleic acids targeting specific bacterial genes such as siRNA, microRNA, miniRNA, lncRNA, antisense oligonucleotides, aptamer. Such nucleic acids can be single-stranded nucleic acids (such as mRNA) or double-stranded nucleic acids (such as DNA) that can translate into an active form of inhibitor of target bacterial RNA under appropriate conditions.

In one embodiment, the inhibitor-encoding nucleic acid is provided in the form of an expression cassette, typically recombinantly produced, having a promoter operably linked to the polynucleotide sequence encoding the inhibitor. In some cases, the promoter is one that directs expression specifically in selected bacterial cells. Administration of such nucleic acids can suppress target bacterial gene expression and therefore suppress the bacterial population. Since virtually all known bacteria have been fully sequenced and information deposited in data banks, one can devise suitable inhibitor nucleic acids based on the sequence information.

Both inhibitors and activators of the pertinent bacterial species can be confirmed in assays where a bacterial culture is exposed to a candidate compound, and the compound's effect on the culture is analyzed. For example, an inhibitor can be observed to exhibit an inhibitory or suppressing effect on the bacterial culture, resulting in reduced growth and/or increased bacterial cell death. In contrast, an activator can be observed to exhibit a positive effect on the bacterial culture, promoting the survival and proliferation/growth of the bacterium. An inhibitory effect is detected when a negative effect on the bacterial culture is established in the test group. Preferably, the negative effect is at least a 10% decrease; more preferably, the decrease is C Similarly, an activator exhibits an effect of at least 10%, 20%, 50%, or higher increase in cell proliferation, more preferably the increase is at least 1 or 2 fold or even 5 fold.

As stated above, these bacterial inhibitors or activators can have diverse chemical and structural features. For instance, an inhibitor or activator can be any small molecule or macromolecule that simply affects the growth or survival of a particular bacterial species. Essentially any chemical compound can be tested as a potential inhibitor or activator. These modulators can be identified by screening a combinatorial library containing a large number of potentially effective compounds. Such combinatorial chemical libraries can be screened in one or more assays, as described herein, to identify those library members (particular chemical species or subclasses) that display a desired characteristic activity. The compounds thus identified can serve as conventional "lead compounds" or can themselves be used as potential or actual therapeutics.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science,* 274:1520-1522 (1996) and U.S. Pat. No. 5,593,853). Other chemistries for generating chemical diversity libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

B. Pharmaceutical Compositions

1. Formulations

The modulators of pertinent bacterial species are useful in the manufacture of a pharmaceutical composition or a medicament. A pharmaceutical composition or medicament can be administered to a subject for the treatment of colon cancer, especially for prophylaxis.

Compounds used in the treatment method of the present invention are useful in the manufacture of a pharmaceutical composition or a medicament comprising an effective amount thereof in conjunction or mixture with excipients or carriers suitable for application.

An exemplary pharmaceutical composition for such therapeutic use comprises (i) an express cassette comprising a polynucleotide sequence encoding an inhibitor (e.g., siRNA, microRNA, miniRNA, lncRNA, antisense oligonucleotides) as described herein, and (ii) a pharmaceutically acceptable excipient or carrier. The terms pharmaceutically-acceptable and physiologically-acceptable are used synonymously herein. The expression cassette may be provided in a therapeutically effective dose for use in a method for treatment as described herein.

An inhibitor or activator can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells, or with other therapeutic or immunogenic compositions. Thus, liposomes filled with a desired modulator of the invention can be directed to the site of treatment, e.g., colon, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) *Ann. Rev. Biophys. Bioeng.* 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a modulator of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., an inhibitor or an activator, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The modulators can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

In some cases, a pharmaceutical composition or medicament of the present invention comprises (i) an effective amount of a compound as described herein that suppresses or promotes the population of one or more of the pertinent bacterial species identified herein, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a modulator of the present invention). Administration may be by the same or different route of administration or together in the same pharmaceutical formulation.

3. Dosage

Pharmaceutical compositions or medicaments can be administered to a subject at a therapeutically effective dose to prevent, treat, or control colon cancer as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of inhibitor or nucleic acid encoding an inhibitor will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for an inhibitor or a nucleic acid encoding an inhibitor described herein are provided. Dosage for an inhibitor-encoding nucleic acid, such as an expression vector, can be between 0.1-0.5 mg with IV administration (e.g., 5-30 mg/kg). Small organic compounds inhibitors can be administered orally at between 5-1000 mg, or by intravenous infusion at between 10-500 mg/ml. Polypeptide inhibitors can be administered by intravenous injection or infusion at 50-500 mg/ml (over 120 minutes); 1-500 mg/kg (over 60 minutes); or 1-100 mg/kg (bolus) five times weekly. Modulators can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, main active ingredient. The additional therapeutic compound can also be administered separately, in a separate composition, or a different dosage form from the main active ingredient. Some doses of the main ingredient can be administered at the same time as the additional therapeutic compound, while others are administered separately, depending on the particular findings of gut bacterial population and characteristics of the individual.

The dosage of a pharmaceutical composition of the invention can be adjusted throughout treatment, depending on various factors including profile of patient's gut bacterial population and physiological response to the therapeutic regimen. Those of skill in the art commonly engage in such adjustments in therapeutic regimen.

VII. Kits and Devices

The invention provides compositions and kits for practicing the methods described herein to assess the level of one or more pertinent bacterial species in a stool sample obtained from in a subject. For example, one or more gene markers indicative of the pertinent bacterial species can be analyzed for the purpose of detecting or diagnosing the presence of colon cancer, determining the risk of developing colon cancer, and monitoring the progression of colon cancer in a patient, such that the patient may have been treated, e.g., by surgery, chemotherapy, and/or radiotherapy. In the case of prophylactic treatment, a patient who has not yet developed colon cancer but has been deemed to have an increased risk of developing the disease at a later time may receive medicament comprising one or more modulator (inhibitor and/or activator) of the pertinent bacterial species.

Kits for carrying out assays for determining a specific bacterial DNA or RNA level typically include at least one oligonucleotide useful for specific hybridization with at least one segment of the target DNA or RAN sequence or its complementary sequence. Optionally, this oligonucleotide is labeled with a detectable moiety. In some cases, the kits may include at least two oligonucleotide primers that can be used in the amplification of at least one segment of the target bacterial DNA or RNA by PCR, including by RT-PCR. Table S27 of Example 1 and Table 8 of Example 2 provide some examples of such primers.

Kits for carrying out assays for determining a bacterial protein level typically include at least one antibody useful for specific binding to the protein. Optionally, this antibody is labeled with a detectable moiety. The antibody can be either a monoclonal antibody or a polyclonal antibody. In some cases, the kits may include at least two different antibodies, one for specific binding to the target bacterial protein (i.e., the primary antibody) and the other for detection of the primary antibody (i.e., the secondary antibody), which is often attached to a detectable moiety.

Typically, the kits also include an appropriate standard control. The standard controls indicate the average level of a chosen bacterial DNA, RNA, or protein as found in the stool of healthy subjects neither suffering from colon cancer nor having any increased risk of developing colon cancer. In some cases, such standard control may be provided in the form of a set value. In addition, the kits of this invention may provide instruction manuals to guide users in analyzing test samples and assessing the presence or risk of colon cancer in a test subject.

In a further aspect, the present invention can also be embodied in a device or a system comprising one or more such devices, which is capable of carrying out all or some of the method steps described herein. For instance, in some cases, the device or system performs the following steps upon receiving a stool sample, assessing the risk of developing colon cancer, or monitored for progression of the condition: (a) determining in sample the amount or level of a pertinent bacterial species (e.g., by way of measuring the amount or level of a bacterial DNA, RNA or protein indicative of the bacterial species); (b) comparing the amount/level with a standard control value; and (c) providing an output indicating whether colon cancer is likely present in the subject or whether the subject is at an increased risk of developing colon cancer in the future, or whether there is a change, i.e., worsening or improvement, in the subject's colon cancer condition, or whether the patient has an increased likelihood of recurrence colon cancer, e.g., after the initial diagnosis and/or treatment. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Example 1: *Parvimonas micra* and *Solobacterium moorei* as Fecal Markers for CRC The objective of this study is to evaluate the potential for diagnosing colorectal cancer (CRC) from fecal metagenomes. The present inventors performed metagenome-wide association studies on fecal samples from 74 patients with CRC and 54 controls from China, and validated the results in 16 patients and 24 controls from Denmark. The biomarkers were further validated in two published cohorts from France and Austria. Finally, targeted quantitative PCR (qPCR) assays were employed to evaluate diagnostic potential of selected biomarkers in an independent Chinese cohort of 47 patients and 109 controls. Besides confirming known associations of *Fusobacterium nucleatum* and *Peptostreptococcus stomatis* with CRC, the inventors found significant associations with several species, including *Parvimonas micra* and *Solobacterium moorei*. 20 microbial gene markers were identified that differentiated CRC and control microbiomes, and 4 markers were validated in the Danish cohort. In the French and Austrian cohorts, these four genes distinguished CRC metagenomes from controls with areas under the receiver-operating curve (AUC) of 0.72 and 0.77, respectively. qPCR measurements of two of these genes accurately classified patients with CRC in the independent Chinese cohort with AUC=0.84 and OR of 23. These genes were enriched in early-stage (I-II) patient microbiomes, highlighting the potential for using fecal metagenomic biomarkers for early diagnosis of CRC. The inventors present the first metagenomic profiling study of CRC fecal microbiomes to discover and validate microbial biomarkers in ethnically different cohorts, and to independently validate selected biomarkers using an affordable clinically relevant technology. This study thus provides important indications for developing affordable, reliable, non-invasive early diagnostic biomarkers for CRC from fecal samples.

Introduction

Colorectal cancer (CRC), the third most common cancer in the world affecting greater than 1.36 million people every year,[1] arises due to complex interactions between genetic, lifestyle and environmental factors. Despite massive efforts in whole-genome sequencing and genome-wide association studies, genetic factors only explain a small proportion of disease variance-heritability may account for up to 35% all CRCs,[3] but only about 5% of cancers occur in the setting of a known genetic predisposition syndrome.[4] These findings support lifestyle and environment as additional major disease determinants.

Emerging evidence indicates that microbial dysbiosis in the human gut may be an important environmental factor in CRC. Early evidence for gut microbial contribution to CRC pathogenesis came from Apc$^{min/+}$ mice, a genetic mouse model of CRC, where mice housed in germ-free conditions showed a reduction of tumor formation in the intestine compared with mice housed in specific pathogen-free conditions.[5] Further studies have suggested that several bacteria, including *Bacteroides fragilis* and a strain of *Escherichia coli*, may promote colorectal carcinogenesis.[6-11] In humans, bacterial culture-based studies have reported associations between CRC and clinical infections by specific bacteria such as *Streptococcus bovis*[12] and *Clostridium septicum*.[13] Additionally, culture-free 16S ribosomal RNA sequencing studies have associated fecal microbial composition with CRC.[14-16] Independent studies have identified *Fusobacterium nucleatum* to be more abundant in human CRC tissues,[17,18] and follow-up studies showed that *F. nucleatum* potentiates intestinal tumorigenesis through recruitment of infiltrating immune cells[19] and by modulating β-catenin signalling.[20] Two recent studies investigated gut microbial dysbiosis in patients with CRC[21,22] and reported diagnostic potential using metagenomics sequencing. These promising results are still far from directly translating to diagnostic tests for CRC, as simple and affordable targeted approaches to diagnosing CRC from fecal samples are yet to be developed.

This is the first study that (i) uses deep metagenomics profiling of CRC fecal microbiomes to discover and validate microbial gene biomarkers in ethnically different cohorts, and (ii) independently validates them using an affordable technology that can translate to clinical practice.

Materials and Methods

Sample Collection and DNA Preparation

Cohorts C1 and C2 were from Hong Kong, China. C1 (see Table 51) comprised 128 individuals: 74 patients with CRC (15 stage I, 21 stage II, 34 stage III and 4 stage IV; median age 67 years; 26 were females) and 54 controls (median age 62 years; 21 were females). C2 (see Table S16) comprised 156 individuals: 47 patients with CRC (4 stage I, 24 stage II, 15 stage III and 4 stage IV; median age 69 years; 22 were females) and 109 controls (median age 58 years; 69 were females). Cohort D from Copenhagen, Denmark (see Table S18), comprised 40 individuals: patients with CRC (n=16; 1 stage I, 9 stage II, 5 stage III and 1 stage IV; median age 67.5 years; 6 were females) and controls (n=24; median age 65.5 years; 17 were females). Cancer staging in all three cohorts was performed using the tumour, node, metastasis staging system[23] maintained by the American Joint Committee on Cancer and the International Union for Cancer Control. Stool samples were collected by individuals at home, followed by immediate freezing at −20° C. DNA from Chinese samples was extracted using Qiagen QIAamp DNA Stool Mini Kit (Qiagen) according to manufacturer's instructions. DNA from Danish samples was extracted using previously published method.[24] For comprehensive description of sample collection and DNA extraction as well as ethical committee approval numbers, see methods for Example 1.

Metagenomic Sequencing and Annotation

Metagenomic sequencing using Illumina HiSeq 2000 platform, generating gene profiles using gene catalogue, constructing metagenomic linkage groups (MLGs), generating Kyoto Encyclopedia of Genes and Genomes (KEGG) ortholog, module and pathway profiles, were all done using previously published methods.[25] Species-level molecular operational taxonomic units (mOTUs) were obtained using mOTU profiling software.[26] Reads were mapped to the Integrated Microbial Genome (IMG) reference database27 (v400) to generate IMG species and IMG genus profiles. Genes of MLGs were mapped to the IMG database, and MLGs were annotated to an IMG genome when >50% of genes were mapped. MLG species were constructed by grouping MLGs using this annotation. For comprehensive description of these procedures, see methods for Example 1.

Data Analysis

Permutational multivariate analysis of variance (PERMANOVA) was used to assess effects of different phenotypes on gene profiles. Enrichments of genes, KEGG features, mOTUs, IMG species and MLG species were calculated using Wilcoxon rank-sum tests. When appropriate, adjustment was made for confounding effects of sample collection before/after colonoscopy: Wilcoxon rank-sum tests were performed using 'colonoscopy before/after sampling' as a stratifying factor using COIN package in R, and ORs were estimated using Mantel-Haenszel test after stratifying by 'colonoscopy before/after sampling'. The inventors controlled for multiple testing with Benjamini-Hochberg false discovery rate (FDR). Minimum-redundancy maximum-relevancy (mRMR) feature selection method[28] was used to select optimal gene markers, which were then used in constructing a CRC index. Co-occurrence networks were constructed using Spearman's correlation coefficient (>0.5 or <−0.5) and visualized in Cytoscape V.3.0.2. Metagenomic sequences from French (F) and Austrian (A) cohorts were downloaded from NCBI Short Read Archive using study identifiers ERP005534 and ERP008729, respectively. For comprehensive description of biodiversity analysis, rarefaction analysis, identification of CRC-associated genes/species, estimation of FDR, mRMR feature selection framework, definition and validation of CRC index, and receiver operator characteristic (ROC) analysis, see methods for Example 1.

Validation of Gene Markers by qPCR

Abundances of selected gene markers were estimated in stool samples using TaqMan probe-based quantitative PCR (qPCR). Primer and probe sequences were designed manually and then tested using Primer Express V.3.0 (Applied Biosystems, Foster City, Calif., USA) for determination of Tm, guanine-cytosine (GC) content and possible secondary structures. Each probe carried a 50 reporter dye 6-carboxy fluorescein or 4,7,20-trichloro-70-phenyl-6-carboxyfluorescein and a 30 quencher dye 6-carboxytetramethylrhodamine. Primers and hydrolysis probes were synthesized by Invitrogen (Carlsbad, Calif., USA). Nucleotide sequences of primers and probes are listed in Table S27. qPCR was performed on an ABI7500 Real-Time PCR System using TaqMan Universal PCR Master Mix reagent (Applied Biosystems). Universal 16S rDNA was used as internal control and abundance of gene markers were expressed as relative levels to 16S rDNA.

Results

Figure 9A:
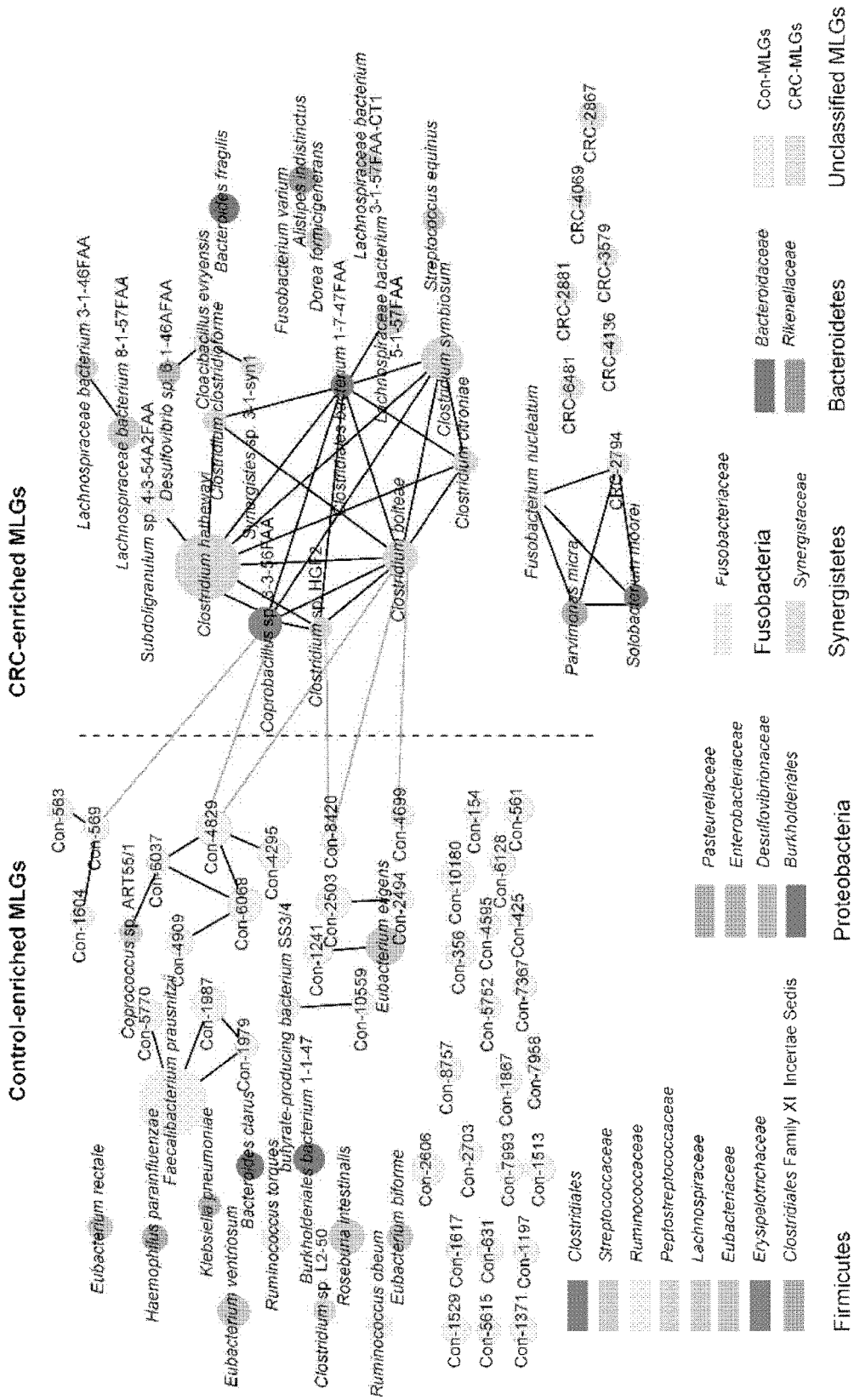
FIG. 9A: Rarefaction curves showing cumulative number of genes sequenced with increasing sample size. The numbers are close to saturation given the current sample sizes for all 128 samples. Inset: colorectal cancer samples have significantly lower gene counts compared to healthy controls. Only the first three points corresponding to sizes of up to 3 samples each are not significant (NS).
Figure 9B:
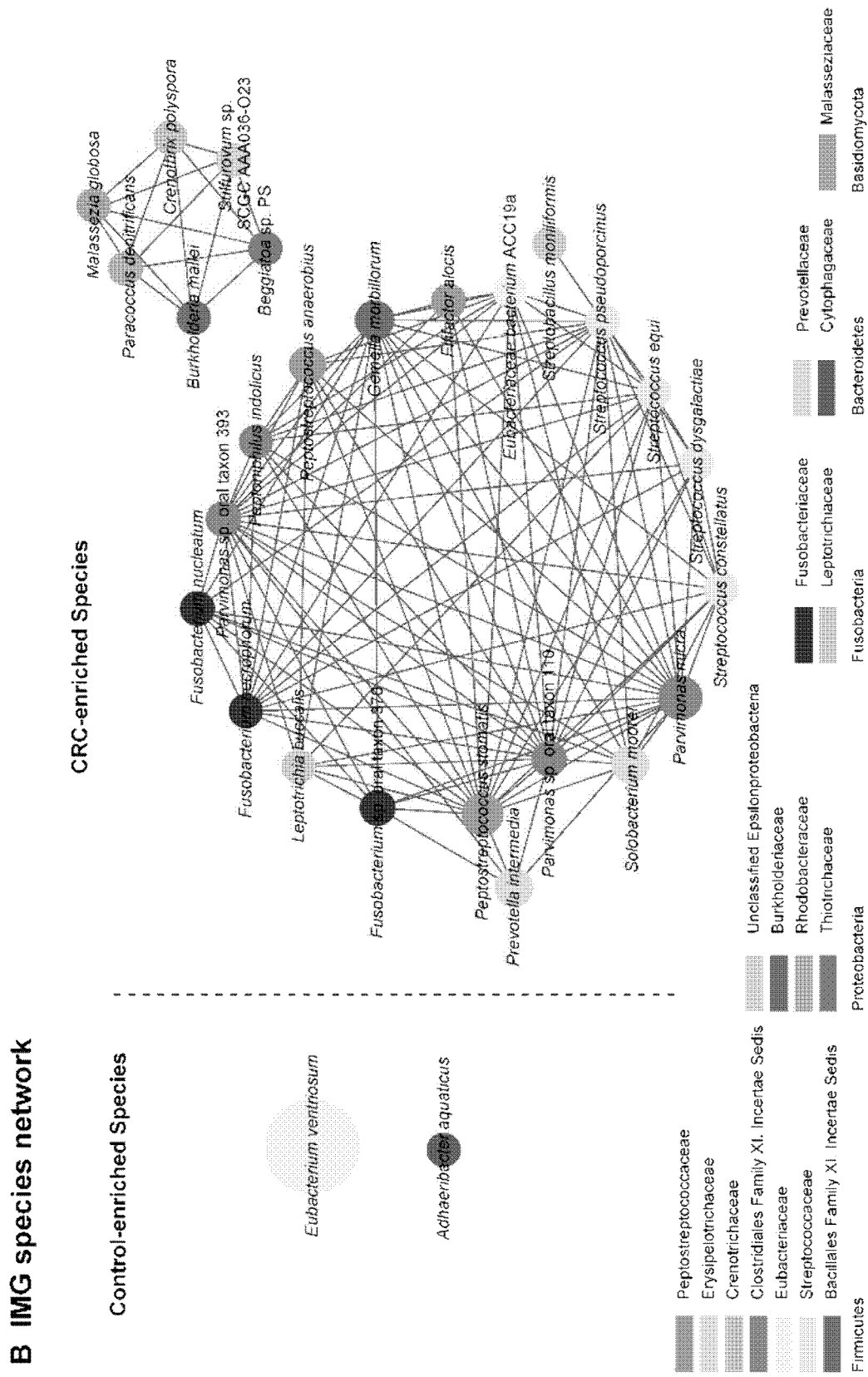
FIG. 9B: Gene count distribution of 128 CRC case and healthy control individuals. The grey line shown corresponds to 400,000 genes, below which 80% individuals had cancer.

Dysbiosis in CRC Gut Microbiome 128 individuals (74 patients with CRC and 54 control subjects) were recruited from China (cohort C1; see Table 51), metagenomic sequencing was performed on their stool samples and generated 751 million metagenomic reads (5.86 million reads per individual on average; see Table S2) using Illumina HiSeq 2000 platform. Among the recorded metabolic parameters, elevated fasting blood glucose and reduced high-density lipoproteins showed significant associations with CRC status (Wilcoxon rank-sum test, q=0.0014 for both) agreeing with previous findings reporting them as risk factors.[29] [30] It was also observed that a significantly higher number of CRC patient samples were collected after colonoscopy than before (Fisher's exact test, q=0.0165; see Table 51). this was adjusted for as a confounding factor in subsequent analyses when appropriate (see section 'Materials and methods'). Rarefaction analysis using a previously published gut microbial gene catalogue consisting of 4 267 985 genes[25] showed a curve reaching plateau, suggesting that this catalogue covers most prevalent microbial genes present in cohort C1 (see FIG. 9A). Therefore, subsequent analyses were based on mapping the metagenomic reads to this catalogue. CRC patient microbiomes exhibited reduced gene richness (see FIG. 9A, B; Wilcoxon rank-sum test, p<0.01) and gene alpha diversity (Wilcoxon rank-sum tests on Shannon and Simpson indices: p=0.075 and 0.028, respectively; see FIG. 9C,D and table S3). However, these differences exhibited p>0.5 after correcting for colonoscopy.

Figure 10A:
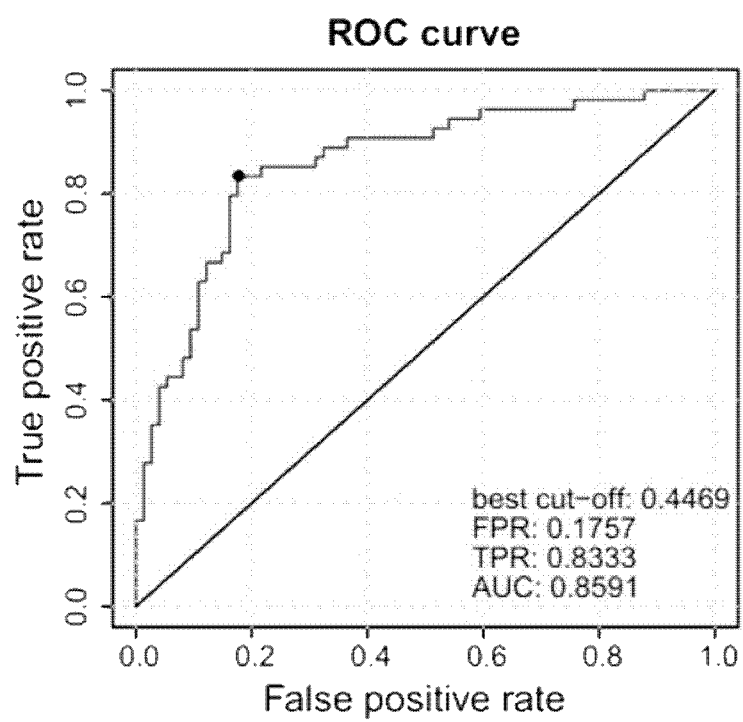
FIG. 10A-FIG. 10C: Principle component analysis using 2,110,489 genes identified in cohort C1.
Figure 10B:
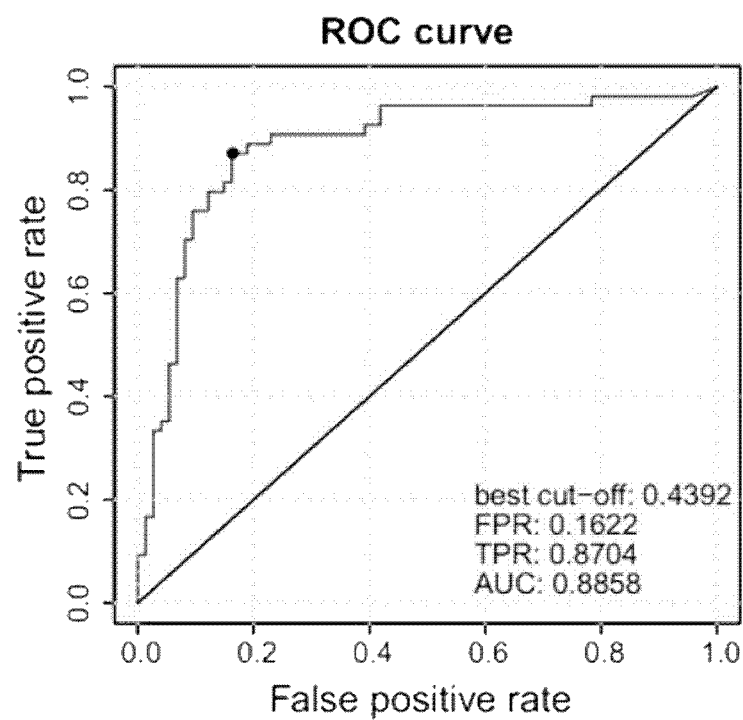
Figure 10C:
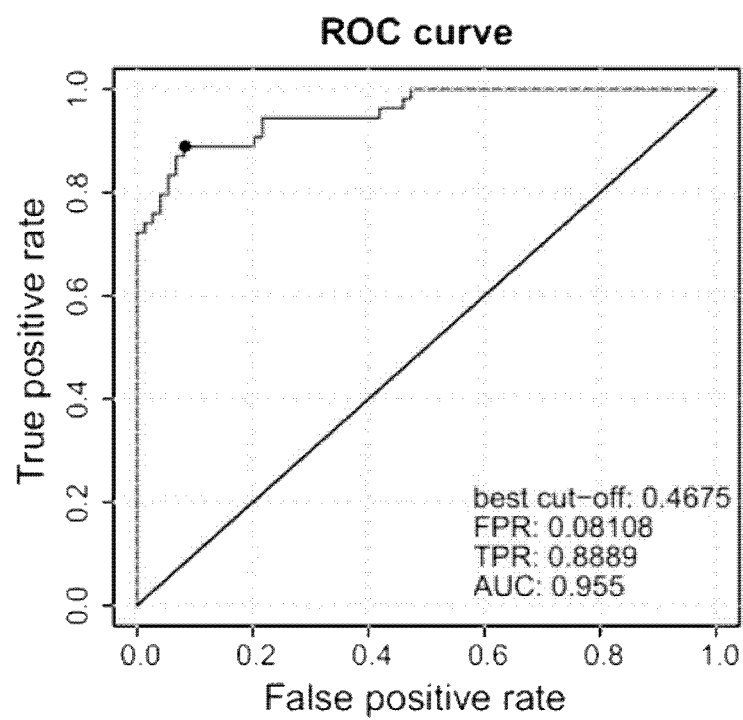

To ensure robust comparison of gene content among 128 metagenomes from cohort C1, a set of 2 110 489 genes was created that were present in at least 6 subjects and generated 128 gene abundance profiles using these 2.1 million genes. When multivariate analysis was performed using PERMANOVA on 17 different covariates, only CRC status and CRC stage were significantly associated with these gene profiles (q<0.06, all other factors: q>0.27; see Table S4). Thus, the data suggest an altered gene composition in CRC patient microbiomes that cannot be explained by other recorded factors. When a principal component analysis (PCA) was performed based on gene profiles, the first and fifth principal components, which explained 6.6% and 3.2% of total variance, respectively, were associated with CRC status (Wilcoxon rank-sum test, PC1: p=0.029; PC5: p=1× 10-6; see FIG. 10 and table S5). Together, these results indicate a state of dysbiosis of the gut microbiome in patients with CRC.

Gut Microbial Genes Associated with CRC

A metagenome-wide association study (MGWAS) was performed to identify genes contributing to the altered gene composition in CRC. From 2.1 million genes, 140 455 genes were identified as being associated with disease status (Wilcoxon rank-sum test p<0.01 and FDR 11.03%; see FIG. 11). Interestingly, CRC-enriched genes occurred less frequently and at lower abundance compared with control-enriched genes (see FIG. 12), indicating that microbial dysbiosis associated with CRC may not involve dominant species. Such patterns of frequency and occurrence have been observed in two earlier metagenomic case-control studies on type 2 diabetes[25] in Chinese individuals and CRC in Austrian individuals,[31] indicating that this may be a common trend in disease-associated gut microbial dysbiosis.

The 140 455 genes were annotated using KEGG32 functional database (V.59) to investigate whether certain microbial functions were associated with CRC. None of the KEGG pathways passed the stringent criteria (Wilcoxon rank-sum test, q<0.05; see Table S6), suggesting that bacterial metabolic pathways present in KEGG database may not be involved in CRC pathogenesis. However, two KEGG modules were enriched in CRC microbiomes: leucine degradation (q=0.0148) and guanine nucleotide biosynthesis (q=0.0241; see Table S6). Leucine stimulates both protein synthesis and degradation,[33] [34] suggesting possible links between leucine metabolism and cancer. At the gene level, several KEGG orthologous groups showed significant associations with disease status (Wilcoxon rank-sum test, q<0.05; see Table S7).

Taxonomic Alterations in CRC Gut Microbiomes

Figure 1A:
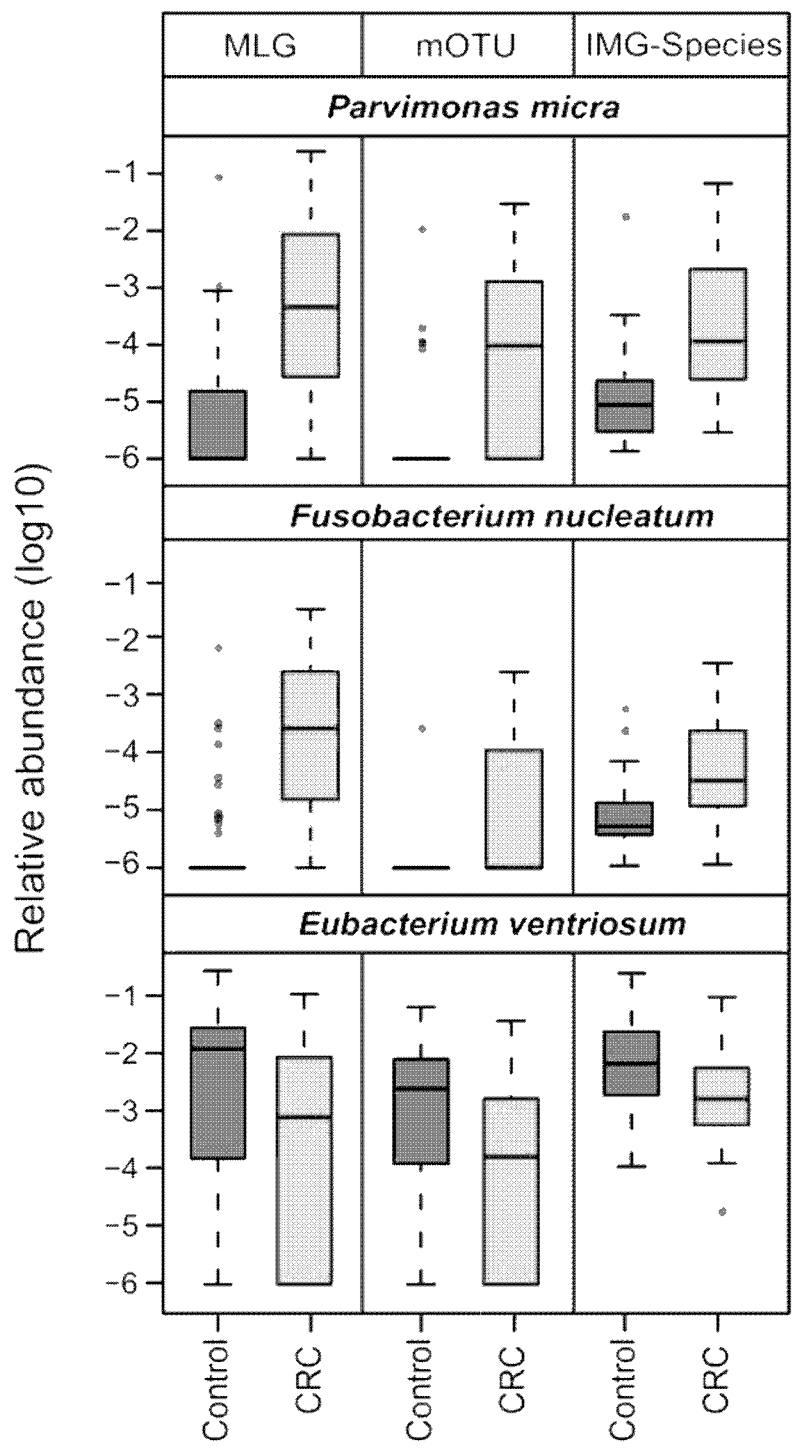
FIG. 1A: Differential relative abundance of two CRC-enriched and one control-enriched microbial species consistently identified using three different methods: metagenomic linkage group (MLG), molecular operational taxonomic unit (mOTU) and Integrated Microbial Genome (IMG) database.

Taxonomic differences between CRC-associated and control microbiomes were examined to identify microbial taxa contributing to the dysbiosis. For this, species profiles derived from three different methods—IMG species, species-level mOTUs and MLG species (see section 'Materials and methods')—were used as supporting evidence from multiple methods would strengthen an association. The analysis identified 28 IMG species, 21 mOTUs and 85 MLG species that were significantly associated with CRC status after adjusting for colonoscopy as a confounding factor (Wilcoxon rank-sum test, q<0.05; see Table S8). *Eubacterium ventriosum* was consistently enriched in control microbiomes across all three methods (IMG: q=0.002; mOTU: q=0.0049; MLG: q=3.33×10-4). On the other hand, *Parvimonas micra* (q<7.73×10-6), *Solobacterium moorei* (q<0.011) and *F. nucleatum* (q<0.00279) were consistently enriched in CRC patient microbiomes across all three methods (FIG. 1A and FIG. 13), while *Peptostreptococcus stomatis* (q<7.73×10-6) was enriched according to two methods. PERMANOVA analysis showed that only CRC status (p<0.013 from all three methods) and colonoscopy (p=0.079 from two methods) explained the quantitative variation in the three CRC-enriched species. All other non-CRC-specific factors could not explain the variation with statistical significance (p>0.18; see Table S9). *P. stomatis* has recently been shown to significantly associate with CRC,[22] and *S. moorei* has previously been associated with bacteraemia.[35] However, a highly significant enrichment of *P. micra*—an obligate anaerobic bacterium that can cause oral infections like *F. nucleatum*[36]—in CRC-associated microbiomes is a novel finding.

Figure 1B:
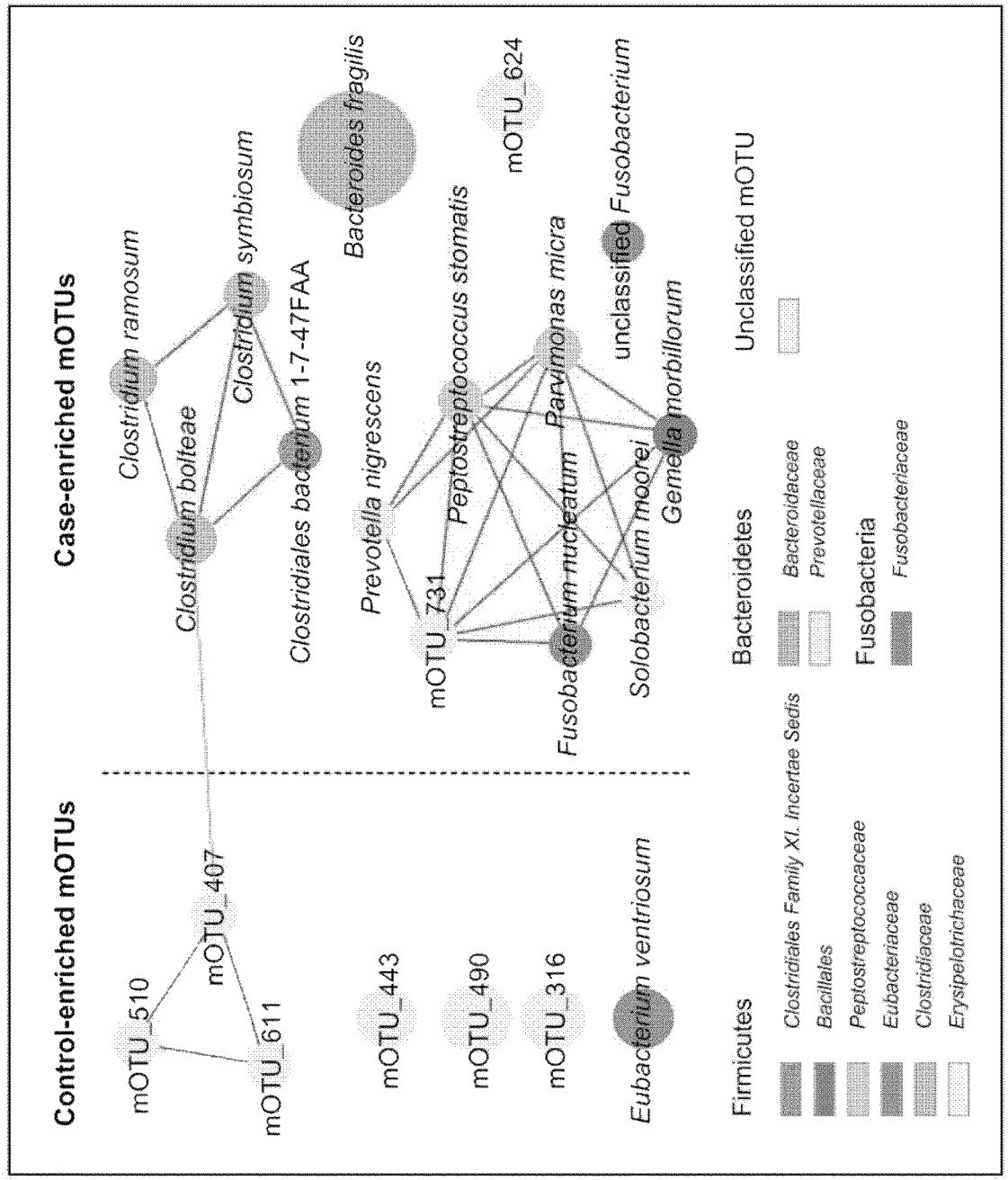
FIG. 1B: A co-occurrence network deduced from relative abundance of 21 mOTUs significantly associated with CRC. Species are rearranged in two sides based on their enrichment in CRC or control microbiomes. Spearman correlation coefficient values below −0.5 (negative correlation) are indicated as light grey edges, and coefficient values above 0.5 (positive correlation) are indicated as dark grey edges. Node size shows the average relative abundance for each species, and node color shows their taxonomic annotation.

Species co-occurrence networks derived from pairwise correlations of species abundances showed a strong positive association between three oral pathogens: *P. micra, F. nucleatum* and *S. moorei* (FIG. 1B and FIG. 14). Previous reports suggest that *P. micra* commonly occurs together with *F. nucleatum* in infected root canals, where they could account for up to 90% of the endodontic microbiome.[36] Given this, these results indicate cooperation between these two species in CRC-associated gut environment.

Although several bacterial genera corresponding to the CRC-associated species identified earlier (including *Parvimonas, Fusobacterium, Solobacterium* and *Peptostreptococcus*) showed significant associations with CRC status (see Table S10), some exceptions were observed as well. While a significant over-representation of *B. fragilis* in patients with CRC (mOTU: q=0.0158; MLG: q=3.02×10-4; see Table S8) was identified, there was no association with *Bacteroides* genus. At the phylum level, only Fusobacteria and *Basidiomycota* were significantly enriched in CRC-associated microbiomes (q<0.0002; see Table S11). In order to evaluate the predictive power of these taxonomic associations, random forest ensemble learning method[37] was used to identify 17 IMG species, 7 species-level mOTUs and 27 MLG species that were highly predictive of CRC status (see Table S12), with predictive power of 0.86, 0.89 and 0.96 in ROC analysis, respectively (see FIG. 15). *P. micra* was identified as a key species from all three methods, while *F. nucleatum, P. stomatis* and *S. moorei* were identified from two out of three methods, providing further statistical support for their association with CRC status.

CRC Biomarker Discovery

Figure 2A:
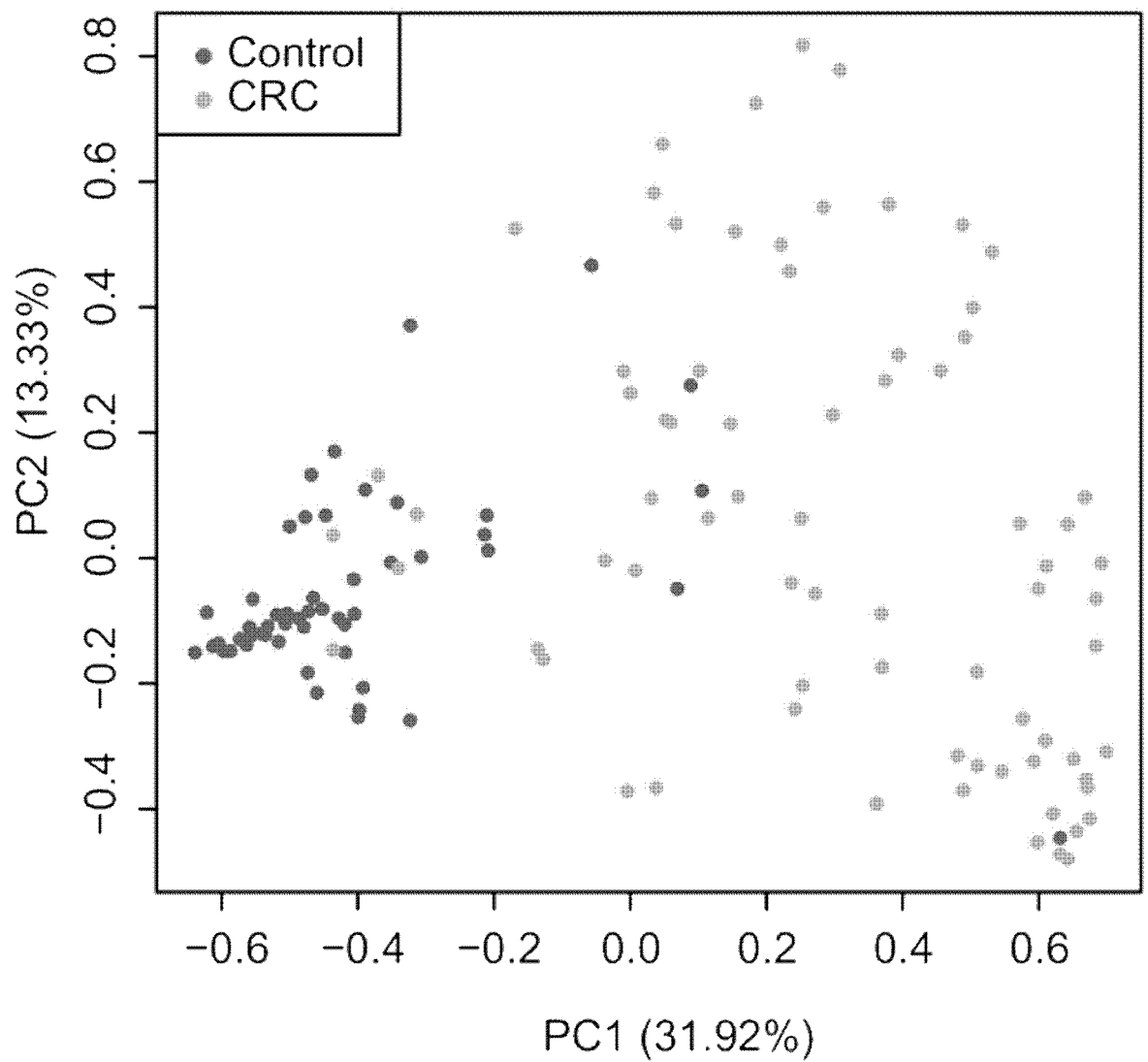
FIG. 2A: Principal component analysis based on abundances of 20 gene markers separates CRC cases and control individuals in cohort C1. First and second principal components associate with CRC status (PC1 and PC2 explain 31.9% and 13.3% of variance, respectively). Compare this with FIG. 10 based on 2.1 million genes, where no separation can be observed.
Figure 2B:
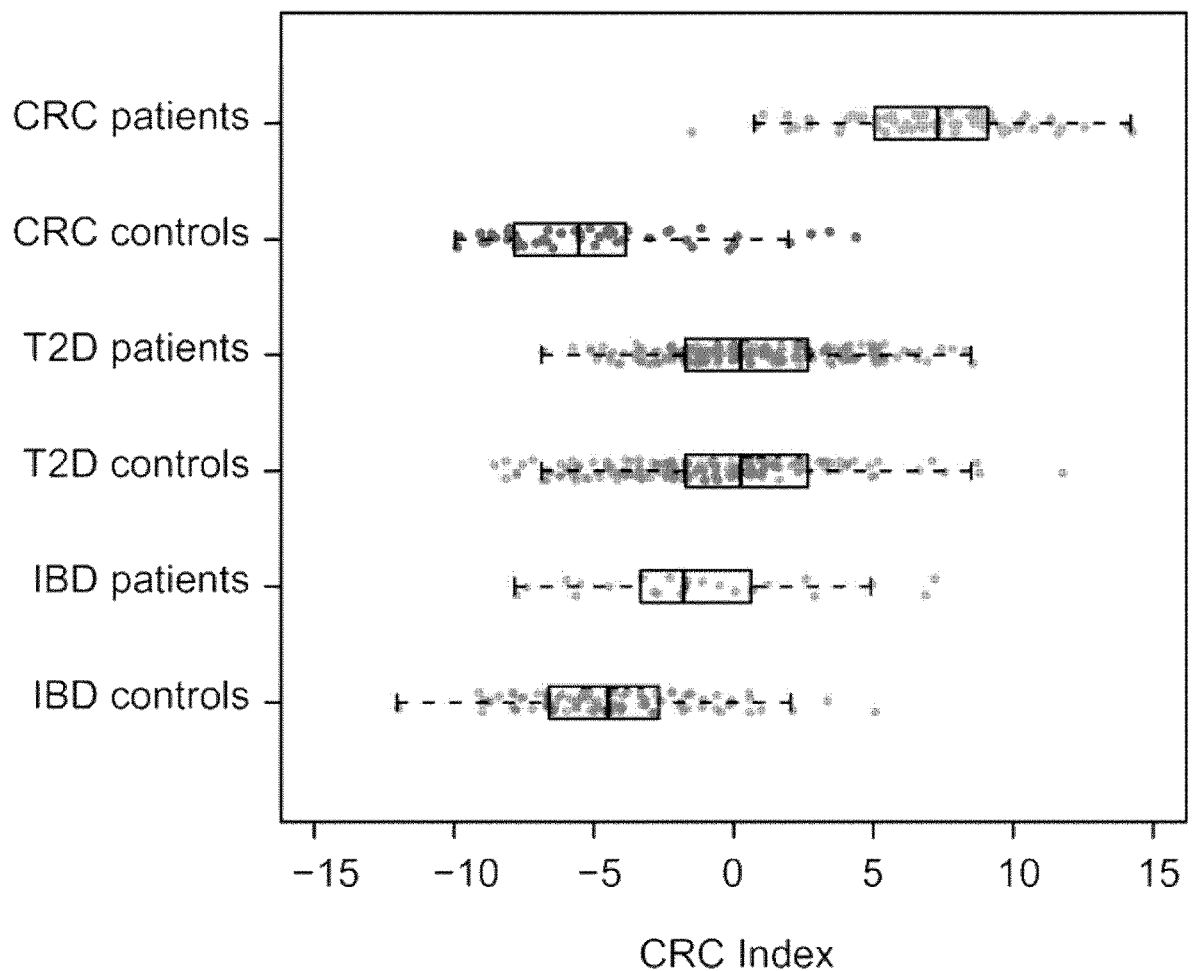
FIG. 2B: CRC index computed using a simple unweighed linear combination of log-abundance of 20 gene markers for patients with CRC and control individuals from this study, shown together with patients and control individuals from earlier studies on type 2 diabetes[25] and IBD.[38] CRC indices for CRC patient microbiomes are significantly different from the rest (p<0.001), indicating that the 20 gene markers are CRC-specific. The box depicts the IQRs between the first and third quartiles, and the line inside denotes the median.

The mRMR feature selection method[28] was used to identify potential CRC biomarkers from the 140 455 genes identified by MGWAS. First, to eliminate confounding effects of colonoscopy, blocked independent Wilcoxon rank-sum tests were performed on these genes with colonoscopy as a stratifying factor. This resulted in 102 514 genes at a significance level of p<0.01 (FDR≤13%) and 24 960 genes at a significance level of p<0.001 (FDR≤5.23%). Then, from the latter, groups of genes were identified that were highly correlated with each other (Kendall's τ>0.9) and chose the longest gene in each group to generate a statistically non-redundant set of 11 128 significant genes. Finally, mRMR method was used and an optimal set of 20 genes were identified that were strongly associated with CRC status (see FIG. 16 and table S13). PCA using these 20 genes showed good separation of patients with CRC from controls (FIG. 2A). PERMANOVA analysis showed that only CRC status, stage and fasting blood glucose explained the variation in the 20 marker gene abundances with statistical significance (p≤0.01; see Table S14). A simple CRC index was computed based on unweighed log relative abundance of these 20 markers, which clearly separated CRC patient microbiomes from control microbiomes, as well as from 490 fecal microbiomes from two previous studies on type 2 diabetes in Chinese individuals[25] and IBD in European individuals' (FIG. 2B; median CRC index for patients and controls in this study were 7.31 and −5.56, respectively; Wilcoxon rank-sum test, q<6×10-11 for all five comparisons; see Table S15).

Evaluating CRC Biomarkers Using Targeted qPCR

Translating these gene markers into diagnostic biomarkers would require reliable measurement by simple, affordable and targeted methods such as qPCR. To verify whether gene abundances measured by metagenomics sequencing and qPCR are comparable, two case-enriched and two control-enriched gene markers were randomly selected and their abundances were measured by qPCR in a subset of cohort C1 (51 cases and 45 controls). Quantification by metagenomic sequencing and qPCR platforms showed strong correlations (Spearman r=0.81-0.95; see FIG. 17), indicating that both measurements are reliable. Next, the abundance of these four gene markers was measured using qPCR in an independent Chinese cohort C2 (156 fecal samples; 47 cases and 109 controls; see Table S16). The two control-enriched genes did not show significant associations in C2 (p>0.31; see Table S17). On the other hand, CRC-enriched gene markers (m1704941, butyryl-CoA dehydrogenase from *F. nucleatum*; m482585, RNA-directed DNA polymerase from an unknown microbe) were also significantly enriched in CRC samples of C2 after adjusting for colonoscopy (p=0.0015 and 0.045, respectively, see Table S17). Among these, only the gene from *F. nucleatum* exhibited a significant OR after a Mantel-Haenszel test adjusted for colonoscopy (OR 18.5, p=0.0051; see Table S17). CRC index based on abundances of the four genes only moderately classified CRC microbiomes from control microbiomes in C2 (areas under the receiver-operating curve (AUC)=0.73; see FIG. 18), suggesting that choosing randomly from the list of 20 biomarkers was not an effective strategy. Nevertheless, the gene from *F. nucleatum* was present only in 4 out of 109 control microbiomes, suggesting a potential for developing specific diagnostic tests for CRC using fecal samples.

Gene Marker Validation in Independent Metagenomic Cohorts

To identify robust biomarkers that can have a more general applicability, all 20 gene markers were evaluated using fecal metagenomes from a cohort with different genetic background and lifestyle: 16 patients with CRC and 24 control individuals from Denmark (cohort D; see Table S18). When mapped to 4.3 million gut microbial genes, Danish metagenomes exhibited significantly higher gene richness and gene alpha diversity, both in cases (Wilcoxon rank-sum tests, gene count: p=1.94×10-5; Shannon's index: p=5.85×10-5) and controls (gene count: p=0.0017; Shannon's index: p=9.34×10-4; see FIG. 19 and table S19), agreeing with a recent study and suggesting differences in gut microbial community structure between Chinese and Danish populations.[39] Among the 102 514 genes associated with CRC status in cohort C1, only 1498 genes could be validated in cohort D. However, CRC-enriched genes were shared significantly more between the two populations than control-enriched genes (1452 out of 35 735 CRC-enriched vs 46 out of 66 779 in control-enriched; two-tailed χ2 test, χ2=2576.57, p<0.0001). Over half (53.6%) of the 1452 CRC-enriched genes were from just three species: *P. micra* (389 genes), *S. moorei* (204 genes) and *Clostridium symbiosum* (177 genes) (see Table S20). At the species level, *P. micra* was enriched in CRC microbiomes using all three methods, while *P. stomatis, Gemella morbillorum* and *S. moorei* were enriched according to two methods (Wilcoxon rank-sum test, q<0.05; see Table S21). Notably, all species that were validated by at least one method were CRC-enriched. These results indicate that changes in colorectal environment during CRC development and progression may facilitate growth of similar species across the two populations, potentially leading to the reduced microbial diversity observed in patients with CRC (see FIG. 9C), in line with earlier observations by others.[40] CRC index using 20 gene markers discovered in cohort C1 marginally differentiated Danish patient microbiomes from controls (Wilcoxon rank-sum test, p=0.029) and exhibited moderate classification potential (area under ROC curve, AUC=0.71; see FIG. 20). Only 4 out of 20 genes (two from *Peptostreptococcus anaerobius* and one each from *P. micra* and *F. nucleatum*) were associated with CRC status in cohort D (Wilcoxon rank-sum test, q≤0.05; all CRC-enriched; see Table S22). Among the factors recorded, only CRC status could explain the variation in these four genes (PERMANOVA p≤0.0001; see Table S23).

For additional unbiased validation of the four gene markers, two recently published metagenomic datasets were used—an Austrian population (cohort A) consisting of 55 controls and 41 patients with CRC[31] and a French population (cohort F) consisting of 61 controls and 53 patients with CRC.[22] As our discovery cohort C1 only included carcinoma samples, all patients with adenoma were excluded, and carcinoma patients were compared with non-adenoma/non-carcinoma controls, contrary to the strategy used by the latter study[22] that included small adenomas in controls and excluded large adenomas. All four genes were significantly enriched in carcinoma fecal samples from both cohorts (Wilcoxon rank-sum test q<0.0035; see Table S24). CRC index using these four genes classified patients with CRC with AUC of 0.77 and 0.72 for cohorts A and F, respectively. When association of all 20 markers was checked, cohorts A and F each could validate an additional gene associated with CRC (see Table S25). Interestingly, one marker enriched in control samples in cohort C1 was enriched in CRC samples in cohort A.

Accurate Classification of CRC Using qPCR

Figure 3A:
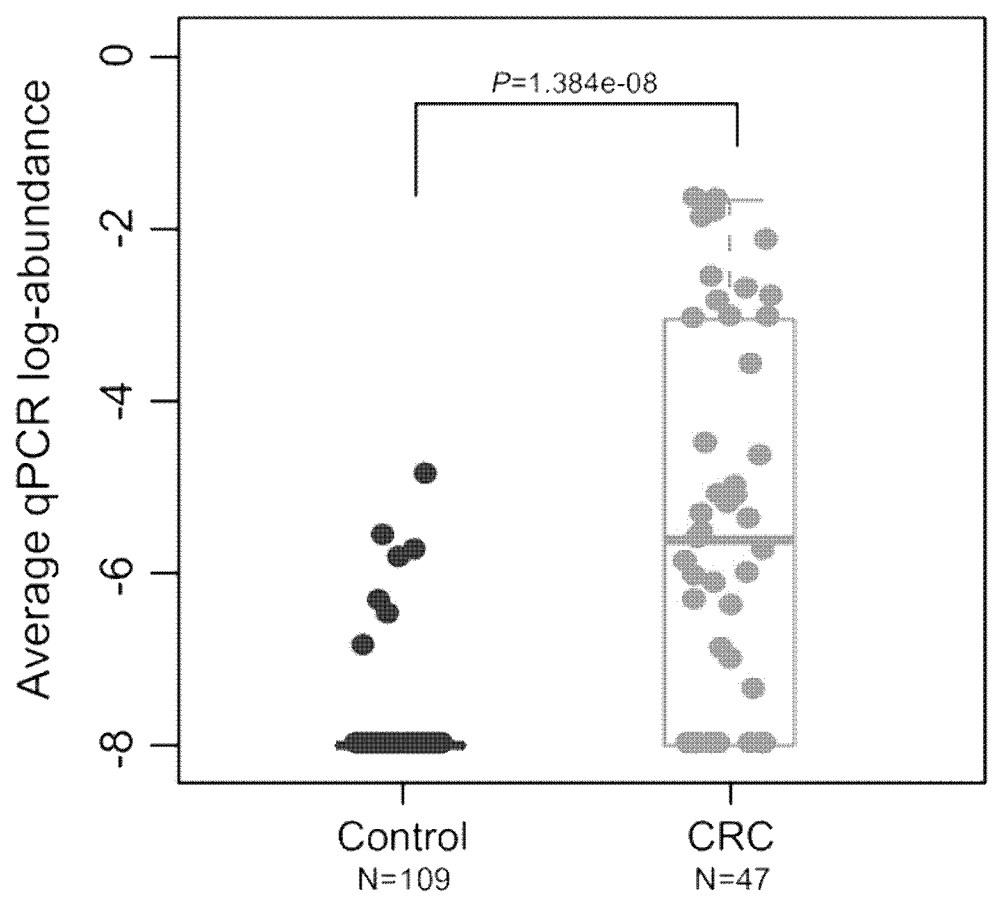
FIG. 3A: Validating robust gene markers associated with colorectal cancer (CRC). Quantitative PCR (qPCR) abundance of two gene markers (m1704941: butyryl-CoA dehydrogenase from *Fusobacterium nucleatum, m*1696299: RNA polymerase subunit (3, rpoB, from *Parvimonas micra*) were measured in cohort C2 consisting of 47 cases and 109 healthy controls. Combined log-abundance of the two genes clearly separates CRC microbiomes from controls.
Figure 3B:
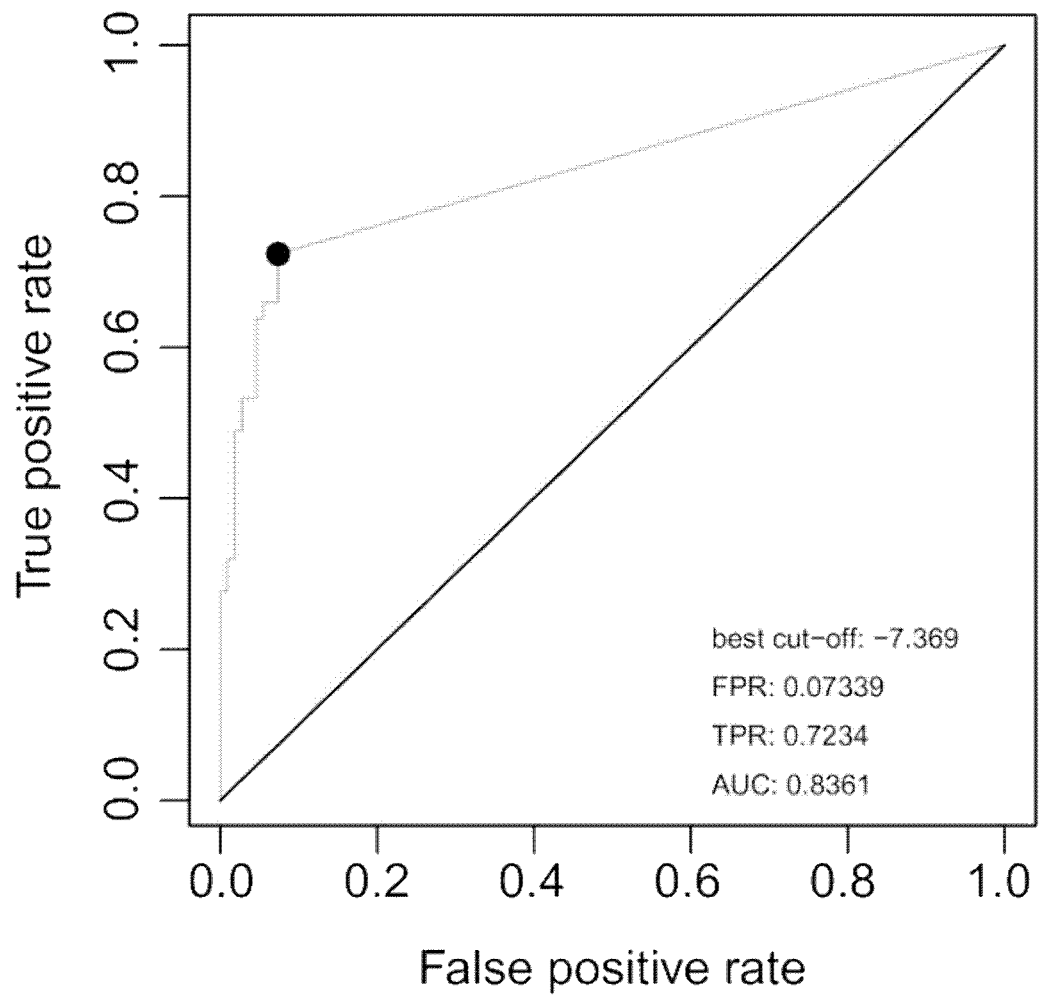
FIG. 3B: combined log-abundance of the two genes classifies CRC microbiomes with an area under the receiver operating characteristic curve of 0.84.
Figure 3C:
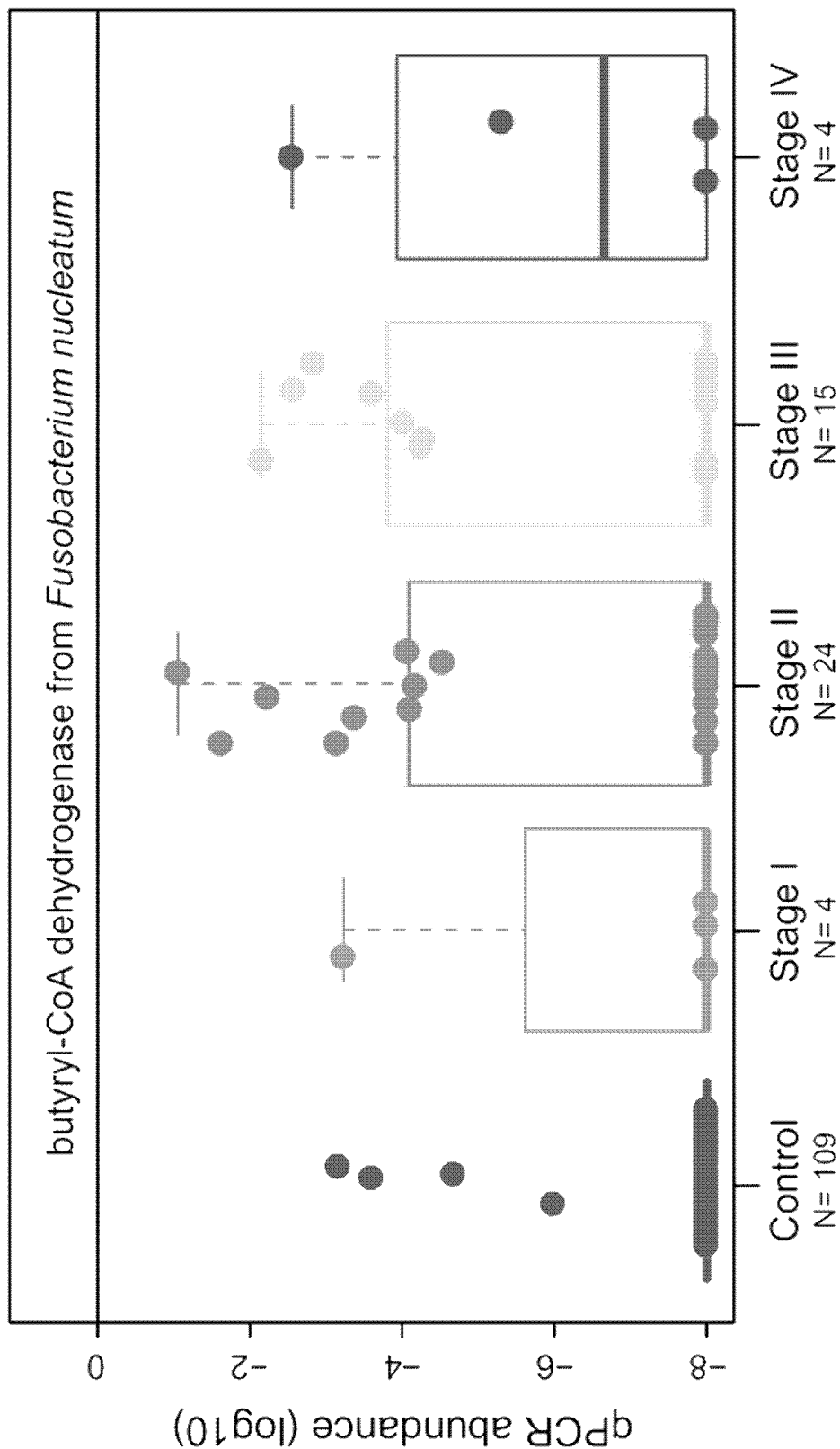
FIG. 3C and FIG. 3D: the two marker genes show relatively higher incidence and abundance in CRC stages II and III compared with control and stage I microbiomes. Abundances are plotted in log 10 scale, and zero abundance is plotted as −8. AUC, areas under the receiver-operating curve; FPR, false-positive rate; TPR, true-positive rate.
Figure 3D:
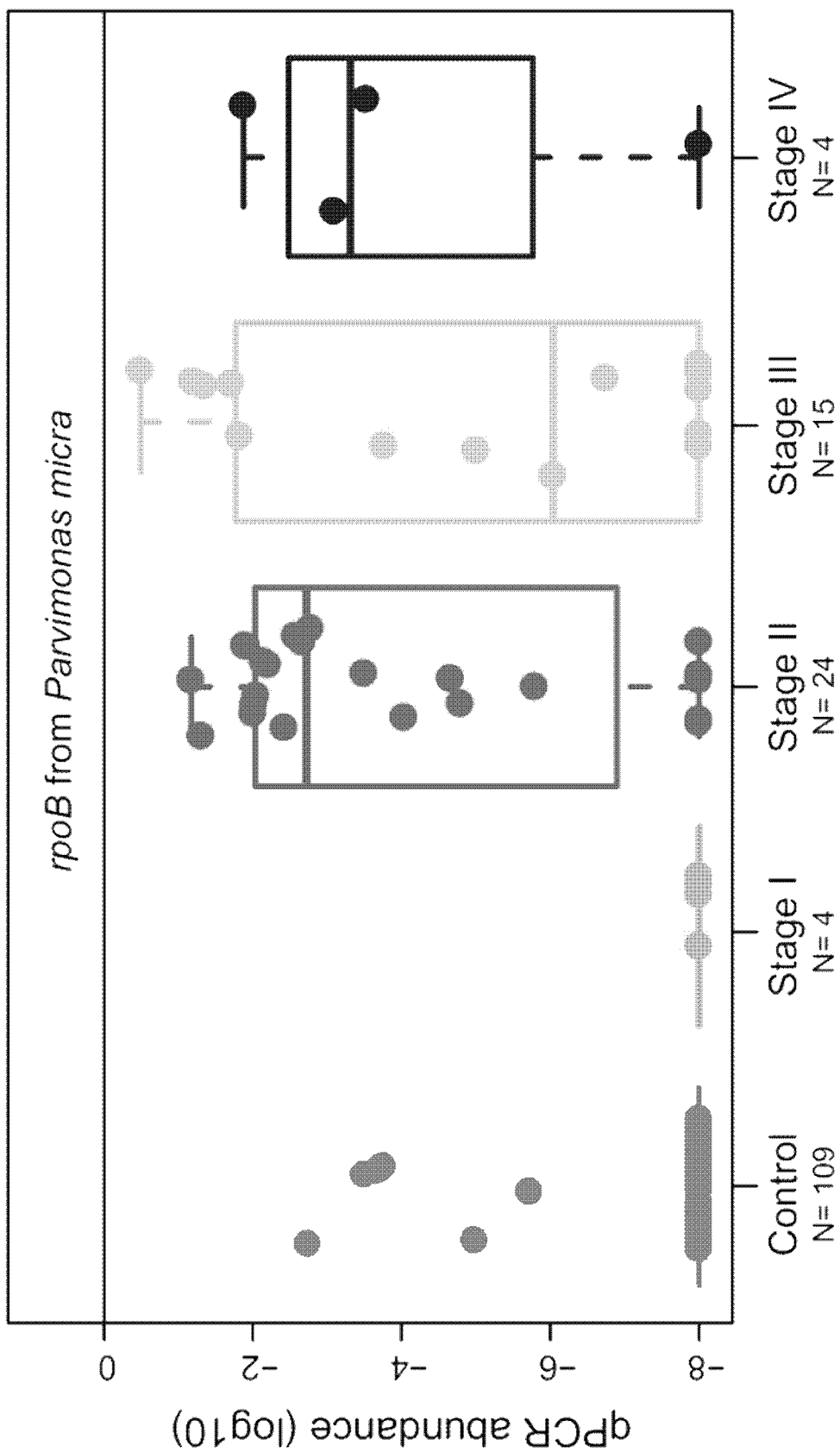

Two of the four cross-ethnically validated gene markers were transposases from *P. anaerobius*. The third gene (m1704941, butyryl-CoA dehydrogenase from *F. nucleatum*) was incidentally among the two genes successfully validated using qPCR in cohort C2. The fourth gene from *P. micra* was the highly conserved rpoB gene encoding RNA polymerase subunit β, often used as a phylogenetic marker.[41] additional qPCR measurements of rpoB from *P. micra* were performed in cohort C2, which showed a significant enrichment in CRC patient microbiomes (Wilcoxon rank-sum test adjusted for colonoscopy, p=8.97×10-8). Mantel-Haenszel O R adjusted for colonoscopy was 20.17 (95% CI 4.59 to 88.6, p=3.36×10-7). Combined qPCR measurements of the two genes clearly separated CRC from control samples in cohort C2 (Wilcoxon rank-sum test adjusted for colonoscopy, p=1.384×10-8, FIG. 3A) and accurately classified CRC samples with an improved AUC of 0.84 (true-positive rate (TPR)=0.723; false-positive rate (FPR)=0.073; FIG. 3B). Accuracy was slightly better than that in a recent study (reporting AUC=0.836, TPR=0.58, FPR=0.08), even though they used a combination of abundances of 22 species using metagenomic sequencing.[22] Mantel-Haenszel O R, adjusted for colonoscopy, for detecting at least one of the two markers by qPCR in patients with CRC was 22.99 (95% CI 5.83 to 90.8, p=5.79×10-8). When stratifying cohort C2 into early-stage (stages I-II) and late-stage (stages III-IV) patients with cancer, classification potential and ORs were still significant (see Table S26). Abundance of these two genes was significantly higher compared with control samples starting from stage II of CRC (FIG. 3C, D), agreeing with the results of this study from species abundances and providing proof-of principle that fecal metagenomes may harbor non-invasive biomarkers for identification of early-stage CRC.

Discussion

The inventors have reported the first successful cross-ethnic validation of metagenomic gene markers for CRC, notably including data from four countries. Two recent studies reported on potential CRC diagnosis using metagenomic sequencing of fecal microbiomes. The first study based on 16S ribosomal RNA gene used five operational taxonomic units to classify CRC from healthy samples in a cohort from the USA.[21] As they did not perform any independent validation, the inventors are unable to compare their validation accuracy with the earlier report. The second study based on shotgun metagenomic sequencing used 21 species discovered in a French cohort to accurately classify patients with CRC in a German cohort.[22] Higher accuracy in their external validation (AUC=0.85 compared with our AUC of 0.77 and 0.72) could be because the validation cohort comes from the same ethnic group. Indeed, when two gene markers discovered in Chinese cohort C1 were validated in the independent Chinese cohort C2 using qPCR, a high accuracy (AUC=0.84) was also achieved even after moving to a different platform. By doing so, the inventors have also demonstrated, for the first time, the potential for CRC diagnosis through affordable targeted detection methods for microbial biomarkers in fecal samples. Significant improvement in the qPCR classification potential (from AUC=0.73 to AUC=0.84) by using a gene (rpoB gene from *P. micra*) validated in cohorts D, F and A reiterates the importance of validating newly discovered biomarkers in independent cohorts with different genetic and environmental background. Further work performing biomarker discovery in high-diversity cohorts or a meta-analysis of published cohorts could reveal whether it leads to increased predictive power. Combining metagenomics markers with the current clinical standard test (fecal occult blood test (FOBT)) has been shown to improve TPR from 49% to 72%. 22 The two markers reported here have reached a comparable TPR without using FOBT. It remains to be seen whether combining FOBT with these markers will further improve accuracy.

Gene markers shared between cohorts from China, Denmark, Austria, and France suggest that even though different populations may have different microbial community structures, signatures of CRC-associated microbial dysbiosis could have universal features. Several important observations should be noted: (i) CRC-enriched gene markers had higher correlation between metagenomic and qPCR abundances (r=0.93 and r=0.95) compared with control-enriched genes (r=0.81 and 0.85) in cohort C1; (ii) among four gene markers randomly tested using qPCR in cohort C2, only CRC-enriched genes were validated; (iii) all four gene markers validated in cohort D, all five markers validated in cohort A and four out of five markers validated in cohort F were CRC-enriched (see Table S25), even though there were 12 control-enriched markers compared with only 8 CRC-enriched markers; (iv) the only marker that switched enrichment during validation in different cohorts was control-enriched; (v) cohort D shared significantly more CRC-enriched genes than control-enriched genes with cohort C1; and (vi) all CRC-associated species from cohort C1 validated in cohort D were CRC-enriched. These features suggest that CRC-enriched biomarkers have a higher chance to be shared across populations and have better diagnostic potential than control-enriched biomarkers. One explanation could be that biomarkers for being healthy are harder to find than biomarkers for a specific disease, which goes against the Anna Karenina principle applied to gut microbiome that predicts higher number of disease-specific disturbed states than undisturbed states.[42] Although it is mandatory to have further validation for all biomarkers in larger cohorts across different populations, these results provide a proof of principle that development of an affordable diagnostic test using fecal microbial gene markers to identify patients with CRC may indeed be possible.

The finding that only two microbial metabolic modules associated with CRC status suggests that the role of microbial pathogens may be more important in disease development than that of functional abnormalities of the gut microbiome. Alternatively, expression levels of microbial genes may be more important than functional potential. Further research employing metatranscriptomic studies of microbial gene expression levels will clarify this.

The fact that only CRC-enriched genes and species could be validated across cohorts limits our conclusions on species depleted in CRC-associated microbiomes. Significant over-representations of several oral pathogens—*P. micra, P. stomatis, S. moorei* and *F. nucleatum* was observed in the stool from patients with CRC, suggesting an oral—gut translocation route associated with CRC. Even though this route cannot be proven without further experiments, a recent study based on 300 healthy individuals reported that oral and gut microbiomes were predictive of each other, supporting this view.[43] While some of these species have been statistically associated with oral cancer in earlier studies,[21][22][40] only *F. nucleatum* has been shown to promote a proinflammatory environment leading to tumorigenesis.[19] This study now introduces *P. micra* as a novel bacterial candidate involved in CRC-associated dysbiosis showing stronger associations with CRC across all five cohorts we investigated. Strong co-occurrence pattern between *P. micra* and the Gram-negative *F. nucleatum*,[44] and the former's ability to increase its capacity to induce inflammatory responses by binding to lipopolysaccharides from Gram-negative bacteria,[45] could mean cooperation between the two, both in terms of colonization strategies and in promoting a proinflammatory tumorigenic microenvironment. Enrichment of these species starts as early as in stage II of CRC, suggesting that they may play a role in the progression of CRC. Further work characterizing *P. micra* could elucidate its role in CRC.

In this study, the present inventors have demonstrated consistent fecal microbial changes in CRC across four cohorts, identified novel bacterial candidates that may be involved in the development and progression of CRC, validated gene markers in three cohorts from three different countries and reported two bacterial genes that could serve as effective diagnostic biomarkers of CRC. Systematic investigation of key species and gene markers identified here might reveal further candidates. Additional work will be imperative (i) to benchmark these observations against currently used diagnostic approaches, (ii) to identify additional markers with improved predictive value and (iii) to eventually validate them in much larger cohorts. The ultimate goal would be to identify fecal metagenomic markers with strong predictive power to detect early stages of CRC, which would significantly reduce CRC-associated mortality.

TABLE A

Primers and probes used in this study

| Targets | (m numbers) | | SEQ ID NO: | Nucleotide sequence (5'->3') |
|---|---|---|---|---|
| 1 | >181682 | Forward Primer | 21 | CGGATTTGCAGTGGCAAGTT |
|   |   | Reverse Primer | 22 | TGATTGCAGACGCCAATGTC |
|   |   | Probe | 23 | CGTGAAAAATCCGCGCATCTGGC |
| 2 | >370640 | Forward Primer | 24 | TCCATCCGCAAGCCTTTACT |
|   |   | Reverse Primer | 25 | GCTTCCGGTGCCATTGACTA |
|   |   | Probe | 26 | TTCATCATCACAGCCGACAACGCA |
| 3 | >482585 | Forward Primer | 27 | AATGGGAATGGAGCGGATTC |
|   |   | Reverse Primer | 28 | CCTGCACCAGCTTATCGTCAA |
|   |   | Probe | 29 | AAGCCTGCGGAACCACAGTTACCAGC |
| 4 | >1696299 | Forward Primer | 30 | AAGAATGGAGAGAGTTGTTAGAGAAAGAA |
|   |   | Reverse Primer | 31 | TTGTGATAATTGTGAAGAACCGAAGA |
|   |   | Probe | 32 | AACTCAAGATCCAGACCTTGCTACGCCTCA |

TABLE A-continued

Primers and probes used in this study

| Targets | (m numbers) | | SEQ ID NO: | Nucleotide sequence (5'->3') |
|---|---|---|---|---|
| 5 | >1704941 (Fn-target 1) | Forward Primer | 33 | TTGTAAGTGCTGGTAAAGGGATTG |
| | | Reverse Primer | 34 | CATTCCTACATAACGGTCAAGAGGTA |
| | | Probe | 35 | AGCTTCTATTGGTTCTTCTCGTCCAGTGGC |
| | Fn-target 2 | Forward Primer | 36 | TTCAATAAAAGTGGCAGGTCAAG |
| | | Reverse Primer | 37 | TAACAACACATGCAGGTCAATGG |
| | | Probe | 38 | ACTCGAACCCCAACCCTCGGTTT |
| 6 | >2736705 | Forward Primer | 39 | GGGCTGCGGAAGCAACTTA |
| | | Reverse Primer | 40 | GATGACCTCGCCCTGATCAT |
| | | Probe | 41 | ACCACCACACAGGACGGAAAGATTCTCC |
| 7 | >3246804 | Forward Primer | 42 | TCGGCACGCTGATTATCACA |
| | | Reverse Primer | 43 | CACACGCCGATCCATCTTC |
| | | Probe | 44 | ACCCACCTGGACGGCTCCGG |
| 8 | >2040133 | Forward Primer | 45 | AAGATCGCGGACGAGTTAGC |
| | | Reverse Primer | 46 | GCTCCCACGCTGACAACAAT |
| | | Probe | 47 | AAAGCTACTATGTCAGCCGGATCGCTGC |
| 9 | >1559769 | Forward Primer | 48 | CCTGGCAGGGTGTAAAAACAC |
| | | Reverse Primer | 49 | TATGCCCGTCGGTACACCAT |
| | | Probe | 50 | CCGGTTATTACCCTCGGCAGCGA |
| 10 | >1804565 | Forward Primer | 51 | AATGGGCGCTTACACCAGAA |
| | | Reverse Primer | 52 | TCACCGCCGGAAAGAGTTC |
| | | Probe | 53 | TTCCCCGCTTAAAGGAACGTACCCG |
| 11 | >2206475 | Forward Primer | 54 | CAGAAGCAACATTGGAAGTTGAA |
| | | Reverse Primer | 55 | TGTAATCCAGTTGCCGTCTGTTC |
| | | Probe | 56 | TCAACAGTAAACGTTAATGCCAACGGCA |
| 12 | >3319526 | Forward Primer | 57 | CGGCCGGAAATGTTCTACAC |
| | | Reverse Primer | 58 | GAAACACGCCGTCTGAGATGA |
| | | Probe | 59 | CCAGACCATTGATTTCGTCACCCTGC |
| 13 | >3611706 | Forward Primer | 60 | CTGGTGGAGTTTGCGAATCA |
| | | Reverse Primer | 61 | CAGCCAGCCGTAAAGCTTGT |
| | | Probe | 62 | CGGAAAATATCCCCGTCGGCAGA |
| 14 | >3976414 | Forward Primer | 63 | GGGCACCTTTCTGCTCACA |
| | | Reverse Primer | 64 | CGGGCTTTACCAGCTTGTTG |
| | | Probe | 65 | AAAAATCAGCCCCTGGCTCGGC |
| 15 | >4171064 | Forward Primer | 66 | GTGCGCAGTCCGATTTCTGT |
| | | Reverse Primer | 67 | CAGCGGCAAATCATAAACGA |
| | | Probe | 68 | TCCGTATTATCCGGCCTACGATACAGCA |
| 16 | >4256106 | Forward Primer | 69 | AGCTTTTTCTCGAATGGTTAGCTTA |
| | | Reverse Primer | 70 | CTGCAATTCCAGACGATCATAGG |
| | | Probe | 71 | AATACGATTCGCAGACATGAACAACACTGG |
| 17 | >2211919 | Forward Primer | 72 | AAAGATGTTGCTGCGCATT |
| | | Reverse Primer | 73 | TTTCCCGCTCATAATTTCTTC |
| | | Probe | 74 | AAATGTTCCTCATTCTGCAATTTCCGA |
| 18 | >2361423 | Forward Primer | 75 | TCCTATCCCTTGAAGGTCAGA |
| | | Reverse Primer | 76 | TGTCAAGAGCTGTACTATATGGAATTT |
| | | Probe | 77 | TTGCCAAGAAGGTCTTTCCAAATGC |
| 19 | >3173495 | Forward Primer | 78 | TGTGGTAAATTCACTGAAATATGACT |
| | | Reverse Primer | 79 | TCCATTAGCATTATCCTTGCC |
| | | Probe | 80 | ACCCTCCACCATGGCATTCGT |
| 20 | >3531210 | Forward Primer | 81 | TGTGTGTAGAGGCGAGAAGG |
| | | Reverse Primer | 82 | CCATTCATTTCGTTCAACATTC |
| | | Probe | 83 | CCCTCTTCCATCCAGGCTCACC |
| 21 | 16S rDNA | Forward Primer | 84 | CGTCAGCTCGTGYCGTGAG |
| | | Reverse Primer | 85 | CGTCRTCCCCRCCTTCC |
| | | Probe | 86 | TTAAGTCCCRYAACGAGCGCAACCC |

Methods for Example 1

Sample Collection and DNA Preparation

Sample Collection in China

The study included adult individuals undergoing colonoscopy at the Shaw Endoscopy Centre at the Prince of Wales Hospital, the Chinese University of Hong Kong. The Chinese cohorts C1 (Table S1) and C2 (Table S16) included individuals presenting symptoms such as change of bowel habit, rectal bleeding, abdominal pain or anaemia, and asymptomatic individuals aged 50 or above undergoing screening colonoscopy. The exclusion criteria were: 1) use of antibiotics within the past 3 months; 2) on a vegetarian diet; 3) had an invasive medical intervention within the past 3 months; 4) had a past history of any cancer, or inflammatory disease of the intestine. Subjects were asked to collect stool samples in standardized containers at home, and store the samples in their home freezer immediately. Frozen samples were then delivered to the hospital in insulating polystyrene foam containers and stored at −80° C. immediately until further analysis. The study protocol in Hong Kong was approved by the Joint Chinese University of Hong Kong—New Territories East Cluster Clinical Research Ethics Committee (CUHK-NTEC CREC).

Sample Collection in Denmark

Cohort D: Stool samples were collected from individuals referred to colonoscopy due to symptoms associated with CRC or from patients who had been diagnosed with CRC and referred to large bowel resection for their primary cancer disease (See Table S18). All individuals were included at their visit to the out-patient clinic either before colonoscopy or before the operation and always before bowel evacuation. The individuals received a stool collection set including a tube without stabilizing buffer and were instructed to collect a stool sample at home one or two days before initiation of large bowel evacuation. Every included individual kept the sample refrigerated at −18° C. and contacted a research nurse who collected the sample. At the laboratory stool samples were immediately snap frozen in liquid nitrogen and subsequently stored at −80° C. under 24/7 electronic surveillance until analysis.

All included individuals thus underwent complete colonoscopy either as the primary examination or after the subsequent operation. Exclusion criteria were previous adenoma, previous CRC and previous or present other malignant diseases.

The recording of data from the included individuals was performed according to the Helsinki II declaration. The protocol was approved by the Ethics Committee of the Capital Region of Denmark (H-3-2009-110) and the Danish Data Protection Agency (2008-41-2252).

DNA Extraction

Chinese samples: Stool samples were thawed on ice and DNA extraction was performed using the Qiagen QIAamp DNA Stool Mini Kit (Qiagen) according to manufacturer's instructions. Extracts were treated with DNase-free RNase to eliminate RNA contamination. DNA quantity was determined using NanoDrop spectrophotometer, Qubit Fluorometer (with the Quant-iTTMdsDNA BR Assay Kit) and gel electrophoresis.

Danish samples: A frozen aliquot (200 mg) of each fecal sample was suspended in 250 µl of 4 M guanidine thiocyanate—0.1 M Tris (pH 7.5) and 40 µl of 10% N-lauroyl sarcosine. Then, DNA extraction was conducted using bead beating method as previously described[24]. The DNA concentration and its molecular size were estimated by nanodrop (Thermo Scientific) and agarose gel electrophoresis.

DNA Library Construction and Sequencing

DNA library construction for samples from cohort C1, C2 and D was performed following the manufacturer's instruction (Illumina) at the same facility. We used a previously described workflow to perform cluster generation, template hybridization, isothermal amplification, linearization, blocking and denaturation, and hybridization of the sequencing primers[25].

We constructed one paired-end (PE) library with insert size of 350 bp for each sample, followed by high-throughput sequencing to obtain around 30 million PE reads of length 2×100 bp. High-quality reads were obtained by filtering low-quality reads with ambiguous 'N' bases, adapter contamination and human DNA contamination from the Illumina raw reads, and by trimming low-quality terminal bases of reads simultaneously.

Gene Profile Analysis

Generating Gene Profiles

We mapped our high-quality reads to a published reference gut microbial gene catalogue derived from European and Chinese adults[25] (using sequence identity >=90%). We then derived the gene profiles using previously described procedures[25].

Bio-Diversity Analysis

Based on the gene profiles, we calculated the within-sample (alpha) diversity to estimate the gene richness using Shannon index and Simpson index of alpha diversity[25], where larger value indicates a higher degree of diversity in the sample. To analyse effects of different phenotype factors, including age, BMI, eGFR, TCHO, LDL, HDL, and TG, on gut microbial diversity, Pearson correlation coefficients between each factor and Shannon index were also calculated.

Rarefaction Analysis Based on Gene Profile

Estimation of total gene richness in a set of metagenomics samples was performed by randomized sampling with replacement. This was done independently for cohort C1, CRC patients group in C1, and non-CRC control group in C1. In each set of size n, we randomly sampled n individual samples with replacement and then calculated the total number of genes that could be identified from these samples. Only genes with ≥1 mapping reads were considered to be present. This was repeated 100 times. The result showed that the control group had higher gene richness than the case group.

Analysis of Factors Influencing Gut Microbial Gene Profile

From the reference gene catalogue[25], we derived a subset of 2.1M genes that appeared in at least 6 samples in all 128 samples from cohort C1 (74 CRC and 54 control). We used the permutational multivariate analysis of variance (PERMANOVA) test to assess the effect of different characteristics, including age, BMI, eGFR, TCHO, LDL, HDL, TG, gender, DM, CRC status and location, on gene profiles of 2.1M genes (see Table 51 for explanation of these factors). We performed the analysis using the implementation in the "vegan" package in R, and the permuted p-value was obtained by performing 10,000 permutations. We also adjusted for multiple testing using the function "p.adjust" in R with Benjamini-Hochberg method to get the corresponding q-values.

Identification of CRC Associated Genes

To identify the association between the metagenomic gene profiles and CRC, a two-tailed Wilcoxon rank-sum test was performed for each of the 2.1M genes. We obtained 140,455 gene markers which were enriched in either case or control with P<0.01. To control for colonoscopy as a confounding factor, we performed the independence test after stratifying by colonoscopy status, using the kruskal test function implemented in COIN package in R.

Estimating the False Discovery Rate (FDR)

Instead of a sequential p-value rejection method, we applied the "qvalue" method proposed in a previous study [46] to estimate the FDR.

Taxonomic Annotation of Genes

Creating IMG Genome Database and Species Annotation of IMG Genomes

Bacterial, archaeal and fungal genome sequences were extracted from IMG v400 reference database[27] downloaded from website: ftp.jgi-psf.org. In total, 522,093 sequences were obtained. For each IMG genome, using the NCBI taxonomy identifier provided by IMG, we identified the corresponding NCBI taxonomic classification at species and genus levels using NCBI taxonomy dump files. The genomes without corresponding NCBI species names were left with their original IMG names, most of which were unclassified at the genus and species levels.

Identification of CRC Associated Metagenomic Linkage Group (MLG) Species

Based on the identified 140,455 CRC associated marker genes, we constructed the CRC associated MLGs using the method described in our previous study on type 2 diabetes [25]. All the above genes were aligned to the reference genomes of IMG database v400 to get genome level annotation. An MLG was assigned to a genome if >50% constituent genes were annotated to that genome, otherwise it was termed as unclassified. 86 MLGs consisting over 100 genes were selected as CRC associated MLGs. These MLGs were grouped based on the species annotation of these genomes to construct MLG species.

Data Profile Construction

Functional Profiles Based on KEGG Database

Based on the gene profiles, we derived the KO profiles using previously described procedures[25]. Functional analysis was performed based on KEGG orthologous group (KO) abundance profiles. KEGG module and pathway (the KEGG Class Level 2) abundance profiles were calculated by summing the abundances of KOs belonging to each functional category.

Molecular Operational Taxonomic Unit (mOTU) Profiles

Clean reads were aligned to mOTU reference database (total 79268 sequences) with default parameters[26]. 549 species level mOTUs were identified, including 307 annotated species and 242 mOTU linkage groups (not to be confused with metagenomics linkage groups) without representative genomes. Most of the mOTU linkage groups were putatively Firmicutes or Bacteroidetes.

IMG-Species and IMG Genus Profiles

SOAP reference index was constructed for the IMG genome database based on 7 equal size chunks of the original file. Clean reads were aligned to reference using SOAP aligner[47] version 2.22, with parameters "-m 4 -s 32 -r 2 -n 100 -x 600 -v 8 -c 0.9 -p 3". Then, SOAP coverage software was used to calculate read coverage of each genome, normalized with genome length, and further normalized to relative abundance for each individual sample. The profile was generated based on uniquely mapped reads only.

MLG-Species and MLG-Genus Profiles

To estimate the relative abundance of an MLG species, we estimated the average abundance of the genes of the MLG species, after removing the 5% lowest and 5% highest abundant genes. Relative abundance of IMG species was estimated by summing the abundance of IMG genomes belonging to that species. Genus abundances were estimated by analogously summing species abundances.

Biomarker Discovery Analysis

Minimum Redundancy Maximum Relevance (mRMR) Framework

To establish CRC classification only using gut metagenomic markers, we adopted the mRMR method[28] to perform feature selection. We used the "sideChannelAttack" package from R to perform an incremental search and found 128 sequential marker sets. For each sequential set, we estimated the error rate by leave-one-out cross-validation (LOOCV) of a linear discrimination classifier. The optimal selection of marker sets was the one corresponding to the lowest error rate. In the present study, we made the feature selection on a set of 102,514 CRC associated gene markers. Since it was computationally prohibitive to perform mRMR using all genes, we derived a statistically non-redundant gene set. Firstly, we pre-grouped the 102,514 CRC associated genes that are highly correlated with each other (Kendall correlation >0.9). Then we chose the longest gene as representative gene for the group, since longer genes have a higher chance of being functionally annotated, and will attract more reads during the mapping procedure. This generated a non-redundant set of 11,128 significant genes. Subsequently, we applied the mRMR feature selection method[28] to the 11,128 significant genes and identified an optimal set of 20 gene biomarkers that are strongly associated with CRC for classification.

Definition of CRC Index

To evaluate the risk of CRC from the gut metagenome, we defined and computed a CRC index for each individual on the basis of the 20 gene markers identified by mRMR procedure. For each individual sample, the CRC index of sample j that denoted by 1 was computed by the formula below:

$$I_j = \left[ \frac{\sum_{i \in N} \log_{10}(A_{ij} + 10^{-20})}{|N|} - \frac{\sum_{i \in M} \log_{10}(A_{ij} + 10^{-20})}{|M|} \right]$$

where $A_{ij}$ is the relative abundance of marker i in sample j. N is a subset of all CRC-enriched markers in these 20 genes. M is a subset of all control-enriched markers in these 20 genes. And |N| and |M| are the sizes of these two sets. The ability of the CRC index to distinguish CRC patient microbiomes from non-CRC microbiomes was examined using Wilcoxon rank-sum test. P-values estimated by these tests were adjusted for multiple testing using Benjamini-Hochberg method, when comparing CRC samples in cohort C1 with several other sample sets.

Receiver Operator Characteristic (ROC) Analysis

We applied the ROC analysis to assess the performance of CRC classification based on metagenomic markers. We used the "Daim" package in R to draw the ROC curve.

Functional Signatures Associated with CRC

Wilcoxon rank-sum test with Benjamini-Hochberg adjustment was employed to identify KEGG KOs, modules and pathways associated with CRC.

Gut Microbial Species Associated with CRC

Out of the 86 MLG species consisting over 100 genes, 85 MLGs were associated with CRC at a significance level of q<0.05 according to Wilcoxon rank-sum tests with Benjamini-Hochberg adjustment. This higher number is expected as the MLGs were constructed with genes that are associated with CRC in the first place. Using the same procedure at the same significance level, 28 IMG species and 21 mOTU species were associated with CRC.

Identifying Gut Microbial Species that can Classify CRC Microbiomes

To evaluate the classification potential of the gut microbial species associated with CRC (identified by three methods: 85 MLG-species, 28 IMG species, and 21 mOTU species), we used "randomForest 4.5-36" package in R vision 2.10 based on these species profiles. For each method, firstly, we sorted all the N species by the importance given by the "randomForest" method. Then we created incremental marker sets by creating subsets of the top ranked species, starting from top 1 species and ending at N species. For each marker set, we calculated the false prediction ratio in Chinese cohort C1. Species from the marker set with lowest false prediction ratio were considered to have high potential for classification of CRC microbiomes from control microbiomes. Furthermore, we drew the ROC curve using the probability of illness based on these selected species markers.

Species Co-Occurrence Network Construction

Co-occurrence networks were constructed for the 85 MLGs, 28 IMG species and 21 mOTUs associated with CRC (q<0.05) using Spearman's correlation coefficient (>0.5 or <−0.5), as described previously[25]. Cytoscape[48] v3.0.2 was used to construct the three networks.

Tables for Example 1

TABLE S1

Baseline characteristics of colorectal cancer (CRC) cases and controls in cohort C1. For quantitative traits, the median, minimum and maximum are shown.

| Parameter | Controls (n = 54) | Cases (n = 74) | P-value | q-value |
|---|---|---|---|---|
| Age | 63 (50, 73) | 67 (34, 89) | 0.007373932[†] | 0.027652245 |
| Gender (M:F) | 33:21 | 48:26 | 0.7124[‡] | 0.875363308 |
| BMI | 22.86341 (17.08744, 35.08618) | 23.89549 (17.28882, 31.25) | 0.1107815[†] | 0.237388929 |
| DM (%) | 16 (29.6%) | 29 (39.2%) | 0.3488[‡] | 0.503844136 |
| Stage of CRC (1:2:3:4) | n.a | 18:22:26:8 | n.a | n.a |
| Distribution of detailed TNM stages (T1N0:T2N0:T3N0:T4N0:T2N1:T3N1:T3N2:T3N+:T4N2:T3N1M1:T3N3M1:T4N1M1:T4N2M1:M:M1:multiple liver met) | n.a | 12:6:21:1:3:14:5:2:2:1:1:1:1:1 | n.a | n.a |
| Leison location(1:2:NA) | n.a | 11:54:9 | n.a | n.a |
| Leison specific location (1:2:3:4:6:7:8:9) | n.a | 3:3:3:2:6:14:5:29 | n.a | n.a |
| Fecal sampling before or after colonoscopy* (before:after) | 30:24 (56%:44%) | 21:52 (29%:71%) | 0.003295[‡] | 0.016475000 |
| Duration between colonoscopy and fecal sample collection* (days) | −1.5 (−34, 106.3438) | 19.89097 (−110.7083, 247) | 0.7586482[†] | 0.875363308 |
| Duration of frozen storage of fecal samples (days) | 185.1076 (86.67708, 2032) | 149 (6.6875, 1280) | 0.3694857[†] | 0.503844136 |
| FBG | 5.1 (4.3, 6.9) | 5.75 (4.3, 13.2) | 0.000131342[†] | 0.001407555 |
| TCHO | 5 (3.2, 6.7) | 4.9 (2.6, 8.6) | 0.299775[†] | 0.503844136 |
| LDL | 2.65 (1.4, 5.2) | 2.9 (0.7, 5) | 0.9413451[†] | 0.989788600 |
| HDL | 1.8 (0.8, 3.5) | 1.3 (0.5, 2.2) | 0.000187674[†] | 0.001407555 |
| TG | 1 (0.37, 2.9) | 1.2 (0.5, 5.1) | 0.01991682[†] | 0.059750460 |
| Cr | 71.5 (43, 101) | 74 (41, 202) | 0.3257186[†] | 0.503844136 |
| ALT GPT | 21 (9, 68) | 18 (10, 69) | 0.05068182[†] | 0.126704550 |
| eGFR | 69.51 (50.82, 115.04) | 71.13 (16.81, 136.52) | 0.9897886[†] | 0.989788600 |

FBG: fasting blood glucose;
ALT/GPT: alanine transaminase/glutamate pyruvated transaminase;
BMI: body mass index;
DM: diabetes mellitus type 2;
HDL: high density lipoprotein;
TG: triglyceride;
eGFR: epidermal growth factor receptor;
TCHO: total cholesterol;
Cr: creatinine;
LDL: low density lipoprotein;
TNM: tumor node metastasis staging system;
Statistical tests used for identifying associations between metadata and CRC:
[†]Wilcoxon test,
[‡]Fisher's exact test.
*Information missing in one CRC patient sample.

TABLE S2

Summary of metagenomic data from C1 and mapping to reference gene catalogue. Fourth column reports results from Wilcoxon rank-sum tests.

| Parameter | Controls | Cases | P-value |
|---|---|---|---|
| Average raw reads | 60162577 | 60496561 | 0.8082 |
| After removing low quality reads | 59423292 (98.77%) | 59715967 (98.71%) | 0.831 |
| After removing human reads | 59380535 ± 7378751 | 58112890 ± 10324458 | 0.419 |
| Mapping rate | 66.82% | 66.27% | 0.276 |

TABLE S3

Gene number and gene alpha diversity of CRC and healthy microbiomes in cohort C1. Diversity was represented by Shannon and Simpson indices.

|  | Controls | | Cases | | |
| --- | --- | --- | --- | --- | --- |
| Parameter | mean | sd | mean | sd | P-value |
| Gene number | 581635 | 165527 | 534440 | 164184 | 0.1127 |
| Shannon index | 11.699 | 0.565 | 11.558 | 0.546 | 0.0746 |
| Simpson index | 0.99997 | 2.71E−05 | 0.99996 | 3.94E−05 | 0.0276 |

TABLE S4

PERMANOVA analysis of microbial gene profiles in cohort C1. The analysis was conducted to test whether clinical parameters and CRC status have significant impact on the gut microbiota with $q < 0.05$.

| Parameter | Df | SumsOfSqs | MeanSqs | F.Model | $R^2$ | Pr (>F) | q-value |
| --- | --- | --- | --- | --- | --- | --- | --- |
| CRC Status | 1 | 0.6792933 | 0.6792933 | 1.9596297 | 0.0153144 | 0.0004 | 0.0076 |
| Stage of CRC | 4 | 1.7697175 | 0.4424294 | 1.2778364 | 0.0398977 | 0.0058 | 0.0551 |
| Lesion location(1:2:NA) | 1 | 0.464298 | 0.464298 | 1.31427 | 0.020435 | 0.0536 | 0.2717 |
| BMI | 1 | 0.4600024 | 0.4600024 | 1.3200099 | 0.0104497 | 0.0572 | 0.2717 |
| DM | 1 | 0.4383585 | 0.4383585 | 1.257642 | 0.0098826 | 0.084 | 0.285 |
| FBG | 1 | 0.4319269 | 0.4319269 | 1.2300105 | 0.0123955 | 0.09 | 0.285 |
| Lesion specific location (1:2:3:4:6:7:8:9:NA) | 1 | 0.421307 | 0.421307 | 1.190278 | 0.018543 | 0.1369 | 0.371586 |
| Age | 1 | 0.3972817 | 0.3972817 | 1.1387282 | 0.0089566 | 0.1923 | 0.456713 |
| HDL | 1 | 0.3641778 | 0.3641778 | 1.0352042 | 0.010246 | 0.3578 | 0.722 |
| eGFR | 1 | 0.3585266 | 0.3585266 | 1.0231375 | 0.0094715 | 0.38 | 0.722 |
| TG | 1 | 0.3522642 | 0.3522642 | 1.001382 | 0.0099145 | 0.4329 | 0.747736 |
| Duration between colonoscopy and fecal sample collection | 1 | 0.3397823 | 0.3397823 | 0.9722612 | 0.0077181 | 0.5036 | 0.761608 |
| Fecal sampling before or after colonoscopy | 1 | 0.3378151 | 0.3378151 | 0.9665887 | 0.0076734 | 0.5211 | 0.761608 |
| TNM | 15 | 5.3000663 | 0.3533378 | 0.9890377 | 0.2036857 | 0.5781 | 0.766587 |
| Cr | 1 | 0.3281613 | 0.3281613 | 0.9330291 | 0.0088077 | 0.6052 | 0.766587 |
| TCHO | 1 | 0.3127842 | 0.3127842 | 0.8878167 | 0.0088 | 0.7198 | 0.854763 |
| LDL | 1 | 0.2994855 | 0.2994855 | 0.8502487 | 0.0084308 | 0.8146 | 0.863233 |
| ALT/GPT | 1 | 0.2976508 | 0.2976508 | 0.847193 | 0.007929 | 0.8178 | 0.863233 |
| Gender | 1 | 0.2677377 | 0.2677377 | 0.7651615 | 0.0060361 | 0.9528 | 0.9528 |

BMI: body mass index;
DM: diabetes mellitus type 2;
FBG: fasting blood glucose;
HDL: high density lipoprotein;
TG: triglyceride;
eGFR: epidermal growth factor receptor;
TNM: tumor node metastasis staging system;
TCHO: total cholesterol;
Cr: creatinine;
LDL; low density lipoprotein.
ALT/GPT: alanine transaminase/glutamate pyruvated transaminase.

TABLE S5

Principal component analysis (PCA) using microbial gene profiles from cohort C1 using 2.1 million genes. Association tests of the first five principal components (PC) with 17 parameters are reported.

| | Gene level P-value | | | | | |
| --- | --- | --- | --- | --- | --- | --- |
| Parameter | PC1 | PC2 | PC3 | PC4 | PC5 | Statistical test for differences |
| CRC Status | 0.029375 | 0.7556469 | 0.0908164 | 0.2458964 | 1.29E−06 | Wilcoxon rank-sum tests |
| Age | 0.1107786 | 0.7187803 | 0.9579642 | 0.3323753 | 0.1740341 | Pearson correlation test |
| BMI | 0.1666538 | 0.349701 | 0.2799689 | 0.9666352 | 0.6664927 | Pearson correlation test |
| Duration between colonoscopy and fecal sample collection | 0.2612967 | 0.3677261 | 0.5027833 | 0.8471867 | 0.985353 | Pearson correlation test |
| Fecal sampling before or after colonoscopy | 0.3051672 | 0.3564576 | 0.6633822 | 0.998038 | 0.2695479 | Wilcoxon rank-sum tests |
| DM | 0.3304729 | 0.7684188 | 0.192732 | 0.4910126 | 0.025695 | Wilcoxon rank-sum tests |
| TNM | 0.3587305 | 0.7179382 | 0.4123964 | 0.6422653 | 0.2646984 | Kruskal-Wallis tests |

TABLE S5-continued

Principal component analysis (PCA) using microbial gene profiles from cohort C1 using 2.1 million genes.
Association tests of the first five principal components (PC) with 17 parameters are reported.

| Parameter | Gene level P-value | | | | | Statistical test for differences |
|---|---|---|---|---|---|---|
| | PC1 | PC2 | PC3 | PC4 | PC5 | |
| Gender | 0.3762511 | 0.692509 | 0.0652127 | 0.6280812 | 0.4261203 | Wilcoxon rank-sum tests |
| TCHO | 0.3918745 | 0.6337139 | 0.8437887 | 0.8920492 | 0.8586685 | Pearson correlation test |
| LDL | 0.3996362 | 0.3026439 | 0.2289333 | 0.8912377 | 0.5012763 | Pearson correlation test |
| eGFR | 0.4185351 | 0.6904019 | 0.4945847 | 0.3171986 | 0.5644339 | Pearson correlation test |
| Stage of CRC | 0.4785966 | 0.4859963 | 0.3868685 | 0.6319499 | 0.1400903 | Kruskal-Wallis tests |
| HDL | 0.4855939 | 0.265294 | 0.9413181 | 0.8985499 | 0.1237575 | Pearson correlation test |
| TG | 0.5435062 | 0.7623276 | 0.4072886 | 0.1106054 | 0.0247417 | Pearson correlation test |
| ALT/GPT | 0.6686028 | 0.819014 | 0.5737057 | 0.3283116 | 0.6117176 | Pearson correlation test |
| Cr | 0.8059999 | 0.5986523 | 0.743814 | 0.7723353 | 0.3177772 | Pearson correlation test |
| FBG | 0.8765164 | 0.6637887 | 0.037985 | 0.8754288 | 0.0596181 | Pearson correlation test |

TABLE S6

List of KEGG modules and pathways associated with CRC status at P-value < 0.01 in cohort C1.

| Module ID | Control rank mean | Case rank mean | Enrichment (0:case/1:control) | P-value | q-value | Definition |
|---|---|---|---|---|---|---|
| KEGG Modules | | | | | | |
| M00036 | 48.72222222 | 76.01351351 | 0 | 4.36E−05 | 0.014810703 | Leucine degradation, leucine => acetoacetate + acetyl-CoA |
| M00050 | 50.2962963 | 74.86486486 | 0 | 0.000141552 | 0.02406378 | Guanine nucleotide biosynthesis, IMP => GDP/dGDP, GTP/dGTP |
| M00037 | 51.72222222 | 73.82432432 | 0 | 0.000655997 | 0.056363614 | Melatonin biosynthesis, tryptophan => serotonin => melatonin |
| M00042 | 52.05555556 | 73.58108108 | 0 | 0.000663101 | 0.056363614 | Catecholamine biosynthesis, tyrosine => dopamine => noradrenaline => adrenaline |
| M00020 | 53.07407407 | 72.83783784 | 0 | 0.002447934 | 0.142598694 | Serine biosynthesis, glycerate-3P => serine |
| M00046 | 54.81481481 | 71.56756757 | 0 | 0.003088118 | 0.142598694 | beta-Alanine biosynthesis, cytosine/uracil => beta-alanine |
| M00055 | 77.38888889 | 55.09459459 | 1 | 0.003404079 | 0.142598694 | N-glycan precursor biosynthesis |
| M00250 | 76.40740741 | 55.81081081 | 1 | 0.003804616 | 0.142598694 | Lipopolysaccharide transport system |
| M00135 | 53.09259259 | 72.82432432 | 0 | 0.004435999 | 0.142598694 | GABA biosynthesis, eukaryotes, putrescine => GABA |
| M00144 | 52.27777778 | 73.41891892 | 0 | 0.004478832 | 0.142598694 | Complex I (NADH dehydrogenase), NADH dehydrogenase I |
| M00267 | 76.2962963 | 55.89189189 | 1 | 0.004613487 | 0.142598694 | PTS system, N-acetylglucosamine-specific II component |
| M00117 | 53.53703704 | 72.5 | 0 | 0.00506723 | 0.143571525 | Ubiquinone biosynthesis, prokaryotes, chorismate => ubiquinone |
| M00319 | 55.03703704 | 71.40540541 | 0 | 0.005986981 | 0.156582578 | Manganese/zinc/iron transport system |
| M00045 | 53.81481481 | 72.2972973 | 0 | 0.006759204 | 0.164152094 | Histidine degradation, histidine => N-formiminoglutamate => glutamate |
| M00318 | 56.85185185 | 70.08108108 | 0 | 0.007585097 | 0.171928858 | Iron/zinc/copper transport system |
| M00209 | 53.72222222 | 72.36486486 | 0 | 0.009495418 | 0.20177763 | Osmoprotectant transport system |
| KEGG Pathways | | | | | | |
| map00901 | 51.72222222 | 73.82432432 | 0 | 0.000655997 | 0.093807599 | Indole alkaloid biosynthesis |
| map00965 | 51.72222222 | 73.82432432 | 0 | 0.000655997 | 0.093807599 | Betalain biosynthesis |
| map00943 | 76.35185185 | 55.85135135 | 1 | 0.001077093 | 0.102682879 | Isoflavonoid biosynthesis |
| map00253 | 76.75925926 | 55.55405405 | 1 | 0.002345148 | 0.167678104 | Tetracycline biosynthesis |
| map00190 | 52.53703704 | 73.22972973 | 0 | 0.003379124 | 0.177259289 | Oxidative phosphorylation |
| map00430 | 52.7962963 | 73.04054054 | 0 | 0.003718726 | 0.177259289 | Taurine and hypotaurine metabolism |
| map00280 | 54.22222222 | 72 | 0 | 0.006119571 | 0.222185359 | Valine, leucine and isoleucine degradation |
| map04724 | 54.68518519 | 71.66216216 | 0 | 0.006639056 | 0.222185359 | Glutamatergic synapse |
| map00562 | 54.07407407 | 72.10810811 | 0 | 0.008048415 | 0.222185359 | Inositol phosphate metabolism |
| map00061 | 74.27777778 | 57.36486486 | 1 | 0.008239217 | 0.222185359 | Fatty acid biosynthesis |
| map00910 | 55.16666667 | 71.31081081 | 0 | 0.008545591 | 0.222185359 | Nitrogen metabolism |
| map04940 | 54.53703704 | 71.77027027 | 0 | 0.009490601 | 0.226192666 | Type I diabetes mellitus |

TABLE S7

List of KEGG orthologous groups (KOs) associated with CRC status at q-value < 0.05 in cohort C1.

| KO ID | Control rank mean | Case rank mean | Enrichment (0:case/1:control) | P-value | q-value | Definition |
|---|---|---|---|---|---|---|
| K09778 | 46.68519 | 77.5 | 0 | 2.91E−06 | 0.017649179 | Hypothetical protein |
| K10670 | 46.44444 | 77.67568 | 0 | 6.94E−06 | 0.020377011 | Glycine reductase |
| K09065 | 49.01852 | 75.7973 | 0 | 1.15E−05 | 0.020377011 | N-acetylornithine carbamoyltransferase |
| K13772 | 47.46296 | 76.93243 | 0 | 1.34E−05 | 0.020377011 | Rrf2 family transcriptional regulator, iron-responsive regulator |
| K01464 | 49.27778 | 75.60811 | 0 | 2.35E−05 | 0.022105986 | Dihydropyrimidinase |
| K02656 | 81.26852 | 52.26351 | 1 | 2.51E−05 | 0.022105986 | Type IV pilus assembly protein PilF |
| K08286 | 81.05556 | 52.41892 | 1 | 2.55E−05 | 0.022105986 | Protein-serine/threonine kinase |
| K01096 | 80.68519 | 52.68919 | 1 | 4.04E−05 | 0.029007909 | Phosphatidylglycerophosphatase B |
| K00087 | 49.61111 | 75.36486 | 0 | 4.56E−05 | 0.029007909 | Xanthine dehydrogenase molybdenum-binding subunit |
| K05020 | 48.07407 | 76.48649 | 0 | 5.26E−05 | 0.029007909 | Glycine betaine transporter |
| K07301 | 81.09259 | 52.39189 | 1 | 5.43E−05 | 0.029007909 | Inner membrane protein |
| K01318 | 79.22222 | 53.75676 | 1 | 5.73E−05 | 0.029007909 | Glutamyl endopeptidase |
| K11786 | 80.85185 | 52.56757 | 1 | 6.74E−05 | 0.031479285 | ATP-dependent helicase STH1/SNF2 |
| K01951 | 49.25926 | 75.62162 | 0 | 7.32E−05 | 0.031758681 | GMP synthase (glutamine-hydrolysing) |
| K01459 | 78.51852 | 54.27027 | 1 | 1.31E−04 | 0.049313518 | NA |
| K00132 | 50.64815 | 74.60811 | 0 | 1.38E−04 | 0.049313518 | Acetaldehyde dehydrogenase (acetylating) |
| K04835 | 51.12963 | 74.25676 | 0 | 1.44E−04 | 0.049313518 | Methylaspartate ammonia-lyase |
| K11337 | 49.16667 | 75.68919 | 0 | 1.51E−04 | 0.049313518 | 3-hydroxyethyl bacteriochlorophyllide a dehydrogenase |
| K04749 | 49.11111 | 75.72973 | 0 | 1.54E−04 | 0.049313518 | Anti-sigma B factor antagonist |

TABLE S8

IMG, mOTU and MLG species associated with CRC with q-value < 0.05 in cohort C1. 86 MLG species were formed after grouping 106 MLGs with more than 100 genes using species annotation when available. MLG species identifiers starting with "Con_" are enriched in control samples, and those starting with "CRC_" are enriched in CRC samples.

| | Control rank mean | Case rank mean | Enrichment (0: case/1: control) | P-value | q-value |
|---|---|---|---|---|---|
| 28 IMG species | | | | | |
| *Peptostreptococcus stomatis* | 37.25926 | 84.37838 | 0 | 5.11E−12 | 1.32E−08 |
| *Parvimonas micra* | 38.43519 | 83.52027 | 0 | 4.21E−11 | 5.43E−08 |
| *Parvimonas* sp. oral taxon 393 | 39.81481 | 82.51351 | 0 | 2.79E−10 | 2.40E−07 |
| *Parvimonas* sp. oral taxon 110 | 43.52778 | 79.80405 | 0 | 6.17E−08 | 3.98E−05 |
| *Gemella morbillorum* | 43.87037 | 79.55405 | 0 | 1.53E−07 | 7.88E−05 |
| *Fusobacterium nucleatum* | 45.09259 | 78.66216 | 0 | 3.86E−07 | 1.56E−04 |
| *Leptotrichia buccalis* | 45.60185 | 78.29054 | 0 | 4.44E−07 | 1.56E−04 |
| *Fusobacterium* sp. oral taxon 370 | 45.02778 | 78.70946 | 0 | 4.83E−07 | 1.56E−04 |
| *Burkholderia mallei* | 45.19444 | 78.58784 | 0 | 7.93E−07 | 2.27E−04 |
| *Prevotella intermedia* | 46.47222 | 77.65541 | 0 | 1.92E−06 | 4.95E−04 |
| *Streptococcus pseudoporcinus* | 47.5 | 76.90541 | 0 | 4.03E−06 | 8.99E−04 |
| *Streptococcus dysgalactiae* | 47.06481 | 77.22297 | 0 | 4.18E−06 | 8.99E−04 |
| *Beggiatoa* sp. PS | 46.53704 | 77.60811 | 0 | 5.03E−06 | 9.97E−04 |
| *Malassezia globosa* | 46.35185 | 77.74324 | 0 | 8.71E−06 | 1.60E−03 |
| *Paracoccus denitrificans* | 47.48148 | 76.91892 | 0 | 1.18E−05 | 2.02E−03 |
| *Eubacterium ventriosum* | 80.98148 | 52.47297 | 1 | 1.27E−05 | 2.05E−03 |
| *Streptococcus constellatus* | 48.2037 | 76.39189 | 0 | 1.66E−05 | 2.52E−03 |
| *Filifactor alocis* | 49.06481 | 75.76351 | 0 | 3.94E−05 | 5.65E−03 |
| *Peptoniphilus indolicus* | 51.2963 | 74.13514 | 0 | 4.53E−05 | 6.14E−03 |
| *Crenothrix polyspora* | 48.76852 | 75.97973 | 0 | 5.14E−05 | 6.63E−03 |
| *Peptostreptococcus anaerobius* | 50.14815 | 74.97297 | 0 | 5.88E−05 | 7.22E−03 |
| *Streptococcus equi* | 50.58333 | 74.65541 | 0 | 6.91E−05 | 8.10E−03 |
| *Solobacterium moorei* | 47.66667 | 76.78378 | 0 | 8.79E−05 | 9.85E−03 |
| *Sulfurovum* sp. SCGC AAA036-O23 | 52.12037 | 73.53378 | 0 | 1.28E−04 | 1.37E−02 |
| *Streptobacillus moniliformis* | 52.35185 | 73.36486 | 0 | 1.44E−04 | 1.49E−02 |
| *Eubacteriaceae bacterium ACC19a* | 51.87037 | 73.71622 | 0 | 1.93E−04 | 1.92E−02 |
| *Fusobacterium necrophorum* | 52.37037 | 73.35135 | 0 | 3.72E−04 | 3.55E−02 |
| *Adhaeribacter aquaticus* | 77.06481 | 55.33108 | 1 | 4.79E−04 | 4.41E−02 |
| 21 mOTU species | | | | | |
| *Parvimonas micra* | 46.2963 | 77.78378 | 0 | 2.31E−08 | 7.73E−06 |
| *Peptostreptococcus stomatis* | 46.25 | 77.81757 | 0 | 2.81E−08 | 7.73E−06 |

TABLE S8-continued

IMG, mOTU and MLG species associated with CRC with q-value < 0.05 in cohort C1. 86 MLG species were formed after grouping 106 MLGs with more than 100 genes using species annotation when available. MLG species identifiers starting with "Con_" are enriched in control samples, and those starting with "CRC_" are enriched in CRC samples.

|  | Control rank mean | Case rank mean | Enrichment (0: case/1: control) | P-value | q-value |
|---|---|---|---|---|---|
| motu_linkage_group_731 | 50.42593 | 74.77027 | 0 | 2.91E−07 | 5.33E−05 |
| *Gemella morbillorum* | 47.93519 | 76.58784 | 0 | 8.63E−07 | 1.18E−04 |
| motu_linkage_group_407 | 81.13889 | 52.35811 | 1 | 8.51E−06 | 9.34E−04 |
| motu_linkage_group_490 | 80.46296 | 52.85135 | 1 | 3.04E−05 | 2.78E−03 |
| *Fusobacterium nucleatum* | 54.62037 | 71.70946 | 0 | 3.56E−05 | 2.79E−03 |
| *Clostridium symbiosum* | 48.66667 | 76.05405 | 0 | 4.50E−05 | 2.99E−03 |
| motu_linkage_group_443 | 79.66667 | 53.43243 | 1 | 4.91E−05 | 2.99E−03 |
| motu_linkage_group_316 | 79.61111 | 53.47297 | 1 | 7.03E−05 | 3.86E−03 |
| *Eubacterium ventriosum* | 78.09259 | 54.58108 | 1 | 9.82E−05 | 4.90E−03 |
| *Solobacterium moorei* | 51.22222 | 74.18919 | 0 | 2.49E−04 | 1.14E−02 |
| *Bacteroides fragilis* | 51.09259 | 74.28378 | 0 | 3.75E−04 | 1.58E−02 |
| unclassified *Fusobacterium* | 54.22222 | 72 | 0 | 4.20E−04 | 1.59E−02 |
| *Clostridiales bacterium* 1_7_47FAA | 51.27778 | 74.14865 | 0 | 4.34E−04 | 1.59E−02 |
| *Clostridium ramosum* | 50.92593 | 74.40541 | 0 | 5.21E−04 | 1.75E−02 |
| motu_linkage_group_611 | 77.2963 | 55.16216 | 1 | 5.50E−04 | 1.75E−02 |
| *Prevotella nigrescens* | 58.09259 | 69.17568 | 0 | 5.72E−04 | 1.75E−02 |
| motu_linkage_group_624 | 51.01852 | 74.33784 | 0 | 1.33E−03 | 3.69E−02 |
| motu_linkage_group_510 | 77.84259 | 54.76351 | 1 | 1.35E−03 | 3.69E−02 |
| *Clostridium bolteae* | 51.81481 | 73.75676 | 0 | 1.41E−03 | 3.69E−02 |
| 85 MLG species | | | | | |
| *Parvimonas micra* | 38.40741 | 83.54054 | 0 | 5.56E−12 | 4.84E−10 |
| *Fusobacterium nucleatum* | 40.32407 | 82.14189 | 0 | 1.72E−10 | 7.48E−09 |
| *Solobacterium moorei* | 42.2037 | 80.77027 | 0 | 4.01E−08 | 1.16E−06 |
| *Clostridium symbiosum* | 46.31481 | 77.77027 | 0 | 2.67E−06 | 5.80E−05 |
| Con 10180 | 82.03704 | 51.7027 | 1 | 6.06E−06 | 1.05E−04 |
| CRC 2881 | 51.25926 | 74.16216 | 0 | 7.57E−06 | 1.10E−04 |
| CRC 2794 | 51.03704 | 74.32432 | 0 | 1.04E−05 | 1.30E−04 |
| *Coprococcus* sp. ART55/1 | 80.85185 | 52.56757 | 1 | 2.09E−05 | 2.05E−04 |
| *Clostridium hathewayi* | 46.77778 | 77.43243 | 0 | 2.12E−05 | 2.05E−04 |
| Clostridiales bacterium 1_7_47FAA | 48.16667 | 76.41892 | 0 | 2.49E−05 | 2.17E−04 |
| CRC 4136 | 50.99074 | 74.35811 | 0 | 2.97E−05 | 2.32E−04 |
| butyrate-producing bacterium SS3/4 | 80.57407 | 52.77027 | 1 | 3.19E−05 | 2.32E−04 |
| *Haemophilus parainfluenzae* | 80.49074 | 52.83108 | 1 | 4.18E−05 | 2.69E−04 |
| Con 154 | 80.35185 | 52.93243 | 1 | 4.45E−05 | 2.69E−04 |
| *Clostridium clostridioforme* | 50.2037 | 74.93243 | 0 | 4.64E−05 | 2.69E−04 |
| *Bacteroides fragilis* | 49.09259 | 75.74324 | 0 | 5.56E−05 | 3.02E−04 |
| Con 1979 | 79.94444 | 53.22973 | 1 | 6.03E−05 | 3.09E−04 |
| *Eubacterium ventriosum* | 78.62963 | 54.18919 | 1 | 6.88E−05 | 3.33E−04 |
| Con 7958 | 75.27778 | 56.63514 | 1 | 7.40E−05 | 3.33E−04 |
| Con 5770 | 79.39815 | 53.62838 | 1 | 7.66E−05 | 3.33E−04 |
| *Clostridium* sp. HGF2 | 48.27778 | 76.33784 | 0 | 8.28E−05 | 3.43E−04 |
| CRC 6481 | 52.09259 | 73.55405 | 0 | 9.87E−05 | 3.90E−04 |
| *Cloacibacillus evryensis* | 52.73148 | 73.08784 | 0 | 1.13E−04 | 4.23E−04 |
| Con 1987 | 79.42593 | 53.60811 | 1 | 1.17E−04 | 4.23E−04 |
| Con 4595 | 77.21296 | 55.22297 | 1 | 1.38E−04 | 4.81E−04 |
| Con 1617 | 76.12963 | 56.01351 | 1 | 1.50E−04 | 5.03E−04 |
| Con 1371 | 78.46296 | 54.31081 | 1 | 2.05E−04 | 6.60E−04 |
| Lachnospiraceae bacterium 5_1_57FAA | 49.96296 | 75.10811 | 0 | 2.49E−04 | 7.73E−04 |
| *Eubacterium biforme* | 74.68519 | 57.06757 | 1 | 3.00E−04 | 8.70E−04 |
| *Faecalibacterium prausnitzii* | 78.25926 | 54.45946 | 1 | 3.00E−04 | 8.70E−04 |
| Con 4699 | 78.78704 | 54.07432 | 1 | 3.13E−04 | 8.79E−04 |
| *Desulfovibrio* sp. 6_1_46AFAA | 53.33333 | 72.64865 | 0 | 3.70E−04 | 9.87E−04 |
| Con 1529 | 75.05556 | 56.7973 | 1 | 3.74E−04 | 9.87E−04 |
| *Ruminococcus torques* | 76.92593 | 55.43243 | 1 | 5.28E−04 | 1.35E−03 |
| *Coprobacillus* sp. 3_3_56FAA | 50.53704 | 74.68919 | 0 | 6.01E−04 | 1.46E−03 |
| *Streptococcus equinus* | 54.52778 | 71.77703 | 0 | 6.02E−04 | 1.46E−03 |
| *Synergistes* sp. 3_1_syn1 | 54.37963 | 71.88514 | 0 | 6.89E−04 | 1.62E−03 |
| Lachnospiraceae bacterium 8_1_57FAA | 51.88889 | 73.7027 | 0 | 7.91E−04 | 1.81E−03 |
| *Klebsiella pneumoniae* | 74.7037 | 57.05405 | 1 | 8.33E−04 | 1.86E−03 |
| *Eubacterium eligens* | 79.53704 | 53.52703 | 1 | 9.07E−04 | 1.97E−03 |
| *Clostridium bolteae* | 51.39815 | 74.06081 | 0 | 9.27E−04 | 1.97E−03 |
| Con 1513 | 76.59259 | 55.67568 | 1 | 1.02E−03 | 2.11E−03 |
| *Clostridium citroniac* | 51.71296 | 73.83108 | 0 | 1.08E−03 | 2.19E−03 |
| *Fusobacterium varium* | 54.57407 | 71.74324 | 0 | 1.15E−03 | 2.28E−03 |
| *Bacteroides clarus* | 75.55556 | 56.43243 | 1 | 1.29E−03 | 2.50E−03 |

TABLE S8-continued

IMG, mOTU and MLG species associated with CRC with q-value < 0.05 in cohort C1. 86 MLG species were formed after grouping 106 MLGs with more than 100 genes using species annotation when available. MLG species identifiers starting with "Con_" are enriched in control samples, and those starting with "CRC_" are enriched in CRC samples.

|  | Control rank mean | Case rank mean | Enrichment (0: case/1: control) | P-value | q-value |
|---|---|---|---|---|---|
| *Ruminococcus obeum* | 77.53704 | 54.98649 | 1 | 1.34E−03 | 2.54E−03 |
| Con 2606 | 77.5 | 55.01351 | 1 | 1.42E−03 | 2.59E−03 |
| Lachnospiraceae bacterium 3_1_46FAA | 52.53704 | 73.22973 | 0 | 1.44E−03 | 2.59E−03 |
| CRC 2867 | 52.31481 | 73.39189 | 0 | 1.46E−03 | 2.59E−03 |
| Con 6037 | 77.5463 | 54.97973 | 1 | 1.56E−03 | 2.71E−03 |
| *Clostridium* sp. L2-50 | 76.37963 | 55.83108 | 1 | 1.61E−03 | 2.75E−03 |
| Con 1867 | 76.38889 | 55.82432 | 1 | 2.13E−03 | 3.57E−03 |
| *Roseburia intestinalis* | 76.99074 | 55.38514 | 1 | 2.20E−03 | 3.58E−03 |
| *Subdoligranulum* sp. 4_3_54A2FAA | 51.56481 | 73.93919 | 0 | 2.24E−03 | 3.58E−03 |
| Con 1197 | 75.42593 | 56.52703 | 1 | 2.26E−03 | 3.58E−03 |
| CRC 4069 | 53.7963 | 72.31081 | 0 | 2.56E−03 | 3.96E−03 |
| Con 8757 | 77.17593 | 55.25 | 1 | 2.60E−03 | 3.96E−03 |
| Con 5752 | 73.65741 | 57.81757 | 1 | 2.71E−03 | 4.07E−03 |
| Con 4295 | 74.98148 | 56.85135 | 1 | 2.95E−03 | 4.34E−03 |
| *Eubacterium rectale* | 75.90741 | 56.17568 | 1 | 3.21E−03 | 4.60E−03 |
| Con 2494 | 74.35185 | 57.31081 | 1 | 3.22E−03 | 4.60E−03 |
| Con 7367 | 76.23148 | 55.93919 | 1 | 3.63E−03 | 5.09E−03 |
| Con 4829 | 76.7963 | 55.52703 | 1 | 3.88E−03 | 5.35E−03 |
| Con 356 | 75.94444 | 56.14865 | 1 | 3.95E−03 | 5.37E−03 |
| *Dorea formicigenerans* | 52.98148 | 72.90541 | 0 | 4.36E−03 | 5.84E−03 |
| Con 10559 | 76.59259 | 55.67568 | 1 | 4.52E−03 | 5.91E−03 |
| Con 563 | 72.7037 | 58.51351 | 1 | 4.55E−03 | 5.91E−03 |
| Con 4909 | 75.72222 | 56.31081 | 1 | 4.79E−03 | 6.12E−03 |
| Con 6128 | 76.22222 | 55.94595 | 1 | 4.86E−03 | 6.13E−03 |
| Con 2503 | 74.14815 | 57.45946 | 1 | 6.02E−03 | 7.46E−03 |
| CRC 3579 | 54.05556 | 72.12162 | 0 | 6.09E−03 | 7.46E−03 |
| Con 2703 | 74.55556 | 57.16216 | 1 | 7.67E−03 | 9.15E−03 |
| Con 6068 | 75.74074 | 56.2973 | 1 | 7.67E−03 | 9.15E−03 |
| Con 1604 | 71.92593 | 59.08108 | 1 | 8.96E−03 | 1.05E−02 |
| Con 5615 | 76.07407 | 56.05405 | 1 | 9.70E−03 | 1.12E−02 |
| Lachnospiraceae bacterium 3_1_57FAA_CT1 | 54.07407 | 72.10811 | 0 | 1.04E−02 | 1.19E−02 |
| Con 569 | 73.41667 | 57.99324 | 1 | 1.30E−02 | 1.46E−02 |
| Con 631 | 70.01852 | 60.47297 | 1 | 1.31E−02 | 1.46E−02 |
| Con 1241 | 76.27778 | 55.90541 | 1 | 1.46E−02 | 1.61E−02 |
| *Alistipes indistinctus* | 54.50926 | 71.79054 | 0 | 1.59E−02 | 1.72E−02 |
| Con 8420 | 72.64815 | 58.55405 | 1 | 2.32E−02 | 2.48E−02 |
| Burkholderiales bacterium 1_1_47 | 72.37963 | 58.75 | 1 | 2.34E−02 | 2.48E−02 |
| Con 7993 | 73.74074 | 57.75676 | 1 | 3.01E−02 | 3.16E−02 |
| Con 425 | 73.19444 | 58.15541 | 1 | 3.87E−02 | 4.01E−02 |
| Con 561 | 70.5 | 60.12162 | 1 | 4.81E−02 | 4.92E−02 |

TABLE S9

PERMANOVA analysis of variation in three CRC-enriched species measured by three different methods in cohort C1. CRC- and colonoscopy-related factors explain the variation in these three species.

| | | mOTU species | | | | | IMG species | | |
|---|---|---|---|---|---|---|---|---|---|
| Parameter | Df | SumsOf Sqs | MeanSqs | F. Model | $R^2$ | Pr (>F) | SumsOf Sqs | MeanSqs | F. Model |
| CRC Status | 1 | 5.85E−05 | 5.85E−05 | 5.1835238 | 0.0395135 | 0.0076 | 2.42E−04 | 2.42E−04 | 4.2189512 |
| Duration between colonoscopy and fecal sample collection | 1 | 4.05E−05 | 4.05E−05 | 3.5159771 | 0.0273583 | 0.0523 | 1.57E−04 | 1.57E−04 | 2.6787139 |
| Fecal sampling before or after colonoscopy | 1 | 3.21E−05 | 3.21E−05 | 2.7722393 | 0.0216967 | 0.0799 | 1.12E−04 | 1.12E−04 | 1.8992995 |
| Stage of CRC | 4 | 8.38E−05 | 2.09E−05 | 1.8432688 | 0.0565537 | 0.1262 | 4.44E−04 | 1.11E−04 | 1.9437773 |
| Lesion location | 1 | 3.02E−05 | 3.02E−05 | 1.5272855 | 0.0236688 | 0.1846 | 1.28E−04 | 1.28E−04 | 1.2152307 |
| LDL | 1 | 2.03E−05 | 2.03E−05 | 1.4217908 | 0.0140186 | 0.2414 | 2.52E−05 | 2.52E−05 | 0.3436566 |
| eGFR | 1 | 5.78E−06 | 5.78E−06 | 0.4256440 | 0.0039622 | 0.5138 | 4.77E−06 | 4.77E−06 | 0.0692402 |
| TCHO | 1 | 1.24E−05 | 1.24E−05 | 0.8618039 | 0.0085444 | 0.3454 | 7.84E−06 | 7.84E−06 | 0.1067080 |
| Lesion specific location | 1 | 4.15E−06 | 4.15E−06 | 0.2052181 | 0.0032469 | 0.6648 | 1.41E−06 | 1.41E−06 | 0.0131386 |

TABLE S9-continued

PERMANOVA analysis of variation in three CRC-enriched species measured by three different methods in cohort C1. CRC- and colonoscopy-related factors explain the variation in these three species.

| | | | | | | | | | |
|---|---|---|---|---|---|---|---|---|---|
| HDL | 1 | 3.24E−07 | 3.24E−07 | 0.0222985 | 0.0002229 | 0.9401 | 4.69E−06 | 4.69E−06 | 0.0638119 |
| Age | 1 | 1.75E−07 | 1.75E−07 | 0.0148715 | 0.0001180 | 0.9652 | 3.05E−06 | 3.05E−06 | 0.0515304 |
| FBG | 1 | 4.03E−06 | 4.03E−06 | 0.2850014 | 0.0028997 | 0.5725 | 1.73E−05 | 1.73E−05 | 0.2322323 |
| BMI | 1 | 1.41E−06 | 1.41E−06 | 0.1195008 | 0.0009551 | 0.749 | 1.07E−05 | 1.07E−05 | 0.1801544 |
| Cr | 1 | 2.32E−06 | 2.32E−06 | 0.1668589 | 0.0015866 | 0.6698 | 3.16E−06 | 3.16E−06 | 0.0449746 |
| ALT/GPT | 1 | 8.01E−07 | 8.01E−07 | 0.0625344 | 0.0005896 | 0.8156 | 6.22E−06 | 6.22E−06 | 0.0929296 |
| TNM | 15 | 5.83E−05 | 3.89E−06 | 0.1815751 | 0.0448528 | 0.9841 | 3.68E−04 | 2.46E−05 | 0.2193220 |
| TG | 1 | 3.80E−07 | 3.80E−07 | 0.0261886 | 0.0002618 | 0.9144 | 6.05E−07 | 6.05E−07 | 0.0082320 |
| Gender | 1 | 1.07E−06 | 1.07E−06 | 0.0908585 | 0.0007206 | 0.8475 | 9.10E−06 | 9.10E−06 | 0.1537437 |
| DM | 1 | 5.19E−07 | 5.19E−07 | 0.0441774 | 0.0003505 | 0.9158 | 4.74E−06 | 4.74E−06 | 0.0800697 |

| | IMG species | | MLG species | | | | | |
|---|---|---|---|---|---|---|---|---|
| Parameter | $R^2$ | Pr (>F) | SumsOfSqs | MeanSqs | F. Model | $R^2$ | Pr (>F) | |
| CRC Status | 0.0323989 | 0.0127 | 7.02E−03 | 7.02E−03 | 5.9492807 | 0.0450876 | 0.0072 | |
| Duration between colonoscopy and fecal sample collection | 0.0209801 | 0.0777 | 4.25E−03 | 4.25E−03 | 3.5265637 | 0.0274384 | 0.0569 | |
| Fecal sampling before or after colonoscopy | 0.0149670 | 0.163 | 3.54E−03 | 3.54E−03 | 2.9217093 | 0.0228398 | 0.0799 | |
| Stage of CRC | 0.0594540 | 0.1157 | 1.27E−02 | 3.17E−03 | 2.7293564 | 0.0815236 | 0.0354 | |
| Lesion location | 0.0189243 | 0.1988 | 2.27E−03 | 2.27E−03 | 1.0493068 | 0.0163828 | 0.3215 | |
| LDL | 0.0034248 | 0.5793 | 6.77E−04 | 6.77E−04 | 0.4524804 | 0.0045044 | 0.5249 | |
| eGFR | 0.0006467 | 0.8438 | 3.31E−04 | 3.31E−04 | 0.2318740 | 0.0021624 | 0.6453 | |
| TCHO | 0.0010659 | 0.7915 | 2.81E−04 | 2.81E−04 | 0.1872153 | 0.0018687 | 0.6821 | |
| Lesion specific location | 0.0002085 | 0.9754 | 8.14E−05 | 8.14E−05 | 0.0370280 | 0.0005874 | 0.9353 | |
| HDL | 0.0006377 | 0.8687 | 3.50E−05 | 3.50E−05 | 0.0232691 | 0.0002326 | 0.955 | |
| Age | 0.0004088 | 0.8841 | 3.47E−05 | 3.47E−05 | 0.0280829 | 0.0002228 | 0.9507 | |
| FBG | 0.0023641 | 0.6205 | 1.70E−03 | 1.70E−03 | 1.1175736 | 0.0112752 | 0.2544 | |
| BMI | 0.0014392 | 0.6958 | 8.11E−05 | 8.11E−05 | 0.0651803 | 0.0005212 | 0.8618 | |
| Cr | 0.0004281 | 0.8759 | 1.61E−04 | 1.61E−04 | 0.1103230 | 0.0010496 | 0.7615 | |
| ALT/GPT | 0.0008759 | 0.7813 | 5.69E−04 | 5.69E−04 | 0.4106836 | 0.0038594 | 0.4907 | |
| TNM | 0.0536766 | 0.9134 | 1.15E−02 | 7.68E−04 | 0.3435946 | 0.0816089 | 0.8323 | |
| TG | 0.0000823 | 0.9827 | 1.39E−04 | 1.39E−04 | 0.0922060 | 0.0009212 | 0.7912 | |
| Gender | 0.0012187 | 0.8233 | 1.65E−04 | 1.65E−04 | 0.1336220 | 0.0010594 | 0.7801 | |
| DM | 0.0006351 | 0.8975 | 2.34E−04 | 2.34E−04 | 0.1895356 | 0.0015020 | 0.7209 | |

TABLE S10

List of 13 genera associated with CRC status in cohort C1.

| | Control rank mean | Case rank mean | Enrichment (0: case/1: control) | P-value | q-value |
|---|---|---|---|---|---|
| *Parvimonas* | 38.55556 | 83.43243 | 0 | 3.97E−11 | 3.86E−08 |
| *Peptostreptococcus* | 40.55556 | 81.97297 | 0 | 5.49E−10 | 2.67E−07 |
| *Fusobacterium* | 45.51852 | 78.35135 | 0 | 6.90E−07 | 2.24E−04 |
| *Beggiatoa* | 45.89815 | 78.07432 | 0 | 1.78E−06 | 4.34E−04 |
| *Malassezia* | 46.35185 | 77.74324 | 0 | 8.71E−06 | 1.70E−03 |
| *Paracoccus* | 47.66667 | 76.78378 | 0 | 1.10E−05 | 1.79E−03 |
| *Leptotrichia* | 48.15741 | 76.42568 | 0 | 3.40E−05 | 4.74E−03 |
| *Filifactor* | 49.06481 | 75.76351 | 0 | 3.94E−05 | 4.80E−03 |
| *Crenothrix* | 48.76852 | 75.97973 | 0 | 5.14E−05 | 5.57E−03 |
| *Solobacterium* | 47.66667 | 76.78378 | 0 | 8.79E−05 | 8.56E−03 |
| *Sulfurovum* | 49.48148 | 75.45946 | 0 | 1.14E−04 | 9.64E−03 |
| *Eubacterium* | 80.07407 | 53.13514 | 1 | 1.19E−04 | 9.64E−03 |
| *Streptobacillus* | 52.35185 | 73.36486 | 0 | 1.44E−04 | 1.08E−02 |
| *Adhaeribacter* | 77.06481 | 55.33108 | 1 | 4.79E−04 | 3.33E−02 |
| *Moniliophthora* | 49.91667 | 75.14189 | 0 | 6.39E−04 | 4.15E−02 |

TABLE S11

List of phyla significantly associating with CRC status in cohort C1.

| Phylum | Control rank mean | Case rank mean | Enrichment (0: case/1: control) | P-value | q-value |
|---|---|---|---|---|---|
| Fusobacteria | 44.68519 | 78.95946 | 0 | 0.00000014 | 0.000005 |
| Firmicutes | 73.44444 | 57.97297 | 1 | 0.02924627 | 0.259876 |
| Cloacimonetes | 69.25926 | 61.02703 | 1 | 0.03419421 | 0.259876 |

TABLE S12

IMG, mOTU and MLG species markers. IMG, mOTU and MLG species markers identified using random forest method among species associated with CRC (Table S8). Marker species are listed by their importance reported by the method. MLG species identifiers starting with "Con_" are enriched in control samples, and those starting with "CRC_" are enriched in CRC samples.

| | Control rank mean | Case rank mean | Enrichment (0: case/1: control) | P-value | q-value |
|---|---|---|---|---|---|
| *17 IMG species markers* | | | | | |
| *Peptostreptococcus stomatis* | 37.25926 | 84.37838 | 0 | 5.11E-12 | 1.32E-08 |
| *Parvimonas micra* | 38.43519 | 83.52027 | 0 | 4.21E-11 | 5.43E-08 |
| *Parvimonas* sp. oral taxon 393 | 39.81481 | 82.51351 | 0 | 2.79E-10 | 2.40E-07 |
| *Parvimonas* sp. oral taxon 110 | 43.52778 | 79.80405 | 0 | 6.17E-08 | 3.98E-05 |
| *Gemella morbillorum* | 43.87037 | 79.55405 | 0 | 1.53E-07 | 7.88E-05 |
| *Fusobacterium nucleatum* | 45.09259 | 78.66216 | 0 | 3.86E-07 | 1.56E-04 |
| *Leptotrichia buccalis* | 45.60185 | 78.29054 | 0 | 4.44E-07 | 1.56E-04 |
| *Fusobacterium* sp. oral taxon 370 | 45.02778 | 78.70946 | 0 | 4.83E-07 | 1.56E-04 |
| *Burkholderia mallei* | 45.19444 | 78.58784 | 0 | 7.93E-07 | 2.27E-04 |
| *Prevotella intermedia* | 46.47222 | 77.65541 | 0 | 1.92E-06 | 4.95E-04 |
| *Streptococcus dysgalactiae* | 47.06481 | 77.22297 | 0 | 4.18E-06 | 8.99E-04 |
| *Beggiatoa* sp. PS | 46.53704 | 77.60811 | 0 | 5.03E-06 | 9.97E-04 |
| *Malassezia globosa* | 46.35185 | 77.74324 | 0 | 8.71E-06 | 1.60E-03 |
| *Paracoccus denitrificans* | 47.48148 | 76.91892 | 0 | 1.18E-05 | 2.02E-03 |
| *Eubacterium ventriosum* | 80.98148 | 52.47297 | 1 | 1.27E-05 | 2.05E-03 |
| *Filifactor alocis* | 49.06481 | 75.76351 | 0 | 3.94E-05 | 5.65E-03 |
| *Solobacterium moorei* | 47.66667 | 76.78378 | 0 | 8.79E-05 | 9.85E-03 |
| *7 mOTU species markers* | | | | | |
| *Gemella morbillorum* | 47.93518519 | 76.58783784 | 0 | 8.63E-07 | 1.18E-04 |
| *Parvimonas micra* | 46.2962963 | 77.78378378 | 0 | 2.31E-08 | 7.73E-06 |
| *Peptostreptococcus stomatis* | 46.25 | 77.81756757 | 0 | 2.81E-08 | 7.73E-06 |
| motu_linkage_group_316 | 79.61111111 | 53.47297297 | 1 | 7.03E-05 | 3.86E-03 |
| motu_linkage_group_407 | 81.13888889 | 52.35810811 | 1 | 8.51E-06 | 9.34E-04 |
| motu_linkage_group_490 | 80.46296296 | 52.85135135 | 1 | 3.04E-05 | 2.78E-03 |
| motu_linkage_group_624 | 51.01851852 | 74.33783784 | 0 | 1.33E-03 | 3.69E-02 |
| *27 MLG species markers* | | | | | |
| *Parvimonas micra* | 38.40741 | 83.54054 | 0 | 5.56E-12 | 4.84E-10 |
| *Fusobacterium nucleatum* | 40.32407 | 82.14189 | 0 | 1.72E-10 | 7.48E-09 |
| *Solobacterium moorei* | 42.2037 | 80.77027 | 0 | 4.01E-08 | 1.16E-06 |
| *Clostridium symbiosum* | 46.31481 | 77.77027 | 0 | 2.67E-06 | 5.80E-05 |
| Con_10180 | 82.03704 | 51.7027 | 1 | 6.06E-06 | 1.05E-04 |
| CRC_2881 | 51.25926 | 74.16216 | 0 | 7.57E-06 | 1.10E-04 |
| *Coprococcus* sp. ART55/1 | 80.85185 | 52.56757 | 1 | 2.09E-05 | 2.05E-04 |
| *Clostridium hathewayi* | 46.77778 | 77.43243 | 0 | 2.12E-05 | 2.05E-04 |
| *Clostridiales bacterium* 1_7_47FAA | 48.16667 | 76.41892 | 0 | 2.49E-05 | 2.17E-04 |
| CRC4136 | 50.99074 | 74.35811 | 0 | 2.97E-05 | 2.32E-04 |
| butyrate-producing bacterium SS3/4 | 80.57407 | 52.77027 | 1 | 3.19E-05 | 2.32E-04 |
| *Haemophilus parainfluenzae* | 80.49074 | 52.83108 | 1 | 4.18E-05 | 2.69E-04 |
| Con_154 | 80.35185 | 52.93243 | 1 | 4.45E-05 | 2.69E-04 |
| *Bacteroides fragilis* | 49.09259 | 75.74324 | 0 | 5.56E-05 | 3.02E-04 |
| Con_1979 | 79.94444 | 53.22973 | 1 | 6.03E-05 | 3.09E-04 |
| Con_7958 | 75.27778 | 56.63514 | 1 | 7.40E-05 | 3.33E-04 |
| Con_5770 | 79.39815 | 53.62838 | 1 | 7.66E-05 | 3.33E-04 |
| CRC_6481 | 52.09259 | 73.55405 | 0 | 9.87E-05 | 3.90E-04 |
| Con_1987 | 79.42593 | 53.60811 | 1 | 1.17E-04 | 4.23E-04 |
| Con_4595 | 77.21296 | 55.22297 | 1 | 1.38E-04 | 4.81E-04 |
| *Eubacterium biforme* | 74.68519 | 57.06757 | 1 | 3.00E-04 | 8.70E-04 |
| *Desulfovibrio* sp. 6_1_46AFAA | 53.33333 | 72.64865 | 0 | 3.70E-04 | 9.87E-04 |
| *Clostridium citroniae* | 51.71296 | 73.83108 | 0 | 1.08E-03 | 2.19E-03 |
| *Fusobacterium varium* | 54.57407 | 71.74324 | 0 | 1.15E-03 | 2.28E-03 |
| *Roseburia intestinalis* | 76.99074 | 55.38514 | 1 | 2.20E-03 | 3.58E-03 |
| *Dorea formicigenerans* | 52.98148 | 72.90541 | 0 | 4.36E-03 | 5.84E-03 |
| CRC_3579 | 54.05556 | 72.12162 | 0 | 6.09E-03 | 7.46E-03 |

TABLE S13

20 gene markers identified by the mRMR feature selection method in cohort C1. Detailed information regarding their enrichment, occurrence in CRC cases and controls, statistical test of association, taxonomy and identity percentage are listed.

| Marker gene id | Enrichment | Wilcoxon rank-sum test P-value | q-value | Occurrence Control (n = 54) N | Rate (%) | Case (n = 74) N | Rate (%) | Identity | Taxonomy (Blastn to IMG v400) | Description (Blastp to KEGG v59) |
|---|---|---|---|---|---|---|---|---|---|---|
| 2361423 | Case | 2.31E−13 | 4.88E−07 | 11 | 20.37037037 | 62 | 83.78378378 | 93.87 | *Peptostreptococcus anaerobius* | transposase |
| 3173495 | Case | 6.24E−13 | 6.58E−07 | 10 | 18.51851852 | 61 | 82.43243243 | 93.98 | *Peptostreptococcus anaerobius* | transposase |
| 2040133 | Case | 7.51E−10 | 4.06E−04 | 14 | 25.92592593 | 62 | 83.78378378 | 99.4 | *Clostridium symbiosum* | cobalt/nickel transport system permease protein |
| 1696299 | Case | 7.70E−10 | 4.06E−04 | 2 | 3.703703704 | 43 | 58.10810811 | 99.78 | *Parvimonas micra* | DNA-directed RNA polymerase subunit beta |
| 482585 | Case | 7.41E−09 | 1.05E−03 | 16 | 29.62962963 | 58 | 78.37837838 | NA | NA | RNA-directed DNA polymerase |
| 2211919 | Control | 4.98E−08 | 2.20E−03 | 49 | 90.74074074 | 47 | 63.51351351 | 80.99 | *Coprobacillus* sp. 8_2_54BFAA | NA |
| 4171064 | Control | 7.50E−08 | 2.61E−03 | 40 | 74.07407407 | 18 | 24.32432432 | 94.94 | *Faecalibacterium prausnitzii* | cytidine deaminase |
| 1704941 | Case | 7.53E−08 | 2.61E−03 | 2 | 3.703703704 | 39 | 52.7027027 | 99.13 | *Fusobacterium nucleatum* | butyryl-CoA dehydrogenase |
| 3319526 | Control | 1.08E−07 | 2.79E−03 | 32 | 59.25925926 | 10 | 13.51351351 | 90.01 | *Faecalibacterium prausnitzii* | NA |
| 3246804 | Case | 1.80E−07 | 3.24E−03 | 1 | 1.851851852 | 35 | 47.2972973 | NA | NA | citrate-$Mg^{2+}$:$H^+$ or citrate-$Ca^{2+}$:$H^+$ symporter, CitMHS family |
| 3976414 | Control | 4.42E−07 | 4.07E−03 | 30 | 55.55555556 | 9 | 12.16216216 | 87.12 | *Faecalibacterium prausnitzii* | adenosylcobinamide-phosphate synthase CobD |
| 4256106 | Control | 7.39E−07 | 4.53E−03 | 28 | 51.85185185 | 9 | 12.16216216 | NA | NA | integrase/recombinase XerD |
| 3531210 | Control | 1.44E−06 | 5.63E−03 | 13 | 24.07407407 | 0 | 0 | NA | NA | GDP-L-fucose synthase |
| 3611706 | Control | 1.68E−06 | 5.82E−03 | 15 | 27.77777778 | 0 | 0 | NA | NA | anti-repressor protein |
| 2206475 | Control | 1.81E−06 | 5.95E−03 | 28 | 51.85185185 | 9 | 12.16216216 | 98.59 | *Eubacterium ventriosum* | beta-glucosidase |
| 181682 | Control | 1.95E−06 | 6.09E−03 | 34 | 62.96296296 | 15 | 20.27027027 | 99.25 | *Roseburia intestinalis* | NA |
| 1804565 | Control | 2.03E−06 | 6.16E−03 | 22 | 40.74074074 | 4 | 5.405405405 | NA | NA | branched-chain amino acid transport system ATP-binding protein |
| 2736705 | Case | 5.71E−06 | 8.55E−03 | 2 | 3.703703704 | 32 | 43.24324324 | 99.68 | *Clostridium hathewayi* | NA |
| 1559769 | Control | 1.03E−05 | 1.04E−02 | 27 | 50 | 7 | 9.459459459 | 88.65 | *Coprococcus catus* | polar amino acid transport system substrate-binding protein |
| 370640 | Control | 2.64E−05 | 1.47E−02 | 14 | 25.92592593 | 0 | 0 | 99.4 | *Bacteroides clarus* | NA |

TABLE S14

PERMANOVA analysis of variation in 20 CRC-associated gene markers in cohort C1. CRC status and stage explain the variation in these gene profiles, while fasting blood glucose (FBG) moderately explains the variation. See Table S4 for explanation of parameters in column 1.

| Parameter | Df | SumsOfSqs | MeanSqs | F.Model | $R^2$ | Pr (>F) | q-value |
|---|---|---|---|---|---|---|---|
| CRC Status | 1 | 5.5793661 | 5.5793661 | 16.626711 | 0.116575 | 0.0001 | 0.00095 |
| Stage of CRC | 4 | 6.7812635 | 1.6953159 | 5.0761083 | 0.1416874 | 0.0001 | 0.00095 |
| FBG | 1 | 0.8119553 | 0.8119553 | 2.154786 | 0.0215146 | 0.0073 | 0.046233 |
| Fecal sampling before or after colonoscopy | 1 | 0.5473702 | 0.5473702 | 1.4588296 | 0.011536 | 0.0978 | 0.46455 |
| Lesion location | 1 | 0.500106 | 0.500106 | 1.4185104 | 0.0220202 | 0.1329 | 0.486163 |
| Lesion specific location | 7 | 2.7831853 | 0.3975979 | 1.1372468 | 0.1225468 | 0.1889 | 0.486163 |
| HDL | 1 | 0.4718905 | 0.4718905 | 1.2480119 | 0.0123263 | 0.203 | 0.486163 |
| ALT/GPT | 1 | 0.4650084 | 0.4650084 | 1.2366953 | 0.0115324 | 0.2047 | 0.486163 |
| Duration between colonoscopy and fecal sample collection | 1 | 0.4170429 | 0.4170429 | 1.1084063 | 0.0087893 | 0.3116 | 0.657822 |
| Age | 1 | 0.3976816 | 0.3976816 | 1.0557238 | 0.0083091 | 0.3669 | 0.676838 |
| TCHO | 1 | 0.3768657 | 0.3768657 | 0.9942006 | 0.0098441 | 0.4287 | 0.676838 |

TABLE S14-continued

PERMANOVA analysis of variation in 20 CRC-associated gene markers in cohort C1. CRC status and stage explain the variation in these gene profiles, while fasting blood glucose (FBG) moderately explains the variation. See Table S4 for explanation of parameters in column 1.

| Parameter | Df | SumsOfSqs | MeanSqs | F.Model | $R^2$ | Pr (>F) | q-value |
|---|---|---|---|---|---|---|---|
| DM | 1 | 0.3653642 | 0.3653642 | 0.9692711 | 0.0076339 | 0.4617 | 0.676838 |
| BMI | 1 | 0.3660728 | 0.3660728 | 0.9708139 | 0.0077067 | 0.4631 | 0.676838 |
| Cr | 1 | 0.3412225 | 0.3412225 | 0.8963725 | 0.0084646 | 0.5617 | 0.719847 |
| TNM | 15 | 5.2686733 | 0.3512449 | 0.9797038 | 0.2021521 | 0.5683 | 0.719847 |
| LDL | 1 | 0.308397 | 0.308397 | 0.8136124 | 0.0080705 | 0.6624 | 0.741782 |
| Gender | 1 | 0.3092058 | 0.3092058 | 0.8193202 | 0.0064605 | 0.6637 | 0.741782 |
| TG | 1 | 0.291975 | 0.291975 | 0.7695216 | 0.0076365 | 0.7334 | 0.774144 |
| eGFR | 1 | 0.2043621 | 0.2043621 | 0.539403 | 0.0050159 | 0.9496 | 0.9496 |

TABLE S15

CRC index estimated in cohort C1, a type 2 diabetes (T2D) cohort and an inflammatory bowel disease (IBD) cohort.

| Cohort/group | Median CRC index | Comparison with C1 patients | |
|---|---|---|---|
| | | P-value | q-value |
| C1 patients | 7.30636 | NA | NA |
| C1 controls | −5.558923 | 3.91E−21 | 4.89E−21 |
| T2D patients | 0.2512602 | 1.71E−26 | 2.85E−26 |
| T2D controls | −1.47849 | 2.00E−30 | 1.00E−29 |
| IBD patients | −1.789305 | 6.00E−11 | 6.00E−11 |
| IBD controls | −4.505388 | 1.27E−28 | 3.16E−28 |

TABLE S16

Baseline characteristics of the Chinese cohort C2 consisting 47 CRC patients and 109 control individuals. For quantitative traits, the median, minimum and maximum are shown.

| Parameter | Controls (n = 109) | Cases (n = 47) | P-value | q-value |
|---|---|---|---|---|
| Age | 58 (43, 68) | 69 (48, 90) | 3.146E−06[†] | 1.363E−05 |
| Gender (M:F) | 40:69 | 25:22 | 0.07626[‡] | 0.1824 |
| BMI | 23.02 (18.59, 30.8) | 20.94 (15.83, 31.68) | 0.7098[†] | 0.7098 |
| Stage of CRC (1:2:3:4) | n.a | 4:24:15:4 | n.a | n.a |
| Distribution of detailed TNM stages (T1N0:T3N0:T1N1:T3N1:T3N2:T4N1:T2N1M1:T3N1M1:T3N2M1:UT4:Mx) | n.a | 4:23:1:9:4:1:1:1:1:1:1 | n.a | n.a |
| Leison location (1:2:NA) | n.a | 9:20:18 | n.a | n.a |
| Leison specific location (2:3:4:6:7:8:9:NA) | n.a | 3:3:3:2:7:4:7:18 | n.a | n.a |
| Fecal sampling before or after colonoscopy (before:after) | 101:8 (93%:7%) | 9:38 (19%:81%) | 6.1669E−20[‡] | 8.017E−19 |
| Duration between colonoscopy and fecal sample collection (days) | −63 (−202, 92) | 18 (−58, 239) | 4.064E−14[†] | 2.642E−13 |
| Duration of frozen storage of fecal samples (days) | 374 (93, 3526) | 297 (30, 3450) | 0.2086[†] | 0.3390 |
| FBG | 5 (4.5, 6.3) | 5.6 (4.5, 7.9) | 0.0842[†] | 0.1824 |
| TCHO | 5.2 (3.8, 5.9) | 4.3 (3.6, 5.3) | 0.0769[†] | 0.1824 |
| LDL | 2.9 (2, 4.2) | 2.5 (2.3, 3.6) | 0.6241[†] | 0.6761 |
| HDL | 1.66 (1, 2.03) | 1.3 (0.9, 2.6) | 0.2822[†] | 0.4076 |
| TG | 0.9 (0.7, 2.08) | 0.8 (0.5, 1.9) | 0.4680[†] | 0.6084 |
| Cr | 74 (58, 129) | 70 (44, 122) | 0.5484[†] | 0.6481 |
| ALT/GPT | 20 (14, 68) | 13 (10, 36) | 0.1043[†] | 0.1937 |

FBG: fasting blood glucose;
ALT/GPT: alanine transaminase/glutamate pyruvated transaminase;
BMI: body mass index;
DM: diabetes mellitus type 2;
HDL: high density lipoprotein;
TG: triglyceride;
eGFR: epidermal growth factor receptor;
TCHO: total cholesterol;
Cr: creatinine;
LDL: low density lipoprotein;
TNM: tumor node metastasis staging system;
Statistical tests used for identifying associations between metadata and CRC:
[†]Wilcoxon test,
[‡]Fisher's exact test.

TABLE S17

Enrichment of two CRC-enriched and two control-enriched genes measured by qPCR in cohort C2.

| Marker gene ID | Gene description | Enrichment | Wilcoxon rank-sum test P-value | Wilcoxon rank-sum test stratified for colonoscopy | Mantel Haenszel Odds Ratio, adjusted for colonoscopy (95% CI) | Mantel Haenszel test P-value |
|---|---|---|---|---|---|---|
| 1704941 | butyryl-CoA dehydrogenase | case | 1.97E−09 | 1.52E−03 | 18.54 (2.62-131) | 0.00509 |
| 482585 | RNA-directed DNA polymerase | case | 2.34E−03 | 4.55E−02 | 1.815 (0.653-5.05) | 0.38 |
| 181682 | gene with unknown function from *Roseburia intestinalis* | control | 2.15E−01 | 3.13E−01 | 1.495 (0.456-4.9) | 0.714 |
| 370640 | gene with unknown function from *Bacteroides clarus* | control | 3.11E−01 | 6.30E−01 | 1.647 (0.395-6.88) | 0.778 |

TABLE S18

Baseline characteristics of the Danish cohort (cohort D) consisting 16 CRC patients and 24 control individuals. For quantitative traits, the median, minimum and maximum are shown.

| Parameter | Control (n = 24) | Case (n = 16) | P-value | q-value |
|---|---|---|---|---|
| Age | 65.5 (30, 87) | 67.5 (47, 78) | 0.4308219[†] | 0.6376 |
| Gender (M:F) | 07:17 | 10:06 | 0.05309[‡] | 0.15927 |
| BMI | 25.88 (18.94, 35.29) | 25.89 (18.83, 33.20) | 0.6328136[†] | 0.6376 |
| DM (YES:NO) | 03:21 | 01:15 | 0.6376[‡] | 0.6376 |
| Stage of CRC (1:2:3:4) | n.a | 1:9:5:1 | n.a | n.a |
| Distribution of detailed TNM stages (T1N0M0V0:T3N0M0V0:T3N0M0V1:T3N1M0V0:T3N2M0V0:T4N0M0:T4N2M0V1:T4NxMx) | n.a | 1:6:3:1:2:1:1:1 | n.a | n.a |
| Cancer location (Distal:Proximal) | n.a | 13:03 | n.a | n.a |
| Cancer location (Adenocarcinom:Ascendens:Coecum:Rectum:Sigmoideum:Transversum) | n.a | 1:1:1:9:3:1 | n.a | n.a |
| Fecal sampling before or after colonoscopy (before:after) | 24:0 (100%:0%) | 12:4 (75%:25%) | 0.0199[‡] | 0.1194 |
| Duration between colonoscopy and fecal sample collection (days) | 7 (3, 89) | 14 (−24, 252) | 0.4466[†] | 0.6376 |

BMI: body mass index;
DM: diabetes mellitus type 2;
TNM: tumor node metastasis staging system;
Statistical tests used for identifying associations between metadata and CRC:
[†]Wilcoxon test,
[‡]Fisher's exact test.

TABLE S19

Community structure differences between cohorts C1 and D.
All comparisons were performed using Wilcoxon rank-sum test.

| | Gene count P-value | | | | Shannon index P-value | | | |
|---|---|---|---|---|---|---|---|---|
| | D: Case | D: Control | C2: Case | C2: Control | D: Case | D: Control | C2: Case | C2: Control |
| D: Case | | 0.25991847 | 1.94E−05 | 0.000294527 | | 0.772788361 | 5.84639E−05 | 4.02E−04 |
| D: Control | | | 7.86E−05 | 0.001729823 | | | 2.25586E−05 | 9.34E−04 |
| C2: Case | | | | 0.212812929 | | | | 0.178412749 |

TABLE S20

Species annotation of the 1498 genes enriched in CRC patient microbiomes, both in cohort C1 and cohort D. A large fraction was annotated to *Parvimonas micra*. Annotated species with more than 10 genes are listed here.

| Species | Gene numbers (Total = 1452) |
|---|---|
| *Parvimonas micra* | 389 |
| *Solobacterium moorei* | 204 |
| *Clostridium symbiosum* | 177 |
| *Clostridium* sp. 7_3_54FAA | 108 |
| *Parvimonas* sp. oral taxon 110 | 93 |
| *Parvimonas* sp. oral taxon 393 | 93 |

TABLE S20-continued

Species annotation of the 1498 genes enriched in CRC patient microbiomes, both in cohort C1 and cohort D. A large fraction was annotated to *Parvimonas micra*. Annotated species with more than 10 genes are listed here.

| Species | Gene numbers (Total = 1452) |
|---|---|
| *Fusobacterium nucleatum* | 64 |
| *Peptostreptococcus stomatis* | 23 |
| *Clostridium hathewayi* | 17 |
| *Clostridium citroniae* | 14 |
| *Akkermansia muciniphila* | 11 |
| *[Clostridium] difficile* | 11 |
| *Peptostreptococcus anaerobius* | 10 |

TABLE S21

List of CRC-associated species predicted from Chinese cohort C1 and validated in Danish cohort D with q < 0.05

| | Control rank mean | Case rank mean | Enrichment (0: case/1: control) | P-value | q-value |
|---|---|---|---|---|---|
| IMG species validated in cohort D | | | | | |
| *Parvimonas* sp. oral taxon 110 | 14.54166667 | 29.4375 | 0 | 9.06E−05 | 0.000808962 |
| *Parvimonas* sp. oral taxon 393 | 14.66666667 | 29.25 | 0 | 0.000127394 | 0.000808962 |
| *Parvimonas micra* | 14.70833333 | 29.1875 | 0 | 0.00015168 | 0.000808962 |
| *Gemella morbillorum* | 15.70833333 | 27.6875 | 0 | 0.001465743 | 0.005862972 |
| *Peptostreptococcus stomatis* | 16.16666667 | 27 | 0 | 0.003409134 | 0.010909228 |
| *Fusobacterium* sp. oral taxon 370 | 16.58333333 | 26.375 | 0 | 0.010235287 | 0.024739601 |
| *Fusobacterium nucleatum* | 16.70833333 | 26.1875 | 0 | 0.010823576 | 0.024739601 |
| *Malassezia globosa* | 17 | 25.75 | 0 | 0.023703729 | 0.047407459 |
| mOTU species validated in cohort D | | | | | |
| *Peptostreptococcus stomatis* | 16.5 | 26.5 | 0 | 0.000139835 | 0.000978842 |
| *Parvimonas micra* | 16.70833333 | 26.1875 | 0 | 0.000749378 | 0.002622823 |
| *Gemella morbillorum* | 18 | 24.25 | 0 | 0.004603221 | 0.010740848 |

| | Control rank mean | Case rank mean | Enrichment (1: case/0: control) | P-value | q-value |
|---|---|---|---|---|---|
| MLG species validated in cohort D | | | | | |
| *Parvimonas micra* | 15.20833333 | 28.4375 | 0 | 9.13E−05 | 0.002329351 |
| *Solobacterium moorei* | 16.22916667 | 26.90625 | 0 | 0.000172545 | 0.002329351 |

TABLE S22

List of four gene markers predicted from cohort C1 that show significant associations in cohort D with q < 0.05.

| Gene Marker ID | Cohort C1 | | | Cohort D | | | Blastn on IMG v400 | Blastp on KEGG v59 | |
|---|---|---|---|---|---|---|---|---|---|
| | P-value | q-value | Enrich | P-value | q-value | Enrich | Species taxonomy | KEGG ID | Gene annotation |
| 2361423 | 2.31148E−13 | 4.87836E−07 | case | 1.16E−04 | 0.00116 | case | *Peptostreptococcus anaerobius* | K07485 | transposase |
| 3173495 | 6.23501E−13 | 6.57946E−07 | case | 1.85E−04 | 0.00123 | case | *Peptostreptococcus anaerobius* | K07485 | transposase |
| 1696299 | 7.69646E−10 | 0.000406082 | case | 7.87E−05 | 0.00116 | case | *Parvimonas micra* | K03043 | DNA-directed RNA polymerase subunit beta |
| 1704941 | 7.53342E−08 | 0.002606428 | case | 2.08E−03 | 0.01040 | case | *Fusobacterium nucleatum* | K00248 | butyryl-CoA dehydrogenase |

TABLE S23

PERMANOVA analysis of variation in four gene markers validated in cohort D
(No. of permutations = 9999). CRC status explains the variation in these gene profiles.

| phenotype | Df | Sums Of Sqs | Mean Sqs | F.Model | $R^2$ | Pr (>F) |
|---|---|---|---|---|---|---|
| CRC Status | 1 | 8.11E−11 | 8.11E−11 | 4.8910108 | 0.1140335 | 0.0001 |
| Stage of CRC | 4 | 1.15E−10 | 2.86E−11 | 1.6816488 | 0.1612064 | 0.1375 |
| Duration between colonoscopy and fecal sample collection | 1 | 2.03E−11 | 2.03E−11 | 1.1199259 | 0.028628 | 0.2265 |
| Cancer location (Distal:Proximal) | 1 | 5.20E−11 | 5.20E−11 | 1.2648699 | 0.0828615 | 0.2383 |
| Cancer location(Adenocarcinom:Ascendens:Coecum:Rectum:Sigmoideum:Transversum) | 5 | 3.12E−10 | 6.24E−11 | 1.9756046 | 0.4969319 | 0.2998 |
| Age | 1 | 1.48E−11 | 1.48E−11 | 0.8097989 | 0.0208658 | 0.3989 |
| DM | 1 | 5.61E−12 | 5.61E−12 | 0.3020817 | 0.0078868 | 0.5654 |
| Gender | 1 | 6.48E−12 | 6.48E−12 | 0.3495622 | 0.0091152 | 0.571 |
| BMI | 1 | 7.51E−12 | 7.51E−12 | 0.4060178 | 0.0105717 | 0.5869 |
| DNA purification date | 1 | 3.66E−12 | 3.66E−12 | 0.1966498 | 0.0051484 | 0.6696 |
| Fecal sampling before or after colonoscopy | 1 | 6.95E−12 | 6.95E−12 | 0.3749813 | 0.0097715 | 0.6878 |
| TNM | 7 | 1.57E−10 | 2.25E−11 | 0.3823119 | 0.2506686 | 0.7061 |

TABLE S24

Enrichment of four marker genes in published Austrian and French cohorts (A and F, respectively).

| Marker Gene ID | Cohort A | | | Cohort F | | | Blastn on IMG v400 | Blastp on KEGG v59 | |
|---|---|---|---|---|---|---|---|---|---|
| | P-value | q-value | Enrich | P-value | q-value | Enrich | Species taxonomy | KEGG ID | Gene annotation |
| 2361423 | 9.465681e−06 | 3.786272e−05 | case | 1.805948e−06 | 7.223791e−06 | case | *Peptostreptococcus anaerobius* | K07485 | transposase |
| 3173495 | 1.021888e−04 | 3.065663e−04 | case | 1.311802e−05 | 3.935405e−05 | case | *Peptostreptococcus anaerobius* | K07485 | transposase |
| 1696299 | 3.089198e−03 | 3.089198e−03 | case | 3.471676e−03 | 3.471676e−03 | case | *Parvimonas micra* | K03043 | DNA-directed RNA polymerase subunit beta |
| 1704941 | 5.007540e−04 | 1.001508e−03 | case | 9.687230e−05 | 1.937446e−04 | case | *Fusobacterium nucleatum* | K00248 | butyryl-CoA dehydrogenase |

TABLE S25

Comparison of enrichment of 20 marker genes in Chinese (C1), Danish (D), Austrian (A) and French (F) cohorts.
Cells marked in red: P < 0.05. Enrichment in case or control is only reported when P < 0.2. Only cohort
C1 was used to discover gene biomarkers, and these 20 genes were among the 102,514 that associated with
CRC. In cohorts D, A and F, association of only these 20 genes were verified.

| | Chinese cohort C1 Case (1) Vs. Controls (0) | | Danish cohort D Case (1) Vs. Controls (0) | | Austrian cohort A Carcinoma (1) Vs Controls (0) | | French cohort F Case (1) Vs. Controls (0) | |
|---|---|---|---|---|---|---|---|---|
| Gene id | p. value | Enrichment | p. value | Enrichment | p. value | Enrichment | p. value | Enrichment |
| 181682 | 1.95E−06 | 0 | 0.900619951 | NA | 0.678813728 | NA | 0.007181249 | 0 |
| 370640 | 2.64E−05 | 0 | 0.495680726 | NA | 0.862554181 | NA | 0.901689843 | NA |
| 482585 | 7.41E−09 | 1 | 0.467868103 | NA | 0.114070684 | 1 | 0.09202366 | 1 |
| 1559769 | 1.03E−05 | 0 | 0.627103852 | NA | 0.613815329 | NA | 0.318983729 | NA |
| 1696299 | 7.70E−10 | 1 | 7.87E−05 | 1 | 0.003089198 | 1 | 0.003471676 | 1 |
| 1704941 | 7.53E−08 | 1 | 0.002080194 | 1 | 0.000500754 | 1 | 9.68723E−05 | 1 |
| 1804565 | 2.03E−06 | 0 | 0.345063544 | NA | 0.719304711 | NA | 1 | NA |
| 2040133 | 7.51E−10 | 1 | 0.923193148 | NA | 0.037408072 | 1 | 0.3620777 | NA |
| 2206475 | 1.81E−06 | 0 | 0.559844892 | NA | 0.239405355 | NA | 0.086939707 | 0 |
| 2211919 | 4.98E−08 | 0 | 0.343905238 | NA | 0.8730299 | NA | 0.403859093 | NA |
| 2361423 | 2.31E−13 | 1 | 0.000116036 | 1 | 9.46568E−06 | 1 | 1.80595E−06 | 1 |
| 2736705 | 5.71E−06 | 1 | 0.653175645 | NA | 0.085244448 | NA | 0.321243655 | NA |
| 3173495 | 6.24E−13 | 1 | 0.00018455 | 1 | 0.000102189 | 1 | 1.3118E−05 | 1 |
| 3246804 | 1.80E−07 | 1 | 0.586270986 | NA | 0.834009147 | NA | 0.893668207 | NA |
| 3319526 | 1.08E−07 | 0 | 0.646619859 | NA | 0.847882874 | NA | 0.085059441 | 0 |
| 3531210 | 1.44E−06 | 0 | 0.23124459 | NA | 0.014329165 | 1 | 0.142060944 | 0 |
| 3611706 | 1.68E−06 | 0 | 1 | NA | 0.889823764 | NA | 0.346149329 | NA |
| 3976414 | 4.42E−07 | 0 | 0.539082044 | NA | 0.748143815 | NA | 0.458758072 | NA |

TABLE S25-continued

Comparison of enrichment of 20 marker genes in Chinese (C1), Danish (D), Austrian (A) and French (F) cohorts. Cells marked in red: P < 0.05. Enrichment in case or control is only reported when P < 0.2. Only cohort C1 was used to discover gene biomarkers, and these 20 genes were among the 102,514 that associated with CRC. In cohorts D, A and F, association of only these 20 genes were verified.

| | Chinese cohort C1 Case (1) Vs. Controls (0) | | Danish cohort D Case (1) Vs. Controls (0) | | Austrian cohort A Carcinoma (1) Vs Controls (0) | | French cohort F Case (1) Vs. Controls (0) | |
|---|---|---|---|---|---|---|---|---|
| Gene id | p. value | Enrichment | p. value | Enrichment | p. value | Enrichment | p. value | Enrichment |
| 4171064 | 7.50E−08 | 0 | 0.705131044 | NA | 0.171937649 | 1 | 0.081938362 | 0 |
| 4256106 | 7.39E−07 | 0 | 0.702861448 | NA | 0.05048434 | 1 | 0.880361689 | NA |

TABLE S26

Classification accuracy of the two marker genes measured by qPCR in cohort C2, stratified into early (I-II) and late (III-IV) stage cancer.

| Group | Marker ID | Enrichment | Wilcox rank-sum test, P-value | Wilcoxon rank-sum test stratified for colonoscopy, P-value | Mantel Haenszel Odds Ratio adjusted for colonoscopy (95% CI) | Mantel-Haenszel test P-value |
|---|---|---|---|---|---|---|
| Stages I and II | 1696299 | case | 6.51E-14 | 3.35E-06 | 21.5 (3.18-146) | 1.38E-05 |
| | 1704941 | case | 4.15E-07 | 0.008654411 | 27.77 (1.64-469) | 0.0322 |
| | 1696299 or 1704941 | | N.A. | N.A. | 33.37 (4.49-248) | 1.68E-06 |
| Stages III and IV | 1696299 | case | 1.51E-11 | 0.00027574 | 15.44 (3.06-77.9) | 0.00109 |
| | 1704941 | case | 4.40E-09 | 0.002700628 | 25.34 (2.91-221) | 0.00842 |
| | 1696299 or 1704941 | | N.A. | N.A. | 15.77 (3.52-70.6) | 0.000653 |

TABLE S27

Primer and probe sequences for qPCR measurement of five gene markers and controls.

| Gene | Sequence type | SEQ ID NO: | Nucleotide sequence |
|---|---|---|---|
| 1696299 | Forward | 30 | AAGAATGGAGAGAGTTGTTAGAGAAAGAA |
| | Reverse | 31 | TTGTGATAATTGTGAAGAACCGAAGA |
| | Probe | 32 | AACTCAAGATCCAGACCTTGCTACGCCTCA |
| 1704941 | Forward | 33 | TTGTAAGTGCTGGTAAAGGGATTG |
| | Reverse | 34 | CATTCCTACATAACGGTCAAGAGGTA |
| | Probe | 35 | AGCTTCTATTGGTTCTTCTCGTCCAGTGGC |
| 181682 | Forward | 21 | CGGATTTGCAGTGGCAAGTT |
| | Reverse | 22 | TGATTGCAGACGCCAATGTC |
| | Probe | 23 | CGTGAAAAATCCGCGCATCTGGC |
| 370640 | Forward | 24 | TCCATCCGCAAGCCTTTACT |
| | Reverse | 25 | GCTTCCGGTGCCATTGACTA |
| | Probe | 26 | TTCATCATCACAGCCGACAACGCA |
| 482585 | Forward | 27 | AATGGGAATGGAGCGGATTC |
| | Reverse | 28 | CCTGCACCAGCTTATCGTCAA |
| | Probe | 29 | AAGCCTGCGGAACCACAGTTACCAGC |
| control | Forward | 87 | CGTCAGCTCGTGTCGTGAG |
| | Reverse | 88 | CGTCGTCCCCACCTTCC |
| | Probe | 89 | TTAAGTCCCACAACGAGCGCAACCC |

Example 2: Use of *Bacteroides clarus, Roseburia Intestinalis, Clostridium Hathewayi*, M7, and *Fusobacterium nucleatum* as Fecal Markers for CRC Gut microbiota is an important etiological factor in the development of colorectal cancer (CRC). The objective of this study is to evaluate the utility of newly identified fecal bacterial marker candidates by metagenome sequencing for CRC diagnosis. In this study, the abundances of five bacteria were quantified in fecal samples of 439 subjects (203 CRC and 236 healthy subjects) from two independent cohorts by duplex quantitative PCR (qPCR) assays. Candidates identified by metagenome sequencing, including *Fusobacterium nucleatum* (Fn), *Bacteroides clarus* (Bc), *Roseburia intestinalis* (Ri), *Clostridium hathewayi* (Ch), and one undefined species (labeled as m7), were examined in fecal samples of 203 CRC patients and 236 healthy controls by duplex-qPCR. Strong positive correlations were demonstrated between the quantification of each candidate by the qPCR assays and metagenomics approach (r=0.801~0.934, all P<0.0001). Among the five candidates, Fn abundance was predominantly higher in CRC than controls (P<0.0001), with area under receiver operating curve (AUROC) of 0.868 (P<0.0001). At the best cutoff value, Fn discriminated CRC from controls with a sensitivity of 77.7%, and specificity of 79.5% in cohort I. Simple linear combination of four bacteria (Fn, Bc, Ch and m7) showed an improved diagnostic ability compared to Fn alone (AUROC=0.886, P<0.0001) in cohort I. These findings were also confirmed in an independent cohort II. In particular, improved diagnostic performances of Fn alone (sensitivity 92.8%, specificity 79.8%) and four-bacteria (sensitivity 92.8%, specificity 81.5%) were achieved in combination with fecal immunochemical test (FIT) for the detection of CRC. In summary, this study provides evidence that stool-based CRC-associated bacteria can serve as novel non-invasive diagnostic biomarkers for CRC.

Introduction

Colorectal cancer (CRC) is one of the most common malignancies worldwide. Many Asian countries including China have experienced a 2 to 4-fold increase in CRC incidence during the past decade (1). Abnormality in the composition of the gut microbiota has been implicated as a potentially important etiological factor in the initiation and progression of CRC (2). With the widespread application of metagenome sequencing and pyrosequencing in the investigation of intestinal microbiota, an increasing number of bacteria have been identified to be positively associated with the incidence of CRC (3-7). Recent studies have shown that *Fusobacterium*, especially Fusobacteriumnucleatum (Fn), is associated with CRC. Fn is enriched in both the feces and colonic mucosa of CRC patients (3, 5, 8) and plays important roles in colorectal carcinogenesis (9, 10). In a recent study using 16SrRNA sequencing to catalogue the microbial communities in human gut mucosa at different stages of colorectal tumorigenesis, *Fusobacterium* was also found to be enriched in colorectal tumors (11). Then by using metagenomics analysis to compare the fecal microbiome of 74 CRC patients and 54 healthy subjects, the inventors have identified bacterial candidates that may serve as non-invasive biomarkers for CRC (12), including Fn, *Bacteroides clarus* (Bc), *Roseburia intestinalis* (Ri), *Clostridium hathewayi* (Ch), one undefined species (labeled as m7). Unlike Fn, the other bacteria have not yet been associated with CRC. Moreover, the translational application of these bacterial candidates into diagnostic biomarkers needs further investigation using simple, cost-effective and targeted methods such as quantitative PCR (qPCR).

In this study, the stool-based bacterial candidate markers were validated in a large cohort of 203 CRC patients and 236 control subjects to identify a panel of markers with good sensitivity and specificity as a novel diagnostic tool for CRC. The inventors established probe-based duplex qPCR assays for the quantification of the bacteria; the technique involved is easy and less costly to perform compared with the currently available tests.

Methods

Human Fecal Sample Collection

Fecal samples (n=439) were collected from the two independent cohorts, including cohort I-Hong Kong: 370 subjects, consisting of 170 patients with CRC (mean age, 67.2±11.6 years; 100 males and 70 females) and 200 normal controls (59.3±5.8 years; 77 males and 123 females), at the Prince of Wales Hospital, the Chinese University of Hong Kong between 2009 and 2013 (Table 6), and cohort II-Shanghai: 69 subjects, consisting of 33 patients with CRC (mean age, 63.4±9.6 years; 17 males and 16 females) and 36 normal controls (53.2±12.2 years; 10 males and 26 females), at Renji Hospital, Shanghai Jiaotong University between 2014 and 2015 (Table 6). Subjects recruited for fecal sample collection included individuals presenting symptoms such as change of bowel habit, rectal bleeding, abdominal pain or anaemia, and asymptomatic individuals aged 50 or above undergoing screening colonoscopy as in our previous metagenomics study (12). Samples were collected before or one month after colonoscopy, when gut microbiome should have recovered to baseline (13). The exclusion criteria were: 1) use of antibiotics within the past 3 months; 2) on a vegetarian diet; 3) had an invasive medical intervention within the past 3 months; 4) had a past history of any cancer, or inflammatory disease of the intestine. Subjects were asked to collect stool samples in standardized containers at home, and store the samples in their home −20° C. freezer immediately. Frozen samples were then delivered to the hospitals in insulating polystyrene foam containers and stored at −80° C. immediately until further analysis. Patients were diagnosed by colonoscopic examination and histopathological review of any biopsies taken. Informed consents were obtained from all subjects. The study was approved by the Clinical Research Ethics Committee of the Chinese University of Hong Kong and the Ethics Committee of Renji Hospital, Shanghai Jiaotong University.

DNA Extraction

Fecal samples were thawed on ice and DNA extraction was performed using the QIAamp DNA Stool Mini Kit according to manufacturer's instructions (Qiagen, Hilden, Germany). Extracts were then treated with DNase-free RNase to eliminate RNA contamination. DNA quality and quantity were determined using a NanoDrop2000 spectrophotometer (Thermo Fisher Scientific, Wilmington, Del.).

Design of Primers and Probes

Primer and probe sequences for the internal control were designed manually on the basis of the conservative fragments in bacterial 16S rRNA genes (14), and then they were tested using the tool PrimerExpress v3.0 (Applied Biosystems, Foster City, Calif.) for determination of Tm, GC content and possible secondary structures. Degenerate sites were included in the primers and probes to increase target coverage; Degenerate sites were not close to 3' ends of primers and 5' end of the probes. Amplicon target was nt1063-1193 of the corresponding *E. coli* genome.

Five bacterial marker candidates identified by previous metagenome sequencing were selected for qPCR quantification, including *F. nucleatum* (Fn), B. *clarus* (Bc), *R. intestinalis* (Ri), *C. hathewayi* (Ch), one undefined species (labeled as m7) (Table 7). These candidates were identified by eliminating confounding effects of colonoscopy using blocked independent Wilcoxon rank-sum tests with colonoscopy as a stratifying factor in one previous metagenome study (12). Fn has also been identified to be enriched in CRC patients by others (3, 5, 8), while the other four have not associated with CRC by other researchers. Primer and probe sequences targeting the nusG gene of Fn (Accession#GMHS-1916) and gene markers identified by our previous metagenome sequencing study, including Bc (ID m370640), Ch (ID m2736705), Ri (ID m181682) and m7(ID m3246804) (12), were designed using PrimerExpress. The primer-probe sets specifically detect the intended targets and not any other known sequences, as confirmed by Blast search. Each probe carried a 5' reporter dye FAM (6-carboxy fluorescein) or VIC (4,7,2'-trichloro-7'-phenyl-6-carboxyfluorescein) and a 3' quencher dye TAMRA (6-carboxytetramethyl-rhodamine). Primers and hydrolysis probes were synthesized by Invitrogen (Carlsbad, Calif.). Nucleotide sequences of the primers and probes are listed in Table 8. PCR amplification specificity was confirmed by direct Sanger sequencing of the PCR products or by sequencing randomly picked TA clones.

Quantitative PCR (qPCR)

qPCR amplifications were performed in a 20 μL reaction system of TaqMan Universal Master Mix II (Applied Biosystems) containing 0.3 μM of each primer and 0.2 μM of each probe in MicroAmp fast optical 96-well reaction plates (Applied Biosystems) with adhesive sealing. Thermal cycler parameters, of an ABI PRISM 7900HT sequence detection system, were 95° C. 10 min and (95° C. 15 s, 60° C. 1 min)×45 cycles. A positive/reference control and a negative control (H$_2$O as template) were included within every experiment. Measurements were performed in triplicates for each sample. qPCR data was analyzed using the Sequence Detection Software (Applied Biosystems) with manual settings of Threshold=0.05 and Baseline from 3-15 cycles for all clinical samples. Experiments were disqualified if their negative control Cq value was <42. Data analysis was carried out according to the ΔCq method, with $\Delta Cq = Cq_{target} - Cq_{control}$ and abundances=POWER (2, −ΔCq).

Fecal Immunochemical Test (FIT)

The HemoSure immunogold labeling FIT dipsticks (WHPM Co. Ltd, Beijing, China), which are certified by the State Food and Drug Administration of China, were used as previously described (15).

Statistical Analysis

Values were all expressed as mean±SD or median (interquartile range [IQR]) as appropriate. The differences in specific bacterial abundance were determined by Wilcoxon signed-rank test or Mann-Whitney U test. Continuous clinical and pathological variables were compared by T-test, whilst categorical variables were compared by Chi-square test. Spearman's correlation coefficient was used to estimate the association of the bacterial abundances and several factors of interest. Factors independently associated with CRC diagnosis were estimated using univariate and multivariate linear regression. Receiver Operating Characteristic (ROC) curve was used to evaluate the diagnostic value of bacterial candidates in distinguishing CRC. Logistic regression model was applied to obtain probability plot values for estimating the incidence of CRC among all subjects. ROC curves were then constructed for the logistic regression models. All tests were done by Graphpad Prism 5.0 (Graphpad Software Inc., San Diego, Calif.) or SPSS software v17.0 (SPSS, Chicago, Ill.). $P<0.05$ was taken as statistical significance.

Results

Figure 4A:
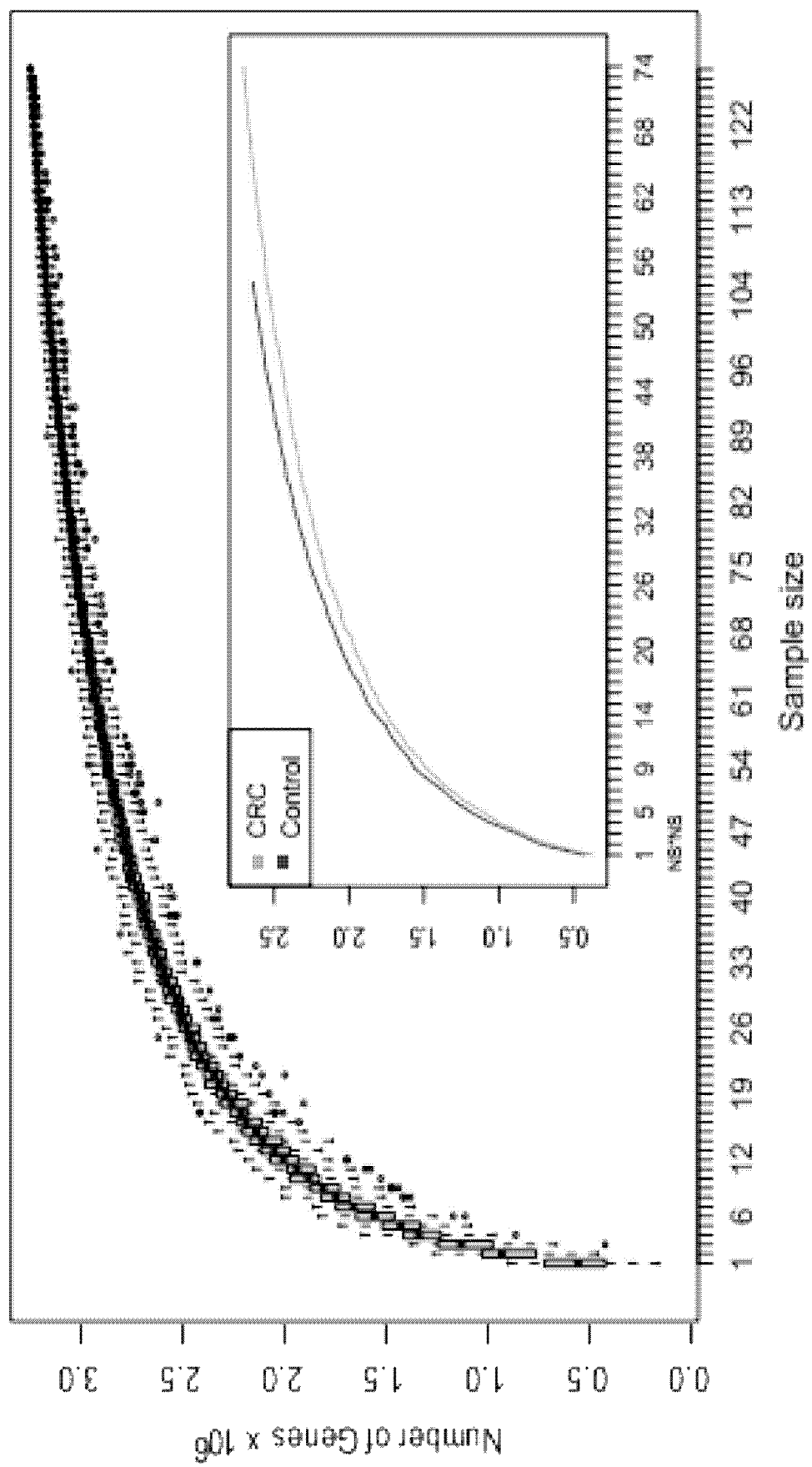
FIG. 4A: Correlation between template quantity and Cq values of the 16S rDNA control. A representative example of qPCR evaluation on samples #1-10 serially diluted from a mixture of 10 randomly selected fecal samples. qPCR results correlated well with template quantity when final DNA concentrations were <10 ng/µL (#4→#10), whilst DNA of >10 ng/µL inhibited PCR amplification (#1→#3).
Figure 4B:
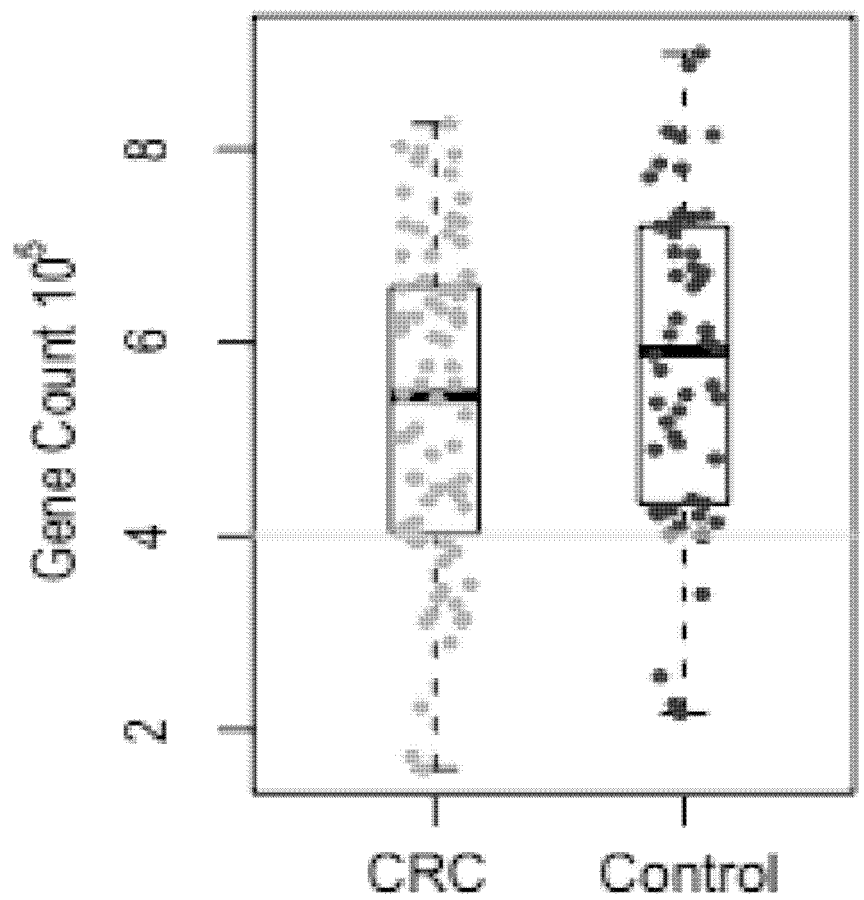
FIG. 4B: Correlation between Cq values of the internal control and DNA quantities (n=29).
Figure 4C:
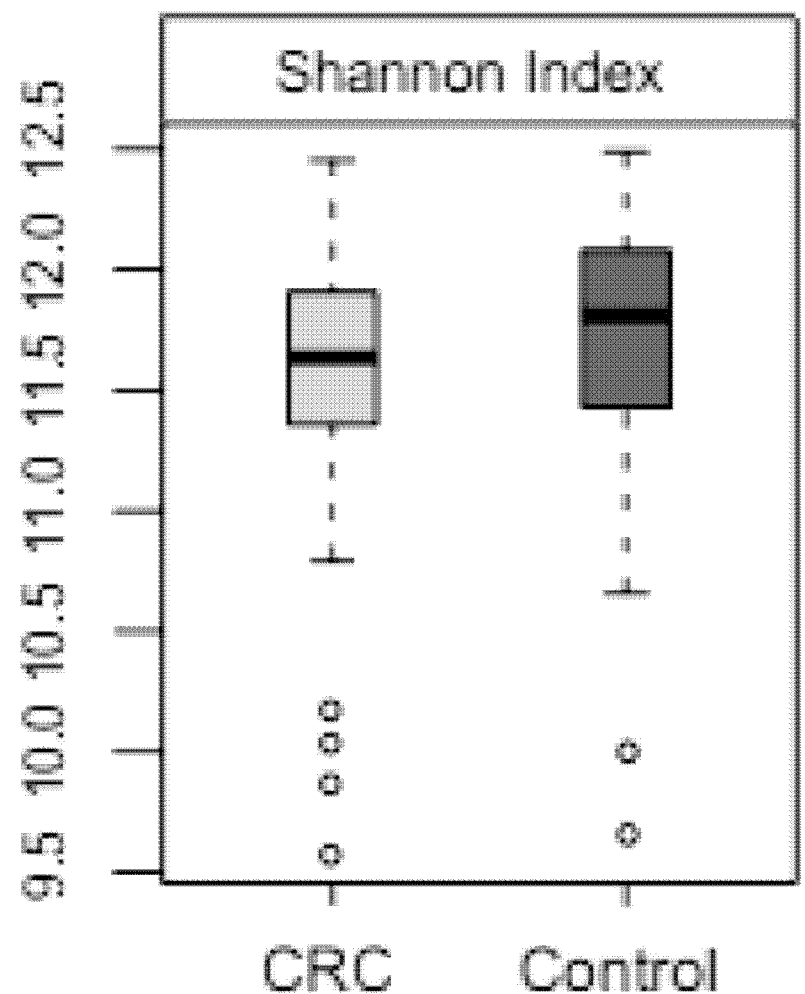
FIG. 4C: The new duplex qPCR assay can stably assess relative target abundance with an appropriate DNA template concentration from fecal samples. An example showing *Fusobacterium nucleatum* (Fn) abundance was stably assessed in one randomly selected fecal sample with several final DNA concentrations<10 ng/µL.
Figure 4D:
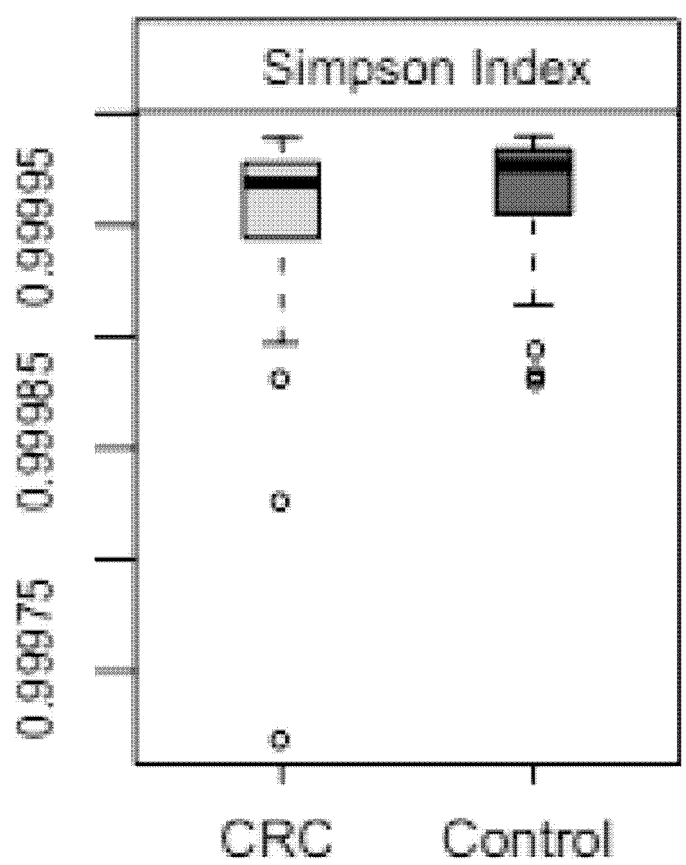
FIG. 4D: Fn abundance was stably assessed in samples, known to have low and very low Fn abundance, with final DNA concentrations<10 ng/µL, but extremely low DNA concentrations may cause false-negative detection in samples of low Fn abundance.

Duplex qPCR Assays for Convenient and Reliable Quantification of Bacterial Abundances To make the quantification of bacterial content convenient, we designed a degenerate primer-probe (VIC-labeled) set with an amplicon size suitable for qPCR quantification to target a 131-bp conserved region of the 16S rRNA genes. The primer and probe sequences cover >90% of the eubacterial population within the Ribosomal Database Project Release version 10.8 (14). Tests using different fecal DNA samples indicated that this internal control assay was capable of evaluating the total bacteria with DNA templates of <10 ng/μL in the final reaction systems (FIG. 4a). Higher template concentrations inhibited PCR amplification probably due to the general impurities within DNA isolated from feces, since no inhibition was observed for pure total DNA extracted from cultured *E. coli* up to at least 25 ng/μL. Using templates with concentration <10 ng/μL, Cq values correlated well with Log2 DNA quantities (R=0.804) (FIG. 4b). Then duplex qPCR assays were developed using the VIC-labeled internal control and FAM-labeled primer-probe sets to specifically target the bacterial candidates. The relative abundance of target bacterium in individual samples could be quantitated consistently with templates of <10 ng/μL (FIG. 4c), but template concentration should be >0.1 ng/μL to avoid false-negative results in samples with low abundance of the target bacterium (FIG. 4d). Quantification of bacterial abundances using our qPCR assays can be well repeated (FIG. 21) and was not interfered by human DNA contamination (FIG. 22). This platform and well-defined experimental conditions may guarantee reliable and convenient quantification of bacterial targets using duplex qPCR assays.

Figure 5:
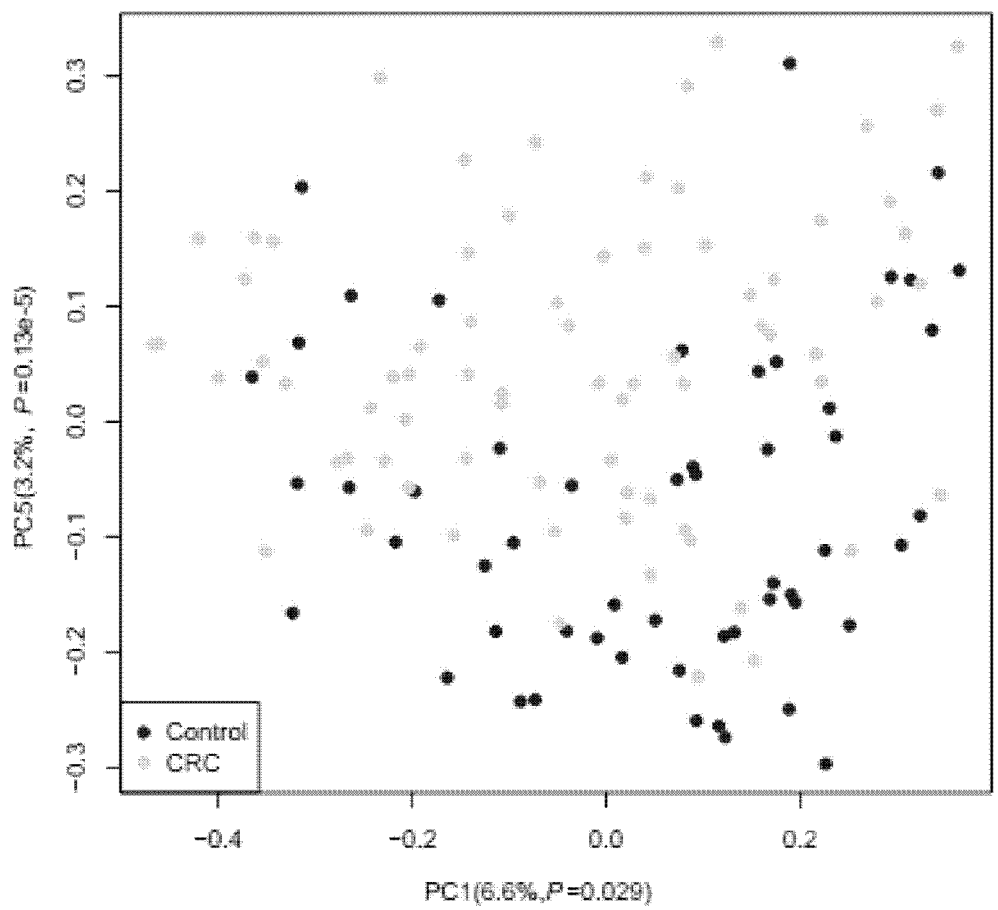
FIG. 5: Good correlation in the quantification of each marker by metagenomics approach and qPCR assays. Correlation for the quantification of *Roseburia intestinalis* (Ri), *Roseburia clarus* (Bc), *Clostridium hathewayi* (Ch) and one undefined species (labeled as m7), by metagenomics approach (gene level, with gene ID shown) and qPCR assay. Corresponding gene marker numbers from metagenomics study were shown. Correlation for the quantification of *Fusobacterium nucleatum* (Fn) by metagenomics approach (species level) and qPCR assay.

The Quantification of Each Bacterial Candidate by Metagenomics Approach are Correlated with qPCR Assays To verify whether gene abundances measured by qPCR assays are comparable with metagenomics sequencing, the abundances of four bacterial candidates (Bc, Ch, Ri and m7) in a subset of subjects (51 CRC and 45 controls) by qPCR were compared to metagenomic sequencing. Quantification of each of these bacteria showed strong correlations by qPCR assays compared to metagenomic sequencing (Spearman r=0.816-0.934; FIG. 5a). The gene marker, butyryl-CoA dehydrogenase from Fn (m1704941; 99.13% identity), showed an occurrence of only 2.7% (39 out of 74) in CRC patients; whilst at the species level, Fn showed an occurrence of 83.8% (62 out of 74) in CRC patients (Table 9), inferring that Fn at species level is better than gene marker m1704941 for the diagnosis of CRC. Therefore, the inventors established a duplex-qPCR assay targeting the nusG gene of Fn, which was reported to be transcriptionally more active in colorectal tumors than in matched normal samples, (5) to assess the diagnostic value of Fn for CRC. This qPCR assay showed good correlation with Fn at species level by metagenome sequencing (FIG. 5b), suggesting qPCR targeting nusG may cover more strains of Fn and could be more sensitive in detecting CRC.

Figure 6:
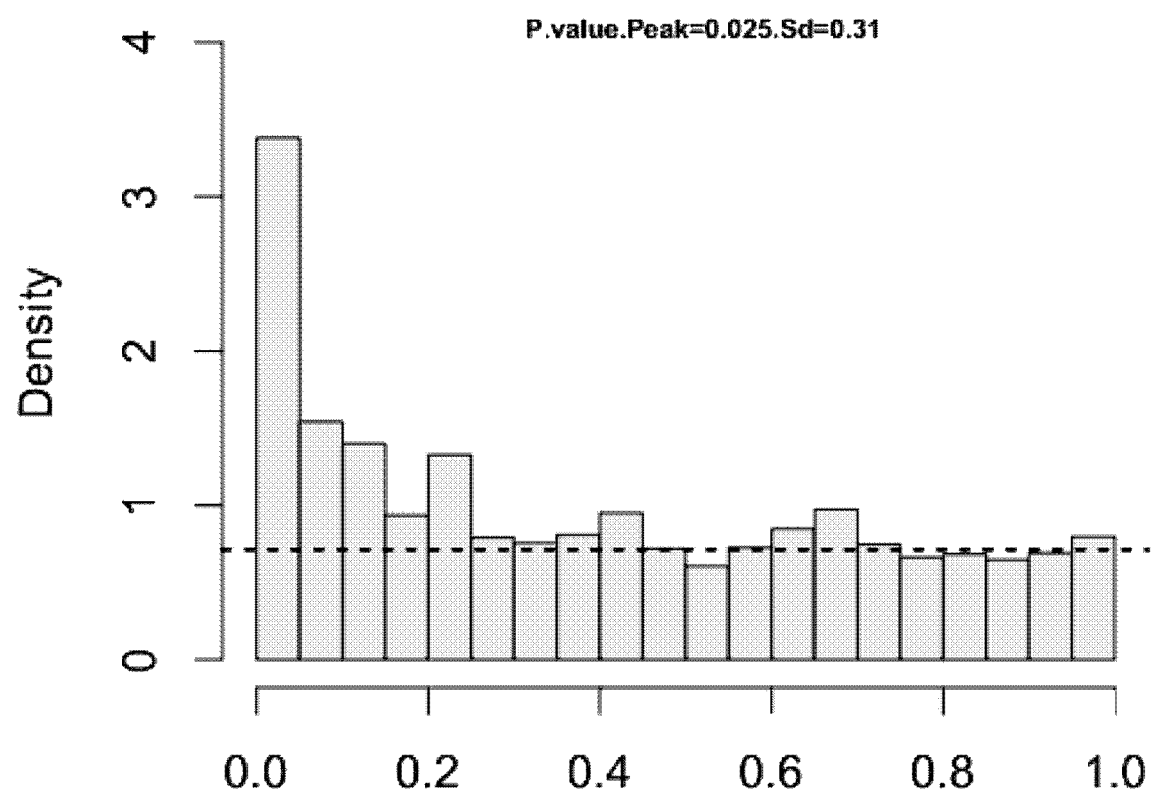
FIG. 6: Quantitative detection of fecal bacterial markers in the diagnosis of CRC patients. Abundances of *Fusobacterium nucleatum* (Fn), *Bacteroides clarus* (Bc), *Roseburia intestinalis* (Ri), *Clostridium hathewayi* (Ch), and one undefined species (label as m7) in fecal samples differed significantly between healthy control subjects (n=200) and CRC patients (n=170) of the first cohort. Receiver Operating Characteristic (ROC) curves for markers Fn, Ch, m7, Bc and Ri in discriminating CRC patients from healthy control subjects of cohort-I. Abundance of Fn in fecal samples of 33 CRC patients and 36 healthy subjects from an independent cohort-II and the corresponding ROC curve for Fn in discriminating CRC patients from healthy control subjects in this cohort. Medians with interquartile ranges are shown in the box and whisker plots by Tukey method.

Significantly Elevated Abundances of Fn, Ch, and m7 and Decreased Abundances of Bc and Ri in CRC Patients Compared to Healthy Controls It was found that the abundance of fecal Fn was predominantly higher in CRC patients (n=170) as compared to healthy controls (n=200). (P<0.0001; FIG. 6a and Table 1) by qPCR quantification. In addition, the significantly elevated abundances of Ch (P<0.0001) and m7 (P<0.0001), and decreased abundances of Bc (P<0.05) and Ri (P<0.05) in CRC patients were also demonstrated compared with control subjects. Bivariate correlation test showed that abundances of all the five bacteria were significantly associated with CRC, but not with tumor-node-metastasis (TNM) staging or tumor location (Table 2). The occurrence rates of these five bacteria differed significantly between CRC patients and healthy control subjects (Table 10). These results collectively confirmed the potential of these bacterial marker candidates in discriminating CRC patients from healthy subjects.

Fn is a Potential Non-Invasive Fecal Biomarker for Diagnosing CRC Patients

Among all the five bacteria, Fn showed the best performance in discriminating CRC from healthy controls, giving an area under receiver operating curve (AUROC) of 0.868 (0.831-0.904, 95% confidence interval; P<0.0001) (FIG. 6b). At the best cut-off value that maximizes the sum of sensitivity and specificity, Fn could discriminate CRC from controls with a sensitivity of 77.7%, specificity of 79.5%, negative predictive value (NPV) of 80.7%, and positive predictive value (PPV) of 76.3% in the first cohort of 170 CRC patients and 200 healthy subjects. This was further verified in a second independent cohort of 33 CRC patients and 36 healthy controls. The abundance of Fn was significantly higher in CRC patients as compared to healthy controls (P=0.012) (FIG. 6c). As a single factor in discriminating between CRC patients and control subjects, fecal Fn had an AUROC of 0.675 (0.545-0.804; P=0.013). The best cut-off value of Fn could discriminate CRC from controls with a sensitivity of 81.8%, specificity of 52.8%, NPV of 76.0%, and PPV of 61.4% in this second cohort.

Figure 7A:
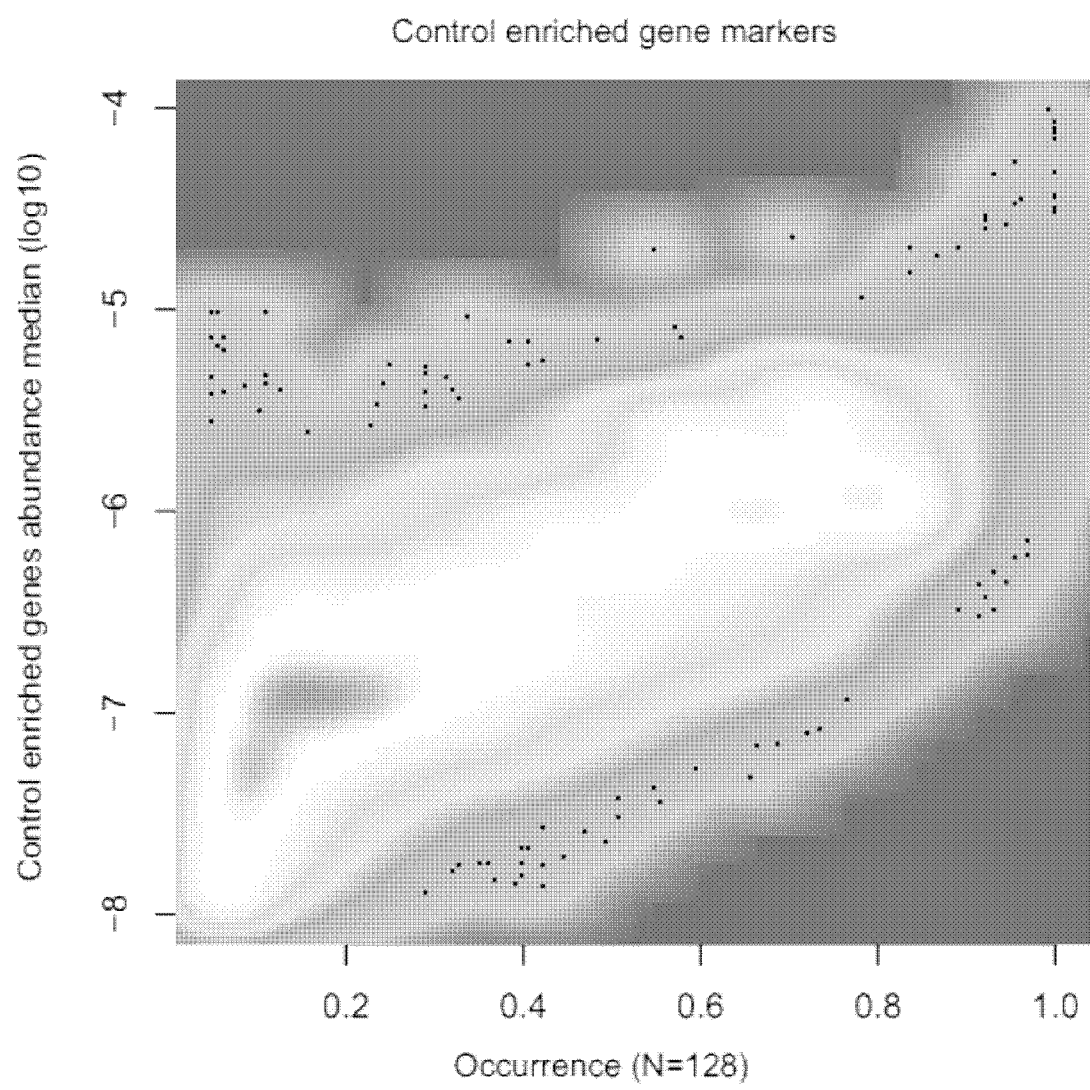
FIG. 7A: ROC curves for simple linear combination of four selected bacterial marker candidates including *Fusobacterium nucleatum* (Fn), *Bacteroides clarus* (Bc), *Clostridium hathewayi* (Ch), and one undefined species (labeled as m7), three selected bacteria (Fn, m7 and Bc), Fn only, and probability plot values of logistic regression model in the first cohort.
Figure 7B:
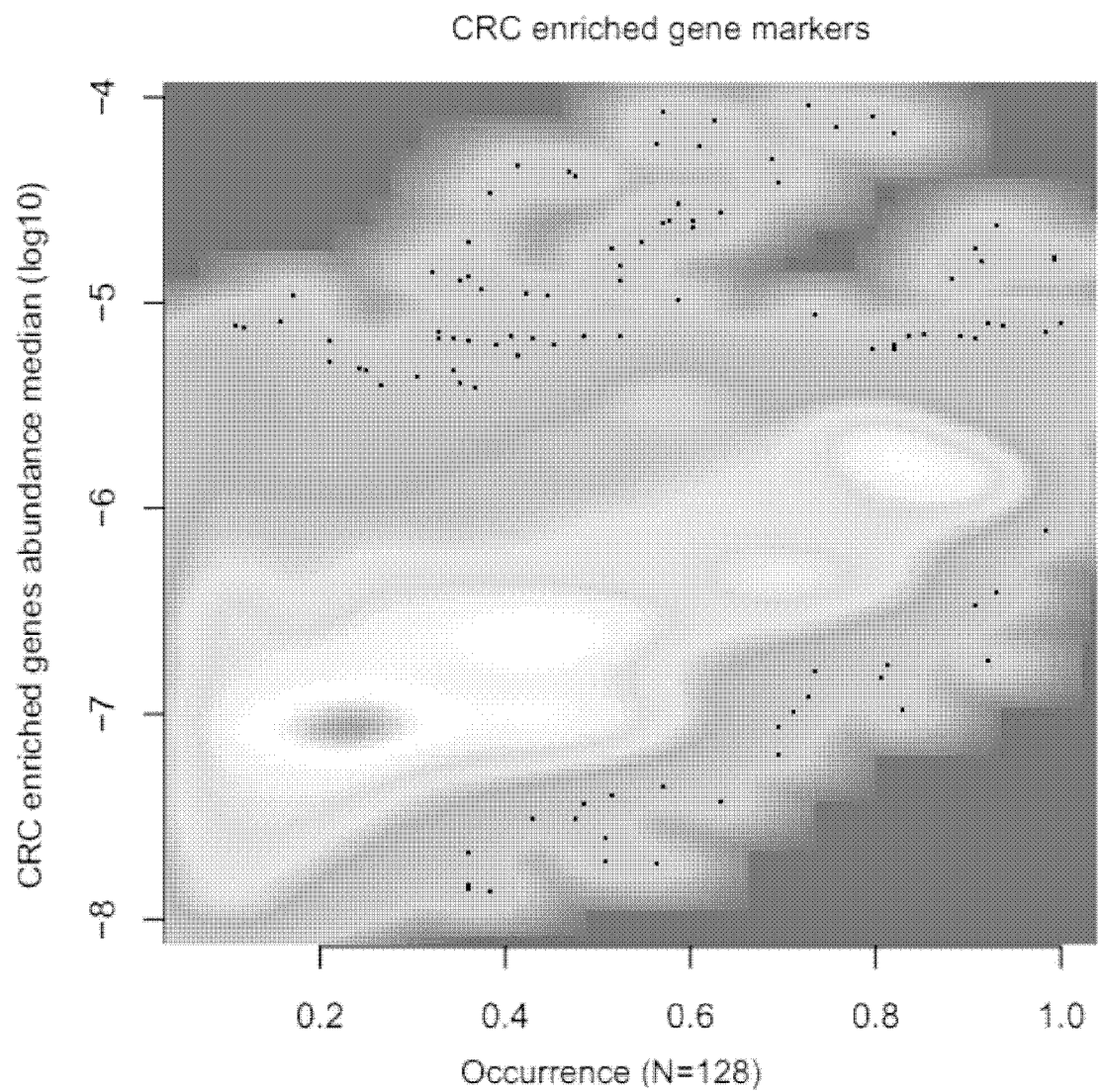
FIG. 7B: Fecal abundances of Fn and four-bacteria (Fn, Bc, Ch and m7) in CRC patients compared to healthy control subjects of the first cohort.

The Combination of Fn, m7,Bc and Chi Improves the Diagnostic Ability of Fn Alone for CRC Patients Linear regression analyses showed that abundances of Fn, m7 and Bc were significantly associated with the diagnosis of CRC (all P<0.05), and the abundance of Ch was marginally associated with CRC (P=0.073), while the association between Ri abundance and CRC was not significant (Table 3). Therefore, the abilities of the three (Fn, m7 and Bc) or four (Fn, m7, Bc and Ch) bacteria for the diagnosis of CRC were evaluated. It was found that a simple linear combination of the four-bacteria (0.886) gave an increased AUROC as compared to three-bacteria (0.877), Fn only (0.868), and the logistic regression model with inclusion of all four bacteria (0.869) in the first cohort (FIG. 7a). The combined abundance of four-bacteria was significantly higher in CRC patients as compared to healthy controls (P<0.0001) (FIG. 7b). At the best cut-off value, this panel of four-bacteria (Fn, m7, Bc and Ch) could discriminate CRC patients from healthy controls with a sensitivity of 77.7%, specificity of 81.5%, NPV of 81.1%, and PPV of 78.1%, showing a better diagnostic performance than Fn only (Table 4). The improved performance of four-bacteria was further validated in the second independent cohort. The combination of the four-bacteria also demonstrated an increased AUROC (0.756) as compared to three-bacteria (0.731), Fn only (0.675) or the logistic regression model (0.746) (FIG. 7c). The combined abundance of the four-bacteria was significantly higher in CRC patients than in healthy controls (P=0.0002) (FIG. 7d). At the best cut-off value, this panel of bacteria could discriminate CRC from controls with a sensitivity of 84.9%, specificity of 61.1%, NPV of 81.5%, and PPV of 66.7%, which also shows a better diagnostic performance than Fn only. Therefore, a bacteria panel of Fn, m7, Bc and Ch could improve the diagnostic ability of Fn alone in discriminating CRC from healthy controls.

Figure 8:
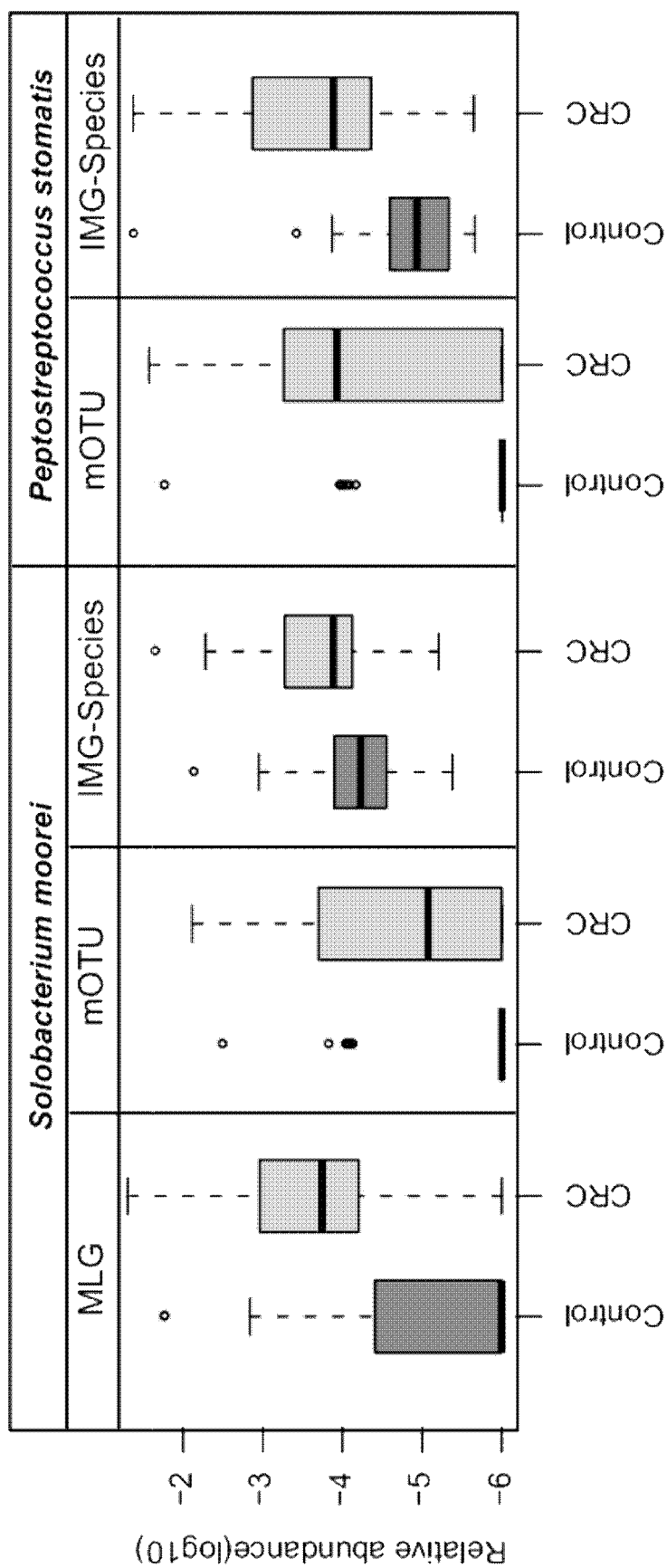
FIG. 8: Sensitivity of the Commercial Fecal Immunochemical Test (FIT) and bacterial markers according to tumor-node-metastasis (TNM) stage subsets. Shown are the sensitivities of FIT, 4-bacteria, and their combination for the detection of colorectal cancer according to tumor stage. The numbers in parentheses are the number of participants in each category.

The Combination of Bacterial Markers with FIT Improves the Diagnostic Ability of Bacteria Alone for CRC Patients FIT was performed on the stool samples of 111 CRC patients and 119 control subjects. It was found that 70.3% (78/111) fecal samples of CRC patients showed FIT positive. The detection rate of FIT was less than the quantification of Fn alone (82.0%) or the four-bacteria panel (83.8%) (both P<0.05 by Chi-square) in this sub-cohort of CRC patients. FIT was marginally associated with TNM staging (P=0.084), while the abundances of the four-bacteria or Fn alone showed no correlation with TNM staging (Table 11). Comparative results for the detection of cancer, according to TNM stage subsets, demonstrated that the quantification of bacterial markers showed significantly higher sensitivities compared to FIT for stage I cancer (FIG. 8). Elevated detection rates of stages II and III cancers were also observed by the bacteria than by FIT but not late stage IV. These results demonstrated that the quantification of bacterial markers was significantly more sensitive than FIT for the detection of CRC, especially for early stage CRC.

The combination of bacterial markers with FIT significantly increased the sensitivity of Fn from 82.0% to 92.8% and the four-bacteria from 83.8% to 92.8%, along with improved PPV and NPV and almost unchanged specificity (Table 5). According to TNM staging, combination of bacterial markers with FIT showed significantly higher sensitivities than using FIT only for stages I, II and III cancers (FIG. 8). These results suggested that the combination of bacterial markers and FIT had the highest sensitivity and specificity for the non-invasive diagnostic value of patients with CRC.

Discussion

According to the most updated Asia Pacific consensus recommendations on CRC screening, FIT is applied to select high-risk patients for colonoscopy (16). FIT has also been widely used in other regions of the world (17). However, the sensitivity of FIT shows limitations for CRC [0.79 (95% CI, 0.69 to 0.86)] and differed greatly among various studies, according to a recent systematic review and meta-analysis by Lee et. al. (17). Nevertheless, the wide application of FIT makes fecal samples easily obtainable. Detection of molecular biomarkers in fecal samples for the non-invasive diagnosis of CRC may be a more promising alternative than blood/plasma biomarkers to be implemented in present clinical settings. With the widespread application of pyrosequencing and metagenome sequencing in the field of microbiota, an increasing number of CRC-associated bacteria have been identified, including those identified by us (12). There is an urgent need to validate these candidate markers and to evaluate their clinical application values by targeted quantification methods.

In order to develop a convenient and reliable method for the targeted quantification of bacterial candidates on their validity and potential clinical implementation, a qPCR platform was established for the quantification in fecal samples. The primer-probe set targeting 16S rRNA genes was designed based on the conserved sequences of all 16S rRNA genes available (14), guaranteeing sufficient coverage and an amplicon size suitable for qPCR (<150 bp). This internal control was confirmed to work well to represent the bacterial DNA content in different samples. Then the probe-based duplex-qPCR assay allows the detection of both internal control and target in the same reaction for each sample, saving both reagents and samples, and producing more reliable data. Target marker abundance is calculated relative to total bacterial content by the ΔCp method. The present inventors defined for the first time that DNA template concentration should be limited (<10 ng/μL) to avoid inhibitory effects caused by fecal DNA and >0.1 ng/μL to avoid false-negative assessments of the targets using our duplex qPCR assays. A good correlation was further shown in the quantification of bacterial candidates by metagenomics approach and qPCR assays. Therefore, the duplex-qPCR assays are reliable, convenient, and of great clinical application value in the quantitative detection of target bacteria.

Using this platform, the potential value of Fn as a biomarker for the stool-based diagnosis of CRC was further corroborated. The abundance of fecal Fn was significantly higher in CRC patients than in healthy control subjects. As a single factor in discriminating CRC patients from healthy subjects, Fn had a sensitivity of 77.7% and specificity of 79.5% in the first cohort of 170 CRC patients and 200 healthy control subjects. The significantly increased or decreased fecal abundances of Bc, Ri, Ch and m7 in CRC patients than in control subjects was also shown, as consistent with metagenomics findings. Although the ability of these individual bacteria to discriminate CRC patients from healthy subjects was limited due to the limited occurrence rates in CRC patients or control subjects, it was found that combining the abundances of Bc, Ch and m7 with that of Fn could improve the diagnostic ability of Fn for CRC. The abundance of Ri did not improve the diagnostic ability of Fn for CRC and was excluded in the further analyses. At the best cutoff value that maximizes the sum of sensitivity and specificity, the combined four-bacteria panel had a sensitivity of 77.7% and specificity of 81.5% in the first cohort of 370 subjects. Importantly, Fn and the combination of four-bacteria markers (Fn, Bc, Ch and m7) for the diagnosis of CRC was also verified in a second independent cohort of fecal samples of CRC patients and healthy controls.

Compared with FIT, the bacterial markers were found to be superior in sensitivity for CRC diagnosis, especially for early stage CRC. It is intriguing that 16 and 15 samples in stage II and III respectively, showed positive in either bacterial markers or FIT (Table 12), summing up to 36.5% of stage II and III cases. Together with the 60% cases (II: 26/42 and III: 25/43) showing positive in both bacterial markers and FIT, the combination of bacteria with FIT detected 96.5% of stages II and III CRC. It has been shown that metagenomic analysis combined with the standard fecal occult blood test (FOBT) improved CRC detection sensitivity (18). It is thus anticipated that the inclusion of the bacterial marker quantification assays, in the non-invasive diagnosis of CRC, with the widely applied FIT may improve diagnosis sensitivity.

Bc is a gram-negative, obligately anaerobic, non-spore-forming, rod-shaped bacterium species that was isolated from human feces in 2010 (19). Ch is a strictly anoxic, gram-positive, spore-forming, rod-shaped bacterium that participates in glucose metabolism using carbohydrates as fermentable substrates to produce acetate, ethanol, carbon dioxide and hydrogen (20). Unlike the well characterized Fn, which is known to promote CRC tumorigenesis, whether the altered abundances of Ri, Bc or m7 play a causative role in CRC development or serve as a consequence of CRC development needs further investigation.

In conclusion, the quantification of Fn alone can serve as a non-invasive diagnostic method for CRC with a moderate sensitivity and specificity. The combination of four bacterial markers (Fn, Bc, Ch and m7) improved the diagnostic ability of Fn alone for CRC. Moreover, the combination of the bacterial markers and FIT showed the highest sensitivity and specificity for the diagnosis of CRC, especially for early stage CRC. Thus, stool-based detection of bacterial markers can serve as a novel non-invasive diagnostic method for patients with CRC.

TABLE 1

Abundances of bacterial candidates in fecal samples of CRC patients and healthy control subjects

| | Bacteria* | | | | | | | | | |
|---|---|---|---|---|---|---|---|---|---|---|
| | Fn | | Ch | | m7 | | Bc | | Ri | |
| | Group** | | | | | | | | | |
| | CRC | control | CRC | control | CRC | control | CRC | control | CRC | control |
| Minimum | 0 | 0 | 0 | 0 | 0 | 0 | 0 | 0 | 0 | 0 |
| 25% Percentile | 0.0008 | 0 | 0 | 0 | 0 | 0 | 0 | 0 | 0 | 0 |
| Median | 0.0288 | 8.1E−06 | 0 | 0 | 1.9E−07 | 0 | 0 | 0 | 0 | 0 |
| 75% Percentile | 0.1011 | 0.0004 | 7.3E−07 | 0 | 0.0002 | 2.3E−06 | 0 | 0 | 6.4E−07 | 0.0004 |
| Maximum | 1.4960 | 0.5826 | 3.2500 | 0.8897 | 0.9908 | 0.1144 | 0.0047 | 0.3563 | 0.2324 | 0.2617 |
| P value (Mann-Whitney test) | <0.0001 | | <0.0001 | | <0.0001 | | <0.05 | | <0.85 | |

Notes:

*Fn, *Fusobacterium nucleatum*; Ch, *Clostridium hathewayi*; m7, in-house label for an unknown species; Bc, *Bacteroides clarus*; Ri, *Roseburia intestinalis*;
**n = 370 (170 CRC and 200 healthy controls).

TABLE 2

Bivariate correlation analysis showing the correlation between bacterial candidates and CRC patients

| Variable | Bacteria* | | | | | | | | | |
|---|---|---|---|---|---|---|---|---|---|---|
| | Fn | | Ch | | m7 | | Bc | | Ri | |
| | Rho | P value | Rho | P value | Rho | P value | Rho | P value | Rho | P value |
| Age | 0.301 | <0.001 | 0.143 | 0.006 | 0.110 | 0.035 | −0.053 | 0.310 | −0.091 | 0.081 |
| Gender | 0.105 | 0.044 | 0.097 | 0.062 | 0.041 | 0.429 | −0.008 | 0.877 | 0.050 | 0.335 |
| CRC** | 0.636 | <0.001 | 0.350 | <0.001 | 0.350 | <0.001 | −0.128 | 0.014 | −0.143 | 0.006 |
| TNM staging | 0.042 | 0.589 | 0.012 | 0.877 | −0.056 | 0.475 | −0.057 | 0.465 | 0.077 | 0.327 |
| Lesion location | −0.023 | 0.769 | 0.029 | 0.709 | 0.008 | 0.915 | 0.020 | 0.796 | 0.068 | 0.386 |
| Differentiation | 0.146 | 0.061 | −0.009 | 0.910 | −0.046 | 0.559 | −0.132 | 0.090 | −0.045 | 0.563 |
| BMI | 0.069 | 0.432 | −0.020 | 0.819 | 0.003 | 0.976 | −0.088 | 0.315 | 0.076 | 0.386 |

Notes:
*Fn, *Fusobacterium nucleatum*; Ch, *Clostridium hathewayi*; m7, in-house label for an unknown species; Bc, *Bacteroides clarus*; Ri, *Roseburia intestinalis*; **n = 170.

TABLE 3

Univariate linear regression analyses of bacteria abundance and CRC status

| Bacteria* | Coefficient | 95% confidence interval | P value |
|---|---|---|---|
| Fn | 0.13 | 0.093-0.167 | <0.001 |
| Ch | 0.035 | (−0.003)-0.073 | 0.073 |
| m7 | 0.016 | 0-0.032 | 0.043 |
| Bc | −0.005 | (−0.010)-0.001 | 0.019 |
| Ri | −0.002 | (−0.007)-0.004 | 0.520 |

Notes:
*Fn, *Fusobacterium nucleatum*; Ch, *Clostridium hathewayi*; m7, in-house label for an unknown species; Bc, *Bacteroides clarus*; Ri, *Roseburia intestinalis*.

TABLE 4

Performance of Fn alone and in combination with other bacteria for CRC diagnosis

| Variable | Fn | Combination of Fn, Bc, Ch and m7 |
|---|---|---|
| AUROC | 0.868 | 0.886 |
| Cutoff | 0.0007072 | 0.001774 |
| Sensitivity | 77.7% | 77.7% |
| specificity | 79.5% | 81.5% |
| PPV | 76.3% | 78.1% |
| NPV | 80.7% | 81.1% |

Notes:
The best cutoff values that maximize sensitivity and specificity were used.
PPV, positive predictive value; NPV, negative predictive value; AUROC, area under receiver operating characteristics curve.
n = 370 (170 CRC and 200 healthy controls).
Fn, *Fusobacterium nucleatum*; Ch, *Clostridium hathewayi*; m7, in-house label for an unknown species; Bc, *Bacteroides clarus*; Ri, *Roseburia intestinalis*.

TABLE 5

Performance of Fit or Fn alone and in combination with other bacteria for CRC diagnosis

| Variable | FIT | Fn | Fn + FIT | 4-Bac | 4-Bac + FIT |
|---|---|---|---|---|---|
| Sensitivity | 70.3% | 82.0% | 92.8% | 83.8% | 92.8% |
| specificity | 98.3% | 80.7% | 79.8% | 83.2% | 81.5% |
| PPV | 97.5% | 79.8% | 81.1% | 82.3% | 82.4% |
| NPV | 78.0% | 82.8% | 92.2% | 84.6% | 92.4% |

Notes:
230 subjects (111 CRC and 119 healthy controls) with FIT result in HK cohort was included.
PPV, positive predictive value; NPV, negative predictive value; AUROC, area under Receiver Operating Characteristics (ROC) curve. 4-Bac includes Fn, Bc, Ch and m7.

TABLE 6

Clinical characteristics of healthy subjects and colorectal cancer patients

| Variables | Hong Kong | | | Hong Kong (subset with FIT) | | | Shanghai | | |
|---|---|---|---|---|---|---|---|---|---|
| | Control (n = 200) | CRC (n = 170) | P value* | Control (n = 119) | CRC (n = 111) | P value* | Control (n = 36) | CRC (n = 33) | P value* |
| Age | 59.3 ± 5.8 | 67.2 ± 11.6 | <0.001 | 59.1 ± 5.3 | 66.8 ± 11.4 | <0.001 | 53.2 ± 12.2 | 63.4 ± 9.6 | <0.001 |
| Gender | | | | | | | | | |
| Male | 77 (38.5%) | 100 (58.8%) | <0.001 | 46 (38.7%) | 73 (65.8%) | <0.001 | 10 (27.8%) | 17 (51.5%) | <0.05 |
| Female | 123 (61.5%) | 70 (41.2%) | | 73 (61.3%) | 38 (34.2%) | | 26 (72.2%) | 16 (48.5%) | |
| BMI | 23.4 ± 2.9 | 23.8 ± 3.4 | 0.443 | 23.1 ± 2.5 | 23.9 ± 3.3 | 0.228 | | | |
| Location | | | | | | | | | |
| Proximal | | 40 (23.5%) | | | 22 (19.8%) | | | 7 (21.2%) | |
| Distal | | 126 (74.1%) | | | 89 (80.2%) | | | 26 (78.8%) | |

TABLE 6-continued

Clinical characteristics of healthy subjects and colorectal cancer patients

| Variables | Hong Kong | | | Hong Kong (subset with FIT) | | | Shanghai | | |
|---|---|---|---|---|---|---|---|---|---|
| | Control (n = 200) | CRC (n = 170) | P value* | Control (n = 119) | CRC (n = 111) | P value* | Control (n = 36) | CRC (n = 33) | P value* |
| TNM stage | | | | | | | | | |
| I | | 27 (15.9%) | | | 17 (15.3%) | | | 4 (12.1%) | |
| II | | 64 (37.6%) | | | 42 (37.8%) | | | 10 (30.3%) | |
| III | | 55 (32.4%) | | | 43 (38.7%) | | | 12 (36.4%) | |
| IV | | 18 (10.6%) | | | 9 (8.1%) | | | 7 (21.2%) | |

CRC, colorectal cancer; FIT, fecal immunochemical test; BMI, body mass index; TNM, tumor-node-metastasis.
*Gender by Chi-square; Age and BMI by T-test.
As the majority of CRC cases were moderately differentiated, differentiation status was not included in further analysis.

TABLE 7

Primers and probes used in this study

| Species* | Label | Control rank mean | CRC rank mean | Enrichment | Wilcoxon rank-sum test | | Gene ID |
|---|---|---|---|---|---|---|---|
| | | | | | P-value | q-value | |
| *Fusobacterium nucleatum* | Fn | 40.32407 | 82.1419 | CRC | 1.72E−10 | 7.48E−09 | 1704941 |
| *Clostridium hathewayi* | Ch | 46.77778 | 77.4324 | CRC | 2.12E−05 | 2.05E−04 | 2736705 |
| undefined species 'm7' | m7 | na | na | CRC | 1.80E−07 | 3.24E−03 | 3246804 |
| *Bacteroides clarus* | Bc | 75.55556 | 56.4324 | Control | 1.29E−03 | 2.50E−03 | 370640 |
| *Roseburia intestinalis* | Ri | 76.99074 | 55.3851 | Control | 2.20E−03 | 3.58E−03 | 181682 |

*MLG species associated with CRC at a significance level of q < 0.05 according to Wilcoxon rank-sum tests with Benjamini-Hochberg adjustment. No species rank mean values could be calculated for the undefined species 'm7', so p-value and q-value shown were based on gene marker '3246804'.

TABLE 8

Primers and probes used in this study (SEQ ID NOS 84-86, 36-44, 24-26 and 21-23, respectively, in order of appearance)

| Targets | | Nucleotide sequence (5'->3') | Size (bp) |
|---|---|---|---|
| Internal control (16S rDNA) | Forward | CGTCAGCTCGTGYCGTGAG | 131 |
| | Reverse | CGTCRTCCCCRCCTTCC | |
| | Probe | VIC-TTAAGTCCCRYAACGAGCGCAACCC-TAMRA | |
| *Fusobacterium nucleatum* | Forward | TTCAATAAAAGTGGCAGGTCAAG | 100 |
| | Reverse | TAACAACACATGCAGGTCAATGG | |
| | Probe | FAM-ACTCGAACCCCCAACCCTCGGTTT-TAMRA | |
| *Clostridium hathewayi* | Forward | GGGCTGCGGAAGCAACTTA | 145 |
| | Reverse | GATGACCTCGCCCTGATCAT | |
| | Probe | FAM-ACCACCACACAGGACGGAAAGATTCTCC-TAMRA | |
| m7 | Forward | TCGGCACGCTGATTATCACA | 119 |
| | Reverse | CACACGCCGATCCATCTTC | |
| | Probe | FAM-ACCCACCTGGACGGCTCCGG-TAMRA | |
| *Bacteroides clarus* | Forward | TCCATCCGCAAGCCTTTACT | 140 |
| | Reverse | GCTTCCGGTGCCATTGACTA | |
| | Probe | FAM-TTCATCATCACAGCCGACAACGCA-TAMRA | |
| *Roseburia intestinalis* | Forward | CGGATTTGCAGTGGCAAGTT | 140 |
| | Reverse | TGATTGCAGACGCCAATGTC | |
| | Probe | FAM-CGTGAAAAATCCGCGCATCTGGC-TAMRA | |

TABLE 9

Abundances of m1704941 (gene maker level, 99.13% identity) and *F. nucleatum* (species level) in fecal samples of CRC patients by metagenome sequencing

| # | CRCsamples | m1704941 (*10e8) | Fn (*10e8) |
|---|---|---|---|
| 1 | A10A | 119.103 | 770.962 |
| 2 | M113A | 0.000 | 0.000 |
| 3 | M115A | 0.000 | 535.076 |
| 4 | M116A | 12.186 | 1172.955 |
| 5 | M117A | 0.000 | 0.000 |
| 6 | M118A | 23.959 | 80.325 |
| 7 | M122A | 76.728 | 620.901 |
| 8 | M123A | 0.000 | 211.109 |
| 9 | M2-Pk-001A | 0.000 | 68.787 |
| 10 | M2-PK002A | 0.000 | 251.341 |
| 11 | M2-PK003A | 0.000 | 66.039 |
| 12 | M2-Pk-004A | 0.000 | 33.969 |
| 13 | M2-Pk-005A | 0.000 | 12.579 |
| 14 | M2-Pk-006A | 0.000 | 112.314 |
| 15 | M2-Pk-007A | 7.492 | 12.558 |
| 16 | M2-Pk-008A | 0.000 | 87.967 |
| 17 | M2-Pk-009A | 0.000 | 6.170 |
| 18 | M2-Pk-010A | 24.677 | 351.666 |
| 19 | M2-Pk-011A | 0.000 | 10.725 |
| 20 | M2-Pk-012A | 0.000 | 0.000 |
| 21 | M2-Pk-013A | 0.000 | 0.000 |
| 22 | M2-Pk-014A | 6.780 | 1066.997 |
| 23 | M2-Pk-015A | 0.000 | 52.238 |
| 24 | M2-Pk-016A | 85.015 | 5278.599 |
| 25 | M2-Pk-017A | 0.000 | 5.224 |
| 26 | M2-PK018A | 0.000 | 0.000 |
| 27 | M2-PK019A | 0.000 | 157.794 |
| 28 | M2-PK021A | 85.513 | 1903.679 |
| 29 | M2-PK022A | 4.441 | 847.987 |
| 30 | M2-PK023A | 4.883 | 11.652 |
| 31 | M2-PK024A | 0.000 | 120.104 |
| 32 | M2-PK026A | 0.000 | 417.015 |
| 33 | M2-PK027A | 0.000 | 144.897 |
| 34 | M2-PK029A | 211.346 | 5178.345 |
| 35 | M2-PK030A | 7.385 | 145.345 |
| 36 | M2-PK032A | 173.798 | 12597.161 |
| 37 | M2-PK037A | 4.656 | 77.877 |
| 38 | M2-PK038A | 5.344 | 87.607 |
| 39 | M2-PK041A | 0.000 | 75.317 |
| 40 | M2-PK042A | 0.000 | 0.000 |
| 41 | M2-PK043A | 0.000 | 80.437 |
| 42 | M2-PK045A | 8.567 | 407.051 |
| 43 | M2-PK046A | 6.250 | 647.331 |
| 44 | M2-PK047A | 5.613 | 119.765 |
| 45 | M2-PK051A | 7.280 | 106.657 |
| 46 | M2-PK052A | 0.000 | 13.354 |
| 47 | M2-PK055A | 5.489 | 19.874 |
| 48 | M2-PK056B | 0.000 | 0.000 |
| 49 | M2-PK059A | 6.495 | 0.000 |
| 50 | M2-PK063A | 0.000 | 31.149 |
| 51 | M2-PK064A | 0.000 | 0.000 |
| 52 | M2-PK065A | 33.082 | 536.173 |
| 53 | M2-PK066A | 0.000 | 0.000 |
| 54 | M2-PK067A | 7.238 | 127.253 |
| 55 | M2-PK069B | 0.000 | 14.021 |
| 56 | M2-PK083B | 38.884 | 498.342 |
| 57 | M2-PK084A | 287.222 | 2738.321 |
| 58 | M2-PK085A | 0.000 | 0.000 |
| 59 | M84A | 19.101 | 176.928 |
| 60 | M89A | 0.000 | 0.000 |
| 61 | MSC103A | 27.599 | 1072.417 |
| 62 | MSC119A | 19.962 | 438.074 |
| 63 | MSC120A | 0.000 | 15.705 |
| 64 | MSC1A | 134.217 | 3162.506 |
| 65 | MSC45A | 7.630 | 691.798 |
| 66 | MSC4A | 0.000 | 44.458 |
| 67 | MSC54A | 36.590 | 347.776 |
| 68 | MSC5A | 33.231 | 874.652 |
| 69 | MSC63A | 13.564 | 41.892 |
| 70 | MSC6A | 7.693 | 90.783 |
| 71 | MSC76A | 79.396 | 877.104 |
| 72 | MSC78A | 7.240 | 21.414 |
| 73 | MSC79A | 240.618 | 2072.609 |
| 74 | MSC81A | 8.325 | 79.723 |
| | Occurrence % | 52.70% | 83.80% |

TABLE 10

The occurrence rates of bacterial candidates in fecal samples of CRC patients and healthy control subjects

| Bacteria | Occurrence in CRC | Occurrence in Control | P value ($x^2$) |
|---|---|---|---|
| *F. nucleatum* (Fn) | 98.2% | 72.0% | <0.0001 |
| *C. hathewayi* (Ch) | 35.3% | 8.0% | <0.0001 |
| m7 | 53.5% | 37.0% | 0.001 |
| *B. clarus* (Bc) | 12.9% | 21.5% | 0.031 |
| *R. intestinalis* (Ri) | 22.9% | 36.0% | 0.006 |

TABLE 11

Correlations of bacterial abundance, FIT with CRC diagnosis and staging

| | Fn | | 4-bacteria | | FIT | |
|---|---|---|---|---|---|---|
| Variable | Rho | p-value | Rho | p-value | Rho | p-value |
| CRC | 0.685 | <0.001 | 0.734 | <0.001 | 0.720 | <0.001 |
| TNM staging | 0.046 | 0.635 | 0.021 | 0.827 | 0.165 | 0.084 |
| Lesion location | 0.002 | 0.982 | −0.074 | 0.440 | 0.122 | 0.204 |

A subset of 230 subjects (111 CRC and 119 healthy controls) with fecal immunochemical test (FIT) result was included.

TABLE 12

Combining bacterial markers and FIT in diagnosing

| TNM | # | Fn | 4markers | FIT | &FIT |
|---|---|---|---|---|---|
| I | 1 | 0.95580 | 0.96380 | 1 | 1 |
| | 2 | 0.90263 | 0.90337 | 1 | 1 |
| | 3 | 0.23575 | 0.23577 | 1 | 1 |
| | 4 | 0.19319 | 0.19202 | 1 | 1 |
| | 5 | 0.04631 | 0.04656 | 1 | 1 |
| | 6 | 0.00965 | 0.00965 | 1 | 1 |
| | 7 | 0.00128 | 0.00185 | 1 | 1 |
| | 8 | 0.42338 | 0.42338 | 0 | 1 |
| | 9 | 0.09616 | 0.09616 | 0 | 1 |
| | 10 | 0.02638 | 0.02638 | 0 | 1 |
| | 11 | 0.00791 | 0.99791 | 0 | 1 |
| | 12 | 0.00185 | 0.00185 | 0 | 1 |
| | 13 | 0.00085 | 0.00098 | 0 | 1/0 |
| | 14 | 0.00000 | 0.00269 | 0 | 0/1 |
| | 15 | 0.00058 | 0.00058 | 0 | 0 |
| | 16 | 0.00001 | 0.00005 | 0 | 0 |
| | 17 | 0.00000 | 0.00000 | 0 | 0 |
| II | 1 | 1.49632 | 1.49640 | 1 | 1 |
| | 2 | 0.87787 | 0.87787 | 1 | 1 |
| | 3 | 0.55448 | 0.55448 | 1 | 1 |
| | 4 | 0.27088 | 0.27089 | 1 | 1 |
| | 5 | 0.11118 | 0.11118 | 1 | 1 |
| | 6 | 0.09866 | 0.09995 | 1 | 1 |
| | 7 | 0.09256 | 0.09256 | 1 | 1 |
| | 8 | 0.09236 | 0.09033 | 1 | 1 |
| | 9 | 0.08412 | 0.08430 | 1 | 1 |

TABLE 12-continued

Combining bacterial markers and FIT in diagnosing

| TNM | # | Fn | 4markers | FIT | &FIT |
|---|---|---|---|---|---|
|  | 10 | 0.07488 | 0.07488 | 1 | 1 |
|  | 11 | 0.07170 | 0.07193 | 1 | 1 |
|  | 12 | 0.05593 | 0.05593 | 1 | 1 |
|  | 13 | 0.05478 | 0.05478 | 1 | 1 |
|  | 14 | 0.04136 | 0.04138 | 1 | 1 |
|  | 15 | 0.03991 | 0.04100 | 1 | 1 |
|  | 16 | 0.03721 | 0.03650 | 1 | 1 |
|  | 17 | 0.03675 | 0.03675 | 1 | 1 |
|  | 18 | 0.02761 | 0.02872 | 1 | 1 |
|  | 19 | 0.01574 | 0.01574 | 1 | 1 |
|  | 20 | 0.01401 | 0.01402 | 1 | 1 |
|  | 21 | 0.00783 | 0.00783 | 1 | 1 |
|  | 22 | 0.00354 | 0.00355 | 1 | 1 |
|  | 23 | 0.00313 | 0.00313 | 1 | 1 |
|  | 24 | 0.00079 | 0.00182 | 1 | 1 |
|  | 25 | 0.00079 | 0.00457 | 1 | 1 |
|  | 26 | 0.00076 | 0.00101 | 1 | 1 |
|  | 27 | 0.22595 | 0.22723 | 0 | 1 |
|  | 28 | 0.08132 | 0.08132 | 0 | 1 |
|  | 29 | 0.05251 | 0.05251 | 0 | 1 |
|  | 30 | 0.04693 | 0.04693 | 0 | 1 |
|  | 31 | 0.04509 | 0.04513 | 0 | 1 |
|  | 32 | 0.03386 | 0.03386 | 0 | 1 |
|  | 33 | 0.02126 | 0.02128 | 0 | 1 |
|  | 34 | 0.01812 | 0.01656 | 0 | 1 |
|  | 35 | 0.00247 | 0.00336 | 0 | 1 |
|  | 36 | 0.00059 | 0.00407 | 1 | 1 |
|  | 37 | 0.00030 | 0.04061 | 1 | 1 |
|  | 38 | 0.00011 | 0.50011 | 1 | 1 |
|  | 39 | 0.00034 | 0.00034 | 1 | 1 |
|  | 40 | 0.00011 | 0.00011 | 1 | 1 |
|  | 41 | 0.00006 | 0.00006 | 1 | 1 |
|  | 42 | 0.00000 | 0.00001 | 1 | 1 |
| III | 1 | 0.97603 | 0.97735 | 1 | 1 |
|  | 2 | 0.60055 | 0.60055 | 1 | 1 |
|  | 3 | 0.35341 | 0.35340 | 1 | 1 |
|  | 4 | 0.24074 | 0.24078 | 1 | 1 |
|  | 5 | 0.18005 | 0.18006 | 1 | 1 |
|  | 6 | 0.11989 | 0.12005 | 1 | 1 |
|  | 7 | 0.08829 | 0.08829 | 1 | 1 |
|  | 8 | 0.08775 | 0.13142 | 1 | 1 |
|  | 9 | 0.07796 | 0.08425 | 1 | 1 |
|  | 10 | 0.07075 | 0.07075 | 1 | 1 |
|  | 11 | 0.06448 | 0.06448 | 1 | 1 |
|  | 12 | 0.06352 | 0.06352 | 1 | 1 |
|  | 13 | 0.04412 | 0.04413 | 1 | 1 |
|  | 14 | 0.03778 | 0.03807 | 1 | 1 |
|  | 15 | 0.03171 | 0.03171 | 1 | 1 |
|  | 16 | 0.02501 | 0.02501 | 1 | 1 |
|  | 17 | 0.02354 | 0.05623 | 1 | 1 |
|  | 18 | 0.02197 | 0.01819 | 1 | 1 |
|  | 19 | 0.01891 | 0.01899 | 1 | 1 |
|  | 20 | 0.01273 | 0.01285 | 1 | 1 |
|  | 21 | 0.01191 | 0.01245 | 1 | 1 |
|  | 22 | 0.00482 | 0.00482 | 1 | 1 |
|  | 23 | 0.00308 | 0.00308 | 1 | 1 |
|  | 24 | 0.00293 | 0.00293 | 1 | 1 |
|  | 25 | 0.00142 | 0.00212 | 1 | 1 |
|  | 26 | 0.75260 | 0.75261 | 0 | 1 |
|  | 27 | 0.74845 | 0.75812 | 0 | 1 |
|  | 28 | 0.65098 | 0.65098 | 0 | 1 |
|  | 29 | 0.04723 | 0.04723 | 0 | 1 |
|  | 30 | 0.04069 | 0.04069 | 0 | 1 |
|  | 31 | 0.03509 | 0.03510 | 0 | 1 |
|  | 32 | 0.01441 | 0.01441 | 0 | 1 |
|  | 33 | 0.01099 | 0.01099 | 0 | 1 |
|  | 34 | 0.00244 | 0.41495 | 0 | 1 |
|  | 35 | 0.00196 | 0.00210 | 0 | 1 |
|  | 36 | 0.00056 | 0.00056 | 1 | 1 |
|  | 37 | 0.00041 | 0.00092 | 1 | 1 |
|  | 38 | 0.00032 | 0.00032 | 1 | 1 |
|  | 39 | 0.00011 | 0.00014 | 1 | 1 |
|  | 40 | 0.00000 | 0.00011 | 1 | 1 |
|  | 41 | 0.00008 | 0.00008 | 0 | 0 |
|  | 42 | 0.00005 | 0.00005 | 0 | 0 |
|  | 43 | 0.00001 | 0.00001 | 0 | 0 |
| IV | 1 | 0.68858 | 0.68858 | 1 | 1 |
|  | 2 | 0.10827 | 0.10401 | 1 | 1 |
|  | 3 | 0.07293 | 0.07293 | 1 | 1 |
|  | 4 | 0.05502 | 0.12836 | 1 | 1 |
|  | 5 | 0.03396 | 0.03397 | 1 | 1 |
|  | 6 | 0.02643 | 0.03824 | 1 | 1 |
|  | 7 | 0.02457 | 0.02458 | 1 | 1 |
|  | 8 | 0.02429 | 0.02430 | 1 | 1 |
|  | 9 | 0.00000 | 0.00121 | 0 | 0 |

The best cutoff values (Fn=0.0007072; 4-markers=0.001774) that maximize sensitivity and specificity were determined in the larger cohort with 170 CRC and 200 controls.

References for Example 1

1. Ferlay J, Soerjomataram I, Ervik M, et al. GLOBOCAN 2012 v1.0, Cancer Incidence and Mortality Worldwide. IARC CancerBase. Lyon, France: International Agency for Research on Cancer, 2013.
2. Galvan A, Ioannidis J P, Dragani T A. Beyond genome-wide association studies: genetic heterogeneity and individual predisposition to cancer. Trends Genet 2010; 26:132-41.
3. Lichtenstein P, Holm N V, Verkasalo P K, et al. Environmental and heritable factors in the causation of cancer—analyses of cohorts of twins from Sweden, Denmark, and Finland. N Engl J Med 2000; 343:78-85.
4. Foulkes W D. Inherited susceptibility to common cancers. N Engl J Med 2008; 359:2143-53.
5. Dove W F, Clipson L, Gould K A, et al. Intestinal neoplasia in the ApcMin mouse: independence from the microbial and natural killer (beige locus) status. Cancer Res 1997; 57:812-14.
6. Arthur J C, Perez-Chanona E, Muhlbauer M, et al. Intestinal inflammation targets cancer-inducing activity of the microbiota. Science 2012; 338:120-3.
7. Cuevas-Ramos G, Petit C R, Marcq I, et al. *Escherichia coli* induces DNA damage in vivo and triggers genomic instability in mammalian cells. Proc Natl Acad Sci USA 2010; 107:11537-42.
8. Grivennikov S I, Wang K, Mucida D, et al. Adenoma-linked barrier defects and microbial products drive IL-23/IL-17-mediated tumour growth. Nature 2012; 491:254-8.
9. Toprak N U, Yagci A, Gulluoglu B M, et al. A possible role of *Bacteroides fragilis* enterotoxin in the aetiology of colorectal cancer. Clin Microbiol Infect 2006; 12:782-6.
10. Uronis J M, Muhlbauer M, Herfarth H H, et al. Modulation of the intestinal microbiota alters colitis-associated colorectal cancer susceptibility. PLoS ONE 2009; 4:e6026.
11. Wu S, Rhee K J, Albesiano E, et al. A human colonic commensal promotes colon tumorigenesis via activation of T helper type 17 T cell responses. Nat Med 2009; 15:1016-22.
12. Boleij A, Schaeps R M, Tjalsma H. Association between *Streptococcus bovis* and colon cancer. J Clin Microbiol 2009; 47:516.
13. Seder C W, Kramer M, Long G, et al. *Clostridium septicum* aortitis: Report of two cases and review of the literature. J Vasc Surg 2009; 49:1304-9.

14. Scanlan P D, Shanahan F, Clune Y, et al. Culture-independent analysis of the gut microbiota in colorectal cancer and polyposis. Environ Microbiol 2008; 10:789-98.
15. Sobhani I, Tap J, Roudot-Thoraval F, et al. Microbial dysbiosis in colorectal cancer (CRC) patients. PLoS ONE 2011; 6:e16393.
16. Chen W, Liu F, Ling Z, et al. Human intestinal lumen and mucosa-associated microbiota in patients with colorectal cancer. PLoS ONE 2012; 7:e39743.
17. Castellarin M, Warren R L, Freeman J D, et al. *Fusobacterium nucleatum* infection is prevalent in human colorectal carcinoma. Genome Res 2012; 22:299-306.
18. Kostic A D, Gevers D, Pedamallu C S, et al. Genomic analysis identifies association of *Fusobacterium* with colorectal carcinoma. Genome Res 2012; 22:292-8.
19. Kostic A D, Chun E, Robertson L, et al. *Fusobacterium nucleatum* Potentiates Intestinal Tumorigenesis and Modulates the Tumor-Immune Microenvironment. Cell Host Microbe 2013; 14:207-15.
20. Rubinstein M R, Wang X, Liu W, et al. *Fusobacterium nucleatum* promotes colorectal carcinogenesis by modulating E-cadherin/beta-catenin signaling via its FadA adhesin. Cell Host Microbe 2013; 14:195-206.
21. Zackular J P, Rogers M A, Ruffin M Tt, et al. The human gut microbiome as a screening tool for colorectal cancer. Cancer Prev Res (Phila) 2014; 7:1112-21.
22. Zeller G, Tap J, Voigt A Y, et al. Potential of fecal microbiota for early-stage detection of colorectal cancer. Mol Syst Biol 2014; 10:766.
23. Edge S B, Compton C C. The American Joint Committee on Cancer: the 7th edition of the AJCC cancer staging manual and the future of TNM. Ann Surg Oncol 2010; 17:1471-4.
24. Godon J J, Zumstein E, Dabert P, et al. Molecular microbial diversity of an anaerobic digestor as determined by small-subunit rDNA sequence analysis. Appl Environ Microbiol 1997; 63:2802-13.
25. Qin J, Li Y, Cai Z, et al. A metagenome-wide association study of gut microbiota in type 2 diabetes. Nature 2012; 490:55-60.
26. Sunagawa S, Mende D R, Zeller G, et al. Metagenomic species profiling using universal phylogenetic marker genes. Nat Methods 2013; 10:1196-9.
27. Markowitz V M, Chen I M, Palaniappan K, et al. IMG: the Integrated Microbial Genomes database and comparative analysis system. Nucleic Acids Res 2012; 40:D115-22.
28. Peng H, Long F, Ding C. Feature selection based on mutual information: criteria of max-dependency, max-relevance, and min-redundancy. IEEE Trans Pattern Anal Mach Intell 2005; 27:1226-38.
29. Kabat G C, Kim M Y, Strickler H D, et al. A longitudinal study of serum insulin and glucose levels in relation to colorectal cancer risk among postmenopausal women. Br J Cancer 2012; 106:227-32.
30. van Duijnhoven F J, Bueno-De-Mesquita H B, Calligaro M, et al. Blood lipid and lipoprotein concentrations and colorectal cancer risk in the European Prospective Investigation into Cancer and Nutrition. Gut 2011; 60:1094-102.
31. Feng Q, Liang S, Jia H, et al. Gut microbiome development along the colorectal adenoma-carcinoma sequence. Nat Commun 2015; 6:6528.
32. Kanehisa M, Goto S, Sato Y, et al. KEGG for integration and interpretation of large-scale molecular data sets. Nucleic Acids Res 2012; 40:D109-14.
33. Baracos V E, Mackenzie M L. Investigations of branched-chain amino acids and their metabolites in animal models of cancer. J Nutr 2006; 136:237S-42S.
34. Gonsalves E M, Salomão E M, Gomes-Marcondes M C C. Leucine modulates the effect of Walker factor, a proteolysis-inducing factor-like protein from Walker tumours, on gene expression and cellular activity in C2C12 myotubes. Cytokine 2013; 64:343-50.
35. Pedersen R M, Holt H M, Justesen U S. *Solobacterium moorei* bacteremia: identification, antimicrobial susceptibility, and clinical characteristics. J Clin Microbiol 2011; 49:2766-8.
36. Sundqvist G. Taxonomy, ecology, and pathogenicity of the root canal flora. Oral Surg Oral Med Oral Pathol 1994; 78:522-30.
37. Knights D, Costello E K, Knight R. Supervised classification of human microbiota. FEMS Microbiol Rev 2011; 35:343-59.
38. Qin J, Li R, Raes J, et al. A human gut microbial gene catalogue established by metagenomic sequencing. Nature 2010; 464:59-65.
39. Li J, Jia H, Cai X, et al. An integrated catalog of reference genes in the human gut microbiome. Nat Biotechnol 2014; 32:834-41.
40. Ahn J, Sinha R, Pei Z, et al. Human gut microbiome and risk for colorectal cancer. J Natl Cancer Inst 2013; 105:1907-11.
41. Ciccarelli F D, Doerks T, von Mering C, et al. Toward automatic reconstruction of a highly resolved tree of life. Science 2006; 311:1283-7.
42. Holmes I, Harris K, Quince C. Dirichlet multinomial mixtures: generative models for microbial metagenomics. PLoS ONE 2012; 7:e30126.
43. Ding T, Schloss P D. Dynamics and associations of microbial community types across the human body. Nature 2014; 509:357-60.
44. Kremer B H, van Steenbergen T J. *Peptostreptococcus micros* coaggregates with *Fusobacterium nucleatum* and non-encapsulated *Porphyromonas gingivalis*. FEMS Microbiol Lett 2000; 182:57-62.
45. Yoshioka M, Grenier D, Mayrand D. Binding of *Actinobacillus* ctinomycetemcomitans lipopolysaccharides to *Peptostreptococcus micros* stimulates tumor necrosis factor alpha production by macrophage-like cells. Oral Microbiol Immunol 2005; 20:118-21.
46 Storey J D, Tibshirani R. Statistical significance for genomewide studies. Proceedings of the National Academy of Sciences of the United States of America 2003; 100:9440-5.
47 Li R, Yu C, Li Y, Lam T W, Yiu S M, Kristiansen K, et al. SOAP2: an improved ultrafast tool for short read alignment. Bioinformatics 2009; 25:1966-7.
48 Shannon P, Markiel A, Ozier O, Baliga N S, Wang J T, Ramage D, et al. Cytoscape: a software environment for integrated models of biomolecular interaction networks. Genome research 2003; 13:2498-504.

References for Example 2

1. Sung J J, Lau J Y, Goh K L, et al. Increasing incidence of colorectal cancer in Asia: implications for screening. Lancet Oncol 2005; 6:871-6.
2. Irrazabal T, Belcheva A, Girardin S E, et al. The multifaceted role of the intestinal microbiota in colon cancer. Mol Cell 2014; 54:309-20.

3. Ahn J, Sinha R, Pei Z, et al. Human gut microbiome and risk for colorectalcancer. J Natl Cancer Inst 2013; 105: 1907-11.
4. Kassinen A, Krogius-Kurikka L, Makivuokko H, et al. The fecal microbiota of irritable bowel syndrome patients differs significantly from that of healthy subjects. Gastroenterology 2007; 133:24-33.
5. Castellarin M, Warren R L, Freeman J D, et al. *Fusobacterium nucleatum* infection is prevalent in human colorectal carcinoma. Genome Res 2012; 22:299-306.
6. Qin J, Li Y, Cai Z, et al. A metagenome-wide association study of gut microbiota in type 2 diabetes. Nature 2012; 490:55-60.
7. Shin N R, Lee J C, Lee H Y, et al. An increase in the Akkermansia spp. population induced by metformin treatment improves glucose homeostasis in diet-induced obese mice. Gut 2014; 63:727-35.
8. McCoy A N, Araujo-Perez F, Azcarate-Peril A, et al. *Fusobacterium* is associated with colorectal adenomas. PLoS One 2013; 8:e53653.
9. Kostic A D, Chun E, Robertson L, et al. *Fusobacterium nucleatum* potentiates intestinal tumorigenesis and modulates the tumor-immune microenvironment. Cell Host Microbe 2013; 14:207-15.23
10. Rubinstein M R, Wang X, Liu W, et al. *Fusobacterium nucleatum* promotes colorectal carcinogenesis by modulating E-cadherin/beta-catenin signaling via its FadA adhesin. Cell Host Microbe 2013; 14:195-206.
11. Nakatsu G, Li X, Zhou H, et al. Gut mucosal microbiome across stages of colorectal carcinogenesis. Nat Commun 2015; 6:8727.
12. Yu J, Feng Q, Wong S H, et al. Metagenomic analysis of faecal microbiome as a tool towards targeted non-invasive biomarkers for colorectal cancer. Gut 2015: September 25. pii: gutjnl-2015-309800.
13. Jalanka J, Salonen A, Salojarvi J, et al. Effects of bowel cleansing on the intestinal microbiota. Gut 2015; 64:1562-8.
14. Wang Y, Qian P Y. Conservative fragments in bacterial 16S rRNA genes and primer design for 16S ribosomal DNAamplicons in metagenomic studies. PLoS One 2009; 4:e7401.
15. Huang Y, Li Q, Ge W, et al. Predictive power of quantitative and qualitative fecal immunochemical tests for hemoglobin in population screening for colorectal neoplasm. Eur J Cancer Prev 2014; 23:27-34.
16. Sung J J, Ng S C, Chan F K, et al. An updated Asia Pacific Consensus Recommendations on colorectal cancer screening. Gut 2015; 64:121-32.
17. Lee J K, Liles E G, Bent S, et al. Accuracy of fecal immunochemical tests for colorectal cancer: systematic review and meta-analysis. Ann Intern Med 2014; 160:171.
18. Zeller G, Tap J, Voigt A Y, et al. Potential of fecal microbiota for early-stage detection of colorectal cancer. Mol Syst Biol 2014; 10:766.24
19. Watanabe Y, Nagai F, Morotomi M, et al. *Bacteroides* clams sp. nov., *Bacteroides* fluxus sp. nov. and *Bacteroides* oleiciplenus sp. nov., isolated from human faeces. Int J Syst Evol Microbiol 2010; 60:1864-9.
20. Steer T, Collins M D, Gibson G R, et al. *Clostridium hathewayi* sp. nov., from human faeces. Syst Appl Microbiol 2001; 24:353-7.

All patents, patent applications, and other publications, including GenBank Accession Numbers, cited in this application are incorporated by reference in the entirety for all purposes.

What is claimed is:

1. A method for assessing risk for colon cancer in a subject, comprising the steps of:
   (a) performing a polymerase chain reaction to amplify the nucleotide sequence set forth in SEQ ID NO:3, thereby quantitatively determining level of a bacterial species whose genome comprises the nucleotide sequence set forth in SEQ ID NO:3 in a stool sample taken from the subject;
   (b) comparing the level obtained in step (a) with a standard control;
   (c) determining the level obtained in step (a) as increased from the standard control;
   (d) determining the subject who has an increased level in step (c) as having an increased risk for colon cancer; and
   (e) administering colonoscopy to the subject who has been determined in step (d) as having an increased risk for colon cancer/examination.

2. The method of claim 1, further comprising quantitatively determining *Parvimonas micra, Solobacterium moorei, Clostridium hathewayi*, or *Fusobacterium nucleatum* level in the sample.

3. The method of claim 1, further comprising quantitatively determining *Bacteroides clarus* or *Roseburia intestinalis* level in the sample.

4. The method of claim 1, wherein step (a) comprises determining the level of a DNA or RNA unique to the bacterial species whose genome comprises the nucleotide sequence set forth in SEQ ID NO:3.

5. The method of claim 2, wherein step (a) comprises determining the level of a DNA or RNA unique to at least one of *Parvimonas micra, Solobacterium moorei, Fusobacterium nucleatum*, and *Clostridium hathewayi*.

6. The method of claim 5, wherein step (a) comprises determining the level of a DNA unique to at least one of *Parvimonas micra, Solobacterium moorei, Fusobacterium nucleatum*, and *Clostridium hathewayi*.

7. The method of claim 3, wherein step (a) comprises determining the level of a DNA or RNA unique to at least one of *Bacteroides clarus* and *Roseburia intestinalis*.

8. The method of claim 7, wherein step (a) comprises determining the level of a DNA unique to at least one of *Bacteroides clarus* and *Roseburia intestinalis*.

9. A method for detecting a bacterial species whose genome comprises the nucleotide sequence set forth in SEQ ID NO:3 in a stool sample, comprising the steps of:
   (a) performing a polymerase chain reaction to amplify the nucleotide sequence set forth in SEQ ID NO:3, thereby quantitatively determining level of the bacterial species whose genome comprises the nucleotide sequence set forth in SEQ ID NO:3 in the stool sample.

10. The method of claim 9, wherein the stool sample is obtained from a human subject.

11. The method of claim 9, further comprising step (b): quantitatively determining *Parvimonas micra, Solobacterium moorei, Clostridium hathewayi, Fusobacterium nucleatum, Bacteroides clarus*, or *Roseburia intestinalis* level in the sample.

12. The method of claim 11, wherein step (b) comprises determining the level of a DNA or RNA unique to *Parvimonas micra, Solobacterium moorei, Clostridium hathewayi, Fusobacterium nucleatum, Bacteroides clarus, Roseburia intestinalis* in the sample.

13. The method of claim 12, wherein step (b) comprises determining the level of a DNA unique to *Parvimonas micra, Solobacterium moorei, Clostridium hathewayi, Fusobacterium nucleatum, Bacteroides clarus, Roseburia intestinalis* in the sample.

14. The method of claim 13, wherein step (b) comprises a polymerase chain reaction.

* * * * *